United States Patent
Missiakas et al.

(10) Patent No.: US 11,214,600 B2
(45) Date of Patent: Jan. 4, 2022

(54) **COMPOSITIONS AND METHODS RELATED TO ANTIBODIES THAT NEUTRALIZE COAGULASE ACTIVITY DURING *STAPHYLOCOCCUS AUREUS* DISEASE**

(71) Applicants: The University of Chicago, Chicago, IL (US); Janssen Pharmaceuticals, Inc., Titusville, NJ (US)

(72) Inventors: Dominique Missiakas, Chicago, IL (US); Olaf Schneewind, Chicago, IL (US); Carla Emolo, Chicago, IL (US); Lena Thomer, Chicago, IL (US); Molly McAdow, Chicago, IL (US); Jeroen Geurtsen, Leiden (NL); Mark De Been, Leiden (NL)

(73) Assignees: The University of Chicago, Chicago, IL (US); Janssen Pharmaceuticals, Inc., Titusville, NJ (US)

( * ) Notice: Subject to any disclaimer, the term of this patent is extended or adjusted under 35 U.S.C. 154(b) by 8 days.

(21) Appl. No.: 16/077,213

(22) PCT Filed: Feb. 10, 2017

(86) PCT No.: PCT/IB2017/050763
§ 371 (c)(1),
(2) Date: Aug. 10, 2018

(87) PCT Pub. No.: WO2017/137954
PCT Pub. Date: Aug. 17, 2017

(65) Prior Publication Data
US 2019/0112342 A1    Apr. 18, 2019

Related U.S. Application Data

(60) Provisional application No. 62/294,413, filed on Feb. 12, 2016.

(51) Int. Cl.
| | | |
|---|---|---|
| *A61K 39/02* | (2006.01) |
| *A61K 39/00* | (2006.01) |
| *A61K 45/00* | (2006.01) |
| *A61K 47/00* | (2006.01) |
| *A61K 39/085* | (2006.01) |
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C07K 14/31* | (2006.01) |
| *C07K 16/12* | (2006.01) |
| *C07K 16/40* | (2006.01) |
| *C12Q 1/689* | (2018.01) |
| *A61K 39/40* | (2006.01) |

(52) U.S. Cl.
CPC ............ *C07K 14/31* (2013.01); *A61K 39/085* (2013.01); *A61K 39/40* (2013.01); *C07K 16/1271* (2013.01); *C07K 16/40* (2013.01); *C12Q 1/689* (2013.01); *A61K 2039/505* (2013.01); *C07K 2317/24* (2013.01); *C07K 2317/92* (2013.01)

(58) Field of Classification Search
CPC ..................................................... C07K 14/31
See application file for complete search history.

(56) References Cited

U.S. PATENT DOCUMENTS

| | | | | |
|---|---|---|---|---|
| 8,632,783 B2* | 1/2014 | Bagnoli | ................. | C07K 14/31 |
| | | | | 424/243.1 |
| 8,703,148 B2* | 4/2014 | Biemans | ............ | A61K 47/6415 |
| | | | | 424/194.1 |
| 8,858,955 B2* | 10/2014 | Biemans | ............... | A61K 39/385 |
| | | | | 424/197.11 |
| 9,085,631 B2* | 7/2015 | Moller | ................... | C07K 14/31 |
| 9,353,189 B2* | 5/2016 | Church | ................. | C07K 16/36 |
| 9,534,022 B2* | 1/2017 | Moller | ................. | C07K 16/1271 |
| 10,548,963 B2* | 2/2020 | Castado | ................. | A61P 31/04 |
| 2011/0008385 A1* | 1/2011 | Castado | ............... | A61K 39/085 |
| | | | | 424/197.11 |

(Continued)

FOREIGN PATENT DOCUMENTS

| | | |
|---|---|---|
| WO | WO 98/57994 | 12/1998 |
| WO | WO 00/12132 | 3/2000 |
| WO | WO 00/15238 | 3/2000 |

(Continued)

OTHER PUBLICATIONS

Kawabata et al., The Journal of Biological Chemistry, 1986; 261(2): 527-531. (Year: 1986).*

(Continued)

*Primary Examiner* — Gary B Nickol
*Assistant Examiner* — Lakia J Jackson-Tongue
(74) *Attorney, Agent, or Firm* — Norton Rose Fulbright US LLP

(57) ABSTRACT

Embodiments concern methods and compositions for treating or preventing a bacterial infection, particularly infection by a *Staphylococcus* bacterium. Aspects include methods and compositions for providing a passive immune response against the bacteria. In certain embodiments, the methods and compositions involve an antibody that binds Coagulase (Coa). Further aspects relate to immunogenic compositions comprising at least one Staphylococcal coagulase R Domain, wherein the R Domain is 80% identical in sequence to a R Domain.

5 Claims, 13 Drawing Sheets
Specification includes a Sequence Listing.

(56) References Cited

U.S. PATENT DOCUMENTS

| | | | | |
|---|---|---|---|---|
| 2013/0171183 A1* | 7/2013 | Schneewind | .......... | C07K 14/31 424/190.1 |
| 2015/0273040 A1* | 10/2015 | McAdow | .............. | C07K 14/31 424/243.1 |
| 2015/0368322 A1 | 12/2015 | McAdow et al. | | |
| 2018/0296659 A1* | 10/2018 | Moller | ................... | C07K 14/31 |

FOREIGN PATENT DOCUMENTS

| | | | |
|---|---|---|---|
| WO | WO2006032475 | * | 3/2006 |
| WO | WO 2007/113222 A | * | 10/2007 |
| WO | WO2007113223 | * | 10/2007 |
| WO | WO 2011/005341 | | 1/2011 |
| WO | WO 2012/003474 | | 1/2012 |
| WO | WO2012136653 | * | 10/2012 |
| WO | WO 2013/162751 | | 10/2013 |
| WO | WO 2013162746 | | 10/2013 |
| WO | WO 2015/057893 A | * | 4/2015 |

OTHER PUBLICATIONS

Watanabe et al., J Bacteriol., 2005; 187(11):3698-707 (Year: 2005).*
Kaida et al., J. Biochem., 1987; 102:1177-1186, 1987 (Year: 1987).*
Kanemitsu et al, Microbiol. Immunol., 2001; 45(1):23-27 (Year: 2001).*
Bae & Schneewind, "Allelic Replacement in *Staphylococcus auereus* with Inducible Counter-Selection," *Plasmid*, 55: 58-63, 2005.
Cheng, et al., Contribution of Coagulases Towards *Staphylococcus aureus* Disease and Protective Immunity. *PLoS Pathogen*, 6; e1001036, 2010.
Fowler, et al., "Effect of an Investigation Vaccine for Preventing *Staphylococcus aureus* Infections After Cardiothoracic Surgery: A Randomized Trial," *JAMA*, 309: 1368-1378, 2013.
International Search Report and Written Report Issued in Corresponding PCT Application No. PCT/IB17/50763, dated Aug. 7, 2017.
McAdow, et al., "Coagulases as Determinants of Protective Immune Responses Against *Staphylococcus aureus*," *Infect. Immun.*, 80: 3389-3398, 2012.
McAdow, et al., "Preventing *Staphylococcus aureus* Sepsis Through the Inhibition of its Agglutination in Blood," *PLoS Pathogen*, 7: e1002307, 2011.
McAdow, et al., "*Staphylococcus aureus* Secretes Coagulase and von Willebrand Factor Binding Protein to Modify the Coagulation Cascade and Establish Host Infections," *Journal of Innate Immunity*, 4: 141-148, 2012.
Panizzi, et al., "In Vivo Detection of *Staphylococcus aureus* Endocarditis by Targeting Pathogen-Specific Prothrombin Activation," *Nat. Med.*, 17(9): 1142-1146, 2011.
Shinefield, et al., "Use of *Staphylococcus aureus* Conjugate Vaccine in patients Receiving Hemodialysis," *New England Journal of Medicine*, 346: 491-496, 2002.
Smith, et al., "The Role of Coagulase in *Staphylococcus* Infections," *Brit. J Exp Pathol.*, 28: 57, 1947.
Spellberg & Daum, "Development of a Vaccine Against *Staphylococcus aureus*," *Semin Immunopathol.*, 34: 335-348, 2012.
Thomer, et al., "Multiple Ligands of von Willebrand Factor-Binding Protein (vWbp) Promote *Staphylococcus aureus* Clot Formation in Human Plasma," *J Biol Chem*, 288: 28283-28292, 2013.
Extended European Search Report and Opinion for EP17749960.5, dated Aug. 8, 2019.
Thomer et al., "Antibodies against a secreted product of *Staphylococcus aureus* trigger phagocytic killing", *The Journal of Experimental Medicine* 213:3, 2016, 283-301.
Office Action issued in Corresponding European Application No. 17749960.5, dated Apr. 6, 2021, Ref # N71886PCEP.

* cited by examiner

Alignment of Coa from five S. aureus strains

```
USA300_Coa    ATGAAAAAGCAAATAATTTCGCTAGGCGCATTAGCAGTTGCATCTAGCTTATTTACATGG 60
N315_Coa      ATGAAAAAGCAAATAATTTCGCTAGGCGCATTAGCAGTTGCATCTAGCTTATTTACATGG 60
MRSA252_Coa   ATGAAAAAGCAAATAATTTCGCTAGGCGCATTAGCAGTTGCATCTAGCTTATTTACATGG 60
MW2_Coa       ATGAAAAAGCAAATAATTTCGCTAGGCGCATTAGCAGTTGCATCTAGCTTATTTACATGG 60
WIS_Coa       ------------------------------------------------------------

USA300_Coa    GATAACAAAGCAGATGCGATAGTAACAAAGGATTATAGTGGGAAATCACAAGTTAATGCT 120
N315_Coa      GATAACAAAGCAGATGCGATAGTAACAAAGGATTATAGTAAAGAATCAAGAGTGAATGAG 120
MRSA252_Coa   GATAACAAAGCAGATGCGATAGTAACTAAAGATTATAGTAAAGAATCAAGAGTGAATGAG 120
MW2_Coa       GATAACAAAGCAGATGCGATAGTAACAAAGGATTATAGTGGGAAATCACAAGTTAATGCT 120
WIS_Coa       ------------------ATAGTAACAAAGGATTATAGTGGGAAATCACAAGTTAATGCT 42
                                ******** ** ********    *****  *** ****

USA300_Coa    GGGAGTAAAAATGGGAC-ATTAAT---AGATAGCAGATATTTAAATTCAGCTCTATATTA 176
N315_Coa      AAAAGTAAAAAGGGAGCTACTGTTTC-AGATTATTACTATTGGAAATAATT---GATAG 176
MRSA252_Coa   AACAGTAAATACGATAC-ACCAATTCCAGATTG---GTATCTAGGTAGTATTTTAAACAG 176
MW2_Coa       GGGAGTAAAAATGGGAA-ACAAATTGCAGATGGATATTATTGGGGAATAATT---GAAAA 176
WIS_Coa       GGGAGTAAAAATGGGAA-ACAAATTGCAGATGGATATTATTGGGGAATAATT---GAAAA 98
                ******  *      *         *    *    ****  ***       *   *

USA300_Coa    TTTGGAAGACTATATAATTTAT----GCTATAGGATTAACTAATAAATATGAATATGGAG 232
N315_Coa      TTTAGAGG----CACAATTTACTGGAGCAATAGACTTATTGGAAGATTATAAATATGGAG 232
MRSA252_Coa   ATTAGGGGATCAAATATACTAC----GCTAAGGAATTAACTAATAAATACGAATATGGTG 232
MW2_Coa       TCTAGAAAACCA---GTTTTAC-AATATTTTTCATTTACTGGATCAGCATAAATATGCAG 232
WIS_Coa       TCTAGAGAACCA---GTTTTAC-AATATTTTTCATTTATTGGATCAGCATAAATATGCAG 154
                * *          **       ***    *  *  * ******    *

USA300_Coa    ATAATATTTATAAAGAAGCTAAAGATAGGTTGTTGGAAAAGGTATTAAGGGAAGATCAAT 292
N315_Coa      ATCCTATCTATAAAGAAGCGAAAGATAGATTGATGACAAGAGTATTAGGAGAAGACCAGT 292
MRSA252_Coa   AGAAAGAGTATAAGCAAGCGATAGATAAATTGATGACTAGAGTTTTGGGAGAAGATCATT 292
MW2_Coa       AAAAAGAATATAAAGATGCAGTAGATAAATTAAAAACTAGAGTTTTAGAGGAAGACCAAT 292
WIS_Coa       AAAAAGAATATAAAGATGCATTAGATAAATTAAAAACTAGAGTTTTAGAGGAAGACCAAT 214
              *    *****  *  ***** **    *  ** **    *****  *

USA300_Coa    ATCTTTTGGAGAGAAAGAAATCTCAATATGAAGATTATAAACAATGGTATGCAAATTATA 352
N315_Coa      ATTTATTAAAGAAAAAGATTGATGAATATGAGCTTTATAAAAAGTGGTATAAAAGTT-CA 351
MRSA252_Coa   ATCTATTAGAAAAAAAGAAAGCCAATATGGTTTGAAAAATGGTTTGAAAAACATA 352
MW2_Coa       ACCTGCTAGAAAAGAAAAAAAGAAAAATACGAAATTTATAAAGAACTATATAAAAATACA 352
WIS_Coa       ACCTGCTAGAAAAGAAAAAAAGAAAAATACGAAATTTATAAAGAACTATATAAAAATACA 274
               *  *  *  * ***   ****  **  ** ***  *   *  * *

USA300_Coa    AAAAAGAAAATCCTCGTACAGATTTAAAAATGGCTAATTTTCATAAATATAATTTAGAAG 412
N315_Coa      AATAAGAACACT------------AATATGCTTACTTTCCATAAATATAATCTTTACA 397
MRSA252_Coa   AAAGTGAAAATCCACATTCTAGTTTAAAAAAGATTAAATTTGACGATTTTGATTTATATA 412
MW2_Coa       AAAAAGAGAATCCTAATACTCAAGTTAAAATGAAAGCATTTGATAAATACGATCTTGGCG 412
WIS_Coa       AAAAAGAGAATCCTAATACTCAGGTTAAAATGAAAGCATTTGATAAATACGATCTTGGCG 334
              **  **  *         ** *   ** *    *  *  **

USA300_Coa    AACTTTCGATGAAAGAATACAATGAACTACAGGATGCATTAAAGAGAGCACTGGATGATT 472
N315_Coa      ATTTAACAATGAATGAATATAACGATATTTTTAACTCTTTGAAAGATGCAGTTTATCAAT 457
MRSA252_Coa   GATTAACGAAGAAAGAATACAATGAGTTACATCAATCATTAAAAGAAGCTGTTGATGAGT 472
MW2_Coa       ATTTAACTATGGAAGAATACAATGACTTATCAAAATTATTAACAAAAGCATTGGATAACT 472
WIS_Coa       ATTTAACTATGGAAGAATACAATGACTTATCAAAATTATTAACAAAAGCATTGGATAACT 394
                * *  ***** ** **  * *   *        *  **  ** * ** * *
```

FIG. 7A

```
USA300_Coa     TTCACAGAGAAGTTAAAGATATTAAGGATAAGAATTCAGACTTGAAAACTTTTAATGCAG 532
N315_Coa       TTAATAAAGAAGTTAAAGAAATAGAGCATAAAAATGTTGACTTGAAGCAGTTTGATAAAG 517
MRSA252_Coa    TTAATAGTGAAGTGAAAAATATTCAATCTAAACAAAAGGATTTATTACCTTATGATGAAG 532
MW2_Coa        TTAAGTTAGAAGTAAAGAAAATTGAATCAGAGAATCCAGATTTAAAACCATATTCTGAAA 532
WIS_Coa        TTAAGTTAGAAGTAAAGAAAATTGAATCAGAGAATCCAGATTTAAGACCATATTCTGAAA 454
                **  *    *****  **   *  **     *       *  *    **  **        *   *   *

USA300_Coa     CAGAAGAAGATAAAGCAACTAAGGAAGTATACGATCTCGTATCTGAAATTGATACATTAG 592
N315_Coa       ATGGAGAAGACAAGGCAACTAAAGAAGTTTATGACCTTGTTTCTGAAATTGATACATTAG 577
MRSA252_Coa    CAACTGAAAATCGAGTAACAAATGGAATATATGATTTTGTTTGCGAGATTGACACATTAT 592
MW2_Coa        GCGAAGAAAGAACAGCATATGGTAAAATAGATTCACTTGTTGATCAAGCATATAGTGTAT 592
WIS_Coa        GTGAAGAGAGAACAGCATATGGTAAAATAGATTCACTTGTTGATCAAGCATATAGTGTAT 514
                **           *  *          *  *   *    *  **       *       *  *       **

USA300_Coa     TTGTATCATATTATGGTGATAAGGATTATGGGGAGCACGCGAAAGAGTTACGAGCAAAAC 652
N315_Coa       TTGTAACTTATTATGCTGATAAGGATTATGGGGAGCATGCGAAAGAGTTACGAGCAAAAC 637
MRSA252_Coa    ACGCAGCATATTTTAATCATAGCCAATATGGTCATAATGCTAAAGAATTAAGAGCAAAGC 652
MW2_Coa        ATTTTGCCTACGTTACAGATGCACAACATAAAACAGAAGCATTAAATCTTAGGGCGAAAA 652
WIS_Coa        ATTTTGCCTACGTTACAGATGCTCAACATAAAACAGAAGCATTAAATCTTAGGGCAAAAA 574
                  *  **    *     **     *   **      *  **        *   *  *    *  **  **

USA300_Coa     TGGACTTAATCCTTGGAGATACAGACAATCCACATAAAATTACAAATGAACGTATTAAAA 712
N315_Coa       TGGACTTAATCCTTGGAGATACAGACAATCCACATAAAATTACAAATGAGCGTATAAAAA 697
MRSA252_Coa    TAGATATAATTCTTGGTGATGCTAAAGATCCTGTTAGAATTACGAATGAAAGAATAAGAA 712
MW2_Coa        TTGATTTGATTTTAGGTGATGAAAAAGATCCAATTAGAGTTACGAATCAACGTACTGAAA 712
WIS_Coa        TAGATTTGATTTTAGGTGATGAAAAAGATCCAATTAGAGTGACGAATCAACGTACTGAAA 634
                *  **    *  **    *  **  ***      *   ****    **  *   *   **  ***   *   *      **

USA300_Coa     AAGAAATGATTGATGACTTAAATTCAATTATTGATGATTTCTTTATGGAAACTAAACA-A 771
N315_Coa       AAGAAATGATCGATGACTTAAATTCAATTATAGATGATTTCTTTATGGAGACTAAACA-A 756
MRSA252_Coa    AAGAAATGATGGATGATTTAAATTCTATTATTGATGATTTCTTTATGGATAC-AAACATG 771
MW2_Coa        AAGAAATGATTAAAGATTTAGAATCTATTATTGATGATTTCTTCATTGAAACCAAGTT-G 771
WIS_Coa        AAGAAATGATTAAAGATTTAGAATCTATTATTGATGATTTCTTCATTGAAACAAAGTT-G 693
                **********   *  *** *  **  *****  ** **********  **  **  **  **

USA300_Coa     AATAGACCGAAATCTATAACGAAATATAATCCTACAACACATAACTATAAAACAAATAGT 831
N315_Coa       AATAGACCGAATTCTATAACAAAATATGATCCAACAAAACACAATTTTAAAGAGAAGAGT 816
MRSA252_Coa    AATAGACCATTAAACATAACTAAATTTAATCGAATATTCATGACTATACTAATAAGCCT 831
MW2_Coa        AATAGACCTAAACACATTACTAGGTATGATGGAACTAAACATGATTACCA--------T 822
WIS_Coa        AATAGACCTCAACACATTACTAGATATGATGGAACTAAACATGATTACCA--------T 744
                *******       **  **  *   *  **    *    *   **  *  *                    *

USA300_Coa     GATAATAAACCTAATTTTGATAAATTAGTTGAAGAAACGAAAAAAGCAGTTAAAGAAGCA 891
N315_Coa       GAAAATAAACCTAATTTTGATAAATTAGTTGAAGAAACAAAAAAAGCAGTTAAAGAAGCA 876
MRSA252_Coa    GAAAATAGAGATAACTTCGATAAATTAGTCAAAGAAACAAGAGAAGCAATCGCAAACGCT 891
MW2_Coa        AAACATAAAGATGGATTTGATGCTCTAGTTAAAGAAACAAGAGAAGCGGTTGCAAAGGCT 882
WIS_Coa        AAACATAAAGATGGATTTGATGCTTTAGTTAAAGAAACAAGAGAAGCGGTTTCTAAGGCT 804
                 *   ***  *    **  ***     ****  ********  *  *   **     *  *  **

USA300_Coa     GATGATTCTTGGAAAAGAAAACTGTCAAAAAATACGGAGAAACTGAAACAAATCGCCA 951
N315_Coa       GACGAATCTTGGAAAATAAAACTGTCAAAAAATACGAGGAAACTGTAACAAATCTCCT 936
MRSA252_Coa    GACGAATCTTGGAAACAAGAACCGTCAAAAATTACGGTGAATCTGAAACAAATCTCCT 951
MW2_Coa        GACGAATCTTGGAAAAATAAAACTGTCAAAAAATACGAGGAAACTGTAACAAATCTCCA 942
WIS_Coa        GACGAATCTTGGAAAACTAAAACTGTCAAAAAATACGGGGAAACTGAAACAAATATCCT 864
                ** ** **********  * ***   ********* ***  ***  *** *********  **
```

FIG. 7B

```
USA300_Coa    GTAGTAAAAGAAGAGAAGAAAGTTGAAGAACCTCAAGCACCTAAAGTTGATAACCAACAA 1011
N315_Coa      GTTGTAAAAGAAGAGAAGAAAGTTGAAGAACCTCAATTACCTAAAGTTGGAAACCAGCAA 996
MRSA252_Coa   GTTGTAAAAGAAGAGAAGAAAGTTGAAGAACCTCAATTACCTAAAGTTGGAAACCAGCAA 1011
MW2_Coa       GTTGTAAAAGAAGAGAAGAAAGTTGAAGAACCTCAATCACCTAAATTTGATAACCAACAA 1002
WIS_Coa       GTTGTAAAAGAAGAGAAGAAAGTTGAAGAACCTCAATCACCTAAAGTTTCTGAAAAAGTG 924
              ** ******************************* ****** **    *  *

USA300_Coa    GAGGTTAAAACTACGGCTGGTAAAGCTGAAGAAACAACACAACCAGTTGCACAACCATTA 1071
N315_Coa      GAGGTTAAAACTACGGCTGGTAAAGCTGAAGAAACAACACAACCAGTGGCACAGCCATTA 1056
MRSA252_Coa   GAGGATAAAATTACAGTTGGTACAACTGAAGAAGCACCATTACCAATTGCGCAACCACTA 1071
MW2_Coa       GAGGTTAAAATTACAGTTGATAAAGCTGAAGAAACAACACAACCAGTGGCACAGCCATTA 1062
WIS_Coa       GATGTTCAGGAAACGGTTGGTACAACTGAAGAAGCACCATTACCAATTGCGCAACCACTA 984
              ** * *      ** * ** ** *  ******* ** **  ****  *  ** ** *** **

USA300_Coa    GTTAAAATTCCACAGGGCACAATTACAGGTGAAATTGTAAAAGGTCCGGAATATCCAACG 1131
N315_Coa      GTAAAAATTCCACAAGAAACAATCTATGGTGAAACTGTAAAAGGTCCAGAATATCCAACG 1116
MRSA252_Coa   GTTAAAATTCCACAGGGCACAATTCAAGGTGAAATTGTAAAAGGTCCGGAATATCTAACG 1131
MW2_Coa       GTTAAAATTCCACAGGGCACAATTACAGGTGAAATTGTAAAAGGTCCGGAATATCCAACG 1122
WIS_Coa       GTTAAATTACCACAAATTGGGACTCAAGGCGAAATTGTAAAAGGTCCCGACTATCCAACT 1044
              ** *** *  *****        *   **  **** ************ ** **** ***

USA300_Coa    ATGGAAAATAAAACGGTACAAGGTGAAATCGTTCAAGGTCCCGATTTTCTAACAATGGAA 1191
N315_Coa      ATGGAAAATAAAACGTTACAAGGTGAAATCGTTCAAGGTCCCGATTTTCTAACAATGGAA 1176
MRSA252_Coa   ATGGAAAATAAAACGTTACAAGGTGAAATCGTTCAAGGTCCAGATTTCCCAACAATGGAA 1191
MW2_Coa       ATGGAAAATAAAACGTTACAAGGTGAAATCGTTCAAGGTCCAGATTTCCCAACAATGGAA 1182
WIS_Coa       ATGGAAAATAAAACGTTACAAGGTGTAATTGTTCAAGGTCCAGATTTCCCAACAATGGAA 1104
              *************** ********  *** *********  ***** * * *********

USA300_Coa    CAAAGCGGCCCATCATTAAGCAATAATTATACAAACCCA-------------------- 1230
N315_Coa      CAAAACAGACCATCTTTAAGCGATAATTATACTCAACCG-------------------- 1215
MRSA252_Coa   CAAAACAGACCATCTTTAAGCGATAATTATACTCAACCG-------------------- 1230
MW2_Coa       CAAAACAGACCATCTTTAAGCGATAATTATACTCAACCG-------------------- 1221
WIS_Coa       CAAAACAGACCATCTTTAAGTGACAATTATACACAACCATCTGTGACTTTACCGTCAATT 1164
              ****  *  **** ***** *  ********  * **

USA300_Coa    -----------CCGTTAACGAACCCTATTTTAGAAGGTCTTGAAGGTAGCTCATCTAAA 1278
N315_Coa      -----------ACGACACCGAACCCTATTTTAGAAGGTCTTGAAGGTAGCTCATCTAAA 1263
MRSA252_Coa   -----------ACGACACCGAACCCTATTTTAAAAGGTATTGAAGGAAACTCAACTAAA 1278
MW2_Coa       -----------ACGACACCGAACCCTATTTTAGAAGGTCTTGAAGGTAGCTCATCTAAA 1269
WIS_Coa       ACAGGTGAAAGTACACCAACGAACCCTATTTTAAAAGGTATTGAAGGAAACTCATCTAAA 1224
                          *  * ************** * **** * ******  * **** *****

USA300_Coa    CTTGAAATAAAACCACAAGGTACTGAATCAACGTTAAAAGGTACTCAAGGAGAATCAAGT 1338
N315_Coa      CTTGAAATAAAACCACAAGGTACTGAATCAACGTTGAAAGGTATTCAAGGAGAATCAAGT 1323
MRSA252_Coa   CTTGAAATAAAACCACAAGGTACTGAATCAACGTTAAAAGGTACTCAAGGAGAATCAAGT 1338
MW2_Coa       CTTGAAATAAAACCACAAGGTACTGAATCAACGTTAAAAGGTACTCAAGGAGAATCAAGT 1329
WIS_Coa       CTTGAAATAAAACCACAAGGTACTGAATCAACGTTGAAAGGTATTCAAGGAGAATCAAGT 1284
              *********************************** ****** ****** **********

USA300_Coa    GATATTGAAGTTAAACCTCAAGCAACTGAAACAACAGAAGCTTCTCAATATGGTCCGAGA 1398
N315_Coa      GATATTGAAGTTAAACCTCAAGCAACTGAAACAACAGAAGCTTCTCAATATGGTCCGAGA 1383
MRSA252_Coa   GATATTGAAGTTAAACCTCAAGCAACTGAAACAACAGAAGCATCACATTATCCAGCAGA  1398
MW2_Coa       GATATTGAAGTTAAACCTCAAGCATCTGAAACAACAGAAGCATCACATTATCCAGCAGA  1389
WIS_Coa       GATATTGAAGTTAAACCTCAAGCAACTGAAACAACAGAAGCATCACATTATCCAGCAGA  1344
              ************************ *************** ** **  *  *   * ***
```

FIG. 7C

```
USA300_Coa    CCGCAATTTAACAAAACACCTAAATATGTTAAATATAGAGATGCTGGTACAGGTATCCGT 1458
N315_Coa      CCGCAATTTAACAAAACACCTAAGTATGTGAAATATAGAGATGCTGGTACAGGTATCCGT 1443
MRSA252_Coa   CCTCAATTTAACAAAACACCTAAGTATGTGAAATATAGAGATGCTGGTACAGGTATCCGT 1458
MW2_Coa       CCTCAATTTAACAAAACACCTAAATATGTTAAATATAGAGATGCTGGTACAGGTATCCGT 1449
WIS_Coa       CCGCAATTTAACAAAACACCTAAATATGTGAAATATAGAGATGCTGGTACAGGTATTCGT 1404
              ** ******************** ***** ************************** ***

USA300_Coa    GAATACAACGATGGAACATTTGGATATGAAGCGAGACCAAGATTCAATAAGCCA------ 1512
N315_Coa      GAATACAACGATGGAACATTTGGATATGAAGCGAGACCAAGATTCAACAAGCCAAGTGAA 1503
MRSA252_Coa   GAATACAACGATGGAACATTTGGATATGAAGCGAGACCAAGATTCAACAAGCCAAG---- 1514
MW2_Coa       GAATACAACGATGGAACATTTGGATATGAAGCGAGACCAAGATTCAATAAGCCATCAGAA 1509
WIS_Coa       GAATACAACGATGGAACTTTTGGATATGAAGCGAGACCAAGATTCAACAAGCCATCAGAA 1464
              ***************** ***************************** ******

USA300_Coa    -----------------------TCA---------------------------------- 1515
N315_Coa      ACAAATGCATACAACGTAACGACAAATCAAGATGGCACAGTATCATACGGAGCTCGCCCA 1563
MRSA252_Coa   -----------------------C------------------------------------ 1515
MW2_Coa       ACAAACGCATACAACGTAACGACAAATCAAGATGGCACAGTAACATATGGCGCTCGCCCA 1569
WIS_Coa       ACAAACGCATACAACGTAACGACAAATCAAGATGGCACAGTATCATATGGGGCTCGCCCA 1524
                                     *

USA300_Coa    ------------------GAAACAAATGCATATAACGTAACAACACATGCAAATGGTCAA 1557
N315_Coa      ACACAAAACAAGCCAAGTGAAACAAACGCATATAACGTAACAACACATGCAAATGGTCAA 1623
MRSA252_Coa   ------------------GAAACAAATGCATACAACGTAACGACAAATCAAGATGGCACA 1557
MW2_Coa       ACACAAAACAAACCAAGCAAAACAAATGCATACAACGTAACAACACATGCAAATGGTCAA 1629
WIS_Coa       ACACAAAACAAGCCAAGCAAAACAAATGCATATAACGTAACAACACATGCAAACGGCCAA 1584
                                ****** ***** ****** **  * ***  *

USA300_Coa    GTATCATACGGAGCTCGTCCGACA------------------------------------ 1581
N315_Coa      GTATCATACGGTGCTCGCCCAACA------------------------------------ 1647
MRSA252_Coa   GTATCATATGGCGCTCGCCCGACA------------------------------------ 1581
MW2_Coa       GTATCATATGGCGCTCGCCCGACA------------------------------------ 1653
WIS_Coa       GTATCATATGGCGCTCGCCCGACATACAACAAGCCAAGTGAAACAAATGCATACAACGTA 1644
              ******** ** ***** ** ***

USA300_Coa    ----------------------------------------------CAAAACAAGCCAAGC 1596
N315_Coa      ----------------------------------------------CAAAAAAAGCCAAGC 1662
MRSA252_Coa   ----------------------------------------------CAAAACAAGCCAAGC 1596
MW2_Coa       ----------------------------------------------CAAAACAAGCCAAGC 1668
WIS_Coa       ACGACAAATCGAGATGGCACAGTATCATATGGCGCTCGCCCGACACAAAAACAAGCCAAGC 1704
                                                            ***** *********

USA300_Coa    AAAACAAACGCATATAACGTAACAACACATGGAAACGGCCAAGTATCATATGGCGCTCGC 1656
N315_Coa      AAAACAAATGCATACAACGTAACAACACATGCAAATGGTCAAGTATCATATGGCGCTCGC 1722
MRSA252_Coa   GAAACAAACGCATATAACGTAACAACACATGCAAACGGCCAAGTATCATACGGAGCTCGT 1656
MW2_Coa       AAAACAAATGCATATAACGTAACAACACATGCAAATGGTCAAGTATCATACGGAGCTCGC 1728
WIS_Coa       GAAACGAATGCATATAACGTAACAACACACGGAAATGGCCAAGTATCATATGGCGCTCGT 1764
              **** ** ***** *************** *  *** ** ********** ** *****

USA300_Coa    CCAACACAAAACAAGCCAAGCAAAACAAATGCATACAACGTAACAACACATGCAAACGGT 1716
N315_Coa      CCGACACAAAAAGCCAAGCAAAACAAATGCATATAACGTAACAACACATGCAAATGGT 1782
MRSA252_Coa   CCGACACAAAACAAGCCAAGCGAAACGAACGCATATAACGTAACAACACACGCAAACGGT 1716
MW2_Coa       CCGACACAAAACAAGCCAAGCAAAACAAATGCATATAACGTAACAACACACGCAAACGGT 1788
WIS_Coa       CCGACACAAAAGAAGCCAAGCAAAACAAATGCATATAACGTAACAACACATGCAAACGGC 1824
              ** ******* *********  *** ** **** *************** ***** **
```

FIG. 7D

```
USA300_Coa    CAAGTGTCATACGGAGCTCGCCCGACATACAAGAAGCCAAGTAAAACAAATGCATACAAT 1776
N315_Coa      CAAGTATCATACGGAGCTCGCCCGACATACAAGAAGCCAAGCGAAACAAATGCATACAAC 1842
MRSA252_Coa   CAAGTGTCATACGGAGCTCGCCCAACACAAAACAAGCCAAGTAAAACAAATGCATACAAT 1776
MW2_Coa       CAAGTGTCATACGGAGCTCGCCCGACATACAAGAAGCCAAGTAAAACAAATGCATACAAT 1848
WIS_Coa       CAAGTATCATATGGCGCTCGTCCGACATACAACAAGCCAAGTAAAACAAATGCATACAAT 1884
              ***** ***** ** ***** ** *** * ** *******  *****************

USA300_Coa    GTAACAACACATGCA--------------------------------------------- 1791
N315_Coa      GTAACAACACATGCAAATGGTCAAGTATCATATGGCGCTCGCCCGACACAAAAAAAGCCA 1902
MRSA252_Coa   GTAACAACACATGCA--------------------------------------------- 1791
MW2_Coa       GTAACAACACATGCA--------------------------------------------- 1863
WIS_Coa       GTAACAACACATGCA--------------------------------------------- 1899
              ***************

USA300_Coa    ---------------------------------------GATGGTACTGCGACATATGGGCCT 1815
N315_Coa      AGCGAAACAAACGCATATAACGTAACAACACATGCAGATGGTACTGCGACATATGGGCCT 1962
MRSA252_Coa   ---------------------------------------GATGGTACTGCGACATATGGTCCT 1815
MW2_Coa       ---------------------------------------GATGGTACTGCGACATATGGGCCT 1887
WIS_Coa       ---------------------------------------GATGGTACTGCGACATATGGTCCT 1923
                                                     ******************* ***

USA300_Coa    AGAGTAACAAAATAA 1830
N315_Coa      AGAGTAACAAAATAA 1977
MRSA252_Coa   AGAGTAACAAAATAA 1830
MW2_Coa       AGAGTAACAAAATAA 1902
WIS_Coa       AGAGTAACAAAATAA 1938
              ***************
```

FIG. 7E

| | | |
|---|---|---|
| CoaST5_1_n191 | 68 | RPRFNKPSETNAYNVTTNQDGTVSYGARPTQNKPSETNAYNVTTHANGQVSYGARPTQKK |
| CoaST5_2_n85 | 69 | RPRFNKPSETNAYNVTTNQDGTVSYGARPTQNKPSETNAYNVTTHANGQVSYGARPTQKK |
| CoaST5_3_n59 | 70 | RPRFNKPSETNAYNVTTNQDGTVSYGARPTQNKPSETNAYNVTTHANGQVSYGARPTYKK |
| CoaST8_1_n57 | 71 | ----------------------------RPRFNKPSETNAYNVTTHANGQVSYGARPTYKK |
| CoaST8_2_n19 | 72 | ---------------------------------------------------------RPRFNK |
| CoaST22_1_n123 | 73 | RPRFNKPSETNAYNVTTNQDGTVTYGARPTQNKPSKTNAYNVTTHANGQVSYGARPTYKK |
| CoaST22_2_n8 | 74 | RPRFNKPSETNAYNVTTNQDGTVTYGARPTQNKPSKTNAYNVTTHANGQVSYGARPTYKK |
| CoaST22_3_n5 | 75 | ------------------------------------------------------------ |
| CoaST30_1_n27 | 76 | ---------------------------------------------------------RPRFNK |
| CoaST30_2_n5 | 77 | RPRFNKPSETNAYNVTTNQDGTVSYGARPTQNKPSETNAYNVTTHANGQVSYGARPTYKK |
| CoaST30_3_n3 | 78 | RPRFNKPSETNAYNVTTNQDGTVSYGARPTQNKPSETNAYNVTTHANGQVSYGARPTYKK |
| ST45_1_n16 | 79 | ------------------------------------------------------------ |
| ST45_2_n15 | 80 | RPRFNKPSETNAYNVTTNQDGTVSYGARPTQNKPSKTNAYNVTTHANGQVSYGARPTYNK |
| ST45_3_n4 | 81 | RPRFNKPSETNAYNVTTNQDGTVSYGARPTQNKPSKTNAYNVTTHANGQVSYGARPTYNK |
| CoaST239_1_n10 | 82 | RPRFNKPSETNAYNVTTNQDGTVSYGARPTQNKPSETNAYNVTTHANGQVSYGARPTYKK |
| CoaST239_2_n4 | 83 | RPRFNKPSETNAYNVTTNQDGTVSYGARPTQNKPSETNAYNVTTHANGQVSYGARPTYKK |
| CoaST239_3_n3 | 84 | ----------------------------------------------------------RPRFNK |

| | | |
|---|---|---|
| CoaST5_1_n191 | 68 | PSKTNAYNVTTHANGQVSYGARPTQKKPSKTNAYNVTTHANGQVSYGARPTYKKPSETNA |
| CoaST5_2_n85 | 69 | PSKTNAYNVTTHANGQVSYGARPTQKKPSKTNAYNVTTHANGQVSYGARPTYKKPSETNA |
| CoaST5_3_n59 | 70 | PSETNAYNVTTHANGQVSYGARPTQKKPSKTNAYNVTTHANGQVSYGARPTYKKPSETNA |
| CoaST8_1_n57 | 71 | PSETNAYNVTTHANGQVSYGARPTQNKPSKTNAYNVTTHGNGQVSYGARPTQNKPSKTNA |
| CoaST8_2_n19 | 72 | PSETNAYNVTTHANGQVSYGARPTQNKPSKTNAYNVTTHGNGQVSYGARPTQNKPSKTNA |
| CoaST22_1_n123 | 73 | PSETNAYNVTTHANGQVSYGARPTQNKASETNAYNVTTHANGQVSYGARPTQNKPSKTNA |
| CoaST22_2_n8 | 74 | PSETNAYNVTTHANGQVSYGARPTQNKASETNAYNVTTHANGQVSYGARPTQNKPSKTNA |
| CoaST22_3_n5 | 75 | ------------------RPRFNKPSETNAYNVTTNQDGTVTYGARPTQNKPSKTNA |
| CoaST30_1_n27 | 76 | PSETNAYNVTTNQDGTVSYGARPTQNKPSETNAYNVTTHANGQVSYGARPTQNKPSETNA |
| CoaST30_2_n5 | 77 | PSETNAYNVTTNQDGTVSYGARPTQNKPSETNAYNVTTHANGQVSYGARPTQNKPSETNA |
| CoaST30_3_n3 | 78 | PSETNAYNVTTNQDGTVSYGARPTQNKPSETNAYNVTTHANGQVSYGARPTQNKPSETNA |
| ST45_1_n16 | 79 | ------------------RPRFNKPSETNAYNVTTNQDGTVSYGARPTQNKPSKTNA |
| ST45_2_n15 | 80 | PSETNAYNVTTNRDGTVSYGARPTQNKPSETNAYNVTTHGNGQVSYGARPTQKKPSKTNA |
| ST45_3_n4 | 81 | PSETNAYNVTTNRDGTVSYGARPTQNKPSETNAYNVTTHGNGQVSYGARPTQKKPSKTNA |
| CoaST239_1_n10 | 82 | PSETNAYNVTTNQDGTVSYGARPTQNKPSETNAYNVTTHANGQVSYGARPTQNKPSETNA |
| CoaST239_2_n4 | 83 | PSETNAYNVTTNQDGTVSYGARPTQNKPSETNAYNVTTHANGQVSYGARPTQNKPSETNA |
| CoaST239_3_n3 | 84 | PSETNAYNVTTNQDGTVSYGARPTQNKPSETNAYNVTTHANGQVSYGARPTQNKPSETNA |
| | | ** :*.*:*********: :* *:**** :*:*** |

| | | |
|---|---|---|
| CoaST5_1_n191 | 68 | YNVTTHANGQVSYGARLTQKKPSETNAYNVTTHADGTATYGP |
| CoaST5_2_n85 | 69 | YNVTTHANGQVSYGARPTQKKPSETNAYNVTTHADGTATYGP |
| CoaST5_3_n59 | 70 | YNVTTHANGQVSYGARPTQKKPSETNAYNVTTHADGTATYGP |
| CoaST8_1_n57 | 71 | YNVTTHANGQVSYGARPTYKKPSKTNAYNVTTHADGTATYGP |
| CoaST8_2_n19 | 72 | YNVTTHANGQVSYGARPTYKKPSKTNAYNVTTHADGTATYGP |
| CoaST22_1_n123 | 73 | YNVTTHGNGQVSYGARPTYKKPSETNAYNVTTHADGTATYGP |
| CoaST22_2_n8 | 74 | YNVTTHGNGQVSYGARPTYKKPSETNAYNVTTHADGTATYGP |
| CoaST22_3_n5 | 75 | YNVTTHANGQVSYGARPTYKKPSETNAYNVTTHANGTATYGP |
| CoaST30_1_n27 | 76 | YNVTTHANGQVSYGARPTQNKPSKTNAYNVTTHADGTATYGP |
| CoaST30_2_n5 | 77 | YNVTTHANGQVSYGARPTQNKPSKTNAYNVTTHADGTATYGP |
| CoaST30_3_n3 | 78 | YNVTTHANGQVSYGARPTQNKPSKTNAYNVTTHADGTATYGP |
| ST45_1_n16 | 79 | YNVTTHANGQVSYGARPTYNKPSKTNAYNVTTHADGTATYGP |
| ST45_2_n15 | 80 | YNVTTHANGQVSYGARPTYNKPSKTNAYNVTTHADGTATYGP |
| ST45_3_n4 | 81 | YNVTTHANGQVSYGARPTQKKPSKTNAYNVTTHADGTATYGP |
| CoaST239_1_n10 | 82 | YNVTTHANGQVSYGARPTQNKPSKTNAYNVTTHADGTATYGP |
| CoaST239_2_n4 | 83 | YNVTTHANGQVSYGARPTQNKPSKTNAYNVTTHADGTATYGP |
| CoaST239_3_n3 | 84 | YNVTTHANGQVSYGARPTQNKPSKTNAYNVTTHADGTATYGP |
| | | ****.******* * :*.*****:***** |

FIG. 8

COMPOSITIONS AND METHODS RELATED TO ANTIBODIES THAT NEUTRALIZE COAGULASE ACTIVITY DURING *STAPHYLOCOCCUS AUREUS* DISEASE

CROSS-REFERENCE TO RELATED APPLICATIONS

This application is a national phase application under 35 U.S.C. § 371 of International Application No. PCT/IB2017/050763 filed Feb. 10, 2017, which claims the benefit of priority of U.S. Provisional Patent Application No. 62/294,413, filed Feb. 12, 2016. The entire contents of each of the above-referenced disclosures are specifically incorporated herein by reference.

STATEMENT OF GOVERNMENT SUPPORT

This invention was made with government support under Grant Nos.: AI52747 and AI110937, awarded by the National Institute of Allergy and Infectious Diseases and Grant No.: HD009007 awarded by the National Institute of Health. The government has certain rights in the invention.

BACKGROUND OF THE DISCLOSURE

Field of the Invention

The present invention relates generally to the fields of immunology, microbiology, and pathology. More particularly, it concerns methods and compositions involving antibodies to bacterial proteins and bacterial peptides used to elicit such antibodies. The proteins include Coagulase (Coa).

Background

North American hospitals are experiencing an epidemic of *Staphylococcus aureus*. This organism causes a wide range of diseases from minor skin infections to life-threatening sepsis, endocarditis, and pneumonia [2]. *S. aureus* is endowed with a wide range of virulence factors that enable its many disease manifestations. One of the defining characteristics of *S. aureus* that distinguishes it from less pathogenic species of Staphylococci is its ability to clot anticoagulated blood [48,75]. This characteristic is due to two proteins, coagulase (Coa) and von Willebrand factor binding protein (vWbp). Coa and vWbp bind to and induce a conformational change in host prothrombin, which mimics the transition from the zymogen to activated thrombin, enabling the complex to cleave fibrinogen to fibrin [66,67,71,72,133,146,188]. Fibrin forms the mesh network of a blood clot.

Coa and vWbp play an important role during the pathogenesis of *S. aureus* infection [212]. Infection with double mutants in coa and vwb results in delayed mortality in a murine sepsis model and nearly eliminates the ability of Staphylococci to form abscesses (Cheng et al. 2010). A humoral immune response against Coa and vWbp provides protection against Staphylococcal infection (Cheng et al. 2010). Pharmacologic inhibition of the coagulases with direct thrombin inhibitors neutralizes the activity of Coa and vWbp and provides prophylactic protection against Staphylococcal sepsis [20,177,213].

*S. aureus* can survive on dry surfaces, increasing the chance of transmission. Any *S. aureus* infection can cause the Staphylococcal scalded skin syndrome, a cutaneous reaction to exotoxin absorbed into the bloodstream. *S. aureus* can also cause a type of septicemia called pyaemia that can be life-threatening. Methicillin-resistant *Staphylococcus aureus* (MRSA) has become a major cause of hospital-acquired infections.

*S. aureus* infections are typically treated with antibiotics, with penicillin being the drug of choice, but vancomycin being used for methicillin resistant isolates. The percentage of Staphylococcal strains exhibiting wide-spectrum resistance to antibiotics has increased, posing a threat to effective antimicrobial therapy. In addition, the recent appearance of vancomycin-resistant *S. aureus* strain has aroused fear that MRSA strains for which no effective therapy is available are starting to emerge and spread.

An alternative approach to antibiotics in the treatment of Staphylococcal infections has been the use of antibodies against Staphylococcal antigens in passive immunotherapy. Examples of this passive immunotherapy involves administration of polyclonal antisera (WO00/15238, WO00/12132) as well as treatment with monoclonal antibodies against lipoteichoic acid (WO98/57994).

The first generation of vaccines targeted against *S. aureus* or against the exoproteins it produces have met with limited success (Lee, 1996) and there remains a need to develop additional therapeutic compositions for treatment of *staphylococcus* infections.

SUMMARY

During infection, *Staphylococcus aureus* secrets two coagulases, Coa and vWbp, which upon association with host prothrombin and fibrinogen, convert soluble fibrinogen to insoluble fibrin, induce the formation of fibrin clots and enable the establishment of Staphylococcal disease. Coa and vWbp are important factors for Staphylococcal coagulation and agglutination and for promoting the pathogenesis of *S. aureus* abscess formation and lethal bacteremia in mice. Here the inventors demonstrate that polypeptides with the R Domain of Coa can be used as vaccines and that antibodies directed against the R Domain of Coa are capable of recognizing many different serotypes, providing broad-spectrum protection against bloodstream infections caused by MRSA isolates. Furthermore, antibodies described herein that are directed to the D1 domain of Coa and/or vWbp also provide protection from infection. *Staphylococcus aureus* is the most frequent cause of bacteremia and hospital-acquired infection in the United States. An FDA approved vaccine that prevents Staphylococcal disease is currently unavailable.

In certain embodiments there are antibody compositions that inhibit, ameliorate, and/or prevent Staphylococcal infection.

Certain embodiments are directed to methods of inhibiting *Staphylococcus* infection in a subject determined to have or be at risk for *Staphylococcus* infection comprising administering to the subject an effective amount of a Coa binding polypeptide that specifically binds to a Staphylococcal Coa polypeptide. In some embodiments, the method further comprises administering an effective amount of two or more Coa binding polypeptides. In some embodiments, the method further comprises administering an antibiotic or a Staphylococcal vaccine composition to the subject. In other embodiments, there are methods for treating a subject with or determined to have a *Staphylococcus* infection. In further embodiments, there are methods for preventing a *Staphylococcus* infection.

In some aspects, the Coa binding polypeptide specifically binds to Domain 1 of a Staphylococcal Coa polypeptide. In other aspects, the Coa binding polypeptide specifically binds to Domain 2 of a Staphylococcal Coa polypeptide. In some aspects, the Coa binding polypeptide specifically binds to R Domain of a Staphylococcal Coa polypeptide. In further embodiments, the Coa binding polypeptide specifically binds to a region on both Domain 1 and Domain 2 of a Staphylococcal Coa polypeptide.

Certain embodiments are directed to a Coa binding polypeptide that specifically binds to an epitope in a polypeptide encoded by any of: 1) a R Domain from the *S. aureus* Coa polypeptides corresponding to SEQ ID NOS:1-8 or 22-38; 2) a R Domain of SEQ ID NOS:39-55, SEQ ID NOS:85-101, or a fragment thereof; or 3) one or more R domain fragments of SEQ ID NOS:57-62 or SEQ ID NOS:102-127. In certain aspects, the Coa binding polypeptide specifically binds to an epitope in amino acids 1-149, 150-282, or 1-282 of a polypeptide encoded by any of SEQ ID NOs: 1-8. In certain aspects, the Coa binding polypeptide specifically binds to an epitope in amino acids 470-605 of *S. aureus* Newman. In certain aspects the epitope comprises at least, or has at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 or more contiguous amino acids (or any range derivable therein) from any of the sequences provided herein or encoded by any of the sequences provided herein.

In particular embodiments, the Coa binding polypeptide competes for binding of Staphylococcal Coa polypeptide with the 5D5.4 or 3B3.14 monoclonal antibody. In further embodiments, the monoclonal antibody is 3B3.14 or 5D5.4. In some embodiments, the Coa binding polypeptide has an association constant for the Staphylococcal Coa polypeptide of between about 0.5 and 20 nM$^{-1}$, 1.0 and 10 nM$^{-1}$, or 1.0 and 6.0 nM$^{-1}$ as measured by ELISA. In certain embodiments, the Coa binding polypeptide has an association constant for the Staphylococcal Coa Domain 1-2 or R Domain of between about 0.5 and 20 nM$^{-1}$ or 1.0 and 10 nM$^{-1}$ as measured by ELISA.

The Coa binding polypeptide may be any polypeptide that specifically binds Coa proteins from *staphylococcus* bacteria. In certain embodiments, the Coa binding polypeptide is a purified monoclonal antibody or a purified polyclonal antibody. The polypeptide may be, for example, an antibody that is single domain, humanized, or chimeric. In some embodiments, two or more Coa binding polypeptides (e.g., two or more purified monoclonal antibodies or purified polyclonal antibodies) may be administered to the subject. In certain aspects, the Coa binding polypeptide is recombinant. In other embodiments, there may be chemical modifications to the polypeptide, such as the addition of one or more chemical modifications or moieties.

Embodiments are provided in which the Coa binding polypeptide comprises one or more CDR domains from an antibody that specifically binds to Domains 1-2 of a Staphylococcal Coa polypeptide. Embodiments are provided in which the Coa binding polypeptide comprises one or more CDR domains from an antibody that specifically binds to an R Domain of a Staphylococcal Coa polypeptide. In particular embodiments, the Coa binding polypeptide comprises one, two, three, four, five, six, or more CDR domains from among the VH or VL domain of the 5D5.4 and 3B3.14 monoclonal antibodies. In certain aspects, the Coa binding polypeptide comprises six CDR domains from among the VH or VL domains of the 5D5.4 and 3B3.14 monoclonal antibodies. In some embodiments, the Coa binding polypeptide comprises a sequence at least or at most 70%, 75%, 80%, 85%, 90%, 95%, or 99% (or any range derivable therein) identical to the VH or VL domain of the 5D5.4 or 3B3.14 monoclonal antibodies. Embodiments are provided in which the Coa binding polypeptide comprises the VH domain from the 5D5.4 or 3B3.14 monoclonal antibody and/or the VL domain the 5D5.4 or 3B3.14 monoclonal antibody. In further embodiments, the monoclonal antibody is 5D5.4 or 3B3.14.

In some embodiments the Coa binding polypeptide comprises one or more CDR domains from a Coa binding polypeptide that specifically binds to Domain 1-2 of a Staphylococcal Coa polypeptide and a scaffold from a polypeptide selected from the group consisting of an immunoglobulin, a fibronectin or a *S. aureus* protein Z.

In some embodiments the Coa binding polypeptide comprises one or more CDR domains from a Coa binding polypeptide that specifically binds to the R Domain of a Staphylococcal Coa polypeptide and a scaffold from a polypeptide selected from the group consisting of an immunoglobulin, a fibronectin or a *S. aureus* protein Z.

The Coa binding polypeptide may be operatively coupled to a second Coa binding polypeptide. In some aspects, the first and second Coa binding peptides are operatively coupled recombinantly. In other aspects, the first and second Coa binding peptides are operatively coupled chemically.

Embodiments are provided in which the Coa binding polypeptide is administered at a dose of about, at least about, or at most about 0.1 mg/kg to 5 mg/kg, 1 mg/kg to 5 mg/kg, 0.1 mg/kg to 1 mg/kg, or 2 mg/kg to 5 mg/kg (or any range derivable therein).

Embodiments also provide a purified polypeptide comprising one or more Coa binding polypeptide CDR domains from an antibody that specifically binds to Domain 1-2 of a Staphylococcal Coa polypeptide. In certain embodiments, the Coa binding polypeptide competes for binding of a Staphylococcal Coa polypeptide with the 5D5.4 or 3B3.14 monoclonal antibody. In certain aspects, the polypeptide has an association constant for a Staphylococcal Coa polypeptide of between about 0.1 and 20 nM$^{-1}$, 0.5 and 10 nM$^{-1}$, or 1.0 and 10 nM$^{-1}$ as measured by ELISA. The polypeptide may comprise, for example, a single domain antibody Coa binding polypeptide, a humanized antibody, or a chimeric antibody.

In certain embodiments, the polypeptide is recombinant. In certain aspects, the recombinant polypeptide comprises at least 90%, 95%, or 99% of one or more CDR domains from the VH or VL domain of the 5D5.4 or 3B3.14 monoclonal antibodies. In some embodiments, the recombinant polypeptide comprises two, three, four, five, six, or more CDR domains from the VH or VL domain of the 5D5.4 and/or 3B3.14 monoclonal antibodies.

In some embodiments, a recombinant polypeptide comprises i) CDR1, CDR2, and/or CDR3 from the variable light chain of 5D5.4; and/or ii) CDR1, CDR2, and/or CDR3 from the variable heavy chain of 5D5.4. In some embodiments, a recombinant polypeptide comprises i) CDR1, CDR2, and/or CDR3 from the variable light chain of 3B3.14; and/or ii) CDR1, CDR2, and/or CDR3 from the variable heavy chain of 3B3.14. The sequences for these CDRs are the following:

TABLE 1

CDR Sequences of 5D5.4 and 3B3.14 Monoclonal Antibodies

| Ab | Variable chain | CDR1 | SEQ ID NO: | CDR2 | SEQ ID NO: | CDR3 | SEQ ID NO: |
|---|---|---|---|---|---|---|---|
| 5D5.4 | Heavy | GASITTSY | 9 | ISYSGNT | 10 | ATYYDFNYDGYLDV | 11 |
| 5D5.4 | Light | SSVSSSY | 12 | STS | 13 | QQYHRSPPT | 14 |
| 3B3.14 | Heavy | GYTFTSFD | 15 | IFPGDGSA | 16 | VKNHGGWYFDV | 17 |
| 3B3.14 | Light | QSIVHSNGNTY | 18 | KVS | 19 | FQGSHVPLT | 20 |

In some embodiments, there is a purified polypeptide comprising one or more Coa binding polypeptide CDR domains from an antibody that specifically binds to Domain 1-2 of a Staphylococcal Coa polypeptide. In some embodiments, there is a purified polypeptide comprising one or more Coa binding polypeptide CDR domains from an antibody that specifically binds to the R Domain of a Staphylococcal Coa polypeptide. As indicated above, the polypeptide may comprise 1, 2, 3, 4, 5, or 6 CDRs from the light and/or heavy chain variable regions of a Coa antibody. Table 1 provides 2 different Coa antibodies and their CDR1, CDR2, and CDR3 sequences from both the light and heavy chain variable regions. In certain embodiments, a polypeptide contains CDR1, CDR2, and/or CDR3 from the light chain variable region of a particular antibody. It is contemplated that while in some embodiments a polypeptide has a CDR1, CDR2, and CDR3 from the variable region of a light chain and/or the variable region of a heavy chain that the CDR1, CDR2, and CDR3 need not be from the same antibody. While some polypeptides have CDR1, CDR2, and CDR3 from the same antibody or based on the same antibody, given the overlap in amino acid sequences, a CDR1 from one antibody may be substituted with a CDR from or based on another antibody. For example, a polypeptide may comprise a CDR1 from or based on the light chain variable region of 5D5.4, a CDR2 from or based on the light chain variable region of 3B3.14, but have a CDR3 from or based on the variable light chain region of 5D5.4. It is generally contemplated, however, that when a single set of CDR1, CDR2, and CDR3 are employed together that they all be from a light chain variable region or from a heavy chain variable region, but not a mix from both.

Alternatively, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs:12 and 18, which are CDR1 sequences from the light chain variable region of a Coa antibody. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs:13 and 19, which are CDR2 sequences from the light chain variable region of a Coa antibody. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs:14 and 20, which are CDR3 sequences from the light chain variable region of a Coa antibody. Alternatively or additionally, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs:9 and 15, which are CDR1 sequences from the heavy chain variable region of a Coa antibody. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs:10 and 16, which are CDR2 sequences from the heavy chain variable region of a Coa antibody. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs:11 and 17, which are CDR3 sequences from the heavy chain variable region of a Coa antibody.

Other embodiments provide a recombinant polypeptide that comprises one or more CDR domain(s) from an antibody that specifically binds to Domains 1-2 or to the R Domain of a Staphylococcal Coa polypeptide and a scaffold from a polypeptide selected from the group consisting of an immunoglobulin, a fibronectin or a S. aureus protein Z. It is further contemplated that any polypeptide may be attached, fused or conjugated to an agent or substance, such a therapeutic moiety or a detectable moity.

In certain aspects, the recombinant polypeptide is operatively coupled to a recombinant polypeptide that specifically binds to a second Staphylococcal protein.

In other embodiments, the polypeptide is an antibody comprising (a) a heavy chain comprising said VH region, and a human hinge, CH1, CH2, and CH3 regions from an IgG1, IgG2, IgG3 or IgG4 subtype; and (b) a light chain comprising said VL region, and either a human kappa CL or human lambda CL.

Certain embodiments provide a purified monoclonal antibody that specifically binds to a Staphylococcal Coa polypeptide, wherein the purified monoclonal antibody is the 5D5.4 or 3B3.14 monoclonal antibody.

In some aspects, the purified polypeptide does not consist of the mouse monoclonal antibody that is 5D5.4 or 3B3.14. In other embodiments the purified polypeptide is not an isolated mouse monoclonal antibody.

Other embodiments provide a pharmaceutical composition comprising one or more purified Coa binding polypeptide. In some embodiments, the pharmaceutical composition provides a single unit dose of the purified polypeptide in a sealed container. The pharmaceutical composition may comprise at least a second anti-bacterial agent including, but not limited to, an antibiotic, a Staphylococcal vaccine composition or a polypeptide that specifically binds to a second Staphylococcal protein.

Certain embodiments, provide a polynucleotide comprising a nucleic acid sequence encoding a Coa binding polypeptide.

Other embodiments provide an expression vector comprising a nucleic acid sequence encoding a Coa binding polypeptide operably linked to an expression control sequence. Some embodiments provide a host cell comprising the expression vector.

Embodiments also provide a method manufacturing a Coa binding polypeptide comprising expressing a nucleic acid sequence encoding the polypeptide operably linked to an expression control sequence in a host cell.

Embodiments also provide for the use of Coa antibodies in methods and compositions for the treatment of bacterial and/or Staphylococcal infection. In certain embodiments, compositions are used in the manufacture of medicaments for the therapeutic and/or prophylactic treatment of bacterial infections, particularly *staphylococcus* infections. Furthermore, in some embodiments there are methods and compositions that can be used to treat (e.g., limiting Staphylococcal abscess formation and/or persistence in a subject) or prevent bacterial infection.

Certain aspects are directed to methods of reducing *Staphylococcus* infection or abscess formation comprising administering to a subject having or suspected of having a *Staphylococcus* infection an effective amount of one or more purified antibodies that specifically bind a Coa polypeptide. The antibody can be a purified polyclonal antibody, a purified monoclonal antibody, a recombinant polypeptide, or a fragment thereof. In certain aspects the antibody is humanized or human. In still further aspects the antibody is a recombinant antibody segment. In certain aspects a monoclonal antibody includes one or more of 5D5.4 or 3B3.14. An antibody can be administered at a dose of 0.1, 0.5, 1, 5, 10, 50, 100 mg or µg/kg to 5, 10, 50, 100, 500 mg or µg/kg, or any range derivable therein. The recombinant antibody segment can be operatively coupled to a second recombinant antibody segment. In certain aspects the second recombinant antibody segment binds a second Staphylococcal protein. The method can further comprise administering a second antibody that binds a second Staphylococcal protein. In certain aspects the method further comprises administering an antibiotic.

Embodiments are directed to monoclonal antibody polypeptides, polypeptides having one or more segments thereof, and polynucleotides encoding the same. In certain aspects a polypeptide can comprise all or part of the heavy chain variable region and/or the light chain variable region of Coa-specific antibodies. In a further aspect, a polypeptide can comprise an amino acid sequence that corresponds to a first, second, and/or third complementary determining regions (CDRs) from the light variable chain and/or heavy variable chain of a Coa-specific antibody.

In still further aspects, embodiments provide a hybridoma cell line that produces a monoclonal antibody of the embodiments. In embodiments the hybridoma cell line is a line that produces the 5B5.4 or 3B3.14 monoclonal antibody. In a further aspect, 1, 2, and/or 3 CDRs from the light and/or heavy chain variable region of a mAb can be comprised in a humanized antibody or variant thereof.

A further aspect of the disclosure relates to an immunogenic composition comprising a polypeptide comprising a Staphylococcal coagulase R Domain or segment thereof. For example, the R Domain can comprise or consist of an amino acid sequence that is at least 80, 85, 90, 95, 98, 99 or 100% identical to an amino acid sequence of the R Domain. In some aspects, a Staphylococcal coagulase R Domain is comprised in a less than full-length coagulase protein. For example, the R Domain can be comprised in a less than full-length Coa protein (e.g., that lacks all or part of a L, 1, or 2 Domain segment). In some aspects, a R Domain is a R Domain segment/fragment wherein the secretion signal sequence has been removed. In some aspects, the R Domain is a R Domain segment/fragment comprising at least one repeat element from the R Domain. In some aspects, the R Domain comprises R Domain segments/fragments (also referred to as R-repeats) comprising 1, 2, 3, 4, 5, 6, 7, 8, 9, 10, 11 or 12 repeat elements from the R Domain. In some embodiments, the R Domain is the full R Domain or a segment/fragment that is repeated in tandem units. In some embodiments, the full R Domain or a segment is repeated in 2, 3, 4, 5, 6, 7, 8, 9, or 10 tandem units (or any derivable range therein). In certain embodiments, an immunogenic composition is provided comprising at least one Staphylococcal coagulase R domain or segment thereof. For example, a composition can comprise at least one Staphylococcal R Domain (or segment/fragment thereof) from a Staphylococcal Coa protein. In some embodiments, the immunogenic composition comprises at least one R Domain. In some embodiments, the immunogenic composition comprises at least two R Domains. In some embodiments, the immunogenic composition comprises at least two different R Domains. In some embodiments, the R Domain (or segment) is comprised in a less than full-length coagulase protein. In certain aspects, the sequence of the R Domain comprises or consists of an amino acid sequence that is at least 80% identical to an amino acid sequence of the R domain (FIG. 1A, a.a. 470-605 of *S. aureus* Newman, for example). Sequences of R domains are described herein. In certain aspects, the sequence of the R Domain comprises or consists of an amino acid sequence that is at least 85, 90, 95, 98, 99 or 100% identical to an amino acid sequence of the R domain described herein. In some embodiments, the R Domains are at least 85%, 90% or 95% identical to an amino acid sequence of 1) a R Domain from the *S. aureus* Coa polypeptides corresponding to SEQ ID NOS:1-8 or 22-38; 2) a R Domain of SEQ ID NOS:39-55, SEQ ID NOS:85-101, or a fragment thereof; or 3) one or more R domain fragments of SEQ ID NOS:57-62 or SEQ ID NOS:102-127. In some embodiments, the R Domains are at least 80, 81, 82, 83, 84, 85, 86, 87, 88, 89, 90, 91, 92, 93, 94, 95, 96, 97, 98, 99, or 100% (or any derivable range therein) identical to an amino acid sequence of a R Domain of SEQ ID NOS:39-55, SEQ ID NOS:85-101, or a segment/fragment thereof. In further aspects, at least one of the R Domains is comprised in a less than full-length coagulase protein sequence. In particular embodiments, the full length coagulase protein is a Coa protein comprising the sequence of SEQ ID NO:1, 2, 3, 4, 5, 6, 7, 8, 22, 23, 24, 25, 26, 27, 28, 29, 30, 31, 32, 33, 34, 35, 36, 37 or 38. In still further aspects, the less than full-length Coa protein lacks all or part of a L Domain segment.

The polypeptides or the disclosure, including those discussed in the above-identified embodiments, as well as the antibody polypeptides, *Staphylococcus* coagulase polypeptides, R domains, and R domain segments/fragments may comprise a sequence that is at least, at most, or exactly 10, 11, 12, 13, 14, 15, 16, 17, 18, 19, 20, 21, 22, 23, 24, 25, 26, 27, 28, 29, 30, 31, 32, 33, 34, 45, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 contiguous amino acids (or any derivable range therein) to a polypeptide sequence described herein and may be at least 70, 75, 80, 85, 86, 87, 88, 89, 90, 91, 92, 93, 94, 95, 96, 97, 98, 99, or 100% (or any range derivable therein) identical to another polypeptide and/or the contiguous polypeptide may be at least 70, 75, 80, 85, 86, 87, 88, 89, 90, 91, 92, 93, 94, 95, 96, 97, 98, 99, or 100% (or any range derivable therein) to a contiguous amino acid sequence described herein.

In certain embodiments, one of the Staphylococcal coagulase R Domains (or segment thereof) is from a coagulase protein from a *S. aureus* Newman, 85/2082, MW2, MSSA476, N315, Mu50, MRSA252, Cowan1, WIS or USA300 strain, or any other *S. aureus* strain.

In certain embodiments, one of the Staphylococcal coagulase R Domains (or segment thereof) is from one of the dominant Coa taken from one of the dominant *S. aureus* lineage ST5, ST8, ST22, ST30, ST45, ST239.

In some aspects, one of the R Domains comprises a Coa R Domain at least 80% identical to an amino acid sequence of the R Domain. In further aspects, one of the R Domains comprises a Coa R Domain at least 85, 90, 95, 98, 99% identical (or any derivable range therein) to an amino acid sequence of the R Domain.

In certain embodiments, one of the R Domains is a Coa R Domain, further comprising an L, 1 (D1), or 2 (D2) Domain from a Staphylococcal Coa protein. In certain embodiments, the polypeptide and/or immunogenic composition does not comprise an L Domain. In certain embodiments, the polypeptide and/or immunogenic composition does not comprise a D1 and or D2 Domain.

In some aspects, an immunogenic composition comprises or consists of at least three, four, or five different Staphylococcal coagulase R Domains. In further aspects, an immunogenic composition comprise at least four different Staphylococcal coagulase R Domains. In particular embodiments, the at least four different Staphylococcal coagulase R Domains are Staphylococcal Coa R Domains from strains MRSA252, MW2, N315 and USA300. In particular embodiments, the at least four different Staphylococcal coagulase R Domains are Staphylococcal Coa R Domains from ST5, ST8, ST22 and ST239. In particular embodiments, the at least four different Staphylococcal coagulase R Domains are Staphylococcal Coa R Domains from ST5, ST8, ST22, ST30, ST45 and/or ST239. In some embodiments, it is contemplated that an immunogenic composition comprises at least two different Staphylococcal coagulase R Domains that are comprised in a fusion protein (i.e. the two R domains are on the same polypeptide). In some embodiments, the polypeptide comprises one or more R domains or R domain segments/fragments; wherein the polypeptide comprises a polypeptide linker before, after, and/or between the R domains or segments/fragments thereof.

Embodiments include a recombinant polypeptide comprising at least one Staphylococcal coagulase R Domain. In some embodiments, the recombinant polypeptide comprises at least two different R Domains. The sequences of the R Domains are at least 80% identical to an amino acid sequence of the R Domain. In some aspects, the sequence of the R Domains are at least 85, 90, 95, 98, 99% identical (or any derivable range therein) to an amino acid sequence of the R Domain. In some embodiments, the R Domains are at least 80, 81, 82, 83, 84, 85, 86, 87, 88, 89, 90, 91, 92, 93, 94, 95, 96, 97, 98, 99, or 100% identical (or any derivable range therein) to an amino acid sequence of: 1) a R Domain from the *S. aureus* Coa polypeptides corresponding to SEQ ID NOS:1-8 or 22-38; 2) a R Domain of SEQ ID NOS:39-55, SEQ ID NOS:85-101, or a fragment thereof; or 3) one or more R domain fragments of SEQ ID NOS:57-62 or SEQ ID NOS:102-127.

In further embodiments, a polynucleotide molecule comprising a nucleic acid sequence encoding a recombinant polypeptide comprising sequence encoding at least one Staphylococcal coagulase R Domain or segment/fragment is contemplated. In some embodiments, the polynucleotide molecule comprises a nucleic acid sequence encoding for at least two different R Domains. In further aspects, an expression vector comprises the nucleic acid sequence operably linked to an expression control sequence. In still further aspects, a host cell comprising the expression vector is also contemplated.

Embodiments include the use of the compositions, the polypeptides, recombinant polypeptides, immunoglobulin preparations, the polynucleotide molecule and the expression vector described throughout the disclosure to treat or prevent a Staphylococcal infection in a subject. In some aspects, a composition comprising at least one Staphylococcal coagulase R Domain is used to treat or prevent a Staphylococcal infection. In some embodiments, the composition comprises at least two different R Domains. The sequences of the R Domains are at least 80% identical to an amino acid sequence of the R domain and at least one of the R Domains is a truncated coagulase protein sequence.

Embodiments include methods of preventing or treating staphylococcal infection comprising the step of administering an immunogenic composition comprising a Staphylococcal coagulase or an immunogenic segment thereof, such as the R domains and R domain fragment/segments described herein.

Certain embodiments are directed to methods of preparing an immunoglobulin for use in prevention or treatment of staphylococcal infection comprising the steps of immunizing a recipient with a coagulase polypeptide polypeptide such as a polypeptide comprising a R domain or R domain segment/fragment described herein and isolating immunoglobulin from the recipient.

In one embodiment, there is a method of preparing an immunoglobulin for use in prevention or treatment of staphylococcal infection comprising the steps of immunizing a recipient with a vaccine, polypeptide, or immunogenic composition of the disclosure and isolating antibody-producing cells from the recipient, fusing the isolated cells with a myeloma cell, and isolating immunoglobulin from the fused cell. In some embodiments, the antibody producing cell comprises a spleen, peripheral blood, or lymph node cell. In some embodiments, the method further comprises sequencing the isolated immunoglobulin. In some embodiments, the method further comprises testing the isolated immunoglobulin for binding to an antigen, wherein the antigen comprises: 1) a R Domain from the *S. aureus* Coa polypeptides corresponding to SEQ ID NOS:1-8 or 22-38; 2) a R Domain of SEQ ID NOS:39-55, SEQ ID NOS:85-101, or a fragment thereof; or 3) one or more R domain fragments of SEQ ID NOS:57-62 or SEQ ID NOS:102-127.

A further embodiment is directed to an immunoglobulin prepared by a method described herein.

A further embodiment is directed to an immunoglobulin that specifically binds to a polypeptide comprising: 1) a R Domain from the *S. aureus* Coa polypeptides corresponding to SEQ ID NOS:1-8 or 22-38; 2) a R Domain of SEQ ID NOS:39-55, SEQ ID NOS:85-101, or a fragment thereof; or 3) one or more R domain fragments of SEQ ID NOS:57-62 or SEQ ID NOS:102-127. The polypeptide that is specifically recognized by the immunoglobulin may be a polypeptide described throughout this disclosure.

A further embodiment is directed to methods for treatment or prevention of staphylococcal infection comprising a step of administering to a subject an effective amount of pharmaceutical preparation of immunoglobulin that binds to a R domain and/or R domain fragment/segments described herein.

Other embodiments are directed to a use of the pharmaceutical preparation of coagulase immunoglobulins in the manufacture of a medicament for the treatment or prevention of staphylococcal infection.

Yet still further embodiments include vaccines comprising a pharmaceutically acceptable composition having an isolated polypeptide described herein, such as the R Domains and/or R domain segments/fragments set forth in SEQ ID NOS:1-8, 22-55, or 85-101 or fragments thereof, or any other combination or permutation of protein(s) or peptide(s) described herein, wherein the composition is capable of stimulating an immune response against a *staphylococcus* bacterium. The vaccine may comprise an isolated polypeptide described herein, or any other combination or permutation of protein(s) or peptide(s) described throughout the disclosure. In certain aspects of the invention the isolated polypeptide, or any other combination or permutation of protein(s) or peptide(s) described are multimerized, e.g., dimerized or concatamerized. In a further aspect, the vaccine composition is contaminated by less than about 10, 9, 8, 7, 6, 5, 4, 3, 2, 1, 0.5, 0.25, 0.05% (or any range derivable therein) of other Staphylococcal proteins. A composition may further comprise an isolated non-coagulase polypeptide. Typically the vaccine comprises an adjuvant. In certain aspects a protein or peptide of the invention is linked (covalently or non-covalently) to the adjuvant, preferably the adjuvant is chemically conjugated to the protein.

In still yet further embodiments, a vaccine composition is a pharmaceutically acceptable composition having a recombinant nucleic acid encoding all or part of a polypeptide described herein, or any other combination or permutation of protein(s) or peptide(s) described herein, wherein the composition is capable of stimulating an immune response against a *staphylococcus* bacterium. The vaccine composition may comprise a recombinant nucleic acid encoding all or part of a polypeptide of the disclosure, or any other combination or permutation of protein(s) or peptide(s) described herein. In certain embodiments the recombinant nucleic acid contains a heterologous promoter. Preferably the recombinant nucleic acid is a vector. More preferably the vector is a plasmid or a viral vector. In some aspects the vaccine includes a recombinant, non-*staphylococcus* bacterium containing the nucleic acid. The recombinant non-staphylococci may be *Salmonella* or another gram-positive bacteria. The vaccine may comprise a pharmaceutically acceptable excipient, more preferably an adjuvant.

In some embodiments, a method to manufacture an immunogenic composition comprising mixing at least one Staphylococcal coagulase R Domain polypeptide with a carrier is contemplated. In some embodiments, the method comprises mixing at least two, three, four, five, six, seven, eight, nine, or ten different (having different amino acid sequences) R Domains. The sequences of the R Domains are at least 80% identical to an amino acid sequence of the R Domain and at least one of the R Domains is a truncated coagulase protein sequence.

In some embodiments, the R Domain is not a full-length Coa protein or comprises less than a full-length Coa protein. In some embodiments, the R Domain (or fragment thereof) comprises at least, at most, or exactly 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 amino acids (or any range derivable therein). In some embodiments, the R Domain comprises a post-translational modification that is not present in the natural form in the *S. aureus* cell (i.e. bacterial-produced form). In some embodiments, the polypeptide is produced in a eukaryotic cell.

In some embodiments, the polypeptide has or lacks one or more post-translational modifications such as myristoylation, palmitoylation, isoprenylation or prenylation, farnesylation, geranylgeranylation, glypiation, acylation, acetylation, formylation, alkylation, methylation, amide bond formation, amidation at C-terminus, arginylation, polyglutamylation, polyglycylation, butyrylation, glycosylation, glycation, polysialylation, malonylation, hydroxylation, iodination, phosphorylation, adenylylation, propionylation, S-glutathionylation, S-nitrosylation, S-sulfenylation (aka S-sulphenylation), succinylation, sulfation, biotinylation, pegylation, SUMOylation, ubiquitination, Neddylation, Pupylation, disulfide bridges, or racemization.

Embodiments include the use of at least one Staphylococcal coagulase R Domain described herein in methods and compositions for the treatment of bacterial and/or Staphylococcal infection. Furthermore, certain embodiments provide methods and compositions that can be used to treat (e.g., limiting Staphylococcal abscess formation and/or persistence in a subject) or prevent bacterial infection. In some cases, methods for stimulating an immune response involve administering to the subject an effective amount of the immunogenic composition described herein and in certain aspects other bacterial proteins. Other bacterial proteins include, but are not limited to (i) a secreted virulence factor, and/or a cell surface protein or peptide, or (ii) a recombinant nucleic acid molecule encoding a secreted virulence factor, and/or a cell surface protein or peptide.

Certain aspects are directed to methods of treating a subject having or suspected of having a *Staphylococcus* infection comprising administering to a subject having or suspected of having a *Staphylococcus* infection an effective amount of a purified antibody or polypeptide that specifically binds a polypeptide of the disclosure.

In a further aspect methods are directed to treating a subject at risk of a *Staphylococcus* infection comprising administering to a subject at risk of a *Staphylococcus* infection an effective amount of an antibody that binds a polypeptide of the disclosure prior to infection with *Staphylococcus*.

Certain embodiments are directed to an antibody or binding polypeptide composition comprising an isolated and/or recombinant antibody or polypeptide that specifically binds a peptide segment as described above. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein.

In additional embodiments, there are pharmaceutical compositions comprising one or more polypeptides, immunogenic compositions, or antibodies or antibody fragments that are discussed herein. Such a composition may or may not contain additional active ingredients.

In certain embodiments there is a pharmaceutical composition consisting essentially of a polypeptide comprising one or more antibodies or antibody fragments, polypeptides, or immunogenic compositions discussed herein. It is contemplated that the composition may contain non-active ingredients.

Other aspects are directed to pharmaceutical compositions comprising an effective anti-bacterial amount of an antibody that specifically binds to a peptide described above and a pharmaceutically acceptable carrier.

The term "providing" is used according to its ordinary meaning to indicate "to supply or furnish for use." In some embodiments, the protein is provided directly by administering a composition comprising antibodies or fragments thereof that are described herein.

The subject typically will have (e.g., diagnosed with a persistent Staphylococcal infection), will be suspected of having, or will be at risk of developing a Staphylococcal infection. In some embodiments, the subject has been diagnosed with a *Staphylococcus* infection, has been previously treated for a *Staphylococcus* infection, has been determined to be resistant to a previous treatment for a *Staphylococcus* infection, is immune deficient, is immunocompromised, is hospitalized, is undergoing an invasive medical procedure, has a respiratory infection, is infected with influenza virus or is on a respirator.

Compositions include Coa-binding polypeptides in amounts effective to achieve the intended purpose—treatment or protection of Staphylococcal infection. The term "binding polypeptide" refers to a polypeptide that specifically binds to a target molecule, such as the binding of an antibody to an antigen. Binding polypeptides may but need not be derived from immunoglobulin genes or fragments of immunoglobulin genes. More specifically, an effective amount means an amount of active ingredients necessary to provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods described herein, an effective amount or dose can be estimated initially from in vitro, cell culture, and/or animal model assays. For example, a dose can be formulated in animal models to achieve a desired response. Such information can be used to more accurately determine useful doses in humans.

Compositions can comprise an antibody that binds Coa. An antibody can be an antibody fragment, a humanized antibody, a monoclonal antibody, a single chain antibody or the like. In certain aspects, the Coa antibody is elicited by providing a Coa peptide or antigen or epitope that results in the production of an antibody that binds Coa in the subject. The Coa antibody is typically formulated in a pharmaceutically acceptable composition. The Coa antibody composition can further comprise at least 1, 2, 3, 4, 5, 6, 7, 8, 9, 10, 11, 12, 13, 14, 15, 16, 17, 18, or 19 for more Staphylococcal antigens or immunogenic fragments thereof. The Staphylococcal antigen, or immunogenic fragment or segment can be administered concurrently with the Coa antibody. The Staphylococcal antigen or immunogenic fragment and the Coa antibody can be administered in the same or different composition and at the same or different times. The composition may comprises multiple (e.g., 2, 3, 4, or more) Coa antibodies that bind Coa polypeptides from multiple strains of *S. aureus*.

The Coa antibody composition can further comprise antibodies, antibody fragments or antibody subfragments to at least 1, 2, 3, 4, 5, 6, 7, 8, 9, 10, 11, 12, 13, 14, 15, 16, 17, 18, or 19 of more (or any range derivable therein) Staphylococcal antigens or immunogenic fragments thereof. The antibodies, antibody fragments or antibody subfragments to other Staphylococcal antigens or immunogenic fragments thereof can be administered concurrently with the Coa antibody. The antibodies, antibody fragments or antibody subfragments to other Staphylococcal antigens or immunogenic fragments thereof can be administered in the same or different composition to the Coa antibody and at the same or different times.

In other aspects, the subject can be administered with the immunogenic composition, the recombinant polypeptide, or the vector described herein. The recombinant polypeptide or the vector can be formulated in a pharmaceutically acceptable composition.

The Staphylococcal antigen or immunogenic fragment can be administered concurrently with the immunogenic composition comprising at least one coagulase R Domain, the recombinant polypeptide comprising at least one R Domain, and/or the vector comprising a nucleic acid sequence encoding at least one R Domain described herein. The Staphylococcal antigen or immunogenic fragment can be administered in the same composition with the immunogenic composition comprising at least one R Domains, the recombinant polypeptide comprising at least one R Domains, and/or the vector comprising a nucleic acid sequence encoding at least one R Domains described herein. As used herein, the term "modulate" or "modulation" encompasses the meanings of the words "enhance," or "inhibit." "Modulation" of activity may be either an increase or a decrease in activity. As used herein, the term "modulator" refers to compounds that effect the function of a moiety, including up-regulation, induction, stimulation, potentiation, inhibition, down-regulation, or suppression of a protein, nucleic acid, gene, organism or the like.

A recombinant nucleic acid molecule can encode at least one Staphylococcal coagulase R Domain and at least one Staphylococcal antigen or immunogenic fragment thereof. In particular aspects, the Staphylococcal coagulase R Domain is a Coa R Domain at least 80% identical to an amino acid sequence of the R Domain. In particular embodiments, the coagulase protein is a Coa protein comprising the sequence of SEQ ID NO: 1-8 or 22-38 or fragment thereof. In some embodiments, the R Domain comprises the sequence of SEQ ID NO:39-55, SEQ ID NOS:85-101, or a fragment thereof. In some embodiments the R domain comprises one or more R domain fragments of SEQ ID NOS:57-62 or SEQ ID NOS:102-127.

In some embodiments, the R Domain comprises an amino acid sequence of $X_d$:

(SEQ ID NO: 57)
RP(T/R)(F/Q)(N/K)K(P/A)S(E/K)TNAYNVTT(H/N)(A/G/Q)

(N/D)G(Q/T)V(S/T)YGARPT(Y/Q)(K/N)KPS(E/K)TNAYNVTTH (A/G)NGQVSYGAR(L/P)T(Q/Y)(N/K)KPS(K/E)TNAYNVTTHA (D/N)GTATYGP;

In some embodiments, the R Domain polypeptide comprises or further comprises an amino acid sequence of $X_a$, $X_b$, and/or $X_c$ wherein: $X_a$ is RPRFNKPSET-NAYNVTTNQDGTV(S/T)YGA (SEQ ID NO:58); $X_b$ is RP(T/R)(Q/F)NKPS(K/E)TNAYNVTTHANGQVSYGA (SEQ ID NO:59); and $X_c$ is RP(T/R)(F/Y/Q)(N/K)KPS(E/K)TNAYNVTT(H/N)(Q/A/R)(N/D)G(Q/T)VSYGA (SEQ ID NO:60). In some embodiments, the R Domain comprises an amino acid sequence of $X_aX_bX_cX_d$. In some embodiments, the R Domain comprises one or more of $X_a$, $X_b$, $X_c$, and/or $X_d$. In some embodiments, the R Domain comprises one or more tandem repeated $X_a$, $X_b$, $X_c$, and/or $X_d$ elements.

In some embodiments, the R Domain comprises an amino acid sequence of $X_b$:

(SEQ ID NO: 123)
ARP(T/R)(F/Q)(N/K)K(P/A)S(E/K)TNAYNVTT(H/N)(A/G/Q)

(N/D)G(Q/T)V(S/T)YGARPT(Y/Q)(K/N)KPS(E/K)TNAYNVTTH (A/G)NGQVSYGAR(L/P)T(Q/Y)(N/K)KPS(K/E)TNAYNVTTHA (D/N)GTATYG;

In some embodiments, the R Domain polypeptide comprises or further comprises an amino acid sequence of $X_e$, $X_f$, and/or $X_g$ wherein: $X_e$ is ARPRFNKPSET-NAYNVTTNQDGTV(S/T)YG (SEQ ID NO:124); $X_f$ is ARP(T/R)(Q/F)NKPS(K/E)TNAYNVTTHANGQVSYG (SEQ ID NO:125); and $X_g$ is ARP(T/R)(F/Y/Q)(N/K)KPS (E/K)TNAYNVTT(H/N)(Q/A/R)(N/D)G(Q/T)VSYG (SEQ ID NO:126).

In some embodiments, the R domain fragment comprises one or more polypeptides with an amino acid sequence of ARX$_1$X$_2$X$_3$X$_4$KX$_5$SX$_6$TNAYNVTTX$_7$X$_8$X$_9$GX$_{10}$X$_{11}$X$_{12}$YG (SEQ ID NO:61) or ARPTX$_3$X$_4$KPSX$_6$TNAYNVTTHX$_8$X$_9$GX$_{10}$X$_{11}$X$_{12}$YG (SEQ ID NO:62), wherein X$_1$, X$_2$, X$_3$, X$_4$, X$_5$, X$_6$, X$_7$, X$_8$, X$_9$, X$_{10}$, X$_{11}$, and X$_{12}$ are any amino acid. In some embodiments, X$_1$ is proline or leucine. In some embodiments, X$_2$ is arginine or threonine. In some embodiments, X$_3$ is phenylalanine, glutamine, or tyrosine. In some embodiments, X$_4$ is asparagine or lysine. In some embodiments, X$_5$ is proline or alanine. In some embodiments, X$_6$ is lysine or glutamate. In some embodiments, X$_7$ is histidine or asparagine. In some embodiments, X$_8$ is alanine, glutamine, glycine, or arginine. In some embodiments, X$_9$ is aspartate or asparagine. In some embodiments, X$_{10}$ is threonine or glutamine. In some embodiments, X$_{11}$ is valine or alanine. In some embodiments, X$_{12}$ is threonine or serine. The polypeptide may comprise one or more segments as defined by SEQ ID NO:61, 62, or any of SEQ ID NO:102-126. For example, the polypeptide may comprises at least, at most, or exactly 1, 2, 3, 4, 5, 6, 7, 8, 9, 10, 11, 12, 13, 14, 15, 20, 25, 30, 35, or 40 (or any derivable rage therein) segments, wherein each segment comprises SEQ ID NO:61, 62, or any of SEQ ID NO:102-126. The segments, which are all in the same continuous polypeptide, may have a peptide linker between the segments or may be joined without any linking amino acids. In some embodiments, the polypeptide comprises two to six segments of SEQ ID NO:61, 62, or any of SEQ ID NO:102-126. Furthermore, it is specifically contemplated that the R domain fragments, as defined by SEQ ID NO:61, 62, or any of SEQ ID NO:102-126 may be used with respect to any embodiment involving a R domain or R domain fragment/segment described throughout this disclosure.

In still further aspects, the isolated recombinant polypeptide comprising at least two different Staphylococcal coagulase R Domains (or segment thereof) described herein is multimerized, e.g., dimerized or a linear fusion of two or more polypeptides or peptide segments. In certain aspects of the disclosure, a composition comprises multimers or concatamers of 1, 2, 3, 4, 5, 6, 7, 8, 9, 10, 11, 12, 13, 14, 15, 16, 17, 18, 19, 20 or more isolated cell surface proteins or segments thereof. Concatamers are linear polypeptides having one or more repeating peptide units. The at least two different Staphylococcal coagulase R Domains (or segment thereof) can be consecutive or separated by a spacer or other peptide sequences, e.g., one or more additional bacterial peptide.

Certain embodiments include methods for eliciting an immune response against a *staphylococcus* bacterium or Staphylococci in a subject comprising providing to the subject an effective amount of an immunogenic composition or a recombinant polypeptide comprising at least one Staphylococcal coagulase R Domain (or segment thereof) or a vector comprising a nucleic acid sequence encoding the same.

Embodiments of the disclosure include compositions that include a polypeptide, peptide, or protein that comprises a sequence that is or is at least 70%, 75%, 80%, 85%, 90%, 95%, 96%, 97%, 98%, or 99% identical or similar to a Staphylococcal coagulase R Domains (or segment thereof), in particular, a Coa R Domain (or segment thereof) (see, the R Domain of FIG. 1A), or a second protein or peptide that is a secreted bacterial protein or a bacterial cell surface protein. Similarity or identity, with identity being preferred, is known in the art and a number of different programs can be used to identify whether a protein (or nucleic acid) has sequence identity or similarity to a known sequence. Sequence identity and/or similarity is determined using standard techniques known in the art, including, but not limited to, the local sequence identity algorithm of Smith & Waterman (1981), by the sequence identity alignment algorithm of Needleman & Wunsch (1970), by the search for similarity method of Pearson & Lipman (1988), by computerized implementations of these algorithms (GAP, BEST-FIT, FASTA, and TFASTA in the Wisconsin Genetics Software Package, Genetics Computer Group, 575 Science Drive, Madison, Wis.), the Best Fit sequence program described by Devereux et al. (1984), preferably using the default settings, or by inspection. Preferably, percent identity is calculated by using alignment tools known to and readily ascertainable to those of skill in the art. Percent identity is essentially the number of identical amino acids divided by the total number of amino acids compared times one hundred.

Still further embodiments include methods for stimulating in a subject a protective or therapeutic immune response against a *staphylococcus* bacterium comprising administering to the subject an effective amount of a composition including (i) a immunogenic composition comprising at least one Staphylococcal coagulase R Domain (or segment/fragment thereof), e.g., a Coa R Domain (see, the R Domain of FIG. 1A or of SEQ ID NO:1-8 or of SEQ ID NO: 22-38; a R Domain of SEQ ID NOS:39-55, SEQ ID NOS:85-101, or a fragment thereof; or 3) one or more R domain fragments of SEQ ID NOS:57-62 or SEQ ID NOS:101-127 or a homologue thereof; or, (ii) a recombinant polypeptide comprising at least one Staphylococcal coagulase R Domain or homogues thereof; or, (iii) a nucleic acid molecule comprises a sequence encoding the at least one Staphylococcal R Domais or homologue thereof, or (iv) administering any of (i)-(iii) with any combination or permutation of bacterial proteins described herein. In a preferred embodiment the composition is not a *staphylococcus* bacterium. In certain aspects the subject is a human or a cow. In some embodiments, the subject is a mammal. In a further aspect the composition is formulated in a pharmaceutically acceptable formulation. The Staphylococci may be *Staphylococcus aureus*.

Yet still further embodiments include vaccines comprising a pharmaceutically acceptable composition having at least one Staphylococcal coagulase R Domain described herein, or any other combination or permutation of protein(s) or peptide(s) described herein, wherein the composition is capable of stimulating an immune response against a *staphylococcus* bacterium. The vaccine may comprise at least one diferent Staphylococcal coagulase R Domain described herein, or any other combination or permutation of protein(s) or peptide(s) described. In certain aspects, at least one Staphylococcal coagulase R Domain described herein, or any other combination or permutation of protein(s) or peptide(s) described are multimerized, e.g., dimerized or concatamerized. In a further aspect, the vaccine composition is contaminated by less than about 10, 9, 8, 7, 6, 5, 4, 3, 2, 1, 0.5, 0.25, 0.05% (or any range derivable therein) of other Staphylococcal proteins. A composition may further comprise an isolated non-coagulase polypeptide. Typically the vaccine comprises an adjuvant. In certain aspects a protein or peptide of the disclosure is linked (covalently or non-covalently) to the adjuvant, preferably the adjuvant is chemically conjugated to the protein.

Yet further embodiments include a method comprising performing a binding assay to test the binding of an antibody and an antigen, wherein the antigen comprises at least 80% identity to: 1) a R Domain from the *S. aureus* Coa polypeptides corresponding to SEQ ID NOS:1-8 or 22-38; 2) a R Domain of SEQ ID NOS:39-55, SEQ ID NOS:85-101, or a fragment thereof; or 3) one or more R domain fragment of SEQ ID NOS:57-62 or SEQ ID NOS:102-127. In some embodiments, the binding assay comprises an ELISA (enzyme-linked immunosorbent assay). Other binding assays are known in the art and include, for example, western blotting, competition assays, capture assays, and FRET. In some embodiments, the method further comprises treating or inhibiting a *Staphylococcus* infection in a subject determined to have or be at risk for *Staphylococcus* infection by administering the tested antibody to the subject. In some embodiments, the method further comprises testing the concentration of the antibody, testing the purity of the antibody, and testing the binding of the antibody to *S. aureus* infected cells.

In still yet further embodiments, a vaccine composition is a pharmaceutically acceptable composition having a recombinant nucleic acid encoding a recombinant polypeptide containing at least one different Staphylococcal coagulase R Domain described herein, or any other combination or permutation of protein(s) or peptide(s) described herein, wherein the composition is capable of stimulating an immune response against a *staphylococcus* bacteria. In certain embodiments the recombinant nucleic acid contains a heterologous promoter. Preferably the recombinant nucleic acid is a vector. More preferably the vector is a plasmid or a viral vector. In some aspects the vaccine includes a recombinant, non-*staphylococcus* bacterium containing the nucleic acid. The recombinant non-Staphylococci may be *Salmonella* or another gram-positive bacteria. The vaccine may comprise a pharmaceutically acceptable excipient, more preferably an adjuvant.

Still further embodiments include methods for stimulating in a subject a protective or therapeutic immune response against a *staphylococcus* bacterium comprising administering to the subject an effective amount of a composition of at least one different Staphylococcal coagulase R Domain described herein, or a recombinant polypeptide containing at least one Staphylococcal coagulase R Domain.

In certain embodiments of the compositions and methods described herein, the Staphylococcal infection is a Staphylococcal *aureus* infection. In some embodiments, the Staphylococcal infection is methicillin resistant. In some embodiments, the Staphylococcal infection is methicillin resistant Staphylococcal *aureus* infection (MRSA).

In certain aspects, a bacterium delivering a composition of the disclosure will be limited or attenuated with respect to prolonged or persistent growth or abscess formation. In yet a further aspect, at least one Staphylococcal coagulase R Domain can be overexpressed in an attenuated bacterium to further enhance or supplement an immune response or vaccine formulation.

The term "vWbp protein" refers to a protein that includes isolated wild-type vWbp (von Willebrand factor binding protein) polypeptides from *staphylococcus* bacteria and segments thereof, as well as variants that stimulate an immune response against *staphylococcus* bacteria vWbp proteins.

The term "vWh protein" refers to a protein that includes isolated wild-type vWh (von Willebrand factor binding protein homolog) polypeptides from *staphylococcus* bacteria and segments thereof, as well as variants that stimulate an immune response against *staphylococcus* bacteria vWh proteins. An immune response refers to a humoral response, a cellular response, or both a humoral and cellular response in an organism. An immune response can be measured by assays that include, but are not limited to, assays measuring the presence or amount of antibodies that specifically recognize a protein or cell surface protein, assays measuring T-cell activation or proliferation, and/or assays that measure modulation in terms of activity or expression of one or more cytokines.

In yet still further embodiments of the disclosure a composition may include a polypeptide, peptide, or protein that is or is at least 70%, 75%, 80%, 85%, 90%, 95%, 96%, 97%, 98%, or 99% identical or similar to a Coa protein.

In yet still further embodiments of the disclosure a composition may include a polypeptide, peptide, or protein that is or is at least 70%, 75%, 80%, 85%, 90%, 95%, 96%, 97%, 98%, or 99% identical or similar to a vWbp protein.

In certain aspects, a polypeptide or segment/fragment can have a sequence that is at least 85%, at least 90%, at least 95%, at least 98%, or at least 99% or more identical to the amino acid sequence of the reference polypeptide. The term "similarity" refers to a polypeptide that has a sequence that has a certain percentage of amino acids that are either identical with the reference polypeptide or constitute conservative substitutions with the reference polypeptides.

The polypeptides described herein may include 1, 2, 3, 4, 5, 6, 7, 8, 9, 10, 11, 12, 13, 14, 15, or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of the sequence of the R domain.

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of the sequence of the R Domain.

In yet still further embodiments, a composition may include a polynucleotide that is or is at least 70%, 75%, 80%, 85%, 90%, 95%, 96%, 97%, 98%, or 99% identical or similar to a nucleic acid sequence encoding a Coa protein. In certain aspects, the nucleic acid sequence encoding a Coa protein of strain USA300 will have all or part of the nucleic acid sequence provided herein. In certain aspects, the nucleic acid sequence encoding a Coa protein of strain N315 will have all or part of the nucleic acid sequence provided herein. In certain aspects, the nucleic acid sequence encoding a Coa protein of strain MW2 will have all or part of the nucleic acid sequence provided herein. In certain aspects, the nucleic acid sequence encoding a Coa protein of strain MRSA252 will have all or part of the nucleic acid sequence provided herein. In certain aspects, the nucleic acid sequence encoding a Coa protein of strain WIS will have all or part of the nucleic acid sequence provided herein. In certain aspects, the nucleic acid sequence encoding a Coa protein of strain MU50 will have all or part of the nucleic acid sequence provided herein. In certain aspects, the nucleic acid sequence encoding a Coa protein of strain 85/2082 will have all or part of the nucleic acid sequence provided herein. In certain aspects, the nucleic acid sequence encoding a Coa protein of strain Newman will have all or part of the nucleic acid sequence provided herein.

In yet still further embodiments, a composition may include a polynucleotide that is or is at least 70%, 75%, 80%, 85%, 90%, 95%, 96%, 97%, 98%, or 99% identical or similar to a nucleic acid sequence encoding a Coa R Domain. In certain aspects, the nucleic acid sequence encoding a Coa R Domain of strain N315 will have all or part of the nucleic acid sequence provided herein. In certain aspects, the nucleic acid sequence encoding a Coa R Domain of strain MW2 will have all or part of the nucleic acid sequence provided herein. In certain aspects, the nucleic acid sequence encoding a Coa R Domain of strain MRSA252 will have all or part of the nucleic acid sequence provided herein. In certain aspects, the nucleic acid sequence encoding a Coa R Domain of strain WIS will have all or part of the nucleic acid sequence provided herein.

In particular aspects, a composition may comprise a polynucleotide that is or is at least 70%, 75%, 80%, 85%, 90%, 95%, 96%, 97%, 98%, or 99% identical or similar to a nucleic acid sequence encoding five different Coa R Domains from strains WIS, MRSA252, N315, MW2, and USA300, respectively. In still further aspects, the nucleic acid sequence encoding five different Coa R Domains will have all or part of the nucleic acid sequence provided herein.

The compositions may be formulated in a pharmaceutically acceptable composition. In certain aspects of the disclosure the *staphylococcus* bacterium is an *S. aureus* bacterium.

In further aspects, a composition may be administered more than one time to the subject, and may be administered 1, 2, 3, 4, 5, 6, 7, 8, 9, 10, 15, 20 or more times. The administration of the compositions include, but is not limited to oral, parenteral, subcutaneous, intramuscular, intravenous, or various combinations thereof, including inhalation or aspiration.

In still further embodiments, a composition comprises a recombinant nucleic acid molecule encoding a polypeptide described herein or segments/fragments thereof. Typically a recombinant nucleic acid molecule encoding a polypeptide described herein contains a heterologous promoter. In certain aspects, a recombinant nucleic acid molecule of the disclosure is a vector, in still other aspects the vector is a plasmid. In certain embodiments the vector is a viral vector. In certain aspects a composition includes a recombinant, non-*staphylococcus* bacterium containing or expressing a polypeptide described herein. In particular aspects the recombinant non-*staphylococcus* bacteria is *Salmonella* or another gram-positive bacteria. A composition is typically administered to mammals, such as human subjects, but administration to other animals that are capable of eliciting an immune response is contemplated. In further aspects the *staphylococcus* bacterium containing or expressing the polypeptide is *Staphylococcus aureus*. In further embodiments the immune response is a protective immune response.

Compositions discussed herein are typically administered to human subjects, but administration to other animals that are capable of eliciting an immune response to a *staphylococcus* bacterium is contemplated, particularly cattle, horses, goats, sheep and other domestic animals, i.e., mammals.

In certain aspects the *staphylococcus* bacterium is a *Staphylococcus aureus*. In further embodiments the immune response is a protective immune response. In still further aspects, the methods and compositions of the disclosure can be used to prevent, ameliorate, reduce, or treat infection of tissues or glands, e.g., mammary glands, particularly mastitis and other infections. Other methods include, but are not limited to prophylactically reducing bacterial burden in a subject not exhibiting signs of infection, particularly those subjects suspected of or at risk of being colonized by a target bacteria, e.g., subjects that are or will be at risk or susceptible to infection during a hospital stay, treatment, and/or recovery.

Any embodiment discussed with respect to one aspect of the disclosure applies to other aspects of the disclosure as well. In particular, any embodiment discussed in the context of a composition comprising at least one Staphylococcal coagulase R Domain or a recombinant polypeotide comprising the same or a nucleic acid encoding the same may be implemented with respect to other antigens such as the fragments of the R Domain defined herein.

Embodiments of the disclosure include a method of treating or inhibiting a *Staphylococcus* infection in a subject determined to have or be at risk for *Staphylococcus* infection comprising administering to the subject an effective amount of the composition comprising an antibody that specifically recognizes an antigenic fragment of the Staphylococcal coagulase protein; wherein the antigenic fragment is less than 200 amino acids in total length; comprises a R domain or fragment thereof; and wherein the R domain or fragment comprises SEQ ID NO:61 wherein $X_1$ is proline or leucine, $X_2$ is arginine or threonine, $X_3$ is phenylalanine, glutamine, or tyrosine, $X_4$ is asparagine or lysine, $X_5$ is proline or alanine, $X_6$ is lysine or glutamate, $X_7$ is histidine or asparagine, $X_8$ is alanine, glutamine, glycine, or arginine, $X_9$ is aspartate or asparagine, $X_{10}$ is threonine or glutamine, $X_{11}$ is valine or alanine, and $X_{12}$ is threonine or serine. A further embodiment relates to an immunogenic composition comprising a polypeptide comprising an R domain or fragment thereof, wherein the R domain or fragment comprises SEQ ID NO:61, wherein $X_1$ is proline or leucine, $X_2$ is arginine or threonine, $X_3$ is phenylalanine, glutamine, or tyrosine, $X_4$ is asparagine or lysine, $X_5$ is proline or alanine, $X_6$ is lysine or glutamate, $X_7$ is histidine or asparagine, $X_8$ is alanine, glutamine, glycine, or arginine, $X_9$ is aspartate or asparagine, $X_{10}$ is threonine or glutamine, $X_{11}$ is valine or alanine, and $X_{12}$ is threonine or serine, and wherein the polypeptide is less than 200 amino acids in length.

Moieties, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the disclosure may further comprise an adjuvant or a pharmaceutically acceptable excipient. An adjuvant may be covalently or non-covalently coupled to a polypeptide or peptide of the disclosure. In certain aspects, the adjuvant is chemically conjugated to a protein, polypeptide, or peptide.

The subject will have (e.g., are diagnosed with a Staphylococcal infection), will be suspected of having, or will be at risk of developing a Staphylococcal infection. Compositions of the present disclosure include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the disclosure, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

The embodiments in the Example section are understood to be embodiments of the disclosure that are applicable to all aspects of the disclosure.

Embodiments include compositions that contain or do not contain a bacterium. A composition may or may not include an attenuated or viable or intact Staphylococcal bacterium. In certain aspects, the composition comprises a bacterium that is not a Staphylococci bacterium or does not contain Staphylococci bacteria. In certain embodiments a bacterial composition comprises an isolated or recombinantly expressed Coa antibody or a nucleic acid encoding the same. In still further aspects, the Coa antibody is multimerized, e.g., a dimer, a trimer, a tertramer, etc.

In certain aspects, a peptide or an antigen or an epitope can be presented as multimers of 1, 2, 3, 4, 5, 6, 7, 8, 9, 10 or more peptide segments or peptide mimetics.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

In some embodiments, the polypeptides of the disclosure are non-naturally occurring polypeptides. In some embodiments, the polypeptides of the disclosure are truncated, chimeric, and/or modified. In some embodiments, the modification comprises a post-translational modification.

Compositions such as antibodies, peptides, antigens, or immunogens may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated.

The term "Coa antibody" refers to an antibody that specifically binds Coa proteins from *Staphylococcus* bacteria. In certain embodiments the antibody may bind a specific Coa protein from a particular *Staphylococcus* bacteria strain. In some embodiments, the antibody is humanized or chimeric.

In further aspects a composition may be administered more than one time to the subject, and may be administered 1, 2, 3, 4, 5, 6, 7, 8, 9, 10, 15, 20 or more times (or any range derivable therein). The administration of the compositions include, but is not limited to oral, parenteral, subcutaneous and intravenous administration, or various combinations thereof, including inhalation or aspiration.

Compositions may be administered to human or non-human subjects. For example, administration to non-human animals that are capable of providing a therapeutic benefit against a *Staphylococcus* bacterium are contemplated, particularly cattle, horses, goats, sheep, birds and other domesticated animals. In further aspects the *Staphylococcus* bacterium is a *Staphylococcus aureus*. In some embodiments, the subject is non-human. In some embodiments, the compositions are administered to non-human subjects for the purposes of generating monoclonal antibodies directed to an antigenic component in the composition. In still further aspects, the methods and compositions may be used to prevent, ameliorate, reduce, or treat infection of tissues or glands. Other methods include, but are not limited to prophylactically reducing bacterial burden in a subject not exhibiting signs of infection, particularly those subjects suspected of or at risk of being colonized by a target bacteria, e.g., subjects that are or will be at risk or susceptible to infection during a hospital stay, treatment, and/or recovery.

Still further embodiments include methods for providing a subject a protective or therapeutic composition against a *staphylococcus* bacterium comprising administering to the subject an effective amount of a composition including (i) a Coa antibody; or, (ii) a nucleic acid molecule encoding the same, or (iii) administering a Coa antibody with any combination or permutation of bacterial proteins described herein.

Further embodiments are described in Internation Publications: WO/2013/162746 and WO/2013/162751, each of which are incorporated by reference for all purposes.

The embodiments in the Example section are understood to be embodiments that are applicable to all aspects of the disclosure, including compositions and methods.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIG. 7: Alignment of Coa sequences from USA300 (SEQ ID NO:63), N315 (SEQ ID NO:64), MRSA252 (SEQ ID NO:65), MW2 (SEQ ID NO:66), and WIS (SEQ ID NO:67). The polypeptide sequences of these genes are provided as SEQ ID NOS:1-5, respectively.

FIG. 8: Alignment of Coa R Domain sequences. (SEQ ID NOS:68-84).

FIG. 10: Anti-R domain IgG improves survival of mice in a *S. aureus* lethal challenge model.

DETAILED DESCRIPTION

Host immunity against bacterial pathogens typically involves antibodies that recognize the microbial surface and promote phagocytic killing. Methicillin-resistant *Staphylococcus aureus* (MRSA) is a frequent cause of lethal bloodstream infection, however vaccines and antibody therapeutics targeting Staphylococcal surface molecules have thus far failed to achieve clinical efficacy. *S. aureus* secretes coagulase (Coa), which activates host prothrombin and generates fibrin fibrils that protect the pathogen against phagocytosis by immune cells. Because of negative selection, the coding sequence for the prothrombin binding D1-D2 domain is highly variable and does not elicit cross-protective immune responses. The R domain, tandem repeats of a 27-residue peptide that bind fibrinogen, is conserved at the C-terminus of all Coa molecules, We show here that the R domain enables bloodstream infections by directing fibrinogen to the Staphylococcal surface, generating a protective fibrin shield that inhibits phagocytosis. The fibrin shield can be marked with R-specific antibodies, which trigger phagocytic killing of Staphylococci and protect mice against lethal bloodstream infections caused by a broad spectrum of MRSA isolates. These findings emphasize the critical role of coagulase in Staphylococcal escape from opsonophagocytic killing and as a protective antigen for *S. aureus* vaccines.

*Staphylococcus aureus*, a Gram-positive bacterium and colonizer of the human nares and skin, is also an invasive pathogen and cause of soft tissue and bloodstream infections (David and Daum, 2010). Drug-resistant strains, designated MRSA (methicillin-resistant *S. aureus*), emerged with antibiotic use for the prevention or therapy of Staphylococcal infections. The recent pandemic of MRSA infections is associated with increased failure of antibiotic therapy and increased mortality of infection (David and Daum, 2010). To address this public health crisis, several vaccines and antibody therapeutics have been developed, each targeting molecules on the Staphylococcal surface including capsule, polyglycerol phosphate lipoteichoic acid, iron-regulated surface determinant protein B (IsdB) and clumping factor A (ClfA)(Spellberg and Daum, 2012). However, the corresponding clinical trials failed to reach their designated endpoints (Fowler et al., 2013; Shinefield et al., 2002).

Figures 1A, 1B, 1C, 1D, 1E:
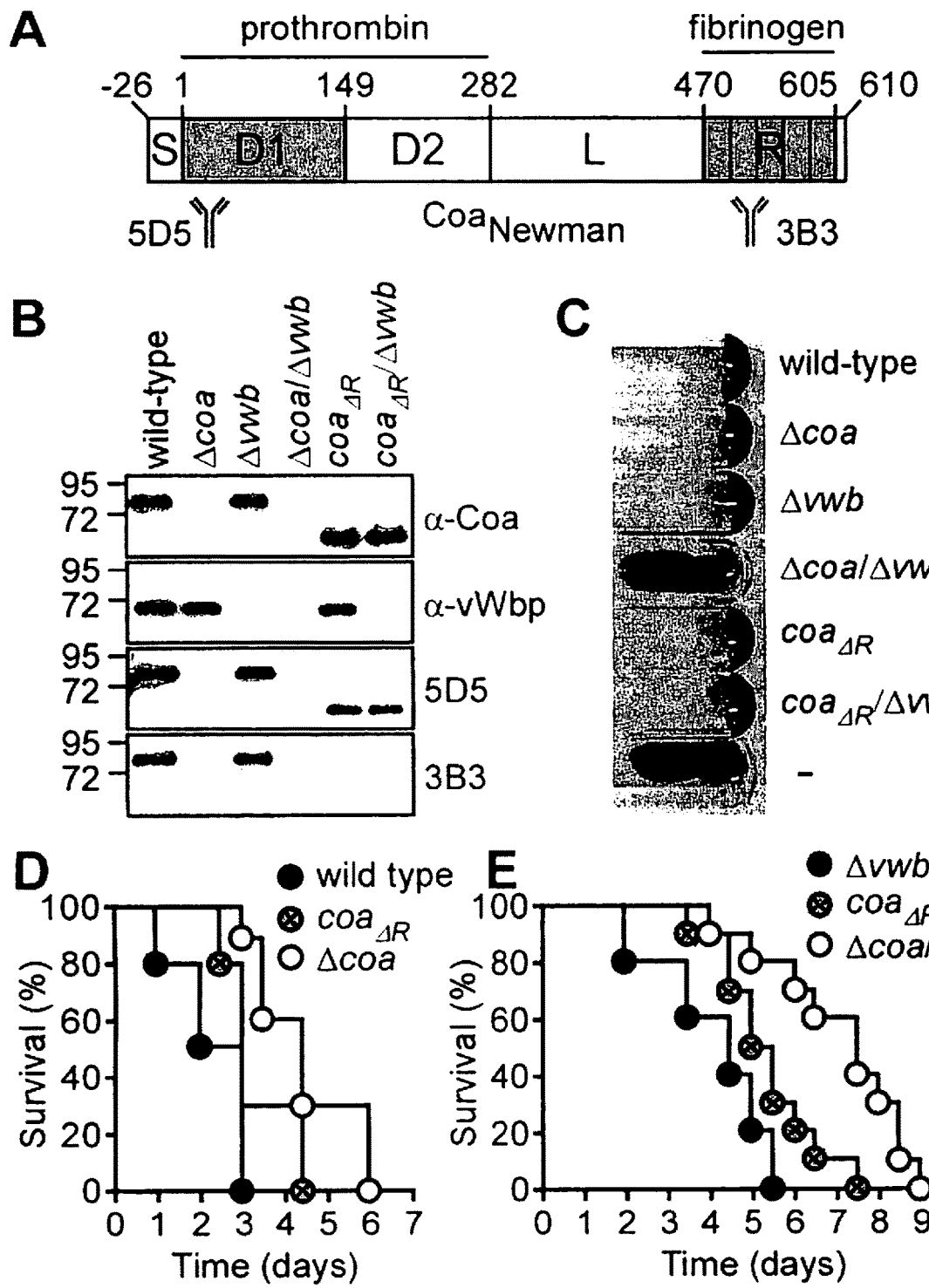
FIGS. 1A-1E: The repeat domain of coagulase contributes to *Staphylococcus aureus* bloodstream infections. (A) Primary structure of coagulase (Coa) with signal sequence (SS), variable D1 and D2 domains involved in prothrombin binding (D1-D2), linker (L) and repeat (R) domains. In *S. aureus* Newman, R comprises of five tandem repeats of a 27 residue peptide that bind fibrinogen. The binding sites for monoclonal antibodies (mAbs) 5D5 (blue) and 3B3 (red) are identified. (B) Secreted proteins of *S. aureus* Newman (wild-type) and coagulase variants were analyzed by immunoblotting with polyclonal α-Coa or α-vWbp and mAbs 5D5 or 3B3. Migratory positions of 72 and 95 kDa markers are indicated. (C) Calcium-chelated mouse blood was inoculated with *S. aureus* strains ($1 \times 10^6$ CFU) at room temperature for 24 hours and coagulation analyzed by inversion of tubes. (D-E) Mice (n=10) were challenged by intravenous injection with $8 \times 10^7$ CFU of *S. aureus* Newman wild-type or coagulase variant strains. Data are representative of two independent analyses; (D-E) statistical significance was assessed with the Log-rank test.

A distinguishing feature of clinical *S. aureus* isolates is their ability to clot human plasma. This unique trait is based on the secretion of coagulase (Coa; FIG. 1A)(Tager, 1956), which associates with human prothrombin to form enzymatically active staphylothrombin, cleaving the A and B peptides of fibrinogen and generating fibrin fibrils (Friedrich et al., 2003). Staphylothrombin does not cut other endogenous substrates of thrombin, causing exuberant polymerization of fibrin while avoiding activation of other clotting and inflammatory factors (McAdow et al., 2012b; Panizzi et al., 2004). The resulting fibrin meshwork protects bacteria from phagocytes and is essential for the formation of *S. aureus* abscess lesions (Cheng et al., 2010; Smith et al., 1947). Activation of prothrombin is mediated by the N-terminal D1-D2 domain of Coa and blocked by specific antibodies, which provide protection from *S. aureus* bloodstream infection in animal models (Cheng et al., 2010; Rammelkamp et al., 1950). Because of negative selection, coa is one of the most variable genes in the core genome of *S. aureus*. Up to 50% sequence variation occurs in the coding sequence for the D1-D2 domain and the corresponding products can be categorized into serotypes without cross-protecting epitopes for the neutralization of staphylothrombin (McAdow et al., 2012a; Watanabe et al., 2009). *S. aureus* secretes a second staphylothrombin, designated von Willebrand factor binding protein (vWbp) with the conserved D1-D2 domain structure mediating association with prothrombin (Bjerketorp et al., 2004). This complex displays different catalytic activity than Coa-staphylothrombin, generating fibrin fibrils at a reduced rate and contributing to abscess formation without affecting Staphylococcal escape from phagocytosis (Guggenberger et al., 2012; Kroh et al., 2009). The structural gene for vWbp, vwb, displays limited sequence variation, and is presumably not subject to negative selection (McAdow et al., 2012a).

*Staphylococcus aureus* is a commensal of the human skin and nares, and the leading cause of bloodstream, skin and soft tissue infections (Klevens et al., 2007). Recent dramatic increases in the mortality of Staphylococcal diseases are attributed to the spread of methicillin-resistant *S. aureus* (MRSA) strains often not susceptible to antibiotics (Kennedy et al., 2008). In a large retrospective study, the incidence of MRSA infections was 4.6% of all hospital admissions in the United States (Klevens et al., 2007). The annual health care costs for 94,300 MRSA infected individuals in the United States exceed $2.4 billion (Klevens et al., 2007). The current MRSA epidemic has precipitated a public health crisis that needs to be addressed by development of a preventive vaccine (Boucher and Corey, 2008). To date, an FDA licensed vaccine that prevents *S. aureus* diseases is not available.

Coagulase (Coa) is an important virulence factor in the pathogenesis of Staphylococcal sepsis. The conversion of fibrinogen to fibrin by the Coa:prothrombin complex enables *Staphylococcus aureus* to evade immune defenses and disseminate throughout the body. Humoral immunity toward Coa is protective in a murine sepsis model. Previous work demonstrated that there are protective epitopes in both the N- and C-terminus and that there is type-specific immunity, attributable to the genetic variation in the N-terminus of Coa among strains.

The inventors describe here Staphylococcal coagulase-binding antibodies and the antigen binding determinants thereof. In particular, a panel of monoclonal antibodies were generated against Coa and characterized based on their affinity for individual domains of the protein and their disturbance of clotting. Based on in vitro characteristics, several monoclonal antibodies were tested for protection in a murine sepsis model resulting in the identification of a protective epitope in the conserved portion of the N-terminus. Importantly, antibodies targeting this epitope are able, when administered to animals, to reduce Staphylococcal sepsis following challenge with virulent *S. aureus*. Because these molecules are able to block the prothrombin-activating effects of Coa, such antibodies may also enhance host immune response following Staphylococcal infection. Thus, the Coa-binding molecules of the embodiments offer a new and effective avenue to treat or prevent Staphylococcal disease.

I. COAGULASE POLYPEPTIDES

Certain aspects of the embodiments concern coagulase (Coa) polypeptides. An illustration of the primary structure of Coa from *S. aureus* Newman ($Coa_{NM}$) is provided in FIG. 1A. Amino acid sequences for Coa from eight *S. aureus* strains are provided in SEQ ID NOs: 1-8 as follows: USA300 (SEQ ID NO: 1), N315 (SEQ ID NO: 2), MW2 (SEQ ID NO: 3), MRSA252 (SEQ ID NO: 4), WIS (SEQ ID NO: 5), MU50 (SEQ ID NO: 6), 85/2082 (SEQ ID NO: 7), and Newman (SEQ ID NO: 8). An alignment of Coa sequences from nucleic acids encoding USA300 (SEQ ID NO: 1), N315 (SEQ ID NO: 2), MRSA252 (SEQ ID NO: 4), MW2 (SEQ ID NO: 3), and WIS (SEQ ID NO: 5) is provided in FIG. 7.

Amino acid sequences from 17 Coa R Domains from one of the dominant Coa taken from dominant *S. aureus* lineages are provided as follows: ST5_1 (SEQ ID NO:22), ST5_2 (SEQ ID NO:23), ST5_3 (SEQ ID NO:24), ST8_1 (SEQ ID NO:25), ST8_2 (SEQ ID NO:26), ST22_1 (SEQ ID NO:27), ST22_2 (SEQ ID NO:28), ST22_3 (SEQ ID NO:29), ST30_1 (SEQ ID NO:30), ST30_2 (SEQ ID NO:31), ST30_3 (SEQ ID NO:32), ST45_1 (SEQ ID NO:33), ST45_2 (SEQ ID NO:34), ST45_3 (SEQ ID NO:35), ST239_1 (SEQ ID NO:36), ST239_2 (SEQ ID NO:37), ST239_3 (SEQ ID NO:38).

Coagulase interacts with host prothrombin through its N-terminal domains, D1 and D2. The three-helix bundles of D1 and D2 share structural similarity but are poorly conserved at the sequence level [66]. The first 150 amino acids comprise the D1 domain [68]. The amino-terminal tetrapeptide of Coa inserts into the activation pocket of prothrombin and forms a salt bridge with prothrombin Asp194 [66]. The first of two high-affinity binding interactions between Coa and prothrombin occurs through a hydrophobic surface groove in D1 with the 148 loop of prothrombin [66]. $SC_{150-282}$ comprises the D2 domain [68]. The second high-affinity binding interaction is between the side chain of Tyr76 of the prothrombin exosite I and D2 alpha helices [66]. Coa forms a dimer in solution, with each monomer binding one molecule of prothrombin [66]. A complex formed by prothrombin and a recombinant construct of the D1D2 domain ($SC_{1-325}$) is able to bind fibrinogen through a distinct interaction from the substrate binding exosite on prothrombin [133].

Two other domains of Coa are less well understood. Following D2, there is a highly conserved Linker (L) region with unknown function [77]. Near the C-terminus is a region of tandem repeats of a 27 amino acid peptide, and the number of repeats varies among strains [77]. The repeat region is thought to be responsible for high affinity binding to fibrinogen [133,214].

The gene encoding Coa (coa) is found on all *S. aureus* chromosomes, yet it is one of the most variable proteins, with twelve known types (Watanabe et al. 2005, Watanabe et al. 2009). The majority of variability among Coa alleles resides in the D1 and D2 domains. The linker region is relatively conserved with 86.7% identity among serotypes (Watanabe et al. 2005). Of note, the amino terminal end of mature Coa, i.e. the first seven residues following the signal peptidase cleavage site, activate prothrombin and these residues are conserved among all strains analyzed [68]. The C-terminal tandem repeats of a 27 residue peptide vary in number from five to nine but have greater than 90% identity among serotypes (Watanabe et al. 2005). Antibodies that recognize epitopes in $SC_{1-282}$ are necessary to block the enzymatic activities of the Coa-prothrombin complex [215]. In vivo, antibodies against the C-terminal repeats also confer protection [215], though the mechanism of protection is not yet clear.

Coa polypeptides can be used as subunit vaccines and raise humoral immune responses and confer protective immunity against *S. aureus* challenge. In certain embodiments, polyvalent vaccines targeting Coa variation across multiple *S. aurueus* strains are contemplated. This embodiment is discussed in a U.S. Provisional Patent Application filed on Apr. 26, 2012 entitled "STAPHYLOCOCCAL COAGULASE ANTIGENS AND METHODS OF THEIR USE" in the names of Molly McAdow, Andrea DeDent, Alice Cheng, Carla Emolo, Dominique Missiakas, Olaf Schneewind, which is hereby incorporated by reference in its entirety.

II. PROTEINACEOUS COMPOSITIONS

As used herein, a "protein" or "polypeptide" refers to a molecule comprising at least ten amino acid residues. In some embodiments, a wild-type version of a protein or polypeptide are employed, however, in many embodiments of the disclosure, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of coagulases, in particular, of coagulase R Domains, SpA and other polypeptides of the disclosure can be substitutional, insertional, or deletion variants. A variation in a polypeptide of the disclosure may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, or 90%, including all values and ranges there between, identical to any sequence provided or referenced herein, e.g., a sequence of the R Domain. A variant can include 2, 3, 4, 5, 6, 7, 8, 9, 10, 11, 12, 13, 14, 15, 16, 17, 18, 19, 20, or more substitute amino acids. A polypeptide processed or secreted by the Ess pathway or other surface proteins (see Table 3) or sortase substrates from any *staphylococcus* species and strain are contemplated for use in compositions and methods described herein.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptides or polypeptides described or referenced herein.

The following is a discussion based upon changing of the amino acids of a protein to create a variant polypeptide or peptide. For example, certain amino acids may be substituted for other amino acids in a protein structure with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence, and in its underlying DNA coding sequence, and nevertheless produce a protein with a desirable property. It is thus contemplated by the inventors that various changes may be made in the DNA sequences of genes.

It is contemplated that in compositions of the disclosure, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a coagulase R Domain or a coagulase or its variant and may be used in combination with other peptides or polypeptides, such as other bacterial peptides and/or antigens.

The present disclosure contemplates the administration of Staphylococcal coagulase R Domains (or segments thereof) or variants thereof to effect a preventative therapy or therapeutic effect against the development of a disease or condition associated with infection by a *staphylococcus* pathogen.

In certain aspects, combinations of Staphylococcal antigens are used in the production of an immunogenic composition that is effective at treating or preventing Staphylococcal infection. Staphylococcal infections progress through several different stages. For example, the Staphylococcal life cycle involves commensal colonization, initiation of infection by accessing adjoining tissues or the bloodstream, and/or anaerobic multiplication in the blood. The interplay between *S. aureus* virulence determinants and the host defense mechanisms can induce complications such as endocarditis, metastatic abscess formation, and sepsis syndrome. Different molecules on the surface of the bacterium are involved in different steps of the infection cycle. Combinations of certain antigens can elicit an immune response which protects against multiple stages of Staphylococcal infection. The effectiveness of the immune response can be measured either in animal model assays and/or using an opsonophagocytic assay.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Codon Table, below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an antibody that binds Coa, and may be used in combination with other Staphylococcal proteins or protein-binding antibodies described herein.

A. Polypeptides and Polypeptide Production

Embodiments involve polypeptides, peptides, and proteins and immunogenic fragments thereof for use in various aspects described herein. For example, specific antibodies are assayed for or used in neutralizing or inhibiting Staphylococcal infection. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects an immunogenic Coa fragment comprises substantially all of the D1 and/or D2 domains and/or R domain of a Coa protein isolatable from *S. aureus*.

Also included in immunogenic compositions are fusion proteins composed of Staphylococcal proteins, or immunogenic fragments of Staphylococcal proteins (e.g., Coa). Alternatively, embodiments also include individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

The present disclosure describes polypeptides, peptides, and proteins and immunogenic fragments thereof for use in various embodiments of the present disclosure. For example, specific polypeptides are assayed for or used to elicit an immune response. In specific embodiments, all or part of the proteins of the disclosure can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

Alternatively, recombinant DNA technology may be employed wherein a nucleotide sequence which encodes a peptide of the disclosure is inserted into an expression vector, transformed or transfected into an appropriate host cell and cultivated under conditions suitable for expression.

One embodiment of the disclosure includes the use of gene transfer to cells, including microorganisms, for the production and/or presentation of polypeptides or peptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified.

Another embodiment of the present disclosure uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Where a protein is specifically mentioned herein, it is preferably a reference to a native or recombinant protein or optionally a protein in which any signal sequence has been removed. The protein may be isolated directly from the Staphylococcal strain or produced by recombinant DNA techniques. Immunogenic fragments of the protein may be incorporated into the immunogenic composition of the disclosure. These are fragments comprising at least 10 amino acids, 20 amino acids, 30 amino acids, 40 amino acids, 50 amino acids, or 100 amino acids, including all values and ranges there between, taken contiguously from the amino acid sequence of the protein. In addition, such immunogenic fragments are immunologically reactive with antibodies generated against the Staphylococcal proteins or with antibodies generated by infection of a mammalian host with Staphylococci. Immunogenic fragments also include fragments that when administered at an effective dose, (either alone or as a hapten bound to a carrier), elicit a protective or therapeutic immune response against Staphylococcal infection, in certain aspects it is protective against S. aureus and/or S. epidermidis infection. Such an immunogenic fragment may include, for example, the protein lacking an N-terminal leader sequence, and/or a transmembrane domain and/or a C-terminal anchor domain. In a preferred aspect the immunogenic fragment according to the disclosure comprises substantially all of the extracellular domain of a protein which has at least 80% identity, at least 85% identity, at least 90% identity, at least 95% identity, or at least 97-99% identity, including all values and ranges there between, to a sequence selected segment of a polypeptide described or referenced herein.

Also included in immunogenic compositions of the disclosure are fusion proteins composed of one or more Staphylococcal proteins, or immunogenic fragments of Staphylococcal proteins. Such fusion proteins may be made recombinantly and may comprise one portion of at least 1, 2, 3, 4, 5, or 6 Staphylococcal proteins or segments. Alternatively, a fusion protein may comprise multiple portions of at least 1, 2, 3, 4 or 5 Staphylococcal proteins. These may combine different Staphylococcal proteins and/or multiples of the same protein or proten fragment, or immunogenic fragments in the same protein (forming a multimer or a concatamer). Alternatively, the disclosure also includes individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, or CRM197.

B. Antibodies and Antibody-Like Molecules

In certain aspects, one or more antibodies or antibody-like molecules (e.g., polypeptides comprising antibody CDR domains) may be obtained or produced which have a specificity for a Coa. In particular embodiments, one or more antibodies or antibody-like molecules (e.g., polypeptides comprising antibody CDR domains) may be obtained or produced which have a specificity for the D1 and/or D2 domain of Coa. These antibodies may be used in various diagnostic or therapeutic applications described herein.

As used herein, the term "antibody" is intended to refer broadly to any immunologic binding agent such as IgG, IgM, IgA, IgD and IgE as well as polypeptides comprsing antibody CDR domains that retain antigen binding activity. Thus, the term "antibody" is used to refer to any antibody-like molecule that has an antigen binding region, and includes antibody fragments such as Fab', Fab, F(ab')2, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region. Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate Coa-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express, and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as SpA binding molecules. Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibitors of neuronal NO synthase (PIN) may also be used in certain aspects.

Monoclonal antibodies (mAbs) are recognized to have certain advantages, e.g., reproducibility and large-scale production. Embodiments include monoclonal antibodies of the human, murine, monkey, rat, hamster, rabbit, and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

C. Methods for Generating Antibodies

Methods for generating antibodies (e.g., monoclonal antibodies and/or monoclonal antibodies) are known in the art. Briefly, a polyclonal antibody is prepared by immunizing an animal with a Coa polypeptide or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig, or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions, or vectors encoding such adjuvants.

Adjuvants that may be used in accordance with embodiments include, but are not limited to, IL-1, IL-2, IL-4, IL-7, IL-12, interferon, GMCSP, BCG, aluminum hydroxide, MDP compounds, such as thur-MDP and nor-MDP, CGP (MTP-PE), lipid A, and monophosphoryl lipid A (MPL). RIB I, which contains three components extracted from bacteria, MPL, trehalose dimycolate (TDM), and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous, and intraperitoneal. The production of antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate mAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography, among others.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (mAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages (Goding, 1986, pp. 60 61). Mice (e.g., BALB/c mice) are routinely used and generally give a high percentage of stable fusions.

The animals are injected with antigen, generally as described above. The antigen may be mixed with adjuvant, such as Freund's complete or incomplete adjuvant. Booster administrations with the same antigen or DNA encoding the antigen may occur at approximately two-week intervals.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Generally, spleen cells are a rich source of antibody-producing cells that are in the dividing plasmablast stage. Typically, peripheral blood cells may be readily obtained, as peripheral blood is easily accessible.

In some embodiments, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and 5194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al. (2002), for a discussion of myeloma expression systems.

One murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, whose clones can then be propagated indefinitely to provide mAbs. The cell lines may be exploited for mAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide mAbs in high concentration. Second, the individual cell lines could be cultured in vitro, where the mAbs are naturally secreted into the culture medium from which they can be readily obtained in high concentrations.

Further, expression of antibodies (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

mAbs produced by either means may be further purified, if desired, using filtration, centrifugation, and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in *E. coli*.

D. Antibody and Polypeptide Conjugates

Embodiments provide antibodies and antibody-like molecules against Coa proteins, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging". Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might use astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often used in certain embodiments, and technicium$^{99m}$ and/or indium$^{111}$ are also often used due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/ or Texas Red, among others.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as sitedirected photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In some embodiments, anti-Coa antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays include, but are not limited to, those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

III. NUCLEIC ACIDS

In certain embodiments, there are recombinant polynucleotides encoding the proteins, polypeptides, or peptides described herein. Polynucleotide sequences contemplated include those encoding antibodies to Coa or Coa-binding portions thereof.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above). A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges therebetween, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular embodiments, there are isolated nucleic acid segments and recombinant vectors incorporating nucleic acid sequences that encode a polypeptide (e.g., an antibody or fragment thereof) that binds to Coa. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody that binds Coa.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present disclosure to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), al-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II—Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); β-Interferon—poly(rI)x/poly(rc) (Tavernier et al., 1983); Adenovirus 5 E2-E1A (Imperiale et al., 1984); Collagenase—Phorbol Ester (TPA) (Angel et al., 1987a); Stromelysin—Phorbol Ester (TPA) (Angel et al., 1987b); SV40—Phorbol Ester (TPA) (Angel et al., 1987b); Murine MX Gene—Interferon, Newcastle Disease Virus (Hug et al., 1988); GRP78 Gene—A23187 (Resendez et al., 1988); α-2-Macroglobulin—IL-6 (Kunz et al., 1989); Vimentin—Serum (Rittling et al., 1989); MHC Class I Gene H-2κb—Interferon (Blanar et al., 1989); HSP70—E1A/SV40 Large T Antigen (Taylor et al., 1989, 1990a, 1990b); Proliferin—Phorbol Ester/TPA (Mordacq et al., 1989); Tumor Necrosis Factor—PMA (Hensel et al., 1989); and Thyroid Stimulating Hormone a Gene—Thyroid Hormone (Chatterjee et al., 1989).

The particular promoter that is employed to control the expression of peptide or protein encoding polynucleotide of the disclosure is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In embodiments in which a vector is administered to a subject for expression of the protein, it is contemplated that a desirable promoter for use with the vector is one that is not down-regulated by cytokines or one that is strong enough that even if down-regulated, it produces an effective amount of at least one Staphylococcal coagulase R Domain for eliciting an immune response. Non-limiting examples of these are CMV IE and RSV LTR. Tissue specific promoters can be used, particularly if expression is in cells in which expression of an antigen is desirable, such as dendritic cells or macrophages. The mammalian MHC I and MHC II promoters are examples of such tissue-specific promoters.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the disclosure, the use of internal ribosome entry sites (IRES) elements are used to create multigene, or polycistronic, messages. IRES elements are able to bypass the ribosome scanning model of 5'☐ methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

3. Selectable and Screenable Markers

In certain embodiments of the disclosure, cells containing a nucleic acid construct of the present disclosure may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

D. Methods of Gene Transfer

Suitable methods for nucleic acid delivery to effect expression of compositions are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Through the application of techniques such as these, organelle(s), cell(s), tissue(s) or organism(s) may be stably or transiently transformed.

IV. IMMUNE RESPONSE AND ASSAYS

As discussed above, the disclosure concerns evoking or inducing an immune response in a subject against a coagulase or one or more coagulase R Domains or variants thereof. In one embodiment, the immune response can protect against or treat a subject having, suspected of having, or at risk of developing an infection or related disease, particularly those related to Staphylococci. One use of the immunogenic compositions of the disclosure is to prevent nosocomial infections by inoculating a subject prior to undergoing procedures in a hospital or other environment having an increased risk of infection.

A. Immunoassays

The present disclosure includes the implementation of serological assays to evaluate whether and to what extent an immune response is induced or evoked by compositions of the disclosure. There are many types of immunoassays that can be implemented. Immunoassays encompassed by the present disclosure include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non-specifically bound immune complexes, the bound antigen or antibody may be detected. Detection is generally achieved by the addition of another antibody, specific for the desired antigen or antibody that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non-specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

B. Diagnosis of Bacterial Infection

In addition to the use of proteins, polypeptides, and/or peptides, as well as antibodies binding these polypeptides, proteins, and/or peptides, to treat or prevent infection as described above, the present disclosure contemplates the use of these polypeptides, proteins, peptides, and/or antibodies in a variety of ways, including the detection of the presence of Staphylococci to diagnose an infection, whether in a subject or on medical equipment which may also become infected. In accordance with the disclosure, a preferred method of detecting the presence of infections involves the steps of obtaining a sample suspected of being infected by one or more Staphylococcal bacteria species or strains, such as a sample taken from an individual, for example, from one's blood, saliva, tissues, bone, muscle, cartilage, or skin. Following isolation of the sample, diagnostic assays utilizing the polypeptides, proteins, peptides, and/or antibodies of the present disclosure may be carried out to detect the presence of Staphylococci, and such assay techniques for determining such presence in a sample are well known to those skilled in the art and include methods such as radioimmunoassay, western blot analysis and ELISA assays. In general, in accordance with the disclosure, a method of diagnosing an infection is contemplated wherein a sample suspected of being infected with Staphylococci has added to it the polypeptide, protein, peptide, antibody, or monoclonal antibody in accordance with the present disclosure, and Staphylococci are indicated by antibody binding to the polypeptides, proteins, and/or peptides, or polypeptides, proteins, and/or peptides binding to the antibodies in the sample.

Accordingly, antibodies in accordance with the disclosure may be used for the prevention of infection from Staphylococcal bacteria (i.e., passive immunization), for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies, including the products of a Fab immunoglobulin expression library. Accordingly, the disclosure contemplates the use of single chains such as the variable heavy and light chains of the antibodies. Generation of any of these types of antibodies or antibody fragments is well known to those skilled in the art. Specific examples of the generation of an antibody to a bacterial protein can be found in U.S. Patent Application Pub. No. 20030153022, which is incorporated herein by reference in its entirety.

Any of the above described polypeptides, proteins, peptides, and/or antibodies may be labeled directly with a detectable label for identification and quantification of Staphylococcal bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

C. Protective Immunity

In some embodiments of the disclosure, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide or peptide refer to a stretch of amino acids covalently linked there amongst via peptide bonds. Different polypeptides have different functionalities according to the present disclosure. While according to one aspect, a polypeptide is derived from an immunogen designed to induce an active immune response in a recipient, according to another aspect of the disclosure, a polypeptide is derived from an antibody which results following the elicitation of an active immune response in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the disclosure in a recipient subject. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils, or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present disclosure can be administered to a subject who then acts as a source or donor for globulin, produced in response to challenge with the antigenic composition ("hyperimmune globulin") that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins according to the disclosure are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Mernaugh et al., 1995).

As used herein and in the claims, the phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

V. METHODS OF TREATMENT

As discussed above, the compositions and methods of using these compositions can treat a subject (e.g., limiting bacterial load or abscess formation or persistence) having, suspected of having, or at risk of developing an infection or related disease, particularly those related to Staphylococci. One use of the compositions is to prevent nosocomial infections by inoculating a subject prior to hospital treatment.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the disclosure in a recipient subject. Treatment or therapy can be an active immune response induced by administration of immunogen or a passive therapy effected by administration of antibody, antibody containing material, or primed T-cells.

As used herein "passive immunity" refers to any immunity conferred upon a subject by administration of immune effectors including cellular mediators or protein mediators (e.g., a polypeptide that binds to Coa protein). An antibody composition may be used in passive immunization for the prevention or treatment of infection by organisms that carry the antigen recognized by the antibody. An antibody composition may include antibodies or polypeptides comprsing antibody CDR domains that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the subject immunoglobulins (Ig) or fragments thereof and/or other immune factors obtained from a donor or other non-patient source having a known immunoreactivity. In other aspects, an antigenic composition can be administered to a subject who then acts as a source or donor for globulin, produced in response to challenge from the composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition caused by a *staphylococcus* pathogen.

In certain aspects embodiments include methods of treatment of Staphylococcal infection, such as hospital acquired nosocomial infections. In some embodiments, the treatment is administered in the presence of Staphylococcal antigens. Furthermore, in some examples, treatment comprises administration of other agents commonly used against bacterial infection, such as one or more antibiotics.

A method of the present disclosure includes treatment for a disease or condition caused by a *staphylococcus* pathogen. An immunogenic polypeptide of the disclosure can be given to induce an immune response in a person infected with *staphylococcus* or suspected of having been exposed to *staphylococcus*. Methods may be employed with respect to individuals who have tested positive for exposure to *staphylococcus* or who are deemed to be at risk for infection based on possible exposure.

In particular, the disclosure encompasses a method of treatment for Staphylococcal infection, particularly hospital acquired nosocomial infections. The immunogenic compositions and vaccines of the disclosure are particularly advantageous to use in cases of elective surgery. Such patients will know the date of surgery in advance and could be inoculated in advance. The immunogenic compositions and vaccines of the disclosure are also advantageous to use to inoculate health care workers.

In some embodiments, the treatment is administered in the presence of adjuvants or carriers or other Staphylococcal antigens. Furthermore, in some examples, treatment comprises administration of other agents commonly used against bacterial infection, such as one or more antibiotics.

The use of peptides for vaccination can require, but not necessarily, conjugation of the peptide to an immunogenic carrier protein, such as hepatitis B surface antigen, keyhole limpet hemocyanin, or bovine serum albumin. Methods for performing this conjugation are well known in the art.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

A. Antibodies and Passive Immunization

Certain aspects are directed to methods of preparing an antibody for use in prevention or treatment of Staphylococcal infection comprising the steps of immunizing a recipient with a vaccine and isolating antibody from the recipient, or producing a recombinant antibody. An antibody prepared by these methods and used to treat or prevent a Staphylococcal infection is a further aspect. A pharmaceutical composition comprising antibodies that specifically bind Coa and a pharmaceutically acceptable carrier is a further aspect that could be used in the manufacture of a medicament for the treatment or prevention of Staphylococcal disease. A method for treatment or prevention of Staphylococcal infection comprising a step of administering to a subject an effective amount of the pharmaceutical preparation is a further aspect.

Inocula for polyclonal antibody production are typically prepared by dispersing the antigenic composition (e.g., a peptide or antigen or epitope of Coa or a consensus thereof) in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies. The antibodies can be isolated to the extent desired by well known techniques such as affinity chromatography (Harlow and Lane, *Antibodies: A Laboratory Manual* 1988). Antibodies can include antiserum preparations from a variety of commonly used animals e.g., goats, primates, donkeys, swine, horses, guinea pigs, rats or man. The animals are bled and serum recovered.

An antibody can include whole antibodies, antibody fragments or subfragments. Antibodies can be whole immunoglobulins of any class (e.g., IgG, IgM, IgA, IgD or IgE), chimeric antibodies, human antibodies, humanized antibodies, or hybrid antibodies with dual specificity to two or more antigens. They may also be fragments (e.g., F(ab')2, Fab', Fab, Fv and the like including hybrid fragments). An antibody also includes natural, synthetic or genetically engineered proteins that act like an antibody by binding to specific antigens with a sufficient affinity.

A vaccine can be administered to a recipient who then acts as a source of antibodies, produced in response to challenge from the specific vaccine. A subject thus treated would donate plasma from which antibody would be obtained via conventional plasma fractionation methodology. The isolated antibody would be administered to the same or different subject in order to impart resistance against or treat Staphylococcal infection. Antibodies are particularly useful for treatment or prevention of Staphylococcal disease in infants, immune compromised individuals or where treatment is required and there is no time for the individual to produce a response to vaccination.

An additional aspect is a pharmaceutical composition comprising two of more antibodies or monoclonal antibodies (or fragments thereof; preferably human or humanized) reactive against at least two constituents of the immunogenic composition, which could be used to treat or prevent infection by Gram positive bacteria, preferably Staphylococci, more preferably *S. aureus* or *S. epidermidis*.

B. Combination Therapy

The compositions and related methods, particularly administration of an antibody that binds Coa or a peptide or consensus peptide thereof to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a therapy is used in conjunction with antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example antibiotic therapy is "A" and an antibody therapy that comprises an antibody that binds Coa or a peptide or consensus peptide thereof is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

C. Vaccines

The present disclosure includes methods for preventing or ameliorating Staphylococcal infections, particularly hospital acquired nosocomial infections. As such, the disclosure contemplates vaccines for use in both active and passive immunization embodiments. Immunogenic compositions, proposed to be suitable for use as a vaccine, may be prepared from immunogenic coagulases or a fragment thereof or a variant thereof, e.g., one or more coagulase R Domains. In other embodiments, coagulases, a fragment thereof or a variant thereof, can be used in combination with other secreted virulence proteins, surface proteins or immunogenic fragments thereof. In certain aspects, antigenic material is extensively dialyzed to remove undesired small molecular weight molecules and/or lyophilized for more ready formulation into a desired vehicle.

Other options for a protein/peptide-based vaccine involve introducing nucleic acids encoding the antigen(s) as DNA vaccines. In this regard, recent reports described construction of recombinant vaccinia viruses expressing either 10 contiguous minimal CTL epitopes (Thomson, 1996) or a combination of B cell, cytotoxic T-lymphocyte (CTL), and T-helper (Th) epitopes from several microbes (An, 1997), and successful use of such constructs to immunize mice for priming protective immune responses. Thus, there is ample evidence in the literature for successful utilization of peptides, peptide-pulsed antigen presenting cells (APCs), and peptide-encoding constructs for efficient in vivo priming of protective immune responses. The use of nucleic acid sequences as vaccines is exemplified in U.S. Pat. Nos. 5,958,895 and 5,620,896.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

1. Carriers

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against a coagulase and or its variant, such as one or more coagulase Domains 1-2, or any other bacterial protein or combination contemplated herein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (Fluosol-DA®) used as a block substitute may also be employed to produce an adjuvant effect.

Examples of and often preferred adjuvants include complete Freund's adjuvant (a non-specific stimulator of the immune response containing killed *Mycobacterium tuberculosis*), incomplete Freund's adjuvants, and aluminum hydroxide.

In some aspects, it is preferred that the adjuvant be selected to be a preferential inducer of either a Th1 or a Th2 type of response. High levels of Th1-type cytokines tend to favor the induction of cell mediated immune responses to a given antigen, while high levels of Th2-type cytokines tend to favor the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4+ T cell clones by Mosmann and Coffman (Mosmann, and Coffman, 1989). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

D. Lipid Components and Moieties

In certain embodiments, the present disclosure concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present disclosure. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-poxvirus-associated composition of the present disclosure is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range therebetween, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present disclosure may comprise any of the lipids, lipid types or other components in any combination or percentage range.

E. General Pharmaceutical Compositions

In some embodiments, pharmaceutical compositions are administered to a subject. Different aspects may involve administering an effective amount of a composition to a subject. In some embodiments, an antibody that binds Coa or a peptide or consensus peptide thereof may be administered to the subject to protect against or treat infection by one or more bacteria from the *Staphylococcus* genus. Alternatively, an expression vector encoding one or more such antibodies or polypeptides or peptides may be given to a subject as a preventative treatment. Additionally, such compositions can be administered in combination with an antibiotic. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

F. In Vitro, Ex Vivo, or In Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject.

In certain aspects of the present disclosure, the compositions may be administered either in vitro, ex vivo, or in vivo. In certain in vitro embodiments, autologous B-lymphocyte cell lines are incubated with a virus vector of the instant disclosure for 24 to 48 hours or with a cogaulase Domains 1-2 and/or a variant thereof and/or any other composition described herein for two hours. The transduced cells can then be used for in vitro analysis, or alternatively for ex vivo administration. U.S. Pat. Nos. 4,690,915 and 5,199,942, both incorporated herein by reference, disclose methods for ex vivo manipulation of blood mononuclear cells and bone marrow cells for use in therapeutic applications.

VI. SEQUENCES

Amino acid sequences from 8 reference *S. aureus* strains are provided in SEQ ID NOs: 1-8 as follows: USA300 (SEQ ID NO: 1), N315 (SEQ ID NO: 2), MW2 (SEQ ID NO: 3), MRSA252 (SEQ ID NO: 4), WIS (SEQ ID NO: 5), MU50 (SEQ ID NO: 6), 85/2082 (SEQ ID NO: 7), and Newman (SEQ ID NO: 8). Amino acid sequences from 17 Coa R Domains from one of the dominant Coa taken from dominant *S. aureus* lineages are provided as follows:

ST5_1, (SEQ ID NO: 22)

ST5_2, (SEQ ID NO: 23)

ST5_3, (SEQ ID NO: 24)

ST8_1, (SEQ ID NO: 25)

ST8_2, (SEQ ID NO: 26)

ST22_1, (SEQ ID NO: 24)

ST22_2, (SEQ ID NO: 28)

ST22_3, (SEQ ID NO: 29)

ST30_1, (SEQ ID NO: 30)

ST30_2, (SEQ ID NO: 31)

ST30_3, (SEQ ID NO: 32)

ST45_1, (SEQ ID NO: 33)

ST45_2, (SEQ ID NO: 34)

ST45_3, (SEQ ID NO: 35)

ST239_1, (SEQ ID NO: 36)

ST239_2, (SEQ ID NO: 37)

ST239_3. (SEQ ID NO: 38)

-continued

Coa of *S. aureus* USA300-
SEQ ID NO: 1
MKKQIISLGALAVASSLFTWDNKADAIVTKDYSGKSQVNAGSKNGTLIDSRYLNSAL

YYLEDYIIYAIGLTNKYEYGDNIYKEAKDRLLEKVLREDQYLLERKKSQYEDYKQW

YANYKKENPRTDLKMANFHKYNLEELSMKEYNELQDALKRALDDFHREVKDIKDK

NSDLKTFNAAEEDKATKEVYDLVSEIDTLVVSYYGDKDYGEHAKELRAKLDLILGD

TDNPHKITNERIKKEMIDDLNSIIDDFFMETKQNRPKSITKYNPTTHNYKTNSDNKPNF

DKLVEETKKAVKEADDSWKKKTVKKYGETETKSPVVKEEKKVEEPQAPKVDNQQE

VKTTAGKAEETTQPVAQPLVKIPQGTITGEIVKGPEYPTMENKTVQGEIVQGPDFLTM

EQSGPSLSNNYTNPPLTNPILEGLEGSSSKLEIKPQGTESTLKGTQGESSDIEVKPQATE

TTEASQYGPRPQFNKTPKYVKYRDAGTGIREYNDGTFGYEARPRFNKPSETNAYNVT

THANGQVSYGARPTQNKPSKTNAYNVTTHGNGQVSYGARPTQNKPSKTNAYNVTT

HANGQVSYGARPTYKKPSKTNAYNVTTHADGTATYGPRVTK

Coa of *S. aureus* N315-
SEQ ID NO: 2
MKKQIISLGALAVASSLFTWDNKADAIVTKDYSKESRVNEKSKKGATVSDYYYWKII

DSLEAQFTGAIDLLEDYKYGDPIYKEAKDRLMTRVLGEDQYLLKKKIDEYELYKKW

YKSSNKNTNMLTFHKYNLYNLTMNEYNDIFNSLKDAVYQFNKEVKEIEHKNVDLK

QFDKDGEDKATKEVYDLVSEIDTLVVTYYADKDYGEHAKELRAKLDLILGDTDNPH

KITNERIKKEMIDDLNSIIDDFFMETKQNRPNSITKYDPTKHNFKEKSENKPNFDKLVE

ETKKAVKEADESWKNKTVKKYEETVTKSPVVKEEKKVEEPQLPKVGNQQEVKTTA

GKAEETTQPVAQPLVKIPQETIYGETVKGPEYPTMENKTLQGEIVQGPDFLTMEQNR

PSLSDNYTQPTTPNPILEGLEGSSSKLEIKPQGTESTLKGIQGESSDIEVKPQATETTEA

SQYGPRPQFNKTPKYVKYRDAGTGIREYNDGTFGYEARPRFNKPSETNAYNVTTNQ

DGTVSYGARPTQNKPSETNAYNVTTHANGQVSYGARPTQKKPSKTNAYNVTTHAN

GQVSYGARPTQKKPSKTNAYNVTTHANGQVSYGARPTYKKPSETNAYNVTTHANG

QVSYGARPTQKKPSETNAYNVTTHADGTATYGPRVTK

Coa of *S. aureus* MW2-
SEQ ID NO: 3
MKKQIISLGALAVASSLFTWDNKADAIVTKDYSGKSQVNAGSKNGKQIADGYYWGI

IENLENQFYNIFHLLDQHKYAEKEYKDAVDKLKTRVLEEDQYLLERKKEKYEIYKEL

YKKYKKENPNTQVKMKAFDKYDLGDLTMEEYNDLSKLLTKALDNFKLEVKKIESE

NPDLKPYSESEERTAYGKIDSLVDQAYSVYFAYVTDAQHKTEALNLRAKIDLILGDE

KDPIRVTNQRTEKEMIKDLESIIDDFFIETKLNRPKHITRYDGTKHDYHKHKDGFDAL

VKETREAVAKADESWKNKTVKKYEETVTKSPVVKEEKKVEEPQSPKFDNQQEVKIT

VDKAEETTQPVAQPLVKIPQGTITGEIVKGPEYPTMENKTLQGEIVQGPDFPTMEQNR

PSLSDNYTQPTTPNPILEGLEGSSSKLEIKPQGTESTLKGTQGESSDIEVKPQASETTEA

SHYPARPQFNKTPKYVKYRDAGTGIREYNDGTFGYEARPRFNKPSETNAYNVTTNQ

DGTVTYGARPTQNKPSKTNAYNVTTHANGQVSYGARPTQNKPSKTNAYNVTTHAN

GQVSYGARPTQNKPSKTNAYNVTTHANGQVSYGARPTYKKPSKTNAYNVTTHADG

TATYGPRVTK

-continued

Coa of *S. aureus* MRSA252-
SEQ ID NO: 4
MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEMMDDLNSIIDDFFMDTNMNRPLNITKFNPNIHDYTNKPENRDNFD

KLVKETREAIANADESWKTRTVKNYGESETKSPVVKEEKKVEEPQLPKVGNQQEDK

ITVGTTEEAPLPIAQPLVKIPQGTIQGEIVKGPEYLTMENKTLQGEIVQGPDFPTMEQN

RPSLSDNYTQPTTPNPILKGIEGNSTKLEIKPQGTESTLKGTQGESSDIEVKPQATETTE

ASHYPARPQFNKTPKYVKYRDAGTGIREYNDGTFGYEARPRFNKPSETNAYNVTTN

QDGTVSYGARPTQNKPSETNAYNVTTHANGQVSYGARPTQNKPSETNAYNVTTHA

NGQVSYGARPTQNKPSKTNAYNVTTHADGTATYGPRVTK

Coa of *S. aureus* WIS-
SEQ ID NO: 5
MKKQIISLGALAVASSLFTWDNKADAIVTKDYSGKSQVNAGSKNGKQIADGYYWGI

IENLENQFYNIFHLLDQHKYAEKEYKDALDKLKTRVLEEDQYLLERKKEKYEIYKEL

YKKYKKENPNTQVKMKAFDKYDLGDLTMEEYNDLSKLLTKALDNFKLEVKKIESE

NPDLRPYSESEERTAYGKIDSLVDQAYSVYFAYVTDAQHKTEALNLRAKIDLILGDE

KDPIRVTNQRTEKEMIKDLESIIDDFFIETKLNRPQHITRYDGTKHDYHKHKDGFDAL

VKETREAVSKADESWKTKTVKKYGETETKYPVVKEEKKVEEPQSPKVSEKVDVQET

VGTTEEAPLPIAQPLVKLPQIGTQGEIVKGPDYPTMENKTLQGVIVQGPDFPTMEQNR

PSLSDNYTQPSVTLPSITGESTPTNPILKGIEGNSSKLEIKPQGTESTLKGIQGESSDIEV

KPQATETTEASHYPARPQFNKTPKYVKYRDAGTGIREYNDGTFGYEARPRFNKPSET

NAYNVTTNQDGTVSYGARPTQNKPSKTNAYNVTTHANGQVSYGARPTYNKPSETN

AYNVTTNRDGTVSYGARPTQNKPSETNAYNVTTHGNGQVSYGARPTQKKPSKTNA

YNVTTHANGQVSYGARPTYNKPSKTNAYNVTTHADGTATYGPRVTK

Coa of *S. aureus* MU50-
SEQ ID NO: 6
MKKQIISLGALAVASSLFTWDNKADAIVTKDYSKESRVNEKSKKGATVSDYYYWKII

DSLEAQFTGAIDLLEDYKYGDPIYKEAKDRLMTRVLGEDQYLLKKKIDEYELYKKW

YKSSNKNTNMLTFHKYNLYNLTMNEYNDIFNSLKDAVYQFNKEVKEIEHKNVDLK

QFDKDGEDKATKEVYDLVSEIDTLVVTYYADKDYGEHAKELRAKLDLILGDTDNPH

KITNERIKKEMIDDLNSIIDDFFMETKQNRPNSITKYDPTKHNFKEKSENKPNFDKLVE

ETKKAVKEADESWKNKTVKKYEETVTKSPVVKEEKKVEEPQLPKVGNQQEVKTTA

GKAEETTQPVAQPLVKIPQETIYGETVKGPEYPTMENKTLQGEIVQGPDFLTMEQNR

PSLSDNYTQPTTPNPILEGLEGSSSKLEIKPQGTESTLKGIQGESSDIEVKPQATETTEA

SQYGPRPQFNKTPKYVKYRDAGTGIREYNDGTFGYEARPRFNKPSETNAYNVTTNQ

DGTVSYGARPTQNKPSETNAYNVTTHANGQVSYGARPTQKKPSKTNAYNVTTHAN

GQVSYGARPTQKKPSKTNAYNVTTHANGQVSYGARPTYKKPSETNAYNVTTHANG

QVSYGARPTQKKPSETNAYNVTTHADGTATYGPRVTK

Coa of S. aureus 85/2082-
SEQ ID NO: 7

MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEMMDDLNSIIDDFFMDTNMNRPLNITKFNPNIHDYTNKPENRDNFD

KLVKETREAVANADESWKTRTVKNYGESETKSPVVKEEKKVEEPQLPKVGNQQED

KITVGTTEEAPLPIAQPLVKIPQGTIQGEIVKGPEYLTMENKTLQGEIVQGPDFPTMEQ

NRPSLSDNYTQPTTPNPILKGIEGNSTKLEIKPQGTESTLKGTQGESSDIEVKPQATETT

EASHYPARPQFNKTPKYVKYRDAGTGIREYNDGTFGYEARPRFNKPSETNAYNVTT

NQDGTVSYGARPTQNKPSETNAYNVTTHANGQVSYGARPTYKKPSETNAYNVTTN

QDGTVSYGARPTQNKPSETNAYNVTTHANGQVSYGARPTQNKPSETNAYNVTTHA

NGQVSYGARPTQNKPSKTNAYNVTTHADGTATYGPRVTK

Coa of S. aureus Newman-
SEQ ID NO: 8

MKKQIISLGALAVASSLFTWDNKADAIVTKDYSGKSQVNAGSKNGTLIDSRYLNSAL

YYLEDYIIYAIGLTNKYEYGDNIYKEAKDRLLEKVLREDQYLLERKKSQYEDYKQW

YANYKKENPRTDLKMANFHKYNLEELSMKEYNELQDALKRALDDFHREVKDIKDK

NSDLKTFNAAEEDKATKEVYDLVSEIDTLVVSYYGDKDYGEHAKELRAKLDILGD

TDNPHKITNERIKKEMIDDLNSIIDDFFMETKQNRPKSITKYNPTTHNYKTNSDNKPNF

DKLVEETKKAVKEADDSWKKKTVKKYGETETKSPVVKEEKKVEEPQAPKVDNQQE

VKTTAGKAEETTQPVAQPLVKIPQGTITGEIVKGPEYPTMENKTVQGEIVQGPDFLTM

EQSGPSLSNNYTNPPLTNPILEGLEGSSSKLEIKPQGTESTLKGTQGESSDIEVKPQATE

TTEASQYGPRPQFNKTPKYVKYRDAGTGIREYNDGTFGYEARPRFNKPSETNAYNVT

THANGQVSYGARPTYKKPSETNAYNVTTHANGQVSYGARPTQNKPSKTNAYNVTT

HGNGQVSYGARPTQNKPSKTNAYNVTTHANGQVSYGARPTYKKPSKTNAYNVTTH

ADGTATYGPRVTK

CoaST5_1-
SEQ ID NO: 22

MKKQIISLGALAVASSLFTWDNKADAIVTKDYSKESRVNEKSKKGATVSDYYYWKII

DSLEAQFTGAIDLLEDYKYGDPIYKEAKDRLMTRVLGEDQYLLKKKIDEYELYKKW

YKSSNKNTNMLTFHKYNLYNLTMNEYNDIFNSLKDAVYQFNKEVKEIEHKNVDLK

QFDKDGEDKATKEVYDLVSEIDTLVVTYYADKDYGEHAKELRAKLDILGDTDNPH

KITNERIKKEMIDDLNSIIDDFFMETKQNRPNSITKYDPTKHNFKEKSENKPNFDKLVE

ETKKAVKEADESWKNKTVKKYEETVTKSPVVKEEKKVEEPQLPKVGNQQEVKTTA

GKAEETTQPVAQPLVKIPQETIYGETVKGPEYPTMENKTLQGEIVQGPDFLTMEQNR

PSLSDNYTQPTTPNPILEGLEGSSSKLEIKPQGTESTLKGIQGESSDIEVKPQATETTEA

SQYGPRPQFNKTPKYVKYRDAGTGIREYNDGTFGYEARPRFNKPSETNAYNVTTNQ

DGTVSYGARPTQNKPSETNAYNVTTHANGQVSYGARPTQKKPSKTNAYNVTTHAN

GQVSYGARPTQKKPSKTNAYNVTTHANGQVSYGARPTYKKPSETNAYNVTTHANG

QVSYGARLTQKKPSETNAYNVTTHADGTATYGPRVTK

CoaST5_2-
SEQ ID NO: 23
MKKQIISLGALAVASSLFTWDNKADAIVTKDYSKESRVNEKSKKGATVSDYYYWKII
DSLEAQFTGAIDLLEDYKYGDPIYKEAKDRLMTRVLGEDQYLLKKKIDEYELYKKW
YKSSNKNTNMLTFHKYNLYNLTMNEYNDIFNSLKDAVYQFNKEVKEIEHKNVDLK
QFDKDGEDKATKEVYDLVSEIDTLVVTYYADKDYGEHAKELRAKLDLILGDTDNPH
KITNERIKKEMIDDLNSIIDDFFMETKQNRPNSITKYDPTKHNFKEKSENKPNFDKLVE
ETKKAVKEADESWKNKTVKKYEETVTKSPVVKEEKKVEEPQLPKVGNQQEVKTTA
GKAEETTQPVAQPLVKIPQETIYGETVKGPEYPTMENKTLQGEIVQGPDFLTMEQNR
PSLSDNYTQPTTPNPILEGLEGSSSKLEIKPQGTESTLKGIQGESSDIEVKPQATETTEA
SQYGPRPQFNKTPKYVKYRDAGTGIREYNDGTFGYEARPRFNKPSETNAYNVTTNQ
DGTVSYGARPTQNKPSETNAYNVTTHANGQVSYGARPTQKKPSKTNAYNVTTHAN
GQVSYGARPTQKKPSKTNAYNVTTHANGQVSYGARPTYKKPSETNAYNVTTHANG
QVSYGARPTQKKPSETNAYNVTTHADGTATYGPRVTK

CoaST5_3-
SEQ ID NO: 24
MKKQIISLGALAVASSLFTWDNKADAIVTKDYSKESRVNEKSKKGATVSDYYYWKII
DSLEAQFTGAIDLLEDYKYGDPIYKEAKDRLMTRVLGEDQYLLKKKIDEYELYKKW
YKSSNKNTNMLTFHKYNLYNLTMNEYNDIFNSLKDAVYQFNKEVKEIEHKNVDLK
QFDKDGEDKATKEVYDLVSEIDTLVVTYYADKDYGEHAKELRAKLDLILGDTDNPH
KITNERIKKEMIDDLNSIIDDFFMETKQNRPNSITKYDPTKHNFKEKSENKPNFDKLVE
ETKKAVKEADESWKNKTVKKYEETVTKSPVVKEEKKVEEPQLPKVGNQQEVKTTA
GKAEETTQPVAQPLVKIPQETIYGETVKGPEYPTMENKTLQGEIVQGPDFLTMEQNR
PSLSDNYTQPTTPNPILEGLEGSSSKLEIKPQGTESTLKGIQGESSDIEVKPQATETTEA
SQYGPRPQFNKTPKYVKYRDAGTGIREYNDGTFGYEARPRFNKPSETNAYNVTTNQ
DGTVSYGARPTQNKPSETNAYNVTTHANGQVSYGARPTYKKPSETNAYNVTTHAN
GQVSYGARPTQKKPSKTNAYNVTTHANGQVSYGARPTYKKPSETNAYNVTTHANG
QVSYGARPTQKKPSETNAYNVTTHADGTATYGPRVTK

CoaST8_1-
SEQ ID NO: 25
MKKQIISLGALAVASSLFTWDNKADAIVTKDYSGKSQVNAGSKNGTLIDSRYLNSAL
YYLEDYIIYAIGLTNKYEYGDNIYKEAKDRLLEKVLREDQYLLERKKSQYEDYKQW
YANYKKENPRTDLKMANFHKYNLEELSMKEYNELQDALKRALDDFHREVKDIKDK
NSDLKTFNAAEEDKATKEVYDLVSEIDTLVVSYYGDKDYGEHAKELRAKLDLILGD
TDNPHKITNERIKKEMIDDLNSIIDDFFMETKQNRPKSITKYNPTTHNYKTNSDNKPNF
DKLVEETKKAVKEADDSWKKKTVKKYGETETKSPVVKEEKKVEEPQAPKVDNQQE
VKTTAGKAEETTQPVAQPLVKIPQGTITGEIVKGPEYPTMENKTVQGEIVQGPDFLTM
EQSGPSLSNNYTNPPLTNPILEGLEGSSSKLEIKPQGTESTLKGTQGESSDIEVKPQATE
TTEASQYGPRPQFNKTPKYVKYRDAGTGIREYNDGTFGYEARPRFNKPSETNAYNVT
THANGQVSYGARPTYKKPSETNAYNVTTHANGQVSYGARPTQNKPSKTNAYNVTT
HGNGQVSYGARPTQNKPSKTNAYNVTTHANGQVSYGARPTYKKPSKTNAYNVTTH
ADGTATYGPRVTK

CoaST8_2-
SEQ ID NO: 26

MKKQIISLGALAVASSLFTWDNKADAIVTKDYSGKSQVNAGSKNGTLIDSRYLNSAL

YYLEDYIIYAIGLTNKYEYGDNIYKEAKDRLLEKVLREDQYLLERKKSQYEDYKQW

YANYKKENPRTDLKMANFHKYNLEELSMKEYNELQDALKRALDDFHREVKDIKDK

NSDLKTFNAAEEDKATKEVYDLVSEIDTLVVSYYGDKDYGEHAKELRAKLDLILGD

TDNPHKITNERIKKEMIDDLNSIIDDFFMETKQNRPKSITKYNPTTHNYKTNSDNKPNF

DKLVEETKKAVKEADDSWKKKTVKKYGETETKSPVVKEEKKVEEPQAPKVDNQQE

VKTTAGKAEETTQPVAQPLVKIPQGTITGEIVKGPEYPTMENKTVQGEIVQGPDFLTM

EQSGPSLSNNYTNPPLTNPILEGLEGSSSKLEIKPQGTESTLKGTQGESSDIEVKPQATE

TTEASQYGPRPQFNKTPKYVKYRDAGTGIREYNDGTFGYEARPRFNKPSETNAYNVT

THANGQVSYGARPTQNKPSKTNAYNVTTHGNGQVSYGARPTQNKPSKTNAYNVTT

HANGQVSYGARPTYKKPSKTNAYNVTTHADGTATYGPRVTK

CoaST22_1-
SEQ ID NO: 27

MKKQIISLGALAVASSLFTWDNKADAIVTKDYNGKSQVKKESKNGTLIDSRYYWEKI

EALEKQFSSALALTDEYQYGGNEYKEAKDKLMERILGEDQYLLKKKIDEYDYYKK

WYKATYPNDNSKMYSFHKYNVYYLTMNEYNEITNSLKDAVEKFNNEVRDIQSKNE

DLKPYDENTEKQETDKIYEFVSEIDTVFAAYYSHEKFGIHAKELRAKLDIILGDVHNP

NRITNERIKKEMMEDLNSIVDDFFMETNQNRPTTIKKYDPNIHDYTKKKENKENFDK

LVKETREAVEKADESWKNKTVKKYEETVTKSPFVKEEKKVEEPQLPKVGNQQEVKT

TAGKAEETTQPLVKIPQGTITGEIVKGPDYPTMENKTLQGEIVQGPDFPTMEQNRPSL

SDNYTQPTTTNPILEGLEGSSSKLEIKPQGTESTLQGTQGESSDIEVKPQATETTEASQ

YGPRPQFNKTPKYVKYRDAGTGIREYNDGTFGYEARPRFNKPSETNAYNVTTNQDG

TVTYGARPTQNKPSKTNAYNVTTHANGQVSYGARPTYKKPSETNAYNVTTHANGQ

VSYGARPTQNKASETNAYNVTTHANGQVSYGARPTQNKPSKTNAYNVTTHGNGQV

SYGARPTYKKPSETNAYNVTTHADGTATYGPRVTK

CoaST22_2-
SEQ ID NO: 28

MKKQIISLGALAVASSLFTWDNKADAIVTKDYNGKSQVKKESKNGTLIDSRYYWEKI

EALEKQFSSALALTDEYQYGGNEYKEAKDKLMERILGEDQYLLKKKIDEYDYYKK

WYKATYPNDNSKMYSFHKYNVYYLTMNEYNEISNSLKDAVEKFNNEVRDIQSKNE

DLKPYDENTEKQETDKIYEFVSEIDTVFAAYYSHEKFGIHAKELRAKLDIILGDVHNP

NRITNERIKKEMMEDLNSIVDDFFMETNQNRPTTIKKYDPNIHDYTKKKENKENFDK

LVKETREAVEKADESWKNKTVKKYEETVTKSPFVKEEKKVEEPQLPKVGNQQEVKT

TAGKAEETTQPLVKIPQGTITGEIVKGPDYPTMENKTLQGEIVQGPDFPTMEQNRPSL

SDNYTQPTTTNPILEGLEGSSSKLEIKPQGTESTLQGTQGESSDIEVKPQATETTEASQ

YGPRPQFNKTPKYVKYRDAGTGIREYNDGTFGYEARPRFNKPSETNAYNVTTNQDG

TVTYGARPTQNKPSKTNAYNVTTHANGQVSYGARPTYKKPSETNAYNVTTHANGQ

VSYGARPTQNKASETNAYNVTTHANGQVSYGARPTQNKPSKTNAYNVTTHGNGQV

SYGARPTYKKPSETNAYNVTTHADGTATYGPRVTK

CoaST22_3-
SEQ ID NO: 29
MKKQIISLGALAVASSLFTWDNKADAIVTKDYNGKSQVKKESKNGTLIDSRYYWEKI

EALEKQFSSALALTDEYQYGGNEYKEAKDKLMERILGEDQYLLKKKIDEYDYYKK

WYKATYPNDNSKMYSFHKYNVYYLTMNEYNEITNSLKDAVEKFNNEVRDIQSKNE

DLKPYDENTEKQETDKIYEFVSEIDTVFAAYYSHEKFGIHAKELRAKLDIILGDVHNP

NRITNERIKKEMMEDLNSIVDDFFMETNQNRPTTIKKYDPNIHDYTKKKENKENFDK

LVKETREAVEKADESWKNKTVKKYEETVTKSPFVKEEKKVEEPQLPKVGNQQEVKT

TAGKAEETTQPLVKIPQGTITGEIVKGPDYPTMENKTLQGEIVQGPDFPTMEQNRPSL

SDNYTQPTTTNPILEGLEGSSSKLEIKPQGTESTLQGTQGESSDIEVKPQATETTEASQ

YGPRPQFNKTPKYVKYRDAGTGIREYNDGTFGYEARPRFNKPSETNAYNVTTNQDG

TVTYGARPTQNKPSKTNAYNVTTHANGQVSYGARPTYKKPSETNAYNVTTHANGT

ATYGPRVTK

CoaST30_1-
SEQ ID NO: 30
MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEMMDDLNSIIDDFFMDTNMNRPLNITKFNPNIHDYTNKPENRDNFD

KLVKETREAIANADESWKTRTVKNYGESETKSPVVKEEKKVEEPQLPKVGNQQEDK

ITVGTTEEAPLPIAQPLVKIPQGTIQGEIVKGPEYLTMENKTLQGEIVQGPDFPTMEQN

RPSLSDNYTQPTTPNPILKGIEGNSTKLEIKPQGTESTLKGTQGESSDIEVKPQATETTE

ASHYPARPQFNKTPKYVKYRDAGTGIREYNDGTFGYEARPRFNKPSETNAYNVTTN

QDGTVSYGARPTQNKPSETNAYNVTTHANGQVSYGARPTQNKPSETNAYNVTTHA

NGQVSYGARPTQNKPSKTNAYNVTTHADGTATYGPRVTK

CoaST30_2-
SEQ ID NO: 31
MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEMMDDLNSIIDDFFMDTNMNRPLNITKFNPNIHDYTNKPENRDNFD

KLVKETREAVANADESWKTRTVKNYGESETKSPVVKEEKKVEEPQLPKVGNQQED

KITVGTTEEAPLPIAQPLVKIPQGTIQGEIVKGPEYLTMENKTLQGEIVQGPDFPTMEQ

NRPSLSDNYTQPTTPNPILKGIEGNSTKLEIKPQGTESTLKGTQGESSDIEVKPQATETT

EASHYPARPQFNKTPKYVKYRDAGTGIREYNDGTFGYEARPRFNKPSETNAYNVTT

NQDGTVSYGARPTQNKPSETNAYNVTTHANGQVSYGARPTYKKPSETNAYNVTTN

QDGTVSYGARPTQNKPSETNAYNVTTHANGQVSYGARPTQNKPSETNAYNVTTHA

NGQVSYGARPTQNKPSKTNAYNVTTHADGTATYGPRVTK

CoaST30_3-
SEQ ID NO: 32
MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEMMDDLNSIIDDFFMDTNMNRPLNITKFNPNIHDYTNKPENRDNFD

KLVKETREAIANADESWKTRTVKNYGESETKSPVVKEEKKVEEPQLPKVGNQQEDK

ITVGTTEEAPLPIAQPLVKIPQGTIQGEIVKGPEYLTMENKTLQGEIVQGPDFPTMEQN

RPSLSDNYTQPTTPNPILKGIEGNSTKLEIKPQGTESTLKGTQGESSDIEVKPQATETTE

ASHYPARPQFNKTPKYVKYRDAGTGIREYNDGTFGYEARPRFNKPSETNAYNVTTN

QDGTVSYGARPTQNKPSETNAYNVTTHANGQVSYGARPTYKKPSETNAYNVTTNQ

DGTVSYGARPTQNKPSETNAYNVTTHANGQVSYGARPTQNKPSETNAYNVTTHAN

GQVSYGARPTQNKPSKTNAYNVTTHADGTATYGPRVTK

CoaST45_1-
SEQ ID NO: 33
MKKQIISLGALAVASSLFTWDNKADAIVTKDYSGKSQVNAGSKNGKQIADGYYWGI

IENLENQFYNIFHLLDQHKYAEKEYKDALDKLKTRVLEEDQYLLERKKEKYEIYKEL

YKKYKKENPNTQVKMKAFDKYDLGDLTMEEYNDLSKLLTKALDNFKLEVKKIESE

NPDLRPYSESEERTAYGKIDSLVDQAYSVYFAYVTDAQHKTEALNLRAKIDLILGDE

KDPIRVTNQRTEKEMIKDLESIIDDFFIETKLNRPQHITRYDGTKHDYHKHKDGFDAL

VKETREAVSKADESWKTKTVKKYGETETKYPVVKEEKKVEEPQSPKVSEKVDVQET

VGTTEEAPLPIAQPLVKLPQIGTQGEIVKGPDYPTMENKTLQGVIVQGPDFPTMEQNR

PSLSDNYTQPSVTLPSITGESTPTNPILKGIEGNSSKLEIKPQGTESTLKGIQGESSDIEV

KPQATETTEASHYPARPQFNKTPKYVKYRDAGTGIREYNDGTFGYEARPRFNKPSET

NAYNVTTNQDGTVSYGARPTQNKPSKTNAYNVTTHANGQVSYGARPTYNKPSKTN

AYNVTTHADGTATYGPRVTK

CoaST45_2-
SEQ ID NO: 34
MKKQIISLGALAVASSLFTWDNKADAIVTKDYSGKSQVNAGSKNGKQIADGYYWGI

IENLENQFYNIFHLLDQHKYAEKEYKDALDKLKTRVLEEDQYLLERKKEKYEIYKEL

YKKYKKENPNTQVKMKAFDKYDLGDLTMEEYNDLSKLLTKALDNFKLEVKKIESE

NPDLRPYSESEERTAYGKIDSLVDQAYSVYFAYVTDAQHKTEALNLRAKIDLILGDE

KDPIRVTNQRTEKEMIKDLESIIDDFFIETKLNRPQHITRYDGTKHDYHKHKDGFDAL

VKETREAVSKADESWKTKTVKKYGETETKYPVVKEEKKVEEPQSPKVSEKVDVQET

VGTTEEAPLPIAQPLVKLPQIGTQGEIVKGPDYPTMENKTLQGVIVQGPDFPTMEQNR

PSLSDNYTQPSVTLPSITGESTPTNPILKGIEGNSSKLEIKPQGTESTLKGIQGESSDIEV

KPQATETTEASHYPARPQFNKTPKYVKYRDAGTGIREYNDGTFGYEARPRFNKPSET

-continued

NAYNVTTNQDGTVSYGARPTQNKPSKTNAYNVTTHANGQVSYGARPTYNKPSETN

AYNVTTNRDGTVSYGARPTQNKPSETNAYNVTTHGNGQVSYGARPTQKKPSKTNA

YNVTTHANGQVSYGARPTYNKPSKTNAYNVTTHADGTATYGPRVTK

CoaST45_3-
SEQ ID NO: 35
MKKQIISLGALAVASSLFTWDNKADAIVTKDYSGKSQVNAGSKNGKQIADGYYWGI

IENLENQFYNIFHLLDQHKYAEKEYKDALDKLKTRVLEEDQYLLERKKEKYEIYKEL

YKKYKKENPNTQVKMKAFDKYDLGDLTMEEYNDLSKLLTKALDNFKLEVKKIESE

NPDLRPYSESEERTAYGKIDSLVDQAYSVYFAYVTDAQHKTEALNLRAKIDLILGDE

KDPIRVTNQRTEKEMIKDLESIIDDFFIETKLNRPQHITRYDGTKHDYHKHKDGFDAL

VKETREAVSKADESWKTKTVKKYGETETKYPVVKEEKKVEEPQSPKVSEKVDVQET

VGTTEEAPLPIAQPLVKLPQIGTQGEIVKGPDYPTMENKTLQGVIVQGPDFPTMEQNR

PSLSDNYTQPSVTLPSITGESTSTNPILKGIEGNSSKLEIKPQGTESTLKGIQGESSDIEV

KPQATETTEASHYPARPQFNKTPKYVKYRDAGTGIREYNDGTFGYEARPRFNKPSET

NAYNVTTNQDGTVSYGARPTQNKPSKTNAYNVTTHANGQVSYGARPTYNKPSETN

AYNVTTNRDGTVSYGARPTQNKPSETNAYNVTTHGNGQVSYGARPTQKKPSKTNA

YNVTTHANGQVSYGARPTQKKPSKTNAYNVTTHADGTATYGPRVTK

CoaST239_1-
SEQ ID NO: 36
MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEMMDDLNSIIDDFFMDTNMNRPLNITKFNPNIHDYTNKPENRDNFD

KLVKETREAVANADESWKTRTVKNYGESETKSPVVKEEKKVEEPQLPKVGNQQED

KITVGTTEEAPLPIAQPLVKIPQGTIQGEIVKGPEYLTMENKTLQGEIVQGPDFPTMEQ

NRPSLSDNYTQPTTPNPILKGIEGNSTKLEIKPQGTESTLKGTQGESSDIEVKPQATETT

EASHYPARPQFNKTPKYVKYRDAGTGIREYNDGTFGYEARPRFNKPSETNAYNVTT

NQDGTVSYGARPTQNKPSETNAYNVTTHANGQVSYGARPTYKKPSETNAYNVTTN

QDGTVSYGARPTQNKPSETNAYNVTTHANGQVSYGARPTQNKPSETNAYNVTTHA

NGQVSYGARPTQNKPSKTNAYNVTTHADGTATYGPRVTK

CoaST239_2-
SEQ ID NO: 37
MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEKMDDLNSIIDDFFMDTNMNRPLNITKFNPNIHDYTNKPENRDNFD

KLVKETREAVANADESWKTRTVKNYGESETKSPVVKEEKKVEEPQLPKVGNQQED

KITVGTTEEAPLPIAQPLVKIPQGTIQGEIVKGPEYLTMENKTLQGEIVQGPDFPTMEQ

NRPSLSDNYTQPTTPNPILKGIEGNSTKLEIKPQGTESTLKGTQGESSDIEVKPQATETT

EASHYPARPQFNKTPKYVKYRDAGTGIREYNDGTFGYEARPRFNKPSETNAYNVTT

NQDGTVSYGARPTQNKPSETNAYNVTTHANGQVSYGARPTYKKPSETNAYNVTTN

-continued

QDGTVSYGARPTQNKPSETNAYNVTTHANGQVSYGARPTQNKPSETNAYNVTTHA

NGQVSYGARPTQNKPSKTNAYNVTTHADGTATYGPRVTK

CoaST239_3-
SEQ ID NO: 38

MKKQIISLGALAVASSLFTWDNKADAIVTKDYSKESRVNENSKYDTPIPDWYLGSIL

NRLGDQIYYAKELTNKYEYGEKEYKQAIDKLMTRVLGEDHYLLEKKKAQYEAYKK

WFEKHKSENPHSSLKKIKFDDFDLYRLTKKEYNELHQSLKEAVDEFNSEVKNIQSKQ

KDLLPYDEATENRVTNGIYDFVCEIDTLYAAYFNHSQYGHNAKELRAKLDIILGDAK

DPVRITNERIRKEKMDDLNSIIDDFFMDTNMNRPLNITKFNPNIHDYTNKPENRDNFD

KLVKETREAVANADESWKTRTVKNYGESETKSPVVKEEKKVEEPQLPKVGNQQED

KITVGTTEEAPLPIAQPLVKIPQGTIQGEIVKGPEYLTMENKTLQGEIVQGPDFPTMEQ

NRPSLSDNYTQPTTPNPILKGIEGNSTKLEIKPQGTESTLKGTQGESSDIEVKPQATETT

EASHYPARPQFNKTPKYVKYRDAGTGIREYNDGTFGYEARPRFNKPSETNAYNVTT

NQDGTVSYGARPTQNKPSETNAYNVTTHANGQVSYGARPTQNKPSETNAYNVTTH

ANGQVSYGARPTQNKPSKTNAYNVTTHADGTATYGPRVTK

Antibody CDR sequences:

| Ab | Variable chain | CDR1 | SEQ ID NO: | CDR2 | SEQ ID NO: | CDR3 | SEQ ID NO: |
|---|---|---|---|---|---|---|---|
| 5D5.4 | Heavy | GASITTSY | 9 | ISYSGNT | 10 | ATYYDFNYDGYLDV | 11 |
| 5D5.4 | Light | SSVSSSY | 12 | STS | 13 | QQYHRSPPT | 14 |
| 3B3.14 | Heavy | GYTFTSFD | 15 | IFPGDGSA | 16 | VKNHGGWYFDV | 17 |
| 3B3.14 | Light | QSIVHSNGNTY | 18 | KVS | 19 | FQGSHVPLT | 20 |

Full length Coa polypeptide-Strain USA300-SEQ ID NO: 21:
MKKQIISLGA LAVASSLFTW DNKADAIVTK DYSGKSQVNA GSKNGTLIDS 50

RYLNSALYYL EDYIIYAIGL TNKYEYGDNI YKEAKDRLLE KVLREDQYLL 100

ERKKSQYEDY KQWYANYKKE NPRTDLKMAN FHKYNLEELS MKEYNELQDA 150

LKRALDDFHR EVKDIKDKNS DLKTFNAAEE DKATKEVYDL VSEIDTLVVS 200

YYGDKDYGEH AKELRAKLDL ILGDTDNPHK ITNERIKKEM IDDLNSIIDD 250

FFMETKQNRP KSITKYNPTT HNYKTNSDNK PNFDKLVEET KKAVKEADDS 300

WKKKTVKKYG ETETKSPVVK EEKKVEEPQA PKVDNQQEVK TTAGKAEETP 350

QPVAQPLVKI PQGTITGEIV KGPEYPTMEN KTVQGEIVQG PDFLTMEQSG 400

PSLSNNYTNP PLTNPILEGL EGSSSKLEIK PQGTESTLKG TQGESSDIEV 450

KPQATETTEA SQYGPRPQFN KTPKYVKYRD AGTGIREYND GTFGYEARPR 500

FNKPSETNAY NVTTHANGQV SYGARPTQNK PSKTNAYNVT THGNGQVSYG 550

ARPTQNKPSK TNAYNVTTHA NGQVSYGARP TYKKPSKTNA YNVTTHADGT 600

ATYGPRVTK

Exemplary R Domains of the Coa polypeptides of SEQ ID NO:22-38 are provided as SEQ ID NOS:39-55 and SEQ ID NOS:85-101 and include fragments and contiguous sequences (see for example, para. [0094]). It is specifically contemplated that R fragments comprise a contiguous amino acid polypeptide comprising amino acid 1-161 of SEQ ID NOs:39-41, 44, 45, 48, 49, and/or 51-54, amino acids 1-133 of SEQ ID NO:42, amino acids 1-107 of SEQ ID NO:43, amino acids 1-80 of SEQ ID NOS:46 and/or 50, and/or amino acids 1-107 of SEQ ID NOS:47 or 55.

```
                                               (SEQ ID NO: 39)
RPRFNKPSETNAYNVTTNQDGTVSYGARPTQNKPSETNAYNVTTHANGQVSYGARP

TQKKPSKTNAYNVTTHANGQVSYGARPTQKKPSKTNAYNVTTHANGQVSYGARPT

YKKPSETNAYNVTTHANGQVSYGARLTQKKPSETNAYNVTTHADGTATYGP;

(SEQ ID NO: 40)
RPRFNKPSETNAYNVTTNQDGTVSYGARPTQNKPSETNAYNVTTHANGQVSYGARP

TQKKPSKTNAYNVTTHANGQVSYGARPTQKKPSKTNAYNVTTHANGQVSYGARPT

YKKPSETNAYNVTTHANGQVSYGARPTQKKPSETNAYNVTTHADGTATYGP;

(SEQ ID NO: 41)
RPRFNKPSETNAYNVTTNQDGTVSYGARPTQNKPSETNAYNVTTHANGQVSYGARP

TYKKPSETNAYNVTTHANGQVSYGARPTQKKPSKTNAYNVTTHANGQVSYGARPT

YKKPSETNAYNVTTHANGQVSYGARPTQKKPSETNAYNVTTHADGTATYGP;

(SEQ ID NO: 42)
RPRFNKPSETNAYNVTTHANGQVSYGARPTYKKPSETNAYNVTTHANGQVSYGARP

TQNKPSKTNAYNVTTHGNGQVSYGARPTQNKPSKTNAYNVTTHANGQVSYGARPT

YKKPSKTNAYNVTTHADGTATYGP;

(SEQ ID NO: 43)
RPRFNKPSETNAYNVTTHANGQVSYGARPTQNKPSKTNAYNVTTHGNGQVSYGAR

PTQNKPSKTNAYNVTTHANGQVSYGARPTYKKPSKTNAYNVTTHADGTATYGP;

(SEQ ID NO: 44)
RPRFNKPSETNAYNVTTNQDGTVTYGARPTQNKPSKTNAYNVTTHANGQVSYGARP

TYKKPSETNAYNVTTHANGQVSYGARPTQNKASETNAYNVTTHANGQVSYGARPT

QNKPSKTNAYNVTTHGNGQVSYGARPTYKKPSETNAYNVTTHADGTATYGP;

(SEQ ID NO: 45)
RPRFNKPSETNAYNVTTNQDGTVTYGARPTQNKPSKTNAYNVTTHANGQVSYGARP

TYKKPSETNAYNVTTHANGQVSYGARPTQNKASETNAYNVTTHANGQVSYGARPT

QNKPSKTNAYNVTTHGNGQVSYGARPTYKKPSETNAYNVTTHADGTATYGP;

(SEQ ID NO: 46)
RPRFNKPSETNAYNVTTNQDGTVTYGARPTQNKPSKTNAYNVTTHANGQVSYGARP

TYKKPSETNAYNVTTHANGTATYGP;

(SEQ ID NO: 47)
RPRFNKPSETNAYNVTTNQDGTVSYGARPTQNKPSETNAYNVTTHANGQVSYGARP

TQNKPSETNAYNVTTHANGQVSYGARPTQNKPSKTNAYNVTTHADGTATYGP;

(SEQ ID NO: 48)
RPRFNKPSETNAYNVTTNQDGTVSYGARPTQNKPSETNAYNVTTHANGQVSYGARP

TYKKPSETNAYNVTTNQDGTVSYGARPTQNKPSETNAYNVTTHANGQVSYGARPT

QNKPSETNAYNVTTHANGQVSYGARPTQNKPSKTNAYNVTTHADGTATYGP;

(SEQ ID NO: 49)
RPRFNKPSETNAYNVTTNQDGTVSYGARPTQNKPSETNAYNVTTHANGQVSYGARP

TYKKPSETNAYNVTTNQDGTVSYGARPTQNKPSETNAYNVTTHANGQVSYGARPT

QNKPSETNAYNVTTHANGQVSYGARPTQNKPSKTNAYNVTTHADGTATYGP;
```

```
                                                          (SEQ ID NO: 50)
RPRFNKPSETNAYNVTTNQDGTVSYGARPTQNKPSKTNAYNVTTHANGQVSYGARP

TYNKPSKTNAYNVTTHADGTATYGP;

(SEQ ID NO: 51)
RPRFNKPSETNAYNVTTNQDGTVSYGARPTQNKPSKTNAYNVTTHANGQVSYGARP

TYNKPSETNAYNVTTNRDGTVSYGARPTQNKPSETNAYNVTTHGNGQVSYGARPTQ

KKPSKTNAYNVTTHANGQVSYGARPTYNKPSKTNAYNVTTHADGTATYGP;

(SEQ ID NO: 52)
RPRFNKPSETNAYNVTTNQDGTVSYGARPTQNKPSKTNAYNVTTHANGQVSYGARP

TYNKPSETNAYNVTTNRDGTVSYGARPTQNKPSETNAYNVTTHGNGQVSYGARPTQ

KKPSKTNAYNVTTHANGQVSYGARPTQKKPSKTNAYNVTTHADGTATYGP;

(SEQ ID NO: 53)
RPRFNKPSETNAYNVTTNQDGTVSYGARPTQNKPSETNAYNVTTHANGQVSYGARP

TYKKPSETNAYNVTTNQDGTVSYGARPTQNKPSETNAYNVTTHANGQVSYGARPT

QNKPSETNAYNVTTHANGQVSYGARPTQNKPSKTNAYNVTTHADGTATYGP;

(SEQ ID NO: 54)
RPRFNKPSETNAYNVTTNQDGTVSYGARPTQNKPSETNAYNVTTHANGQVSYGARP

TYKKPSETNAYNVTTNQDGTVSYGARPTQNKPSETNAYNVTTHANGQVSYGARPT

QNKPSETNAYNVTTHANGQVSYGARPTQNKPSKTNAYNVTTHADGTATYGP;

(SEQ ID NO: 55)
RPRFNKPSETNAYNVTTNQDGTVSYGARPTQNKPSETNAYNVTTHANGQVSYGARP

TQNKPSETNAYNVTTHANGQVSYGARPTQNKPSKTNAYNVTTHADGTATYGP;

(SEQ ID NO: 85)
ARPRFNKPSETNAYNVTTNQDGTVSYGARPTQNKPSETNAYNVTTHANGQVSYGAR

PTQKKPSKTNAYNVTTHANGQVSYGARPTQKKPSKTNAYNVTTHANGQVSYGARP

TYKKPSETNAYNVTTHANGQVSYGARLTQKKPSETNAYNVTTHADGTATYG;

(SEQ ID NO: 86)
ARPRFNKPSETNAYNVTTNQDGTVSYGARPTQNKPSETNAYNVTTHANGQVSYGAR

PTQKKPSKTNAYNVTTHANGQVSYGARPTQKKPSKTNAYNVTTHANGQVSYGARP

TYKKPSETNAYNVTTHANGQVSYGARPTQKKPSETNAYNVTTHADGTATYG;

(SEQ ID NO: 87)
ARPRFNKPSETNAYNVTTNQDGTVSYGARPTQNKPSETNAYNVTTHANGQVSYGAR

PTYKKPSETNAYNVTTHANGQVSYGARPTQKKPSKTNAYNVTTHANGQVSYGARP

TYKKPSETNAYNVTTHANGQVSYGARPTQKKPSETNAYNVTTHADGTATYG;

(SEQ ID NO: 88)
ARPRFNKPSETNAYNVTTHANGQVSYGARPTYKKPSETNAYNVTTHANGQVSYGA

RPTQNKPSKTNAYNVTTHGNGQVSYGARPTQNKPSKTNAYNVTTHANGQVSYGAR

PTYKKPSKTNAYNVTTHADGTATYG;

(SEQ ID NO: 89)
ARPRFNKPSETNAYNVTTHANGQVSYGARPTQNKPSKTNAYNVTTHGNGQVSYGA

RPTQNKPSKTNAYNVTTHANGQVSYGARPTYKKPSKTNAYNVTTHADGTATYG;

(SEQ ID NO: 90)
ARPRFNKPSETNAYNVTTNQDGTVTYGARPTQNKPSKTNAYNVTTHANGQVSYGA

RPTYKKPSETNAYNVTTHANGQVSYGARPTQNKASETNAYNVTTHANGQVSYGAR

PTQNKPSKTNAYNVTTHGNGQVSYGARPTYKKPSETNAYNVTTHADGTATYG;
```

(SEQ ID NO: 91)
ARPRFNKPSETNAYNVTTNQDGTVTYGARPTQNKPSKTNAYNVTTHANGQVSYGA
RPTYKKPSETNAYNVTTHANGQVSYGARPTQNKASETNAYNVTTHANGQVSYGAR
PTQNKPSKTNAYNVTTHGNGQVSYGARPTYKKPSETNAYNVTTHADGTATYG;

(SEQ ID NO: 92)
ARPRFNKPSETNAYNVTTNQDGTVTYGARPTQNKPSKTNAYNVTTHANGQVSYGA
RPTYKKPSETNAYNVTTHANGTATYG;

(SEQ ID NO: 93)
ARPRFNKPSETNAYNVTTNQDGTVSYGARPTQNKPSETNAYNVTTHANGQVSYGAR
PTQNKPSETNAYNVTTHANGQVSYGARPTQNKPSKTNAYNVTTHADGTATYG;

(SEQ ID NO: 94)
ARPRFNKPSETNAYNVTTNQDGTVSYGARPTQNKPSETNAYNVTTHANGQVSYGAR
PTYKKPSETNAYNVTTNQDGTVSYGARPTQNKPSETNAYNVTTHANGQVSYGARPT
QNKPSETNAYNVTTHANGQVSYGARPTQNKPSKTNAYNVTTHADGTATYG;

(SEQ ID NO: 95)
ARPRFNKPSETNAYNVTTNQDGTVSYGARPTQNKPSETNAYNVTTHANGQVSYGAR
PTYKKPSETNAYNVTTNQDGTVSYGARPTQNKPSETNAYNVTTHANGQVSYGARPT
QNKPSETNAYNVTTHANGQVSYGARPTQNKPSKTNAYNVTTHADGTATYG;

(SEQ ID NO: 96)
ARPRFNKPSETNAYNVTTNQDGTVSYGARPTQNKPSKTNAYNVTTHANGQVSYGA
RPTYNKPSKTNAYNVTTHADGTATYG;

(SEQ ID NO: 97)
ARPRFNKPSETNAYNVTTNQDGTVSYGARPTQNKPSKTNAYNVTTHANGQVSYGA
RPTYNKPSETNAYNVTTNRDGTVSYGARPTQNKPSETNAYNVTTHGNGQVSYGARP
TQKKPSKTNAYNVTTHANGQVSYGARPTYNKPSKTNAYNVTTHADGTATYG;

(SEQ ID NO: 98)
ARPRFNKPSETNAYNVTTNQDGTVSYGARPTQNKPSKTNAYNVTTHANGQVSYGA
RPTYNKPSETNAYNVTTNRDGTVSYGARPTQNKPSETNAYNVTTHGNGQVSYGARP
TQKKPSKTNAYNVTTHANGQVSYGARPTQKKPSKTNAYNVTTHADGTATYG;

(SEQ ID NO: 99)
ARPRFNKPSETNAYNVTTNQDGTVSYGARPTQNKPSETNAYNVTTHANGQVSYGAR
PTYKKPSETNAYNVTTNQDGTVSYGARPTQNKPSETNAYNVTTHANGQVSYGARPT
QNKPSETNAYNVTTHANGQVSYGARPTQNKPSKTNAYNVTTHADGTATYG;

(SEQ ID NO: 100)
ARPRFNKPSETNAYNVTTNQDGTVSYGARPTQNKPSETNAYNVTTHANGQVSYGAR
PTYKKPSETNAYNVTTNQDGTVSYGARPTQNKPSETNAYNVTTHANGQVSYGARPT
QNKPSETNAYNVTTHANGQVSYGARPTQNKPSKTNAYNVTTHADGTATYG;

(SEQ ID NO: 101)
ARPRFNKPSETNAYNVTTNQDGTVSYGARPTQNKPSETNAYNVTTHANGQVSYGAR
PTQNKPSETNAYNVTTHANGQVSYGARPTQNKPSKTNAYNVTTHADGTATYG.

Exemplary R Domain fragments:

(SEQ ID NO: 102)
ARPTYNKPSETNAYNVTTNRDGTVSYG;

(SEQ ID NO: 103)
ARPTYKKPSETNAYNVTTNQDGTVSYG;

(SEQ ID NO: 104)
ARPRFNKPSETNAYNVTTNQDGTVSYG;

-continued (SEQ ID NO: 105)
ARPRFNKPSETNAYNVTTNQDGTVTYG;

(SEQ ID NO: 106)
ARPTYNKPSKTNAYNVTTHADGTATYG;

(SEQ ID NO: 107)
ARPTYKKPSKTNAYNVTTHADGTATYG;

(SEQ ID NO: 108)
ARPTYKKPSETNAYNVTTHANGTATYG;

(SEQ ID NO: 109)
ARPTYKKPSETNAYNVTTHADGTATYG;

(SEQ ID NO: 110)
ARPTQNKPSKTNAYNVTTHADGTATYG;

(SEQ ID NO: 111)
ARPTQKKPSKTNAYNVTTHADGTATYG;

(SEQ ID NO: 112)
ARPTQKKPSETNAYNVTTHADGTATYG;

(SEQ ID NO: 113)
ARLTQKKPSETNAYNVTTHADGTATYG;

(SEQ ID NO: 114)
ARPTYKKPSETNAYNVTTHANGQVSYG;

(SEQ ID NO: 115)
ARPRFNKPSETNAYNVTTHANGQVSYG;

(SEQ ID NO: 116)
ARPTQKKPSKTNAYNVTTHANGQVSYG;

(SEQ ID NO: 117)
ARPTQNKPSKTNAYNVTTHANGQVSYG;

(SEQ ID NO: 118)
ARPTQNKPSKTNAYNVTTHGNGQVSYG;

(SEQ ID NO: 119)
ARPTQNKASETNAYNVTTHANGQVSYG;

(SEQ ID NO: 120)
ARPTQNKPSETNAYNVTTHANGQVSYG;

(SEQ ID NO: 121)
ARPTQNKPSETNAYNVTTHGNGQVSYG;

(SEQ ID NO: 122)
ARPTQNKPSETNAYNVTTHANGQVSYGARPTQNKPSETNAYNVTTHANGQVSYG;

(SEQ ID NO: 57)
RP(T/R)(F/Q)(N/K)K(P/A)S(E/K)TNAYNVTT(H/N)(A/G/Q)(N/D)G(Q/T)V(S/T)YGARPT(Y/Q)(K/N)KPS(E/K)TNAYNVTTH(A/G)NGQVSYGAR(L/P)T(Q/Y)(N/K)KPS(K/E)TNAYNVTTHA(D/N)GTATYGP;

(SEQ ID NO: 58)
RPRFNKPSETNAYNVTTNQDGTV(S/T)YGA;

(SEQ ID NO: 59)
$X_b$ is RP(T/R)(Q/F)NKPS(K/E)TNAYNVTTHANGQVSYGA;

(SEQ ID NO: 60)
RP(T/R)(F/Y/Q)(N/K)KPS(E/K)TNAYNVTT(H/N)(Q/A/R)(N/D)G(Q/T)VSYGA;

(SEQ ID NO: 123)
ARP(T/R)(F/Q)(N/K)K(P/A)S(E/K)TNAYNVTT(H/N)(A/G/Q)(N/D)G(Q/T)V(S/T)YGARPT(Y/Q)(K/N)KPS(E/K)TNAYNVTTH(A/G)NGQVSYGAR(L/P)T(Q/Y)(N/K)KPS(K/E)TNAYNVTTHA(D/N)GTATYG;

-continued (SEQ ID NO: 124)
ARPRFNKPSETNAYNVTTNQDGTV(S/T)YG;

(SEQ ID NO: 125)
ARP(T/R)(Q/F)NKPS(K/E)TNAYNVTTHANGQVSYG;

(SEQ ID NO: 126)
ARP(T/R)(F/Y/Q)(N/K)KPS(E/K)TNAYNVTT(H/N)(Q/A/R)(N/D)G(Q/T)VSYG;

(SEQ ID NO: 61)
$ARX_1X_2X_3X_4KX_5SX_6TNAYNVTTX_7X_8X_9GX_{10}X_{11}X_{12}YG$
or (SEQ ID NO: 62)
$ARPTX_3X_4KPSX_6TNAYNVTTHX_8X_9GX_{10}X_{11}X_{12}YG$, wherein $X_1$, $X_2$, $X_3$, $X_4$, $X_5$, $X_6$, $X_7$, $X_8$, $X_9$, $X_{10}$, $X_{11}$, and $X_{12}$ are any amino acid. In some embodiments, $X_1$ is proline or leucine. In some embodiments, $X_2$ is arginine or threonine. In some embodiments, $X_3$ is phenylalanine, glutamine, or tyrosine. In some embodiments, $X_4$ is asparagine or lysine. In some embodiments, $X_5$ is proline or alanine. In some embodiments, $X_6$ is lysine or glutamate. In some embodiments, $X_7$ is histidine or asparagine. In some embodiments, $X_8$ is alanine, glutamine, glycine, or arginine. In some embodiments, $X_9$ is aspartate or asparagine. In some embodiments, $X_{10}$ is threonine or glutamine. In some embodiments, $X_{11}$ is valine or alanine. In some embodiments, $X_{12}$ is threonine or serine.

VII. EXAMPLES

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Antibodies Against a Secreted Product of *Staphylococcus aureus* Trigger Phagocytic Killing Host immunity against bacterial pathogens typically involves antibodies that recognize the microbial surface and promote phagocytic killing. Methicillin-resistant *Staphylococcus aureus* (MRSA) is a frequent cause of lethal bloodstream infection, however vaccines and antibody therapeutics targeting Staphylococcal surface molecules have thus far failed to achieve clinical efficacy. *S. aureus* secretes coagulase (Coa), which activates host prothrombin and generates fibrin fibrils that protect the pathogen against phagocytosis by immune cells. Because of negative selection, the coding sequence for the prothrombin binding D1-D2 domain is highly variable and does not elicit cross-protective immune responses. The R domain, tandem repeats of a 27-residue peptide that bind fibrinogen, is conserved at the C-terminus of all Coa molecules, however its functional significance is not known. Inventors show here that the R domain enables bloodstream infections by directing fibrinogen to the Staphylococcal surface, generating a protective fibrin shield that inhibits phagocytosis. The fibrin shield can be marked with R-specific antibodies, which trigger phagocytic killing of Staphylococci and protect mice against lethal bloodstream infections caused A. R Domain of Coagulase Supports *S. aureus* Bloodstream Infection The C-terminal domain of Coa is conserved and comprised of tandem repeats of a 27-residue peptide each of which binds fibrinogen (FIG. 1A) (Panizzi et al., 2011; Watanabe et al., 2009). The number of tandem repeats varies between Coa molecules from different isolates of *S. aureus* (Watanabe et al., 2009). To characterize the contribution of the R domain to the pathogenesis of Staphylococcal disease, inventors generated isogenic *S. aureus* variants with a truncated coa, lacking the R domain ($coa_{\Delta R}$), in either wild-type or Δvwb backgrounds. When probed by immunoblotting with Coa- and vWbp-specific antibodies and compared with Coa from wild-type Staphylococci, *S. aureus* $coa_{\Delta R}$ and $coa_{\Delta R}$/Δvwb strains secreted a truncated protein into the extracellular medium (FIG. 1B). Monoclonal antibody mAb 5D5, which recognizes the D1 domain of Coa (vide infra), bound to both Coa and $Coa_{\Delta R}$, whereas mAb 3B3, specific for the R domain (vide infra), only bound Coa, but not $Coa_{\Delta R}$ (FIG. 1AB). When inoculated into calcium-chelated mouse blood and incubated for 24 hours, wild-type *S. aureus* produced a firm clot, whereas mock-infected blood did not (FIG. 1C). Staphylococci rely on secretion of both coagulases for clotting, as only Δcoa/Δvwb but not Δcoa or Δvwb variant strains displayed a defect in this assay (FIG. 1C). Compared to their respective parent strains, the $coa_{\Delta R}$ and $coa_{\Delta R}$/Δvwb mutants were also not defective for clotting, indicating that the R domain of Coa is dispensable for Staphylococcal clot formation (FIG. 1C).

When inoculated intravenously into BALB/c mice, wild-type *S. aureus* Newman causes a lethal bloodstream infection within 2-3 days, where Δcoa or Δvwb mutations each cause a delay in time-to-death that is additive for the Δcoa/Δvwb mutant [median survival time 60 hours (wild-type), 108 hours (Δcoa or Δvwb) and 180 hours (Δcoa/Δvwb)](FIG. 1D, E). Surprisingly, the $coa_{\Delta R}$ mutation also caused a delay in time-to-death [median survival time 72 ($coa_{\Delta R}$) and 126 hours ($coa_{\Delta R}$/Δvwb)], which could be quantified in strains with (wild-type vs. $coa_{\Delta R}$, P=0.0308; Δcoa vs. $coa_{\Delta R}$, P=0.0229) or without vwb expression (Δvwb vs. $coa_{\Delta R}$/Δvwb, P=0.043; Δcoa/Δvwb vs. $coa_{\Delta R}$/Δvwb, P=0.0084). Thus, the R domain of Coa, although dispensable for staphylothrombin-mediated clotting, contributes to the pathogenesis of *S. aureus* infection in mice.

B. R Domain Enables Assembly of the Staphylococcal Fibrin Shield

Figures 2A, 2B:
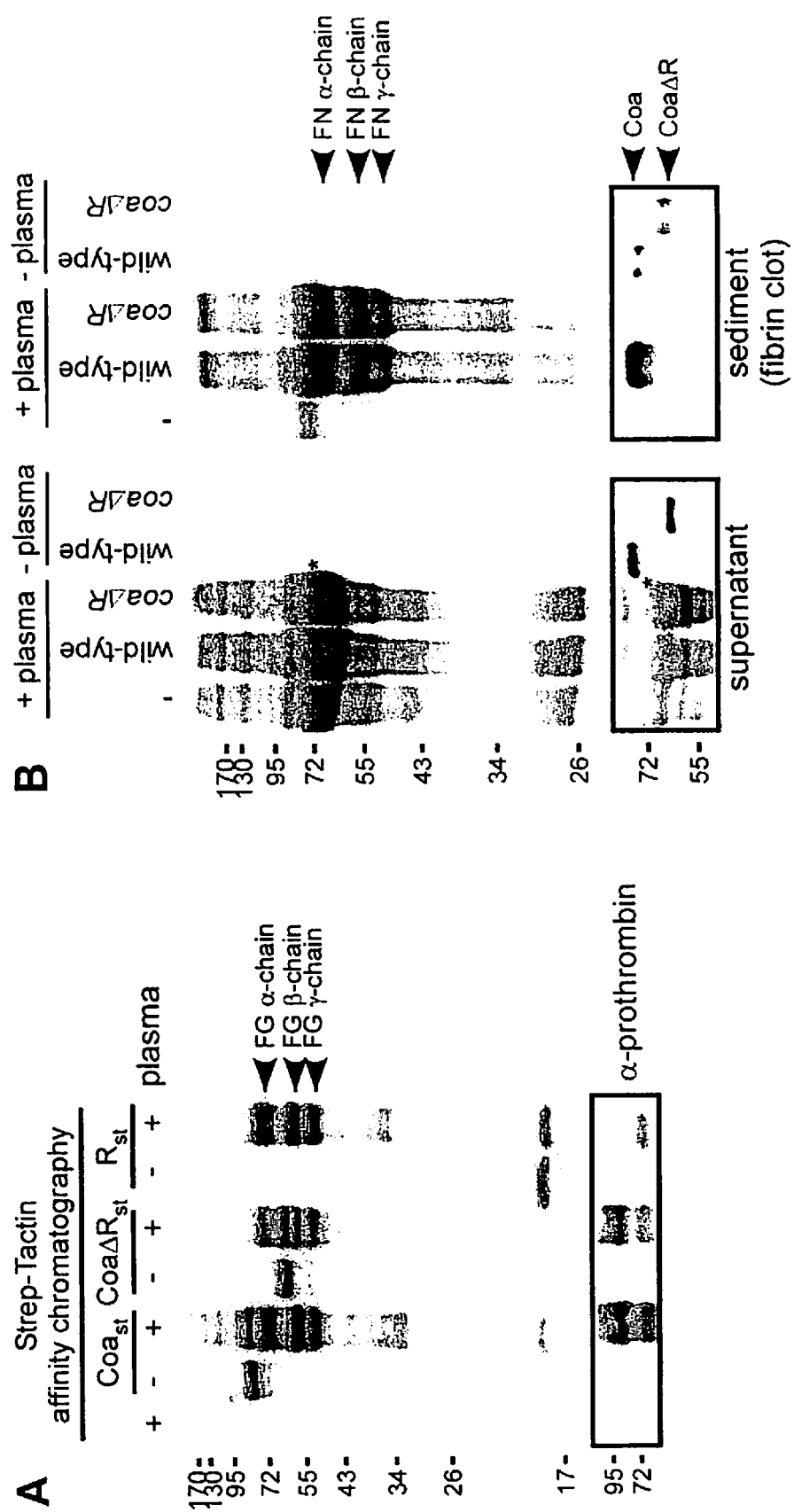
FIGS. 2A-B: The repeat domain of coagulase promotes assembly of a fibrin sheet on the surface of *S. aureus*. (A) Human plasma (+) or PBS control (−) were subjected to chromatography on Strep-Tactin resin pre-charged with full-length coagulase ($Coa_{ST}$), coagulase truncated for the R domain ($Coa_{\Delta R/ST}$), the R domain ($R_{ST}$) alone or without affinity bait. Proteins retained on the affinity column were analyzed by Coomassie-stained SDS-PAGE or immunoblotting with antibodies against prothrombin (α-PT). FG denotes fibrinogen. (B) Human plasma (+) or PBS (−) was added to cultures of *S. aureus* Newman (wild-type) or the $coa_{\Delta R}$ variant or to medium control (−). Plasma proteins in the supernatant and sediment containing fibrin clots or not (+/−plasma) were separated by centrifugation and analyzed by Coomassie-stained SDS-PAGE or immunoblotting against Coa (α-Coa). Asterisks identifies albumin; its abundance affects the eletrophoretic mobility of $Coa_{\Delta R}$ (lower left panel). Numbers indicate the migratory positions of mass standards. FN denotes fibrin. (C) *S. aureus* wild-type or $coa_{\Delta R}$ bacteria expressing mCherry were mixed with human citrate-plasma supplemented with 5% Alexa488-conjugated human fibrinogen and incubated at room temperature for 5 minutes. Incorporation of Alexa488-fibrinogen into fibrin and association with bacteria was imaged by fluorescence microscopy. Data are representative of two independent analyses.

Full-length strep-tagged Coa ($Coa_{ST}$), Coa truncated for the R domain ($Coa_{\Delta R/ST}$), and R domain alone ($R_{ST}$) were purified and used for affinity chromatography experiments with citrate-plasma (FIG. 2A). $Coa_{ST}$ and $R_{ST}$ retained molar excess of fibrinogen, whereas $Coa_{\Delta R/ST}$ retained only equimolar amounts of fibrinogen (FIG. 2A). This can be explained by the equimolar association between fibrinogen and the exosite of staphylothrombin within $Coa_{ST}$ or $Coa_{\Delta R/ST}$, whereas the R domain of $Coa_{ST}$ and $R_{ST}$ associates with 3-4 moles of fibrinogen (FIG. 2A). As expected, $Coa_{ST}$ and $Coa_{\Delta R/ST}$ bound prothrombin via their D1-D2 domain, whereas $R_{ST}$ did not (FIG. 2A). Staphylococci display surface proteins, for example clumping factor A (ClfA), that promote association of bacteria with fibrinogen (McAdow et al., 2012a; McDevitt et al., 1994). Mixed with dilute plasma, mid-log Staphylococcal cultures formed fibrin clots that, when centrifuged, sedimented with the bacteria and could be solubilized with urea (FIG. 2B). When analyzed by Coomassie-stained SDS-PAGE, fibrin was found associated with the bacterial sediment, whereas albumin remained in the supernatant of agglutinated Staphylococci (FIG. 2B). Immunoblotting revealed that full-length Coa sedimented with the bacterial clot, whereas $Coa_{\Delta R}$ did not (FIG. 2B). Association of Coa with Staphylococci occurred in the presence of the fibrin clot and was not observed for Staphylococcal cultures centrifuged without human plasma (FIG. 2B). To visualize the contribution of the R domain towards Staphylococcal fibrin formation, mCherry-expressing bacteria were added to plasma samples with Alexa488-conjugated fibrinogen and clot formation was viewed by fluorescence microscopy. Unlike wild-type Staphylococci, which generated large fibrin deposits in the vicinity of bacteria, the $coa_{\Delta R}$ mutant produced long fibrin strands that were only loosely associated with the pathogen (FIG. 2C). Thus, by augmenting the recruitment of soluble fibrinogen, the C-terminal repeats favor Coa-induced fibrin clots and limit diffusion of Coa away from Staphylococci, thereby localizing the staphylothrombin-generated fibrin shield in the immediate vicinity of the bacteria. R domain interaction with fibrinogen may also explain early observations of cell bound coagulase (Coa) and free coagulase (vWbp) (Duthie, 1954).

C. R Domain Antibody Protects Mice Against Bloodstream Infection

Figures 3A, 3B, 3C, 3D, 3E, 3F:
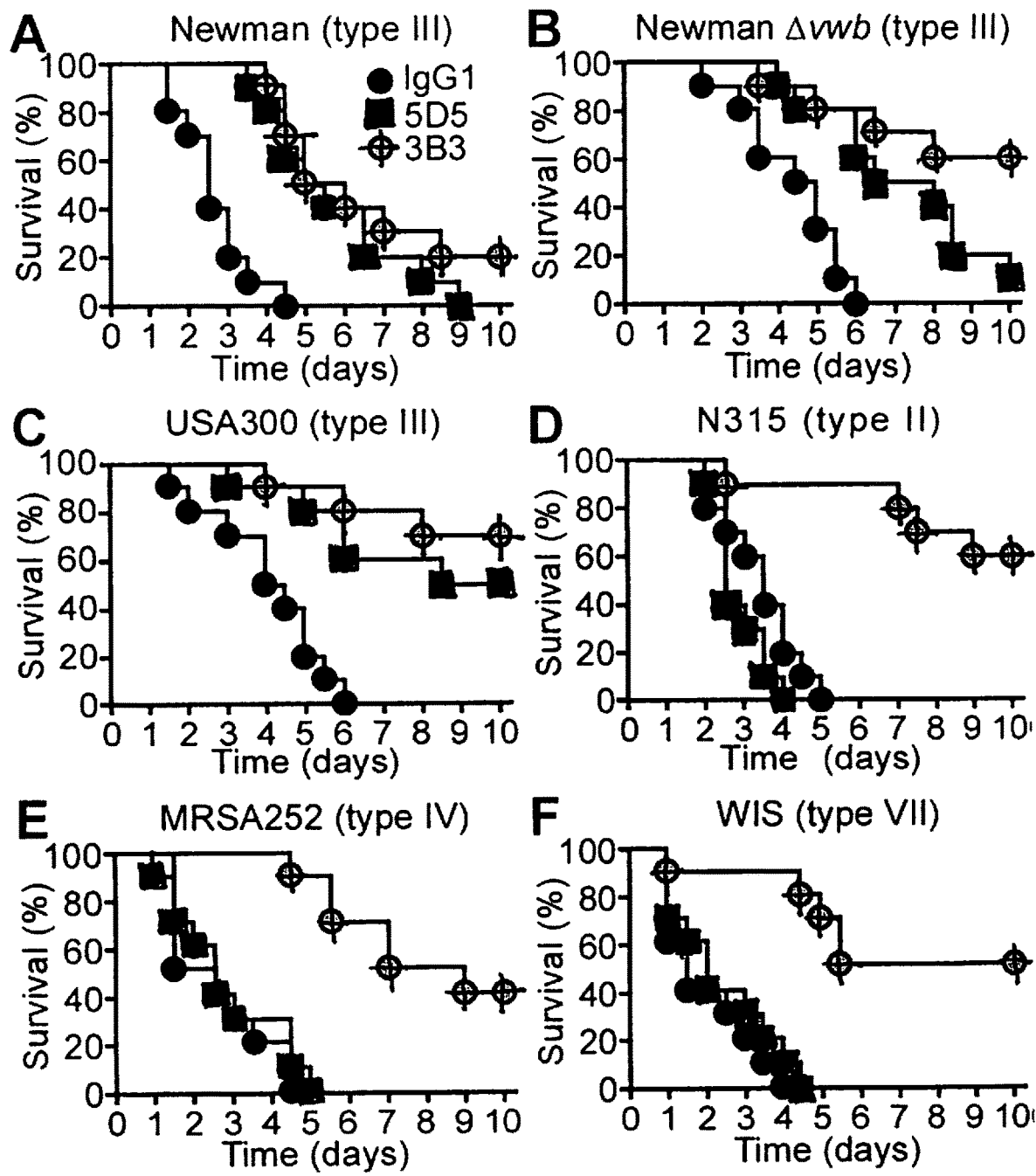
FIGS. 3A-F: Monoclonal antibody against the R domain of coagulase protects against *S. aureus* bloodstream infection. Purified monoclonal antibodies 5D5, 3B3, or IgG1 isotype control, were injected at a concentration of 5 mg $kg^{-1}$ body weight into the peritoneal cavity of naïve BALB/c mice. Animal cohorts (n=10) were challenged by intravenous injection with *S. aureus* strains Newman (A), the Δvwb variant of Newman (B), MRSA USA300 (C), MRSA N315 (D), MRSA252 (E), or WIS (F) and survival monitored over 10 days. Data are representative of two independent analyses; statistical significance was assessed with the Logrank test.
Figures 5A, 5B, 5C, 5D:
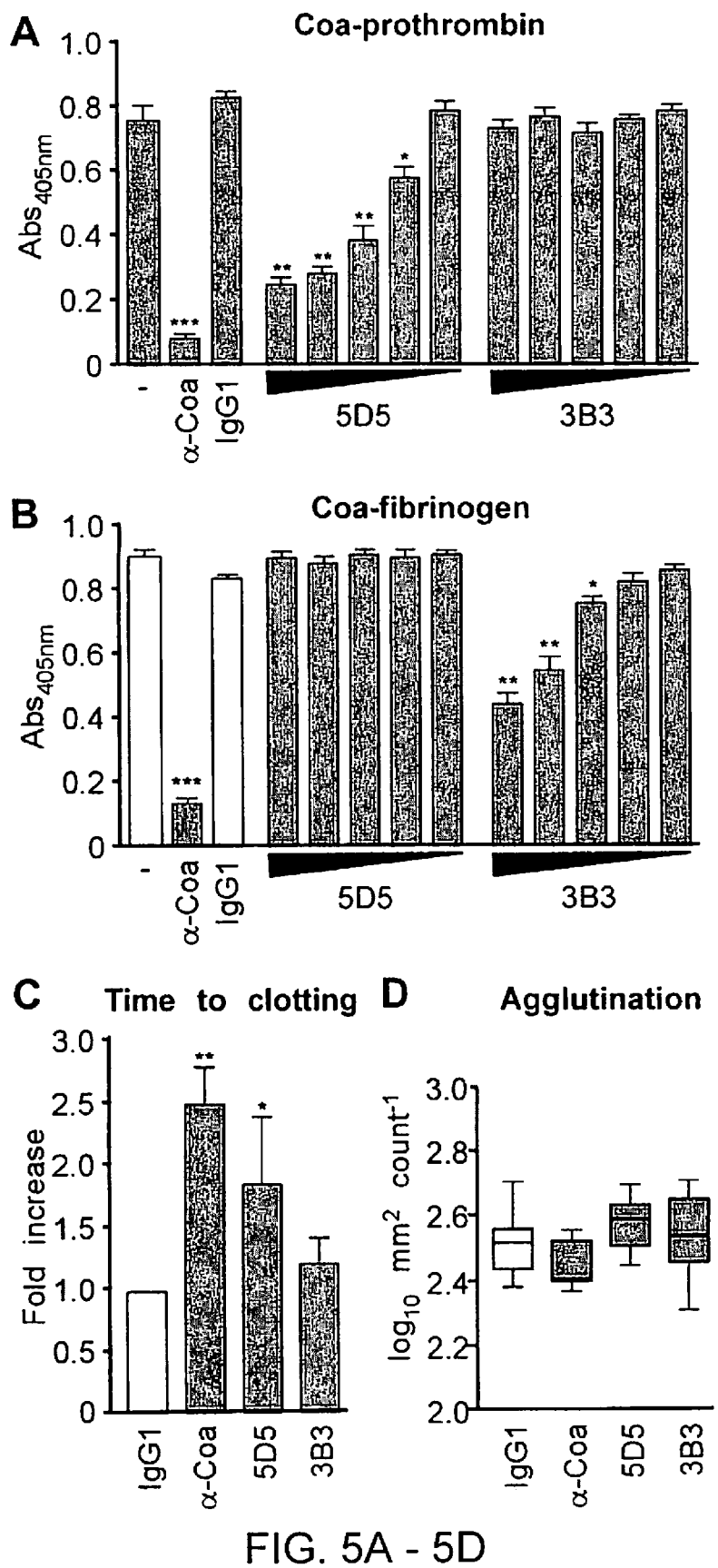
FIG. 5A-D: Monoclonal antibodies 5D5 and 3B3 disrupt specific activities of Coa. (A) Association of Coa with human prothrombin was measured by ELISA and perturbed with increasing concentrations of affinity-purified 5D5, affinity-purified 3B3, polyclonal antibodies (α-Coa), or IgG1 isotype control. (B) Association of Coa with human fibrinogen was measured by ELISA and perturbed with increasing concentrations of affinity-purified 5D5, affinity-purified 3B3, polyclonal antibodies (α-Coa), or IgG1 isotype control. (C) Calcium-chelated mouse blood was inoculated with *S. aureus* Newman wild-type bacteria (1×10⁶ CFU) in the presence of 3 μM of 5D5, 3B3, polyclonal antibodies (α-Coa), or IgG1 isotype control. Samples were incubated at room temperature and monitored for coagulation. (D) Rabbit EDTA-plasma was mixed with SYTO9 stained *S. aureus* Newman wild-type bacteria (1×10⁷ CFU) in the presence of 3 μM of 5D5, 3B3, polyclonal antibodies (α-Coa) or IgG1 isotype control. Samples were incubated at room temperature for 10 minutes, analyzed by fluorescence microscopy, and quantified by calculating means±SEM from 12 fields of microscopic view. Statistical significance was assessed with one-way ANOVA and Bonferroni post-test: *, P<0.01; , P<0.001; *, P<0.0001.

Mouse monoclonal antibodies were raised by immunizing mice with full-length Coa of *S. aureus* Newman. Thirteen antibodies reactive to Coa, but not to vWbp or IsdA controls, were characterized for their affinity and specificity to D1, D2, D1-D2, D1 lacking the first 18 residues ($D1_{\Delta 1-18}$), L (linker) and R domains (FIG. 1A). Two antibodies targeting the variable or conserved domains of Coa, 5D5 and 3B3, were used for further study. mAb 5D5, which bound to the D1 domain within the first 18 residues of D1 that insert into the prothrombin active site to generate active staphylothrombin (Table 1), prevented $Coa_{ST}$ binding to prothrombin but not to fibrinogen (FIG. 5AB). mAb 3B3, on the other hand, bound to the R domain (Table S) and blocked $Coa_{ST}$ association with fibrinogen but not with prothrombin (FIG. 5AB). Further, mAb 5D5, but not mAb 3B3, inhibited *S. aureus* Newman mediated clotting of mouse blood in vitro, similar to polyclonal antibodies raised against Coa from strain Newman (FIG. 5C). Neither 5D5, 3B3 nor polyclonal Coa antibodies inhibited *S. aureus* Newman agglutination of EDTA-rabbit plasma in vitro (FIG. 5D). Purified mAbs, 5D5 or 3B3, were injected at a concentration of 5 mg antibody/kg body weight into the peritoneal cavity of BALB/c mice and compared with IgG1 isotype control mAb (FIG. 3). Both 5D5 and 3B3 provided protection against lethal bloodstream infection with *S. aureus* Newman (IgG1 vs. 5D5, P<0.0001; IgG1 vs. 3B3, P<0.0001; FIG. 3A). Similar results were obtained when the *S. aureus* Δvwb variant was used as a challenge strain (IgG1 vs. 5D5, P=0.0011; IgG1 vs. 3B3, P=0.0004; FIG. 3B). In ELISA assays, mAb 3B3 was observed to bind coagulase from different serotypes including type II ($Coa_{N315}$), type III ($Coa_{USA300}$), type IV ($Coa_{MRSA252}$ and $Coa_{85/2082}$) and type VII ($Coa_{WIS}$) (Table 2). In contrast, mAb 5D5 recognized only $Coa_{USA300}$ and to a lesser degree $Coa_{WIS}$ (Table 2). When analyzed for the prevention of lethal bloodstream infections, both 3B3 and 5D5 provided protection against MRSA strain USA300, with a type III coagulase similar to *S. aureus* Newman (IgG1 vs. 5D5, P=0.0007; IgG1 vs. 3B3, P<0.0001; FIG. 3C). However, only mAb 3B3 protected mice against lethal bloodstream challenge with *S. aureus* N315 (IgG1 vs. 5D5, P=0.1186; IgG1 vs. 3B3, P<0.0001), MRSA252 (IgG1 vs. 5D5, P=0.5993; IgG1 vs. 3B3, P<0.0001), and MRSA isolate WIS (IgG1 vs. 5D5, P=0.4243; IgG1 vs. 3B3, P<0.0001; FIG. 3DEF). Thus, monoclonal antibody against the R domain recognized coagulase of all serotypes, providing broad-spectrum protection against bloodstream infections caused by MRSA isolates.

TABLE 1

Attributes of mAbs raised against $Coa_{Newman}$

| | | Affinity (nM$^{-1}$)[c] | | | | | |
|---|---|---|---|---|---|---|---|
| mAb[a] | Isotype[b] | Coa | D1-D2 | D1 | $D1_{\Delta 1-18}$ | D2 | L | R |
| 5D5 | IgG1 | 5.02 | 5.4 | 4.09 | 1.32 | < | < | < |
| 3B3 | IgG1 | 7.58 | < | < | < | < | < | 8.03 |

[a]Mouse monoclonal antibodies were purified from isolated hybridoma clones.
[b]Immunoglobulin call and subclass of mAbs.
[c]Affinity was determined by ELISA as the association constant ($K_a$) in nM$^{-1}$ for the coagulase protein (Coa) from strain Newman. Mapping of mAb binding sites was performed by using either the full-length Coa or its sub-domains D1-D2, D1, $D1_{\Delta 1-18}$, D2, linker (L) and repeat (R) domains.

TABLE 2

Affinity of mAbs toward Coa proteins of different strains

| | | Affinity (nM$^{-1}$)[c] | | | | | |
|---|---|---|---|---|---|---|---|
| mAb[a] | Domain[b] | $Coa_{NM}$ | $Coa_{USA300}$ | $Coa_{N315}$ | $Coa_{MRSA252}$ | $Coa_{85/2082}$ | $Coa_{WIS}$ |
| 5D5 | D1 | 5.02 | 5.20 | < | < | < | 4.00 |
| 3B3 | R | 7.58 | 6.55 | 7.20 | 6.76 | 7.41 | 6.75 |

[a]Mouse monoclonal antibodies were purified from isolated hybridoma clones.
[b]Coa subdomains D1 or R recognized by mAb 5D5 and 3B3, respectively as shown in Table S1.
[c]Affinity was determined by ELISA as the association constant ($K_a$) in nM$^{-1}$ for each protein domain.

D. *S. aureus* Agglutination in Human Blood

Figures 4A, 4B, 4C, 4D, 4E, 4F:
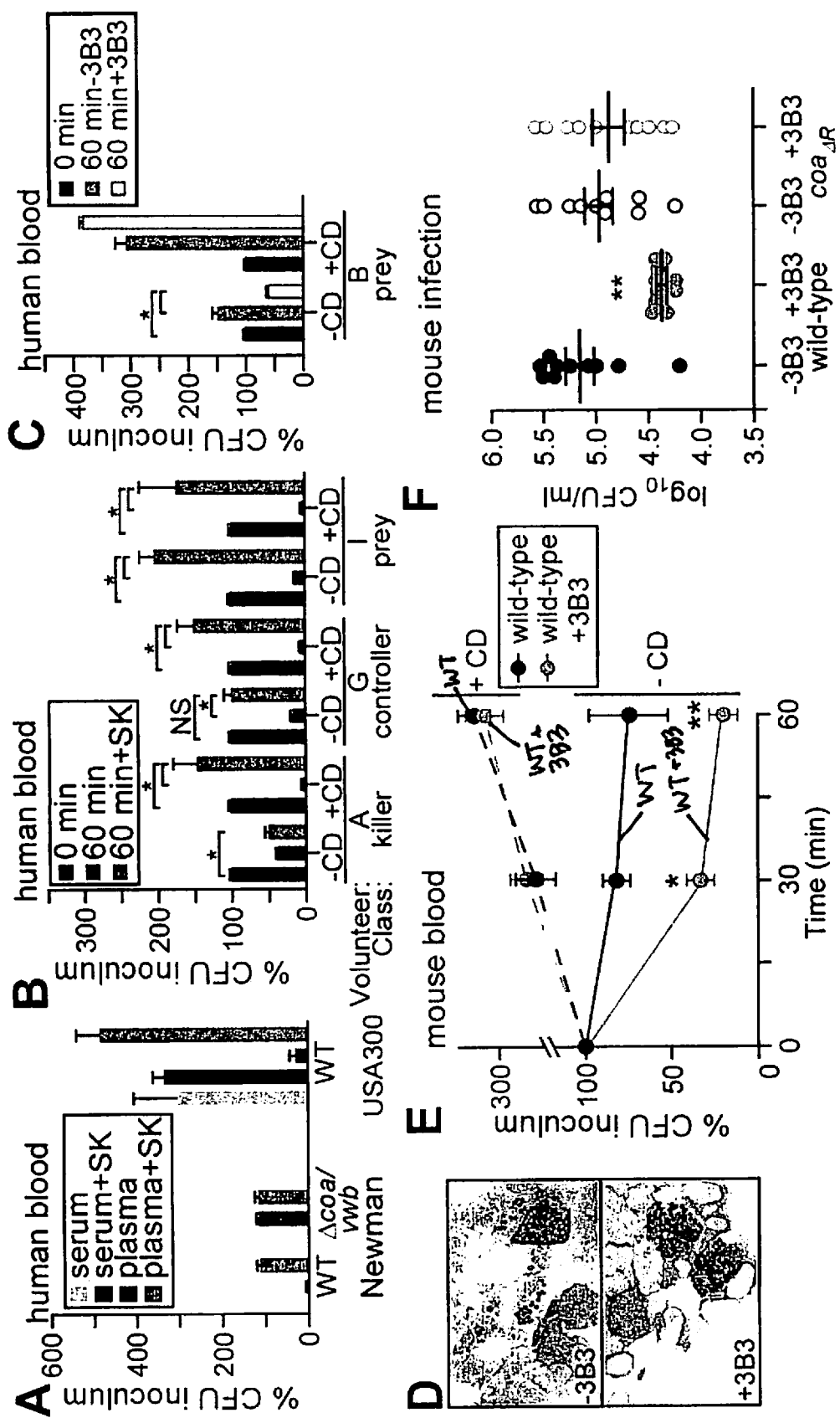
FIG. 4A-F: Monoclonal antibody against the repeat domain of coagulase promotes opsonophagocytic killing of Staphylococci. (A) Anticoagulated human plasma or serum were inoculated with $5 \times 10^6$ CFU *S. aureus* Newman (WT), Δcoa/Δvwb, or MRSA isolate USA300 LAC and incubated for 60 min prior to dilution and plating for CFU. Agglutinated Staphylococci were released by streptokinase (SK) treatment. Experiments were performed in duplicate, results averaged, SEM calculated and data recorded as percent inoculum. The bars representing the data show, from left to right, plasma, plasma+SK (WT group 1), plasma, plasma+SK (Δcoa/vwb group 2), and serum, serum SK, plasma, plasma+SK (WT, group 3). (B) Anticoagulated blood from human volunteers was inoculated with 5×10⁶ CFU USA300 LAC, incubated for 60 min and CFU enumerated with or without SK treatment. Blood samples were pre-treated with cytochalasin D (CD) to block phagocytosis. The bars represent, from left to right 0 min, 60 min, and 60 min+SK for each X-axis group of data. (C) Addition of mAb 3B3 to blood samples promoted OPK of USA300 LAC. The bars represent, from left to right 0 min, 60 min-3B3, and 60 min+3B3 for each X-axis group of data. (D) Mouse blood was incubated for 30 minutes with wild-type *S. aureus* in the absence or presence of mAb 3B3, stained with Giemsa and viewed by microscopy. (E) *S. aureus* Newman was incubated with anticoagulated mouse blood without or with cytochalasin D (CD) and without (mock) or with mAb 3B3; Staphylococcal survival and replication was assessed by CFU enumeration at timed intervals. (A-E) Data were generated from at least two trials. (F) mAb 3B3 or an IgG1 isotype antibody were administered into the peritoneal cavity of mice (n=10). Animals were challenged by intravenous injection with *S. aureus* Newman (wild-type) or the coaΔR variant. After 30 min, animals were bled via cardiac puncture and CFU enumerated. Data are representative of two independent analyses; error bars indicate SEM. Statistical analyses were performed with the two-tailed Student's t-test (A-C, F) or with two-way ANOVA with Bonferroni post-test (E); *, P<0.05 and **, P<0.01.

Blood from human volunteers was anticoagulated with desirudin to inhibit endogenous thrombin without affecting staphylothromin (McAdow et al., 2011). Blood cells were removed by centrifugation and 0.5 ml human plasma was inoculated with *S. aureus* Newman ($5\times10^6$ CFU). At timed intervals, 0 min and 60 min incubation at 37° C., Staphylococcal CFU were enumerated. Within 60 min, CFU for wild-type *S. aureus* dropped from $5\times10^6$ (100%) to $0.15\times10^6$ (3%), whereas CFU for the isogenic Δcoal Δvwb variant were not reduced (FIG. 4A). Treatment of plasma samples with streptokinase (SK), the plasminogen activator of fibrinolysis, did not affect bacterial CFU in the 0 min samples yet liberated wild-type *S. aureus* agglutinated over 60 min (FIG. 4A). USA300 LAC agglutinated in human plasma and replicated quickly to generate a large bacterial load. USA300 LAC agglutination did not occur in defibrinated human serum (FIG. 4A).

Figures 6A, 6B, 6C:
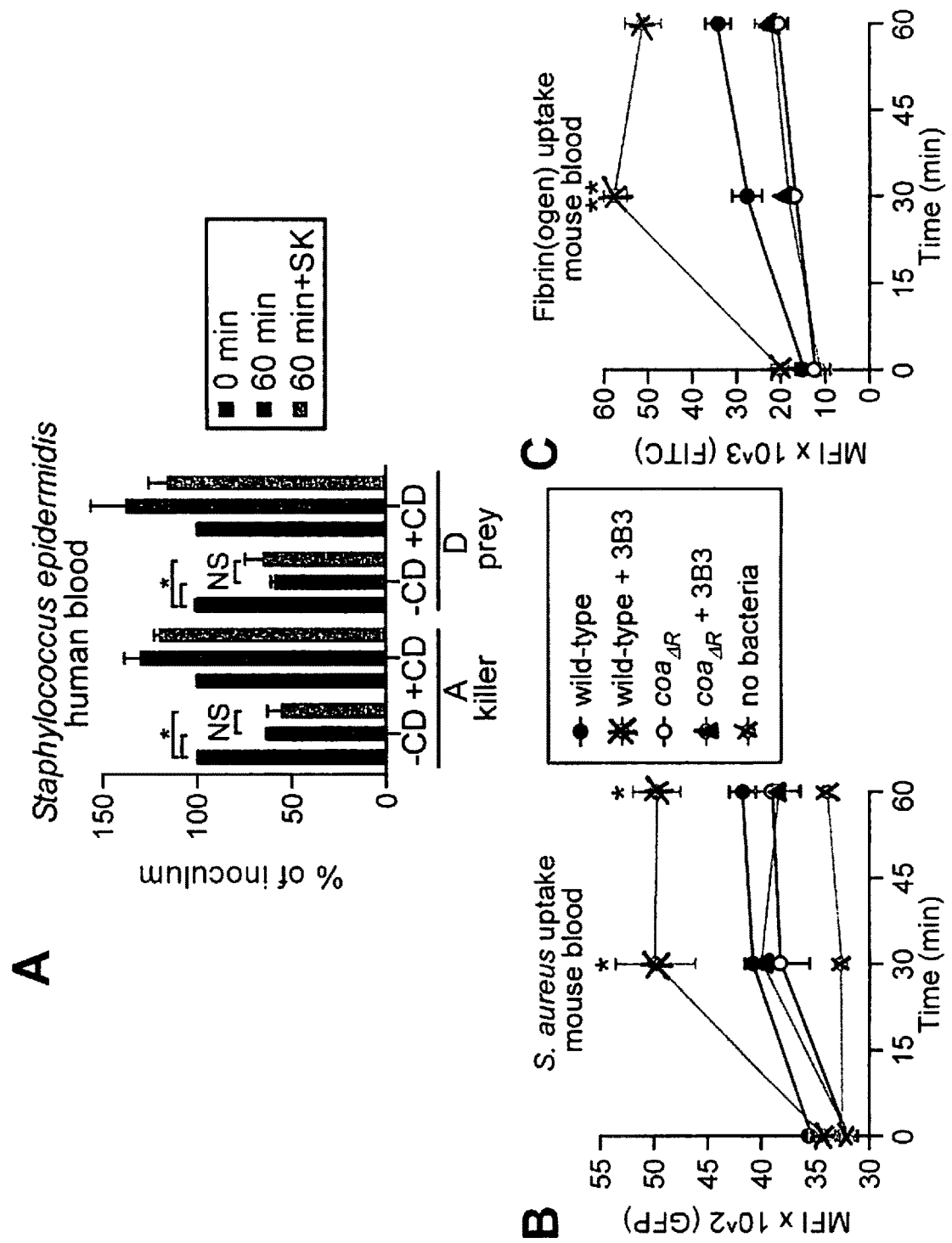
FIG. 6A-C: Agglutination impedes *S. aureus* killing in human blood. (A) *Staphylococcus epidermidis* (5×10⁶ CFU) was incubated with desirudin anticoagulated human blood for 0 and 60 minutes with or without cytochalasin D (CD). Samples were treated with PBS saponin buffer or agglutination lysis buffer (+SK). Experiments were performed in duplicate, results averaged, SEM calculated and data recorded as percent inoculum. Statistical analysis was performed with the two-tailed Student's t-test. The bars represent, from left to right 0 min, 60 min, and 60 min+SK for each X-axis group of data. (B) Anticoagulated mouse blood with or without mAb 3B3 was inoculated with *S. aureus* Newman (pGFP), *S. aureus* coaAR (pGFP) or left uninfected. At 0, 30 and 60 min, extracellular bacteria were first killed with lysostaphin and neutrophils were stained with α-GR1. The mean fluorescence intensity (MFI) of GFP was used as a measure for phagocytosed bacteria. (C) Mouse blood was supplemented with 5% Alexa488-conjugated human fibrinogen. Incorporation of Alexa488-fibrinogen into fibrin and association with neutrophils was measured by FITC fluorescence. Data in B and C are representative of two independent analyses conducted in triplicate; error bars indicate SEM. Statistical significance between wild-type−/+ 3B3 was assessed using two-way ANOVA with Bonferroni post-test: *, P<0.05; **, P<0.01.

*S. aureus* phagocytosis and opsonophagocytic killing (OPK) were measured in blood samples from 20 healthy human volunteers infected with $5\times10^6$ CFU USA300 LAC for 60 min. Bacterial CFU were quantified with or without SK treatment (Table 3). Control blood samples were pre-treated with cytochalasin D (CD), thereby preventing *S. aureus* phagocytosis (Mimura and Asano, 1976). At a challenge dose of 10 bacteria per leukocyte, the assay quantifies OPK of $5\times10^6$ CFU USA300 LAC as the percent CFU reduction from 0 to 60 min in SK treated blood. Phagocytes in blood samples of volunteer A killed $2.552\times10^6$ CFU (51.04%) within 60 min (FIG. 4B). A fraction (64.62%) of the total Staphylococcal load could be enumerated in blood without SK treatment (Table 3). When pre-treated with CD, 97.92% of Staphylococcal CFU were agglutinated in blood from volunteer A. Agglutination was calculated as the percent *S. aureus* CFU requiring SK-treatment for enumeration after 60 min incubation. For volunteer A, 35.38% of the Staphylococcal load had agglutinated within 60 min, whereas 64.62% had been phagocytosed (Table 3). Phagocytes in blood samples from volunteer G were unable to kill *S. aureus*: 99.68% of the inoculum was recovered in SK-blood (FIG. 4B). Here, 21.93% of the bacterial load had been phagocytosed, while 78.07% were agglutinated (Table 3). USA300 LAC expanded in blood samples from volunteer I to 204.42% of the initial inoculum; 85.75% of the load were agglutinated (FIG. 4B). On the basis of these phenotypes, inventors categorized human blood samples as Staphylococcal killer, controller or prey (Table 3). This classification applies only to *S. aureus*, as both killer and prey blood samples were active in phagocytosis and OPK of *Staphylococcus epidermidis*, a commensal that does not express coagulases (FIG. 6A). Antibody titers against the D1-D2 or the C-terminal R domain were not correlated with OPK of USA300 LAC in human blood (Table 3).

TABLE S3

Phagocytosis and opsonophagocytic killing of MRSA USA300 LAC in human blood

| | Serum IgG titer[2] | | | without cytochalasin D | | | | | | |
|---|---|---|---|---|---|---|---|---|---|---|
| | | | | | | streptokinase (SK) | with cytochalasin D[5] | streptokinase | | |
| Donor[1] | Hla | D1-D2$_{ST}$ | R$_{N12D}$ | mock (% total)[3] | (% inoculum)[4] | mock (% total)[3] | (% inoculum)[4] | Agglutinated (%)[6] | OPK (%)[7] | Category[8] |
| A | 2599 | 320 | 716 | 64.62 (±20.53) | 48.96 (±4.48) | 2.08 (±0.31) | 145.59 (±32.82) | 35.38 | 51.04 | K |
| B | 1936 | 546 | 245 | 63.16 (±8.01) | 124.77 (±6.02) | 5.07 (±0.57) | 236.51 (±6.14) | 36.84 | 0 | P |
| C | 3176 | 1550 | 276 | 31.28 (±0.53) | 90.4 (±2.95) | 3.98 (±2.81) | 87.65 (±18.98) | 68.72 | 9.60 | K |
| D | 1134 | 85 | 134 | 37.79 (±6.30) | 139.97 (±5.78) | 1.90 (±0.21) | 218.46 (±5.15) | 62.79 | 0 | P |
| E | 1365 | 278 | 226 | 39.40 (±3.42) | 115.52 (±30.84) | 3.83 (±1.06) | 246.74 (±39.85) | 60.60 | 0 | C |
| F | 6849 | 4470 | 2905 | 14.35 (±1.23) | 130.93 (±11.2) | 2.1 (±1.79) | 117.08 (±22.04) | 85.65 | 0 | P |
| G | 8688 | 2308 | 2760 | 21.93 (±1.94) | 99.68 (±8.25) | 2.58 (±0.47) | 149.60 (±18.75) | 78.07 | 0.32 | C |
| H | 3541 | 553 | 167 | 72.35 (±8.22) | 117.51 (±9.59) | 7.05 (±1.09) | 321.39 (±24.81) | 27.65 | 0 | P |
| I | 1680 | 245 | 250 | 14.25 (±1.74) | 204.42 (±29.76) | 10.49 (±0.75) | 174.60 (±1.95) | 85.75 | 0 | P |
| J | 554 | 281 | 178 | 48.12 (±0.60) | 177.97 (±3.19) | 5.59 (±0.44) | 218.06 (±11.31) | 51.88 | 0 | P |
| K | 2066 | 383 | 520 | 85.24 (±3.36) | 122.63 (±28.2) | 17.45 (±0.78) | 300.6 (±14.15) | 14.76 | 0 | C |
| L | 2333 | 185 | 667 | 63.17 (±6.08) | 176.42 (±29.9) | 3.00 (±0.08) | 354.94 (±19.19) | 36.83 | 0 | P |
| M | 955 | 1343 | 1940 | 75.56 (±1.23) | 173.73 (±2.73) | 7.49 (±0.80) | 392.53 (±68.16) | 24.44 | 0 | P |
| N | 2109 | 575 | 323 | 77.61 (±12.31) | 149.42 (±9.46) | 16.43 (±9.36) | 308.80 (±30.28) | 22.39 | 0 | P |
| O | 1881 | 148 | 216 | 66.91 (±14.36) | 195.00 (±28.06) | 9.10 (±2.92) | 310.92 (±6.27) | 33.09 | 0 | P |
| P | 459 | 80 | 57 | 65.30 (±0.55) | 110.80 (±8.02) | 4.36 (±0.46) | 355.53 (±33.92) | 34.70 | 0 | C |
| Q | 2469 | 1156 | 414 | 39.26 (±10.55) | 203.63 (±17.23) | 13.30 (±2.08) | 196.19 (±38.14) | 60.74 | 0 | P |

TABLE S3-continued

Phagocytosis and opsonophagocytic killing of MRSA USA300 LAC in human blood

| | Serum IgG titer[2] | | | without cytochalasin D | | with cytochalasin D[5] | | | | |
|---|---|---|---|---|---|---|---|---|---|---|
| | | | | | streptokinase (SK) | | streptokinase | | | |
| Donor[1] | Hla | D1-D2$_{ST}$ | R$_{N12D}$ | mock (% total)[3] | (% inoculum)[4] | mock (% total)[3] | (% inoculum)[4] | Agglutinated (%)[6] | OPK (%)[7] | Category[8] |
| R | 5934 | 1114 | 907 | 26.77 (±0.04) | 241.30 (±23.59) | 12.97 (±0.16) | 342.54 (±17.54) | 73.23 | 0 | P |
| S | 4070 | 225 | 300 | 66.06 (±8.19) | 113.39 (±21.00) | 10.89 (±5.89) | 132.24 (±18.5) | 33.94 | 0 | C |
| T | 1878 | 319 | 507 | 55.32 (±0.72) | 90.86 (±3.65) | 7.99 (±2.94) | 292.10 (±46.85) | 44.68 | 9.14 | K |

[1]Blood from human volunteers obtained was anticoagulated with desirudin (10 µg/ml), dispensed into 0.5 ml aliquots and inoculated with 5 × 10⁶ CFU USA300 LAC. The inoculum was enumerated by lysing blood with 0.5 ml PBS (with 0.5% saponin, 100 U streptokinase K, 50 µg trypsin, 1 µg DNAse and 5 µg RNAse), prior to plating on agar for CFU enumeration.
[2]Serum from coagulated blood of human volunteers was examined by ELISA for the half-maximal IgG titer against purified recombinant proteins derived from of S. aureus Newman genome sequence: α-hemolysin (Hla), D1-D2 domain (D1-D2) or a tandem repeat of the R domain carrying the N12D substitution.
[3]Blood samples were lysed after 60 min at 37° C. with 0.5 ml PBS (0.5% saponin, 1 µg DNAse, 5 µg RNAse), followed by CFU enumeration. Data were averaged from two independent determinations, SEM and percent amount of total (60 min streptokinase treated sample) were calculated.
[4]Blood samples were lysed after 60 min at 37° C. with 0.5 ml PBS (0.5% saponin, 100 U streptokinase, 50 µg trypsin, 1 µg DNAse, 5 µg RNAse), followed by CFU enumeration. Data were averaged from two independent determinations, SEM and % of inoculum (0 min = 5 × 10⁶ CFU) calculated.
[5]Blood was pretreated with 10 µg cytochalasin D/ml prior to infection with 5 × 10⁶ CFU USA300 LAC.
[6]Agglutination (%) was calculated from the percent mock treated CFU after 60 min (without cytochalasin D) and the Staphylococcal load enumerated with streptokinase treatment.
[7]Opsonophagocytic killing (OPK) (%) was calculated as the Δ0-60 min load in streptokinase treated blood without cytochalasin D treatment.
[8]Human blood samples were categorized as killer (K), controllers (C) or prey (P) of MRSA isolate USA300 LAC.

E. R Domain Antibody Promotes Phagocytosis of Fibrin-Coated Sstaphylococci

When added to blood samples of volunteer B (prey), mAb 3B3 reduced the bacterial load to 63%, whereas USA300 LAC expanded to 128% in blood without antibody (3B3 vs. mock, P<0.05; FIG. 4C). Pretreatment of blood with CD abolished phagocytosis and OPK of USA300 LAC in the presence of mAb 3B3 (FIG. 4C). S. aureus Newman expressing GFP was inoculated into mouse blood and neutrophils were isolated by GR1-staining and flow cytometry (FIG. 6BC). Although phagocytosis of Staphylococci occurred in the absence of antibody, association of Staphylococci with neutrophils was increased in the presence of mAb 3B3 (FIG. 6B). Further, GFP fluorescence did not increase after 30 min, indicating that bacterial replication had been arrested (Thammavongsa et al., 2013). Antibody-mediated uptake of Staphylococci was not observed in neutrophils from S. aureus coa$_{AR}$ samples (FIG. 6B). Neutrophil uptake of wild-type S. aureus was accompanied by uptake of fibrin, detected by adding Alexa488-conjugated human fibrinogen to blood samples and measuring neutrophil fluorescence (FIG. 6C). Mouse blood infected with S. aureus was Giemsa staining, which revealed large clumps of fibrin-agglutinated Staphylococci outside of neutrophils (FIG. 4D). When treated with mAb 3B3, Staphylococci appeared to be internalized by mouse neutrophils (FIG. 4D). Mouse blood was infected with USA300 LAC and analyzed for CFU after 30 and 60 min incubation. Compared to mock control, mAb 3B3 promoted phagocytic killing of USA300 LAC. As expected, OPK was blocked by pre-treatment with CD (FIG. 4E). OPK of S. aureus was quantified in vivo in mice with intravenous challenge of S. aureus followed by CFU enumeration in cardiac blood 30 minutes post infection. mAb 3B3 reduced the bacterial load in mice infected with wild-type S. aureus but not in mice infected with the coa$_{AR}$ variant (FIG. 4F).

Inventors report that S. aureus evolved a unique mechanism to escape phagocytic killing: coagulase-mediated assembly of a fibrin shield protecting the pathogen against uptake by phagocytes. The R domain drives the formation of the bacterial fibrin shield that protects bacteria but also exposes trapped Coa for antibody deposition. To avoid neutralizing antibody responses against its key virulence determinant, coa, i.e. the coding sequence for the D1-D2 domain, is subject to negative selection, generating variant products that cannot be neutralized by antibodies against the D1-D2 domain of another coagulase serotype (McAdow et al., 2012a; Watanabe et al., 2009). Inventors also show that monoclonal antibody against the R domain target Staphylococci for OPK destruction. If so, some R domain-specific antibodies, either elicited through active vaccination or passively transferred monoclonal, may protect against S. aureus bloodstream infection and may be used to combat MRSA infections. Successful vaccines generally rely on antibodies against bacterial surface structures to implement pathogen destruction (Robbins et al., 1996). However, S. aureus can escape antibody-mediated destruction by a number of different immune evasion mechanisms, for example blocking neutrophil chemotaxis, phagocytosis, complement activation and antibody deposition (Spaan et al., 2013). Vaccine development relies on standardized assays measuring OPK in cultured HL60 phagocytes supplemented with complement and antibody but not with hemostasis factors (Nanra et al., 2013). This assay cannot assess the immune evasive attributes of Staphylococcal coagulase and may overestimate the role of antibodies against surface molecules to promote OPK.

F. Materials and Methods

Bacterial growth, strains and plasmids. S. aureus and Escherichia coli were grown in tryptic soy and Luria broth or agar, with ampicillin (100 µg ml⁻¹) or chloramphenicol (10 µg ml⁻¹) when necessary. Earlier work reported S. aureus Newman and its variants Δcoa, Δvwb and Δcoa/Δvwb with or without plasmid expressing GFP or mCherry (Cheng et al., 2010). pKOR1 was used to introduce the coa$_{AR}$ allele (deletions of codons 470-605) into wild-type or Δvwb Newman (Bae and Schneewind, 2005). Earlier work generated E. coli plasmids for purification of full-length mature Coa (*S. aureus* Newman, USA300, N315, MRSA252, 85/2082, or WIS)(McAdow et al., 2012a; Thomer et al., 2013) or Coa Newman domains (D1, D1-D2, D1 $_{\Delta 1-18}$, D2 and L)(McAdow et al., 2012a). Plasmid pET15b-r$_{ST}$ harbors coding sequence for the R domain (codons 470-605) and a C-terminal Strep tag.

Identification of coagulases in cultures and clots. To examine the secretion of coagulases, cultures of Staphylococci were grown to an optical density $A_{600}$ 0.4 (~$10^8$ colony forming units (CFU) ml$^{-1}$). Proteins in the supernatant, i.e. 1 ml of centrifuged culture, were precipitated with 75 µl of trichloroacetic acid 100% (w/v), washed with acetone, dried and solubilized in 50 µl sample buffer (62.5 mM Tris-HCl, pH 6.8, 2% SDS, 10% glycerol, 5% 2-mercaptoethanol, 0.01% bromophenol blue). To examine the fate of coagulase in fibrin clots, 950 µl of bacterial culture (~$10^8$ CFU ml$^{-1}$) or broth were mixed with 50 µl of PBS or human citrate-plasma for 10 min at 37° C. and centrifuged at 13,000×g for 10 min to separate soluble and clotted materials. 4 M urea was used to solubilize fibrin clots prior to separation of extracts by SDS-PAGE. Proteins were visualized with Coomassie staining or transferred to polyvinylidene difluoride (PVDF) membranes for immunoblotting using rabbit affinity-purified antibodies against Coa (α-Coa) or vWbp (α-vWbp)(Thomer et al., 2013) and mouse affinity-purified monoclonal antibodies 3B3 or 5D5.

Pull down experiments. Coa$_{ST}$, Coa$_{\Delta R/ST}$ and R$_{ST}$ were purified over Strep-Tactin-Sepharose (IBA) following methods described earlier for Coa subdomains and Coa strain variants (McAdow et al., 2012a; Thomer et al., 2013). All purified proteins were stored in PBS. For pull-down experiments, citrate-plasma from healthy human volunteers (500 µl) diluted 1:1 in PBS was applied by gravity flow over Strep-Tactin-Sepharose beads pre-charged or not with 100 nmoles of purified Coa$_{ST}$, Coa$_{\Delta RST}$ or R$_{ST}$. Bound proteins were recovered by boiling the resin in sample buffer and analyzed by SDS-PAGE separation followed by Coomassie staining or immunoblot.

Coagulation assay. 10 µl of bacterial suspension (~$10^8$ CFU ml$^{-1}$) was added to 90 µl of freshly collected mouse blood anti-coagulated with sodium citrate (10 mM final concentration) in a sterile plastic test tube (BD falcon). Samples were incubated at room temperature and blood coagulation was verified by tipping the tubes to 45° angles at timed intervals. Where indicated, antibodies were added at a final concentration of 3 µM. Statistical analysis was performed by two-tailed Student's t-test using Prism (GraphPad Software).

Microscopy. For visualization of bacteria in clots, 5 µl of Staphylococci expressing mCherry (~$10^8$ CFU ml$^{-1}$) were mixed for 5 min with 5 µl of human citrate-plasma supplemented with 5% Alexa488-conjugated human fibrinogen (Life Technologies). Images of samples placed on glass slides were captured on a SP5 tandem scanner spectral 2-photon confocal microscope (Leica) using a 100× objective. For assessment of agglutination, 1 ml of Staphylococci (~$10^8$ CFU ml$^{-1}$) were incubated with 1:500 SYTO9 (Invitrogen) for 15 min, washed twice and suspended in 1 ml of PBS. Bacteria were incubated 1:1 for 15 min with human citrate-plasma on glass microscope slides. Where indicated, antibodies were added at a final concentration of 3 µM. Images were captured on an 1X$_{81}$ live cell total internal reflection fluorescence microscope (Olympus) using a 20× objective. The threshold function in ImageJ software was used to convert the image into a dichromatic format in which Staphylococci are black and the background is white. Statistical significance was determined by two-way analysis of variance using Prism (GraphPad Software).

Production of monoclonal antibodies against coagulase. Three 8-week old BALB/c female mice (Jackson Laboratory) were immunized by intraperitoneal injection with 100 µg of purified recombinant Coa$_{NM}$ emulsified 1:1 in Complete Freund's Adjuvant (DIFCO) for the first immunization. On days 21 and 42, animals were boosted with 100 µg Coa$_N$m emulsified 1:1 in Incomplete Freund's Adjuvant (DIFCO). On days 31 and 52, animals were bled and screened by ELISA on Nunc MaxiSorp 96-well flat bottom plates coated with Coa. Seventy-nine days after the initial immunization, mice that showed strong immunoreactivity to antigen were boosted with 25 µg Coa in PBS. Three days later splenocytes were harvested and fused with the mouse myeloma cell line SP2/mIL-6, an interleukin 6 secreting derivative of SP2/0 myeloma cell line. Hybridomas were screened by ELISA and antigen-specific clones subcloned by limiting dilution, to produce monoclonal antibody-secreting hybridomas arising from single cells. Hybridoma cell lines were grown until a density of $10^6$ cells ml$^{-1}$ in DMEM-10 medium with 10% FBS and left spending for 6 weeks. Antibodies were purified from filtered culture supernatants by affinity chromatography as described (McAdow et al., 2012a; Thomer et al., 2013).

ELISA. To determine the binding affinity and specificity of mAbs, Nunc MaxiSorp 96-well plates were coated with the various Coa variant serotypes and sub-domains prepared at a concentration of 20 nM in 0.1 M sodium bicarbonate and affinities were measured as described earlier (McAdow et al., 2012a). ELISA plates coated with vWbp and IsdA served as negative controls. The ability of mAbs to interfere with the binding of prothrombin or fibrinogen was measured as described earlier (McAdow et al., 2012a) and statistical analyses were performed using one-way ANOVA with Bonferroni post-test. Half-maximal IgG titers in serum from human volunteers for binding to purified Hla, D1-D2$_{ST}$ or R$_{N12D}$ were determined by ELISA as described previously (McAdow et al., 2012a). R$_{N12D}$ is a translational hybrid between SpA$_{KKAA}$, a variant of SpA that does not bind immunoglobulin, and two 27 residue repeats of the R domain from Coa$_{Newman}$, with Asn$^{12}$Asp at position 12 of each repeat, followed by a C-terminal Strep tag; purified R$_{N12D}$ for is defective fibrinogen binding.

Animal infection and immunization studies. Animals (cohorts of 10), 6-week old, female BALB/c mice (Charles River Laboratories) anesthetized with 100 mg ml$^{-1}$ ketamine and 20 mg ml$^{-1}$ xylazine per kilogram of body weight were inoculated into the peri-orbital venous plexus with 100 µl of bacterial suspension in PBS at a concentration of 2×$10^8$ CFU ml$^{-1}$ (USA300), 8×$10^8$ CFU ml$^{-1}$ (Newman, N315, WIS) or 2×$10^9$ CFU ml$^{-1}$ (MRSA252). mAbs were injected at a concentration of 5 mg kg$^{-1}$ into the peritoneal cavity 10 hours prior to challenges. Statistical analyses were performed by two-tailed Log Rank test using Prism (GraphPad Software). To assess the fate of Staphylococci in blood (in vivo blood survival assay), animals were euthanized by CO2 inhalation 30 min post infection and cardiac puncture was performed. Blood samples were treated with 0.5% saponin to lyse eukaryotic cells, serially diluted in PBS and plated on agar for enumeration of CFU. Statistical analysis was performed using two-tailed Student's t test. Animal experiments were performed in accordance with the institutional guidelines following experimental protocol review and approval by the Institutional Biosafety Committee (IBC) and the Institutional Animal Care and Use Committee (IACUC).

Bacterial survival in blood, opsonophagocytosis assay and flow cytometry analysis. To measure bacterial replication and survival ex vivo, 0.5 ml of freshly drawn mouse or human blood anticoagulated with 0.005 mg desirudin per ml was incubated with 50 µl of a bacterial suspension containing $5\times10^5$ CFU (mouse) or $5\times10^6$ CFU (human). Where indicated human blood was processed to generate desirudin-plasma or serum. Where indicated, 5% Alexa488-conjugated human fibrinogen (Life Technologies), cytochalasin D (0.04 mM), or purified mouse monoclonal antibodies (~10 µg ml$^{-1}$ final concentration) were added to the samples. Following incubation at 37° C. for 0, 30 or 60 min, 0.5 ml of PBS with 0.5% saponin or 0.5 ml agglutination lysis buffer (0.5% saponin, 200 U streptokinase K, 100 µg trypsin, 2 µg DNAse, 10 µg RNAse per ml PBS), were added to each sample for 10 min at 37° C., prior to plating on agar for enumeration of CFU. Treatment with agglutination lysis buffer is annotated as +SK in the figures. Statistical analysis was performed by two-tailed Student's t-test. For flow cytometry analysis, samples were incubated first with lysostaphin (10 µg ml$^{-1}$) for 5 min to lyse extracellular bacteria and next with erythrocyte lysis buffer (QIAGEN) for 30 min on ice. Blood leukocytes were recovered following centrifugation at 400×g, washed three times and suspended in PBS containing 1% FBS. Cells were stained with allophycocyanin-conjugated α-GR1 and analyzed using a FACSCanto (BD). The data were analyzed with the two-tailed Student's t-test. Human volunteers were enrolled under a protocol that was reviewed and approved by the University of Chicago's Institutional Review Board.

Example 2

Selection of prototype Staphylocoagulase protein sequences in dominant clinical *Staphylococcus aureus* lineages using molecular epidemiology and whole-genome sequencing for inclusion into a multicomponent Staphylococcal vaccine composition.

A. Purpose:

To collect and analyze currently available genomic information of *Staphylococcus aureus* strain diversity for the purpose of prevalence-based selection of prototype Staphylocoagulase (Coa) sequences. These dominant full-length Coa sequences will form the basis for selecting the most representative R-domains from clinically relevant *Staphylococcus aureus* strains.

B. Methods

1. Molecular Epidemiology of Dominant Staphylococcal Sequence Types (STs)

A Sequence Type (ST) is defined by the Multi Locus Sequence Typing (MLST) technique, which characterizes the nucleotide sequences of a number of housekeeping genes. For each housekeeping gene in an isolate an allele number is assigned to the corresponding sequence according to an existing nomenclature (i.e. each unique allele sequence has its own unique allele number). The resulting combination of allele numbers defines the allelic profile or Sequence Type (ST), according to the defined nomenclature. In the case of *S. aureus,* 7 housekeeping genes are used for defining the ST. The *S. aureus* MLST nomenclature is found on the world wide web at http://saureus.mlst.net.

USA: Dominant Methicillin-Resistant *Staphylococcus aureus* (MRSA) sequence types (STs) in the USA were identified based on prevalence data as reported by the Active Bacterial Core Surveillance (ABCs) as part of the Emerging Infections Program Network on Methicillin-Resistant *Staphylococcus aureus* infections (Center for Disease Control (CDC), for the period 2005-2013, described on the world wide web at cdc.gov/abcs/reports-findings/survreports/mrsa13.pdf).

EU: Dominant Methicillin-Sensitive *Staphylococcus aureus* (MSSA) & MRSA STs in the EU were identified based on prevalence data as reported by Grundmann et al. (Grundmann et al. 2010 PLoS Med. 7(1): e1000215, PMID20084094; Grundmann et al. 2014 Euro Surveill. 19(49). pii: 20987, PMID25523972).

Asia: Dominant MSSA & MRSA STs in Asia were identified based on multiple reviews and meta-analyses including Chen and Huang, 2014, Clin Microbiol Infection PMID: 24888414; Chuang and Huang, 2013, Lancet Infect Disease PMID:23827369; and Chung et al., 2015 IJAA (PMID:25982914).

2. Whole-Genome Sequence Data & Assembly.

Publicly available whole-genome sequence (WGS) assemblies for *S. aureus* were extracted from GenBank on 16Jul. 2015. Additional *S. aureus* WGS data were collected from two publicly available repositories of the Wellcome Trust Sanger Institute (described on the world wide web at sanger.ac.uk/resources/downloads/bacteria/*staphylococcus-aureus*.html). The first repository contained data from the British Society for Antimicrobial Chemotherapy (BSAC, described on the world wide web at bsac.org.uk/) (#project 2036 on the Sanger website). BSAC collects a broad selection of microorganisms from both community- and hospital-acquired infections. Up to 6000 clinical isolates are collected each year across the UK and Ireland. Paired-end Illumina reads for 203 *S. aureus* isolates were downloaded from this repository on 20Nov. 2014. Assemblies were built with SPAdes 3.1.1 (Bankevitch et al. 2012 J Comput Biol. 19(5):455-77, PMID: 22506599) using default settings. All 203 isolates were MRSA from human blood, isolated in the years 2009 and 2010. The second repository contained data from a study describing the genetic diversity of *S. aureus* in Europe (see, eg. world wide web at sanger.ac.uk/resources/downloads/bacteria/*Staphylococcus aureus*.html. on the Sanger website). Collection and typing of these European isolates has been described in two studies by Grundmann and colleagues (Grundmann et al. 2010 PLoS Med. 7(1): e1000215, PMID20084094; Grundmann et al. 2014 Euro Surveill. 19(49). pii: 20987, PMID25523972). In the first study, MSSA and MRSA isolates had been collected from 450 hospitals in 26 European countries in 2006 and 2007. Of these isolates, 90.1% were isolated from blood. In the second study, MSSA and MRSA isolates had been collected from 453 hospitals in 25 European countries in 2011. These isolates came from subjects with *S. aureus* bloodstream infections. The available WGS data on the Sanger website corresponded to a representative selection of 589 *S. aureus* isolates from the two studies described above. Paired-end Illumina reads for these isolates were downloaded on 26 Aug. 2015. Reads were quality-filtered using the Nesoni toolset 0.131 (see, eg. github.com/Victorian-Bioinformatics-Consortium/nesoni). Default settings were used, including clipping of low-quality and ambiguous bases and adapter sequences. Reads shorter than 51 bp as well as their paired reads were discarded. Quality-filtered reads were assembled with SPAdes 3.6.0, using the “careful” option and k-mer values 27, 37 and 47.

3. In Silico Multi-Locus Sequence Typing (MLST).

*S. aureus* WGS assemblies were typed using the available MLST scheme for *S. aureus*. Alleles were typed on the basis of perfect BLAST matches.

4. Gene Prediction and Annotation.

Genes were predicted and annotated in WGS assemblies using Prokka 1.11 (see, eg. github.com/tseemann/prokka). Coa (annotated as "staphylocoagulase") protein sequences were extracted from the Prokka annotations. Full-length Coa sequences were defined as those Coa sequences that contained the N-terminal 3-amino-acid stretch "MKK" and the C-terminal 3-amino-acid stretch "VTK". Assessment of the Coa sequence variation within specific Coa collections was determined using CD-HIT 4.6 (described on the world wide web at bioinformatics.org/cd-hit/). CD-HIT was run using 100% identity clustering (option: −c 1.0), allowing no redundancy (option: −t 0) and using the most accurate clustering approach (option: −g 1).

C. Results:

1. Molecular Epidemiology

A detailed analysis of molecular epidemiological data was used to identify dominant *S. aureus* lineages in USA, Europe and Asia:

a. USA

Prevalence data as reported by the Active Bacterial Core Surveillance (ABCs) as part of the Emerging Infections Program Network on Methicillin-Resistant *Staphylococcus aureus* infections demonstrates that MRSA multilocus sequence type ST5_(USA100) and ST8 (USA300) are predominantly associated with invasive MRSA infections in the USA hospital (HA) and community (CA) settings.

b. EU

Based on the large European surveillance studies performed in 2006 and 2011 (Grundmann et al. 2010 PLoS Med. 7(1): e1000215, PMID20084094; Grundmann et al. 2014 Euro Surveill. 19(49). pii: 20987, PMID25523972) we identified ST22 (i.e. EMRSA-15), first detected in UK in early 1990s, as a dominant clone throughout healthcare settings across Europe. Other important European clones are ST8=CC8 (USA300), ST5, ST125, ST225=CC5 (USA100), ST30 and ST45.

c. Asia

The epidemiology of *S. aureus* in both healthcare facilities and communities in Asia has been extensively addressed, with an emphasis on the prevalence, clonal structure and antibiotic resistant profiles of the MRSA strains in several recent reviews (Chen and Huang, 2014, Clin Microbiol Infection PMID: 24888414 and Chuang and Huang, 2013, Lancet Infect Disease PMID:23827369). Two dominant HA-MRSA clones, namely ST239 and ST5, are disseminated throughout Asia.

In conclusion, we identified 6 dominant clinically-relevant *S. aureus* lineages (or sequence types, ST) in USA, Europe and Asia, corresponding to ST5, ST8, ST22, ST30, ST45 and ST239.

2. *S. aureus* Whole-Genome Sequences

4512 *S. aureus* WGS assembly projects were available in GenBank. Based on available publications and meta-data, an initial selection was made, thereby discarding all non-human isolates and isolates without sufficient meta-data. Isolates with associated publications were kept anyway, because these are often well-characterized reference isolates. The initial screening resulted in 2177 relevant isolates, including 166 with associated publications. Further searches in GenBank and PubMed showed that among the remaining 2011 isolates, 1951 could be manually linked to sequencing projects/studies. Finally, the collection was split into two collections: the first one being of primary interest and containing 1043 recent (from year 1995 or later) clinical human isolates, the other one being of secondary interest and containing 1134 older (from before 1995) and/or non-clinical isolates (e.g. from eye, throat, nares, skin, stool, household surfaces, etc). The primary collection was supplemented with (i) 203 WGS assemblies from the BSAC collection, which comprised MRSA blood isolates from the UK from the years 2009 and 2010 and (ii) 376 assembled genomes from the Grundmann collection, which comprised MRSA and MSSA blood isolates from Europe from the years 2006 and 2011. In summary, our final primary WGS collection consisted of 1043 (GenBank)+203 (BSAC)+376 (Grundmann)=1622 WGS assemblies. Our final secondary collection consisted of 1134 WGS assemblies (GenBank).

3. MLST Profiling

In silico MLST profiling of the final primary WGS collection (n=1622 genomes) showed that all six dominant lineages were present in the following amounts: ST5_ (n=540), ST8 (n=84), ST22 (n=205), ST30 (n=38), ST45 (n=60), ST239 (n=17). In silico MLST profiling of the final secondary WGS collection (n=1134 genomes) showed that all six dominant lineages were present in the following amounts: ST5_(n=493), ST8 (n=252), ST22 (n=2), ST30 (n=5), ST45 (n=17), ST239 (n=7).

4. Identification of Full-Length Coa Sequences

Identification of Coa sequences in the WGS assemblies belonging to the 6 dominant *S. aureus* lineages indicated that the majority of these isolates have a full-length Coa, containing the N-terminal 3-amino-acid stretch "MKK" and the C-terminal 3-amino-acid stretch "VTK". Within the primary WGS collection, the percentage of isolates with a full-length Coa ranged from 82% (ST239) to 98% (ST8) (Table 1). Within the secondary collection, the percentage of isolates with a full-length Coa ranged from 0% (ST22) to 100% (ST8 and ST239) (Table 2).

TABLE 1

Identification of full-length Coa in six dominant *S. aureus* lineages in the primary WGS collection.

| LINEAGE (ST) | # ISOLATES IN COLLECTION | # ISOLATES WITH FULL-LENGTH COA | % ISOLATES WITH FULL-LENGTH COA |
|---|---|---|---|
| ST5 | 540 | 457 | 85% |
| ST8 | 84 | 82 | 98% |
| ST22 | 205 | 165 | 80% |
| ST30 | 38 | 37 | 97% |
| ST45 | 60 | 57 | 95% |
| ST239 | 17 | 14 | 82% |

TABLE 2

Identification of full-length Coa in six dominant *S. aureus* lineages in the secondary WGS collection.

| LINEAGE (ST) | # ISOLATES IN COLLECTION | # ISOLATES WITH FULL-LENGTH COA | % ISOLATES WITH FULL-LENGTH COA |
|---|---|---|---|
| ST5 | 493 | 300 | 61% |
| ST8 | 252 | 251 | 100% |
| ST22 | 2 | 0 | 0% |
| ST30 | 5 | 4 | 80% |
| ST45 | 17 | 16 | 94% |
| ST239 | 7 | 7 | 100% |

5. Coa Sequence Variation

To assess the Coa sequence variation within the dominant *S. aureus* lineages, we collected all corresponding full-length Coa sequences from the primary collection. Since the number of WGS assemblies (and hence full-length Coa) in the primary collection was limited for ST30 and ST239 (i.e. below n=50 for both), we also used the full-length Coa sequences found in the secondary collection for these STs.

a. ST5

Sequence analysis of the 457 full-length Coa sequences identified in the ST5 isolates revealed a total of 42 unique sequences, of which 24 were found once (i.e. each one in one single isolate). Another 5 unique sequences were found twice (i.e. each one found in two isolates). Of the remaining 13 unique sequences the three most dominant ones were found in 191, 85 and 59 isolates. Thus the 3 most dominant Coa sequences represented 73% of the full-length Coa sequences in ST5_(i.e. 191+85+59=335 of the 457). The reference isolates N315 and Mu50 both contain the second most dominant Coa found within ST5. The 3 dominant ST5 Coa sequences are listed below in fasta-format, in the order from most to least dominant. R domains are underlined. Reference isolate(s) in which the corresponding sequence is found is/are given in brackets in the sequence header.

```
>CoaST5_1_n191
                                            (SEQ ID NO: 22)
MKKQIISLGALAVASSLFTWDNKADAIVTKDYSKESRVNEKSKKGATVSD
YYYWKIIDSLEAQFTGAIDLLEDYKYGDPIYKEAKDRLMTRVLGEDQYLL
KKKIDEYELYKKWYKSSNKNTNMLTFHKYNLYNLTMNEYNDIFNSLKDAV
YQFNKEVKEIEHKNVDLKQFDKDGEDKATKEVYDLVSEIDTLVVTYYADK
DYGEHAKELRAKLDLILGDTDNPHKITNERIKKEMIDDLNSIIDDFFMET
KQNRPNSITKYDPTKHNFKEKSENKPNFDKLVEETKKAVKEADESWKNKT
VKKYEETVTKSPVVKEEKKVEEPQLPKVGNQQEVKTTAGKAEETTQPVAQ
PLVKIPQETIYGETVKGPEYPTMENKTLQGEIVQGPDFLTMEQNRPSLSD
NYTQPTTPNPILEGLEGSSSKLEIKPQGTESTLKGIQGESSDIEVKPQAT
ETTEASQYGPRPQFNKTPKYVKYRDAGTGIREYNDGTFGYEARPRFNKPS
ETNAYNVTTNQDGTVSYGARPTQNKPSETNAYNVTTHANGQVSYGARPTQ
KKPSKTNAYNVTTHANGQVSYGARPTQKKPSKTNAYNVTTHANGQVSYGA
RPTYKKPSETNAYNVTTHANGQVSYGARLTQKKPSETNAYNVTTHADGTA
TYGPRVTK

R Domain:
                                            (SEQ ID NO: 85)
ARPRFNKPSETNAYNVTTNQDGTVSYGARPTQNKPSETNAYNVTTHANGQ
VSYGARPTQKKPSKTNAYNVTTHANGQVSYGARPTQKKPSKTNAYNVTTH
ANGQVSYGARPTYKKPSETNAYNVTTHANGQVSYGARLTQKKPSETNAYN
VTTHADGTATYG >CoaST5_2_n85 (Mu50, N315)
                                            (SEQ ID NO: 23)
MKKQIISLGALAVASSLFTWDNKADAIVTKDYSKESRVNEKSKKGATVSD
YYYWKIIDSLEAQFTGAIDLLEDYKYGDPIYKEAKDRLMTRVLGEDQYLL
KKKIDEYELYKKWYKSSNKNTNMLTFHKYNLYNLTMNEYNDIFNSLKDAV
YQFNKEVKEIEHKNVDLKQFDKDGEDKATKEVYDLVSEIDTLVVTYYADK
DYGEHAKELRAKLDLILGDTDNPHKITNERIKKEMIDDLNSIIDDFFMET
KQNRPNSITKYDPTKHNFKEKSENKPNFDKLVEETKKAVKEADESWKNKT
VKKYEETVTKSPVVKEEKKVEEPQLPKVGNQQEVKTTAGKAEETTQPVAQ
PLVKIPQETIYGETVKGPEYPTMENKTLQGEIVQGPDFLTMEQNRPSLSD
NYTQPTTPNPILEGLEGSSSKLEIKPQGTESTLKGIQGESSDIEVKPQAT
ETTEASQYGPRPQFNKTPKYVKYRDAGTGIREYNDGTFGYEARPRFNKPS
ETNAYNVTTNQDGTVSYGARPTQNKPSETNAYNVTTHANGQVSYGARPTQ
KKPSKTNAYNVTTHANGQVSYGARPTQKKPSKTNAYNVTTHANGQVSYGA
RPTYKKPSETNAYNVTTHANGQVSYGARPTQKKPSETNAYNVTTHADGTA
TYGPRVTK R Domain:
                                            (SEQ ID NO: 86)
ARPRFNKPSETNAYNVTTNQDGTVSYGARPTQNKPSETNAYNVTTHANGQ
VSYGARPTQKKPSKTNAYNVTTHANGQVSYGARPTQKKPSKTNAYNVTTH
ANGQVSYGARPTYKKPSETNAYNVTTHANGQVSYGARPTQKKPSETNAYN
VTTHADGTATYG >CoaST5_3_n59
                                            (SEQ ID NO: 24)
MKKQIISLGALAVASSLFTWDNKADAIVTKDYSKESRVNEKSKKGATVSD
YYYWKIIDSLEAQFTGAIDLLEDYKYGDPIYKEAKDRLMTRVLGEDQYLL
KKKIDEYELYKKWYKSSNKNTNMLTFHKYNLYNLTMNEYNDIFNSLKDAV
YQFNKEVKEIEHKNVDLKQFDKDGEDKATKEVYDLVSEIDTLVVTYYADK
DYGEHAKELRAKLDLILGDTDNPHKITNERIKKEMIDDLNSIIDDFFMET
KQNRPNSITKYDPTKHNFKEKSENKPNFDKLVEETKKAVKEADESWKNKT
VKKYEETVTKSPVVKEEKKVEEPQLPKVGNQQEVKTTAGKAEETTQPVAQ
PLVKIPQETIYGETVKGPEYPTMENKTLQGEIVQGPDFLTMEQNRPSLSD
NYTQPTTPNPILEGLEGSSSKLEIKPQGTESTLKGIQGESSDIEVKPQAT
ETTEASQYGPRPQFNKTPKYVKYRDAGTGIREYNDGTFGYEARPRFNKPS
ETNAYNVTTNQDGTVSYGARPTQNKPSETNAYNVTTHANGQVSYGARPTY
KKPSETNAYNVTTHANGQVSYGARPTQKKPSKTNAYNVTTHANGQVSYGA
RPTYKKPSETNAYNVTTHANGQVSYGARPTQKKPSETNAYNVTTHADGTA
TYGPRVTK R Domain:
                                            (SEQ ID NO: 87)
ARPRFNKPSETNAYNVTTNQDGTVSYGARPTQNKPSETNAYNVTTHANGQ
VSYGARPTYKKPSETNAYNVTTHANGQVSYGARPTQKKPSKTNAYNVTTH
ANGQVSYGARPTYKKPSETNAYNVTTHANGQVSYGARPTQKKPSETNAYN
VTTHADGTATYG
``` b. ST8

Sequence analysis of the 82 full-length Coa sequences identified in the ST8 isolates revealed a total of 6 unique sequences, of which 2 were found once (i.e. each one in one single isolate). Another 2 unique sequences were found twice (i.e. each one found in two isolates). The remaining 2 unique sequences were the most dominant ones and were found in 57 and 19 isolates. Thus the 2 most dominant Coa sequences represented 93% of the full-length Coa sequences in ST8 (i.e. 57+19=76 of the 82). The reference isolates Newman and USA300 contain the most dominant and second most dominant Coa found within ST8, respectively. The 2 dominant ST8 Coa sequences are listed below in fasta-format, in the order from most to least dominant. R domains are underlined. Reference isolate(s) in which the corresponding sequence is found is/are given in brackets in the sequence header.

>CoaST8_1_n57 (Newman)
(SEQ ID NO: 25)
MKKQIISLGALAVASSLFTWDNKADAIVTKDYSGKSQVNAGSKNGTLIDS
RYLNSALYYLEDYIIYAIGLTNKYEYGDNIYKEAKDRLLEKVLREDQYLL
ERKKSQYEDYKQWYANYKKENPRTDLKMANFHKYNLEELSMKEYNELQDA
LKRALDDFHREVKDIKDKNSDLKTFNAAEEDKATKEVYDLVSEIDTLVVS
YYGDKDYGEHAKELRAKLDLILGDTDNPHKITNERIKKEMIDDLNSIIDD
FFMETKQNRPKSITKYNPTTHNYKTNSDNKPNFDKLVEETKKAVKEADDS
WKKKTVKKYGETETKSPVVKEEKKVEEPQAPKVDNQQEVKTTAGKAEETT
QPVAQPLVKIPQGTITGEIVKGPEYPTMENKTVQGEIVQGPDFLTMEQSG
PSLSNNYTNPPLTNPILEGLEGSSSKLEIKPQGTESTLKGTQGESSDIEV
KPQATETTEASQYGPRPQFNKTPKYVKYRDAGTGIREYNDGTFGYEARPR
FNKPSETNAYNVTTHANGQVSYGARPTYKKPSETNAYNVTTHANGQVSYG
ARPTQNKPSKTNAYNVTTHGNGQVSYGARPTQNKPSKTNAYNVTTHANGQ
VSYGARPTYKKPSKTNAYNVTTHADGTATYGPRVTK R Domain:
(SEQ ID NO: 88)
ARPRFNKPSETNAYNVTTHANGQVSYGARPTYKKPSETNAYNVTTHANGQ
VSYGARPTQNKPSKTNAYNVTTHGNGQVSYGARPTQNKPSKTNAYNVTTH
ANGQVSYGARPTYKKPSKTNAYNVTTHADGTATYG >CoaST8_2_n19 (USA300)
(SEQ ID NO: 26)
MKKQIISLGALAVASSLFTWDNKADAIVTKDYSGKSQVNAGSKNGTLIDS
RYLNSALYYLEDYIIYAIGLTNKYEYGDNIYKEAKDRLLEKVLREDQYLL
ERKKSQYEDYKQWYANYKKENPRTDLKMANFHKYNLEELSMKEYNELQDA
LKRALDDFHREVKDIKDKNSDLKTFNAAEEDKATKEVYDLVSEIDTLVVS
YYGDKDYGEHAKELRAKLDLILGDTDNPHKITNERIKKEMIDDLNSIIDD
FFMETKQNRPKSITKYNPTTHNYKTNSDNKPNFDKLVEETKKAVKEADDS
WKKKTVKKYGETETKSPVVKEEKKVEEPQAPKVDNQQEVKTTAGKAEETT
QPVAQPLVKIPQGTITGEIVKGPEYPTMENKTVQGEIVQGPDFLTMEQSG
PSLSNNYTNPPLTNPILEGLEGSSSKLEIKPQGTESTLKGTQGESSDIEV
KPQATETTEASQYGPRPQFNKTPKYVKYRDAGTGIREYNDGTFGYEARPR
FNKPSETNAYNVTTHANGQVSYGARPTQNKPSKTNAYNVTTHGNGQVSYG
ARPTQNKPSKTNAYNVTTHANGQVSYGARPTYKKPSKTNAYNVTTHADGT
ATYGPRVTK R Domain:
(SEQ ID NO: 89)
ARPRFNKPSETNAYNVTTHANGQVSYGARPTQNKPSKTNAYNVTTHGNGQ
VSYGARPTQNKPSKTNAYNVTTHANGQVSYGARPTYKKPSKTNAYNVTTH
ADGTATYG c. ST22

Sequence analysis of the 165 full-length Coa sequences identified in the ST22 isolates revealed a total of 25 unique sequences, of which 17 were found once (i.e. each one in one single isolate). Another 3 unique sequences were found three times (i.e. each one found in three isolates). Of the remaining 5 unique sequences, the three most dominant Coa sequences were found in 123, 8 and 5 isolates. Thus the 3 most dominant Coa sequences represented 82% of the full-length Coa sequences in ST22 (i.e. 123+8+5=136 of the 165). The 3 dominant ST22 Coa sequences are listed below in fasta-format, in the order from most to least dominant. R domains are underlined.

>CoaST22_1_n123
(SEQ ID NO: 27)
MKKQIISLGALAVASSLFTWDNKADAIVTKDYNGKSQVKKESKNGTLIDS
RYYWEKIEALEKQFSSALALTDEYQYGGNEYKEAKDKLMERILGEDQYLL
KKKIDEYDYYKKWYKATYPNDNSKMYSFHKYNVYYLTMNEYNEITNSLKD
AVEKFNNEVRDIQSKNEDLKPYDENTEKQETDKIYEFVSEIDTVFAAYYS
HEKFGIHAKELRAKLDIILGDVHNPNRITNERIKKEMMEDLNSIVDDFFM
ETNQNRPTTIKKYDPNIHDYTKKKENKENFDKLVKETREAVEKADESWKN
KTVKKYEETVTKSPFVKEEKKVEEPQLPKVGNQQEVKTTAGKAEETTQPL
VKIPQGTITGEIVKGPDYPTMENKTLQGEIVQGPDFPTMEQNRPSLSDNY
TQPTTTNPILEGLEGSSSKLEIKPQGTESTLQGTQGESSDIEVKPQATET
TEASQYGPRPQFNKTPKYVKYRDAGTGIREYNDGTFGYEARPRFNKPSET
NAYNVTTNQDGTVTYGARPTQNKPSKTNAYNVTTHANGQVSYGARPTYKK
PSETNAYNVTTHANGQVSYGARPTQNKASETNAYNVTTHANGQVSYGARP
TQNKPSKTNAYNVTTHGNGQVSYGARPTYKKPSETNAYNVTTHADGTATY
GPRVTK

R Domain:
(SEQ ID NO: 90)
ARPRFNKPSETNAYNVTTNQDGTVTYGARPTQNKPSKTNAYNVTTHANGQ
VSYGARPTYKKPSETNAYNVTTHANGQVSYGARPTQNKASETNAYNVTTH
ANGQVSYGARPTQNKPSKTNAYNVTTHGNGQVSYGARPTYKKPSETNAYN
VTTHADGTATYG >CoaST22_2_n8
(SEQ ID NO: 28)
MKKQIISLGALAVASSLFTWDNKADAIVTKDYNGKSQVKKESKNGTLIDS
RYYWEKIEALEKQFSSALALTDEYQYGGNEYKEAKDKLMERILGEDQYLL
KKKIDEYDYYKKWYKATYPNDNSKMYSFHKYNVYYLTMNEYNEISNSLKD
AVEKFNNEVRDIQSKNEDLKPYDENTEKQETDKIYEFVSEIDTVFAAYYS
HEKFGIHAKELRAKLDIILGDVHNPNRITNERIKKEMMEDLNSIVDDFFM
ETNQNRPTTIKKYDPNIHDYTKKKENKENFDKLVKETREAVEKADESWKN
KTVKKYEETVTKSPFVKEEKKVEEPQLPKVGNQQEVKTTAGKAEETTQPL
VKIPQGTITGEIVKGPDYPTMENKTLQGEIVQGPDFPTMEQNRPSLSDNY
TQPTTTNPILEGLEGSSSKLEIKPQGTESTLQGTQGESSDIEVKPQATET
TEASQYGPRPQFNKTPKYVKYRDAGTGIREYNDGTFGYEARPRFNKPSET
NAYNVTTNQDGTVTYGARPTQNKPSKTNAYNVTTHANGQVSYGARPTYKK
PSETNAYNVTTHANGQVSYGARPTQNKASETNAYNVTTHANGQVSYGARP
TQNKPSKTNAYNVTTHGNGQVSYGARPTYKKPSETNAYNVTTHADGTATY
GPRVTK R Domain:
(SEQ ID NO: 91)
ARPRFNKPSETNAYNVTTNQDGTVTYGARPTQNKPSKTNAYNVTTHANGQ
VSYGARPTYKKPSETNAYNVTTHANGQVSYGARPTQNKASETNAYNVTTH
ANGQVSYGARPTQNKPSKTNAYNVTTHGNGQVSYGARPTYKKPSETNAYN
VTTHADGTATYG >CoaST22_3_n5
(SEQ ID NO: 29)
MKKQIISLGALAVASSLFTWDNKADAIVTKDYNGKSQVKKESKNGTLIDS
RYYWEKIEALEKQFSSALALTDEYQYGGNEYKEAKDKLMERILGEDQYLL
KKKIDEYDYYKKWYKATYPNDNSKMYSFHKYNVYYLTMNEYNEITNSLKD
AVEKFNNEVRDIQSKNEDLKPYDENTEKQETDKIYEFVSEIDTVFAAYYS
HEKFGIHAKELRAKLDIILGDVHNPNRITNERIKKEMMEDLNSIVDDFFM
ETNQNRPTTIKKYDPNIHDYTKKKENKENFDKLVKETREAVEKADESWKN
KTVKKYEETVTKSPFVKEEKKVEEPQLPKVGNQQEVKTTAGKAEETTQPL
VKIPQGTITGEIVKGPDYPTMENKTLQGEIVQGPDFPTMEQNRPSLSDNY
TQPTTTNPILEGLEGSSSKLEIKPQGTESTLQGTQGESSDIEVKPQATET
TEASQYGPRPQFNKTPKYVKYRDAGTGIREYNDGTFGYEARPRFNKPSET
NAYNVTTNQDGTVTYGARPTQNKPSKTNAYNVTTHANGQVSYGARPTYKK
PSETNAYNVTTHANGTATYGPRVTK R Domain:
(SEQ ID NO: 92)
ARPRFNKPSETNAYNVTTNQDGTVTYGARPTQNKPSKTNAYNVTTHANGQ
VSYGARPTYKKPSETNAYNVTTHANGTATYG d. ST30

Sequence analysis of the 41 full-length Coa sequences identified in the ST30 isolates revealed a total of 9 unique sequences, of which 6 were found once (i.e. each one in one single isolate). The remaining 3 unique sequences were the most dominant ones and were found in 27, 5 and 3 isolates. Thus the 3 most dominant Coa sequences represented 85% of the full-length Coa sequences in ST30 (i.e. 27+5+3=35 of the 41). The reference isolate MRSA252, which is not an ST30 but an ST36 isolate (a single locus variant of ST30), contains the most dominant Coa found within ST30. The reference isolate 85/2082, which is not an ST30 but an ST239 isolate, contains the second most dominant Coa found within ST30 (this Coa was found to be identical to the most dominant Coa within ST239: see below). The 3 dominant ST30 Coa sequences are listed below in fasta-format, in the order from most to least dominant. R domains are underlined. Reference isolate(s) in which the corresponding sequence is found is/are given in brackets in the sequence header.

>CoaST30_1_n27 (MRSA252)
(SEQ ID NO: 30)
MKKQIISLGALAVASSLFTWDNKADAIVTKDYSKESRVNENSKYDTPIPD
WYLGSILNRLGDQIYYAKELTNKYEYGEKEYKQAIDKLMTRVLGEDHYLL
EKKKAQYEAYKKWFEKHKSENPHSSLKKIKFDDFDLYRLTKKEYNELHQS
LKEAVDEFNSEVKNIQSKQKDLLPYDEATENRVTNGIYDFVCEIDTLYAA
YFNHSQYGHNAKELRAKLDIILGDAKDPVRITNERIRKEMMDDLNSIIDD
FFMDTNMNRPLNITKFNPNIHDYTNKPENRDNFDKLVKETREAIANADES
WKTRTVKNYGESETKSPVVKEEKKVEEPQLPKVGNQQEDKITVGTTEEAP
LPIAQPLVKIPQGTIQGEIVKGPEYLTMENKTLQGEIVQGPDFPTMEQNR
PSLSDNYTQPTTPNPILKGIEGNSTKLEIKPQGTESTLKGTQGESSDIEV
KPQATETTEASHYPARPQFNKTPKYVKYRDAGTGIREYNDGTFGYEARPR
FNKPSETNAYNVTTNQDGTVSYGARPTQNKPSETNAYNVTTHANGQVSYG
ARPTQNKPSETNAYNVTTHANGQVSYGARPTQNKPSKTNAYNVTTHADGT
ATYGPRVTK

R Domain:
(SEQ ID NO: 93)
ARPRFNKPSETNAYNVTTNQDGTVSYGARPTQNKPSETNAYNVTTHANGQ
VSYGARPTQNKPSETNAYNVTTHANGQVSYGARPTQNKPSKTNAYNVTTH
ADGTATYG >CoaST30_2_n5 (85/2082)
(SEQ ID NO: 31)
MKKQIISLGALAVASSLFTWDNKADAIVTKDYSKESRVNENSKYDTPIPD
WYLGSILNRLGDQIYYAKELTNKYEYGEKEYKQAIDKLMTRVLGEDHYLL
EKKKAQYEAYKKWFEKHKSENPHSSLKKIKFDDFDLYRLTKKEYNELHQS
LKEAVDEFNSEVKNIQSKQKDLLPYDEATENRVTNGIYDFVCEIDTLYAA
YFNHSQYGHNAKELRAKLDIILGDAKDPVRITNERIRKEMMDDLNSIIDD
FFMDTNMNRPLNITKFNPNIHDYTNKPENRDNFDKLVKETREAVANADES
WKTRTVKNYGESETKSPVVKEEKKVEEPQLPKVGNQQEDKITVGTTEEAP
LPIAQPLVKIPQGTIQGEIVKGPEYLTMENKTLQGEIVQGPDFPTMEQNR
PSLSDNYTQPTTPNPILKGIEGNSTKLEIKPQGTESTLKGTQGESSDIEV
KPQATETTEASHYPARPQFNKTPKYVKYRDAGTGIREYNDGTFGYEARPR
FNKPSETNAYNVTTNQDGTVSYGARPTQNKPSETNAYNVTTHANGQVSYG
ARPTYKKPSETNAYNVTTNQDGTVSYGARPTQNKPSETNAYNVTTHANGQ
VSYGARPTQNKPSETNAYNVTTHANGQVSYGARPTQNKPSKTNAYNVTTH
ADGTATYGPRVTK R Domain:
(SEQ ID NO: 94)
ARPRFNKPSETNAYNVTTNQDGTVSYGARPTQNKPSETNAYNVTTHANGQ
VSYGARPTYKKPSETNAYNVTTNQDGTVSYGARPTQNKPSETNAYNVTTH
ANGQVSYGARPTQNKPSETNAYNVTTHANGQVSYGARPTQNKPSKTNAYN
VTTHADGTATYG >CoaST30_3_n3
(SEQ ID NO: 32)
MKKQIISLGALAVASSLFTWDNKADAIVTKDYSKESRVNENSKYDTPIPD
WYLGSILNRLGDQIYYAKELTNKYEYGEKEYKQAIDKLMTRVLGEDHYLL
EKKKAQYEAYKKWFEKHKSENPHSSLKKIKFDDFDLYRLTKKEYNELHQS
LKEAVDEFNSEVKNIQSKQKDLLPYDEATENRVTNGIYDFVCEIDTLYAA
YFNHSQYGHNAKELRAKLDIILGDAKDPVRITNERIRKEMMDDLNSIIDD
FFMDTNMNRPLNITKFNPNIHDYTNKPENRDNFDKLVKETREAIANADES
WKTRTVKNYGESETKSPVVKEEKKVEEPQLPKVGNQQEDKITVGTTEEAP LPIAQPLVKIPQGTIQGEIVKGPEYLTMENKTLQGEIVQGPDFPTMEQNR
PSLSDNYTQPTTPNPILKGIEGNSTKLEIKPQGTESTLKGTQGESSDIEV
KPQATETTEASHYPARPQFNKTPKYVKYRDAGTGIREYNDGTFGYEARPR
FNKPSETNAYNVTTNQDGTVSYGARPTQNKPSETNAYNVTTHANGQVSYG
ARPTYKKPSETNAYNVTTNQDGTVSYGARPTQNKPSETNAYNVTTHANGQ
VSYGARPTQNKPSETNAYNVTTHANGQVSYGARPTQNKPSKTNAYNVTTH
ADGTATYGPRVTK R Domain:
(SEQ ID NO: 95)
ARPRFNKPSETNAYNVTTNQDGTVSYGARPTQNKPSETNAYNVTTHANGQ
VSYGARPTYKKPSETNAYNVTTNQDGTVSYGARPTQNKPSETNAYNVTTH
ANGQVSYGARPTQNKPSETNAYNVTTHANGQVSYGARPTQNKPSKTNAYN
VTTHADGTATYG e. ST45

Sequence analysis of the 57 full-length Coa sequences identified in the ST45 isolates revealed a total of 19 unique sequences, of which 12 were found once (i.e. each one in one single isolate). Another 2 unique sequences were found twice (i.e. each one found in two isolates). Of the remaining 5 unique sequences the three most dominant ones were found in 16, 15 and 4 isolates. Thus the 3 most dominant Coa sequences represented 61% of the full-length Coa sequences in ST45 (i.e. 16+15+4=35 of the 57). The reference isolates WIS contains the second most dominant Coa found within ST45. The 3 dominant ST45 Coa sequences are listed below in fasta-format, in the order from most to least dominant. R domains are underlined. Reference isolate(s) in which the corresponding sequence is found is/are given in brackets in the sequence header.

>ST45_1_n16
(SEQ ID NO: 33)
MKKQIISLGALAVASSLFTWDNKADAIVTKDYSGKSQVNAGSKNGKQIAD
GYYWGIIENLENQFYNIFHLLDQHKYAEKEYKDALDKLKTRVLEEDQYLL
ERKKEKYEIYKELYKKYKKENPNTQVKMKAFDKYDLGDLTMEEYNDLSKL
LTKALDNFKLEVKKIESENPDLRPYSESEERTAYGKIDSLVDQAYSVYFA
YVTDAQHKTEALNLRAKIDLILGDEKDPIRVTNQRTEKEMIKDLESIIDD
FFIETKLNRPQHITRYDGTKHDYHKHKDGFDALVKETREAVSKADESWKT
KTVKKYGETETKYPVVKEEKKVEEPQSPKVSEKVDVQETVGTTEEAPLPI
AQPLVKLPQIGTQGEIVKGPDYPTMENKTLQGVIVQGPDFPTMEQNRPSL
SDNYTQPSVTLPSITGESTPTNPILKGIEGNSSKLEIKPQGTESTLKGIQ
GESSDIEVKPQATETTEASHYPARPQFNKTPKYVKYRDAGTGIREYNDGT
FGYEARPRFNKPSETNAYNVTTNQDGTVSYGARPTQNKPSKTNAYNVTTH
ANGQVSYGARPTYNKPSKTNAYNVTTHADGTATYGPRVTK

R Domain:
(SEQ ID NO: 96)
ARPRFNKPSETNAYNVTTNQDGTVSYGARPTQNKPSKTNAYNVTTHANGQ
VSYGARPTYNKPSKTNAYNVTTHADGTATYG >ST45_2_n15 (WIS)
(SEQ ID NO: 34)
MKKQIISLGALAVASSLFTWDNKADAIVTKDYSGKSQVNAGSKNGKQIAD
GYYWGIIENLENQFYNIFHLLDQHKYAEKEYKDALDKLKTRVLEEDQYLL
ERKKEKYEIYKELYKKYKKENPNTQVKMKAFDKYDLGDLTMEEYNDLSKL
LTKALDNFKLEVKKIESENPDLRPYSESEERTAYGKIDSLVDQAYSVYFA
YVTDAQHKTEALNLRAKIDLILGDEKDPIRVTNQRTEKEMIKDLESIIDD
FFIETKLNRPQHITRYDGTKHDYHKHKDGFDALVKETREAVSKADESWKT
KTVKKYGETETKYPVVKEEKKVEEPQSPKVSEKVDVQETVGTTEEAPLPI
AQPLVKLPQIGTQGEIVKGPDYPTMENKTLQGVIVQGPDFPTMEQNRPSL
SDNYTQPSVTLPSITGESTPTNPILKGIEGNSSKLEIKPQGTESTLKGIQ
GESSDIEVKPQATETTEASHYPARPQFNKTPKYVKYRDAGTGIREYNDGT
FGYEARPRFNKPSETNAYNVTTNQDGTVSYGARPTQNKPSKTNAYNVTTH
ANGQVSYGARPTYNKPSETNAYNVTTNRDGTVSYGARPTQNKPSETNAYN
VTTHGNGQVSYGARPTQKKPSKTNAYNVTTHANGQVSYGARPTYNKPSKT
NAYNVTTHADGTATYGPRVTK R Domain:
(SEQ ID NO: 97)
ARPRFNKPSETNAYNVTTNQDGTVSYGARPTQNKPSKTNAYNVTTHANGQ
VSYGARPTYNKPSETNAYNVTTNRDGTVSYGARPTQNKPSETNAYNVTTH
GNGQVSYGARPTQKKPSKTNAYNVTTHANGQVSYGARPTYNKPSKTNAYN
VTTHADGTATYG >ST45_3_n4
(SEQ ID NO: 35)
MKKQIISLGALAVASSLFTWDNKADAIVTKDYSGKSQVNAGSKNGKQIAD
GYYWGIIENLENQFYNIFHLLDQHKYAEKEYKDALDKLKTRVLEEDQYLL
ERKKEKYEIYKELYKKYKKENPNTQVKMKAFDKYDLGDLTMEEYNDLSKL
LTKALDNFKLEVKKIESENPDLRPYSESEERTAYGKIDSLVDQAYSVYFA
YVTDAQHKTEALNLRAKIDLILGDEKDPIRVTNQRTEKEMIKDLESIIDD
FFIETKLNRPQHITRYDGTKHDYHKHKDGFDALVKETREAVSKADESWKT
KTVKKYGETETKYPVVKEEKKVEEPQSPKVSEKVDVQETVGTTEEAPLPI
AQPLVKLPQIGTQGEIVKGPDYPTMENKTLQGVIVQGPDFPTMEQNRPSL
SDNYTQPSVTLPSITGESTSTNPILKGIEGNSSKLEIKPQGTESTLKGIQ
GESSDIEVKPQATETTEASHYPARPQFNKTPKYVKYRDAGTGIREYNDGT
FGYEARPRFNKPSETNAYNVTTNQDGTVSYGARPTQNKPSKTNAYNVTTH
ANGQVSYGARPTYNKPSETNAYNVTTNRDGTVSYGARPTQNKPSETNAYN
VTTHGNGQVSYGARPTQKKPSKTNAYNVTTHANGQVSYGARPTQKKPSKT
NAYNVTTHADGTATYGPRVTK R Domain:
(SEQ ID NO: 98)
ARPRFNKPSETNAYNVTTNQDGTVSYGARPTQNKPSKTNAYNVTTHANGQ
VSYGARPTYNKPSETNAYNVTTNRDGTVSYGARPTQNKPSETNAYNVTTH
GNGQVSYGARPTQKKPSKTNAYNVTTHANGQVSYGARPTQKKPSKTNAYN
VTTHADGTATYG f. ST239

Sequence analysis of the 21 full-length Coa sequences identified in the ST239 isolates revealed a total of 7 unique sequences, of which 4 were found once (i.e. each one in one single isolate). The remaining 3 unique sequences were the most dominant ones and were found in 10, 4 and 3 isolates. Thus the 3 most dominant Coa sequences represented 81% of the full-length Coa sequences in ST239 (i.e. 10+4+3=17 of the 21). The reference isolate 85/2082 contains the most dominant Coa found within ST239, which is identical to the second most dominant Coa within ST30. The 3 dominant ST239 Coa sequences are listed below in fasta-format, in the order from most to least dominant. R domains are underlined. Reference isolate(s) in which the corresponding sequence is found is/are given in brackets in the sequence header.

>CoaST239_1_n10 (85/2082)
(SEQ ID NO: 36)
MKKQIISLGALAVASSLFTWDNKADAIVTKDYSKESRVNENSKYDTPIPD
WYLGSILNRLGDQIYYAKELTNKYEYGEKEYKQAIDKLMTRVLGEDHYLL
EKKKAQYEAYKKWFEKHKSENPHSSLKKIKFDDFDLYRLTKKEYNELHQS
LKEAVDEFNSEVKNIQSKQKDLLPYDEATENRVTNGIYDFVCEIDTLYAA
YFNHSQYGHNAKELRAKLDIILGDAKDPVRITNERIRKEMMDDLNSIIDD
FFMDTNMNRPLNITKFNPNIHDYTNKPENRDNFDKLVKETREAVANADES
WKTRTVKNYGESETKSPVVKEEKKVEEPQLPKVGNQQEDKITVGTTEEAP
LPIAQPLVKIPQGTIQGEIVKGPEYLTMENKTLQGEIVQGPDFPTMEQNR
PSLSDNYTQPTTPNPILKGIEGNSTKLEIKPQGTESTLKGTQGESSDIEV
KPQATETTEASHYPARPQFNKTPKYVKYRDAGTGIREYNDGTFGYEARPR
FNKPSETNAYNVTTNQDGTVSYGARPTQNKPSETNAYNVTTHANGQVSYG
ARPTYKKPSETNAYNVTTNQDGTVSYGARPTQNKPSETNAYNVTTHANGQ
VSYGARPTQNKPSETNAYNVTTHANGQVSYGARPTQNKPSKTNAYNVTTH
ADGTATYGPRVTK

R Domain:
(SEQ ID NO: 99)
ARPRFNKPSETNAYNVTTNQDGTVSYGARPTQNKPSETNAYNVTTHANGQ
VSYGARPTYKKPSETNAYNVTTNQDGTVSYGARPTQNKPSETNAYNVTTH
ANGQVSYGARPTQNKPSETNAYNVTTHANGQVSYGARPTQNKPSKTNAYN
VTTHADGTATYG >CoaST239_2_n4
(SEQ ID NO: 37)
MKKQIISLGALAVASSLFTWDNKADAIVTKDYSKESRVNENSKYDTPIPD
WYLGSILNRLGDQIYYAKELTNKYEYGEKEYKQAIDKLMTRVLGEDHYLL
EKKKAQYEAYKKWFEKHKSENPHSSLKKIKFDDFDLYRLTKKEYNELHQS
LKEAVDEFNSEVKNIQSKQKDLLPYDEATENRVTNGIYDFVCEIDTLYAA
YFNHSQYGHNAKELRAKLDIILGDAKDPVRITNERIRKEKMDDLNSIIDD
FFMDTNMNRPLNITKFNPNIHDYTNKPENRDNFDKLVKETREAVANADES
WKTRTVKNYGESETKSPVVKEEKKVEEPQLPKVGNQQEDKITVGTTEEAP
LPIAQPLVKIPQGTIQGEIVKGPEYLTMENKTLQGEIVQGPDFPTMEQNR
PSLSDNYTQPTTPNPILKGIEGNSTKLEIKPQGTESTLKGTQGESSDIEV
KPQATETTEASHYPARPQFNKTPKYVKYRDAGTGIREYNDGTFGYEARPR
FNKPSETNAYNVTTNQDGTVSYGARPTQNKPSETNAYNVTTHANGQVSYG
ARPTYKKPSETNAYNVTTNQDGTVSYGARPTQNKPSETNAYNVTTHANGQ
VSYGARPTQNKPSETNAYNVTTHANGQVSYGARPTQNKPSKTNAYNVTTH
ADGTATYGPRVTK R Domain:
(SEQ ID NO: 100)
ARPRFNKPSETNAYNVTTNQDGTVSYGARPTQNKPSETNAYNVTTHANGQ
VSYGARPTYKKPSETNAYNVTTNQDGTVSYGARPTQNKPSETNAYNVTTH
ANGQVSYGARPTQNKPSETNAYNVTTHANGQVSYGARPTQNKPSKTNAYN
VTTHADGTATYG >CoaST239_3_n3
(SEQ ID NO: 38)
MKKQIISLGALAVASSLFTWDNKADAIVTKDYSKESRVNENSKYDTPIPD
WYLGSILNRLGDQIYYAKELTNKYEYGEKEYKQAIDKLMTRVLGEDHYLL
EKKKAQYEAYKKWFEKHKSENPHSSLKKIKFDDFDLYRLTKKEYNELHQS
LKEAVDEFNSEVKNIQSKQKDLLPYDEATENRVTNGIYDFVCEIDTLYAA
YFNHSQYGHNAKELRAKLDIILGDAKDPVRITNERIRKEKMDDLNSIIDD
FFMDTNMNRPLNITKFNPNIHDYTNKPENRDNFDKLVKETREAVANADES
WKTRTVKNYGESETKSPVVKEEKKVEEPQLPKVGNQQEDKITVGTTEEAP
LPIAQPLVKIPQGTIQGEIVKGPEYLTMENKTLQGEIVQGPDFPTMEQNR
PSLSDNYTQPTTPNPILKGIEGNSTKLEIKPQGTESTLKGTQGESSDIEV
KPQATETTEASHYPARPQFNKTPKYVKYRDAGTGIREYNDGTFGYEARPR
FNKPSETNAYNVTTNQDGTVSYGARPTQNKPSETNAYNVTTHANGQVSYG
ARPTQNKPSETNAYNVTTHANGQVSYGARPTQNKPSKTNAYNVTTHADGT
ATYGPRVTK R Domain:
(SEQ ID NO: 101)
ARPRFNKPSETNAYNVTTNQDGTVSYGARPTQNKPSETNAYNVTTHANGQ
VSYGARPTQNKPSETNAYNVTTHANGQVSYGARPTQNKPSKTNAYNVTTH
ADGTATYG 6. Identification of a Consensus R-Repeat Sequence Coa R-domains consist of one to several 27 amino acid tandem repeats (R-repeats). To identify the consensus R-repeat for invasive *S. aureus* strains, all unique R-repeat sequences were extracted from the R domain sequences listed above (i.e. SEQ ID NO: 39-55), resulting in a set of 20 sequences, which were aligned manually. A 90% consensus R-repeat sequence was defined on the basis of this alignment (Table 3).

TABLE 3

Identification of a 90% consensus R-repeat in six dominant *S. aureus* lineages.

| SEQ ID NO. | R-REPEAT SEQUENCE |
| --- | --- |
| 102 | ARPTYNKPSETNAYNVTTNRDGTVSYG |
| 103 | ARPTYKKPSETNAYNVTTNQDGTVSYG |
| 104 | ARPRFNKPSETNAYNVTTNQDGTVSYG |

TABLE 3-continued

Identification of a 90% consensus R-repeat in six dominant *S. aureus* lineages.

| SEQ ID NO. | R-REPEAT SEQUENCE |
|---|---|
| 105 | ARPRFNKPSETNAYNVTTNQDGTVTYG |
| 106 | ARPTYNKPSKTNAYNVTTHADGTATYG |
| 107 | ARPTYKKPSKTNAYNVTTHADGTATYG |
| 108 | ARPTYKKPSETNAYNVTTHANGTATYG |
| 109 | ARPTYKKPSETNAYNVTTHADGTATYG |
| 110 | ARPTQNKPSKTNAYNVTTHADGTATYG |
| 111 | ARPTQKKPSKTNAYNVTTHADGTATYG |
| 112 | ARPTQKKPSETNAYNVTTHADGTATYG |
| 113 | ARLTQKKPSETNAYNVTTHADGTATYG |
| 114 | ARPTYKKPSETNAYNVTTHANGQVSYG |
| 115 | ARPRFNKPSETNAYNVTTHANGQVSYG |
| 116 | ARPTQKKPSKTNAYNVTTHANGQVSYG |
| 117 | ARPTQNKPSKTNAYNVTTHANGQVSYG |
| 118 | ARPTQNKPSKTNAYNVTTHGNGQVSYG |
| 119 | ARPTQNKASETNAYNVTTHANGQVSYG |
| 120 | ARPTQNKPSETNAYNVTTHANGQVSYG |
| 121 | ARPTQNKPSETNAYNVTTHGNGQVSYG |
| 90% consensus (SEQ ID NO: 127) | ARP---KPS-TNAYNVTT---G---YG |

D. Conclusions:

It was identified that ST5_(USA100), ST8 (USA300), ST22, and ST239 are dominant MRSA clones found in USA, Europe and Asia. Other relevant MSSA *S. aureus* clones linked to invasive infections are ST30 and ST45 that appear to be spread predominantly in several EU member states. For each lineage we have identified the most dominant two or three full-length Coa sequences, which can be used for selecting representative R-domains from clinically relevant *Staphylococcus aureus* strains to be used in a vaccine composition.

Example 3

A polypeptide comprising the R-domain subunit of the coagulase protein from *Staphylococcus aureus* USA300LAC (SEQ ID NO:1) was produced recombinantly in *Escherichia coli* with an N-terminal His-SUMO tag, which was removed after purification. The R domain was defined as amino acid positions 470-583 of the full length mature coagulase protein, and the R-domain subunit expressed was, after tag removal, unchanged from that present in the full-length protein. The sequence of the purified R-domain subunit was:

```
                                           (SEQ ID NO: 56)
EARPRFNKPSETNAYNVTTHANGQVSYGARPTQNKPSKTNAYNVTTHGNG

QVSYGARPTQNKPSKTNAYNVTTHANGQVSYGARPTYKKPSKTNAYNVTT

HADGTATYGPRVTK,
``` which comprises the R domain as defined in SEQ ID NO:43 and 89

Antibodies were produced by immunization of a New Zealand White rabbit with 3 intramuscular doses of 100 μg recombinant R-domain adsorbed to aluminium hydroxide adjuvant. Doses were administered 3 weeks apart, with a final bleed taken 3 weeks after the last dose. Total IgG was obtained from sera using Protein G purification and stored in PBS.

Mouse challenge studies were performed with *S. aureus* strain USA300LAC as described previously (Thomer L. et al., J Exp Med. 2016 Mar. 7; 213(3):293-301).

The Whole Blood Killing Assay (WBKA) measures the ability of fresh blood to kill bacteria. For *S. aureus*, killing requires opsonization of the bacteria with antibodies and complement proteins, followed by phagocytosis and subsequent killing. Supplementing additional antibodies into the blood tests the ability of those antibodies to improve killing either by increasing the degree of opsonization or by inhibiting the activity of Staphylococcal proteins that prevent phagocytosis. WBKAs were performed with fresh (<1 hour old) heparinated blood from healthy human donors. *S. aureus* strain USA300LAC was grown to early-log phase and added to the healthy donor blood at $5 \times 10^5$ CFU/mL in the presence of 5 μg/mL purified IgG or PBS. Cytochalasin D was added to control tubes to inhibit killing by phagocytosis. After 60 minutes incubation, the colony counts were determined as described previously (Thomer L. et al., J Exp Med. 2016 Mar. 7; 213(3):293-301). The percentage of survival of the bacteria at Time=60 minutes was calculated relative to the number of bacteria measured at Time=0 minutes.

Figure 9:
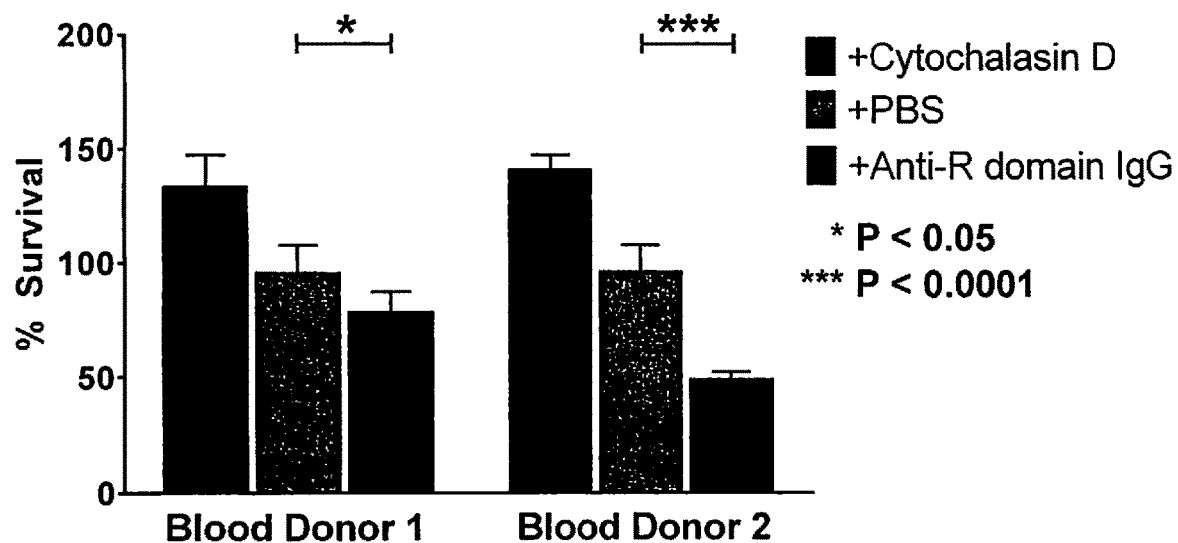
FIG. 9: Anti-R domain IgG enhances opsonophagocytic killing of *S. aureus* by human whole blood.

As shown in FIG. 9, anti-R domain IgG enhances opsonophagocytic killing of *S. aureus* by human whole blood. Purified rabbit anti-R domain IgG was tested for the capacity to induce killing of *S. aureus* by phagocytosis in human whole blood. Blood from two donors was tested independently. With both blood donors the addition of the phagocytosis-inhibitor Cytochalasin D increased survival of the bacteria, indicating that the donor blood was already capable of some phagocytic killing of *S. aureus*. The addition of anti-R domain IgG significantly decreased bacterial survival in the blood of both donors compared to the PBS controls, indicating that anti-R domain IgG enhances opsonophagocytic killing of *S. aureus* by human cells.

Figure 10:
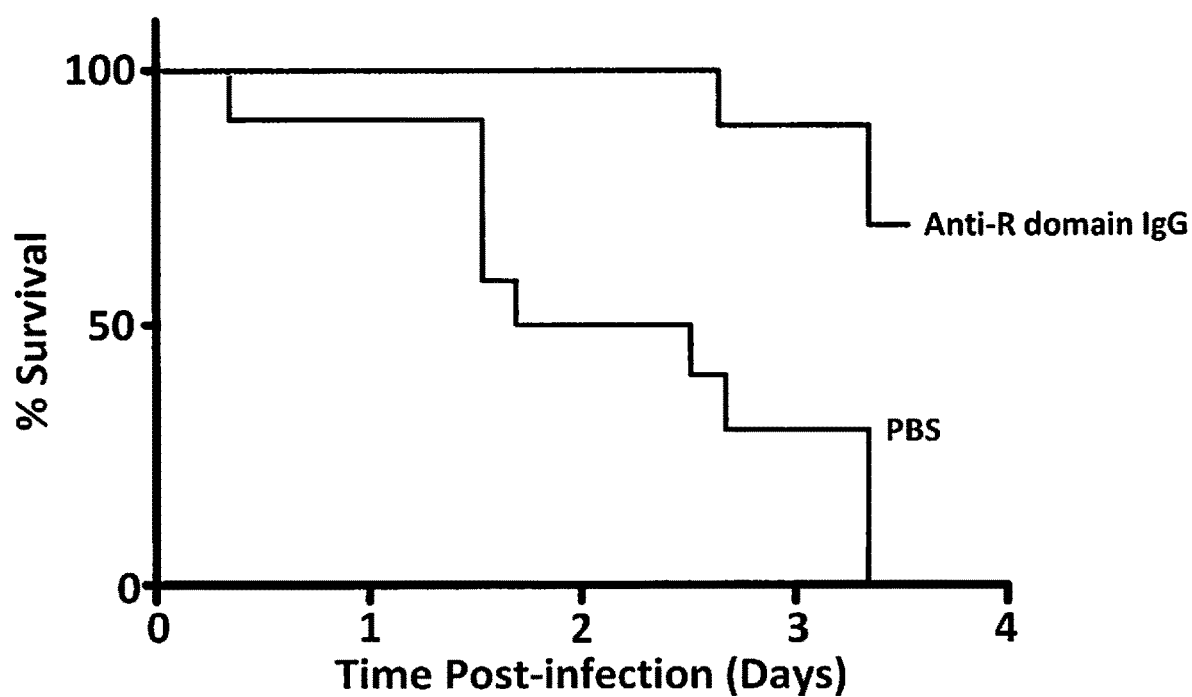
As shown in FIG. 10, anti-R domain IgG improves survival of mice in a *S. aureus* lethal challenge model. The bars represent, from left to right+Cytochalasin D, +PBS, and +anti-R domain IgG for each X-axis group of data.

As shown in FIG. 10, anti-R domain IgG improves survival of mice in a *S. aureus* lethal challenge model. Mice were passively immunized with anti-R domain IgG or a PBS control prior to lethal infection with *S. aureus*. Mice given anti-R domain IgG showed significantly improved survival compared to those given only PBS ($P<0.0005$).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All references cited in this application are specifically incorporated by reference for all purposes.

REFERENCES

The following references, to the extent that they provide exemplary procedural or other details supplementary to those set forth herein, are specifically incorporated herein by reference.

Bae, T., and O. Schneewind. 2005. Allelic replacement in Staphylococcus aureus with inducible counter-selection. Plasmid 55:58-63.

Bjerketorp, J., K. Jacobsson, and L. Frykberg. 2004. The von Willebrand factor-binding protein (vWbp) of Staphylococcus aureus is a coagulase. FEMS Microbiol. Lett. 234:309-314.

Cheng, A. G., M. McAdow, H. K. Kim, T. Bae, D. M. Missiakas, and O. Schneewind. 2010. Contribution of coagulases towards Staphylococcus aureus disease and protective immunity. PLoS Pathog. 6:e1001036.

David, M. Z., and R. S. Daum. 2010. Community-associated methicillin-resistant Staphylococcus aureus: epidemiology and clinical consequences of an emerging epidemic. Clin. Microbiol. Rev. 23:616-687.

Duthie, E. S. 1954. Evidence for two forms of Staphylococcal coagulase. Journal of general microbiology 10:427-436.

Fowler, V. G., K. B. Allen, E. D. Moreira, M. Moustafa, F. Isgro, H. W. Boucher, G. R. Corey, Y. Carmeli, R. Betts, J. S. Hartzel, I. S. Chan, T. B. McNeely, N. A. Kartsonis, D. Guris, M. T. Onorato, S. S. Smugar, M. J. DiNubile, and A. Sobanjo-ter Meulen. 2013. Effect of an investigational vaccine for preventing Staphylococcus aureus infections after cardiothoracic surgery: a randomized trial. JAMA 309:1368-1378.

Friedrich, R., P. Panizzi, P. Fuentes-Prior, K. Richter, I. Verhamme, P. J. Anderson, S. Kawabata, R. Huber, W. Bode, and P. E. Bock. 2003. Staphylocoagulase is a prototype for the mechanism of cofactor-induced zymogen activation. Nature 425:535-539.

Guggenberger, C., C. Wolz, J. A. Morrissey, and J. Heesemann. 2012. Two distinct coagulase-dependent barriers protect Staphylococcus aureus from neutrophils in a three dimensional in vitro infection model. PLoS Pathog. 8:e1002434.

Kroh, H. K., P. Panizzi, and P. E. Bock. 2009. von Willebrand factor-binding protein is a hysteretic conformational activator of prothrombin. Proc. Natl. Acad. Sci. USA 106:7786-7791.

McAdow, M., A. C. DeDent, C. Emolo, A. G. Cheng, B. N. Kreiswirth, D. M. Missiakas, and O. Schneewind. 2012a. Coagulases as determinants of protective immune responses against Staphylococcus aureus. Infect. Immun. 80:3389-3398.

McAdow, M., H. K. Kim, A. C. DeDenta, A. P. A. Hendrickx, O. Schneewind, and D. M. Missiakas. 2011. Preventing Staphylococcus aureus sepsis through the inhibition of its agglutination in blood. PLoS Pathog. 7:e1002307.

McAdow, M., D. M. Missiakas, and O. Schneewind. 2012b. Staphylococcus aureus secretes coagulase and von Willebrand factor binding protein to modify the coagulation cascade and establish host infections. J. Innate Immun. 4:141-148.

McDevitt, D., P. Francois, P. Vaudaux, and T. J. Foster. 1994. Molecular characterization of the clumping factor (fibrinogen receptor) of Staphylococcus aureus. Mol. Microbiol. 11:237-248.

Mimura, N., and A. Asano. 1976. Synergistic effect of colchicine and cytochalasin D on phagocytosis by peritoneal macrophages. Nature 261:319-321.

Nanra, J. S., S. M. Buitrago, S. Crawford, J. Ng, P. S. Fink, J. Hawkins, I. L. Scully, L. K. McNeil, J. M. Aste-Amézaga, D. Cooper, K. U. Jansen, and A. S. Anderson. 2013. Capsular polysaccharides are an important immune evasion mechanism for Staphylococcus aureus. Hum. Vaccin. Immunother. 9:480-487.

Panizzi, P., R. Friedrich, P. Fuentes-Prior, W. Bode, and P. E. Bock. 2004. The staphylocoagulase family of zymogen activator and adhesion proteins. Cell. Mol. Life Sci. 61:2793-2798.

Panizzi, P., M. Nahrendorf, J. L. Figueiredo, J. Panizzi, B. Marinelli, Y. Iwamoto, E. Keliher, A. A. Maddur, P. Waterman, H. Kroh, F. Leuschner, E. Aikawa, F. K. Swirski, M. J. Pittet, T. M. Hackeng, P. Fuentes-Prior, O. Schneewind, P. E. Bock, and R. Weissleder. 2011. In vivo detection of Staphylococcus aureus endocarditis by targeting pathogen-specific prothrombin activation. Nat. Med. 17:1142-1146.

Rammelkamp, C. H., M. M. Hezebicks, and J. H. Dingle. 1950. Specific coagulases of Staphylococcus aureus. J. Exp. Med. 91:295-307.

Robbins, J. B., R. Schneerson, and S. C. Szu. 1996. Hypothesis: how licensed vaccines confer protective immunity. Adv. Exp. Med. Biol. 397:169-182.

Shinefield, H., S. Black, A. Fattom, G. Horwith, S. Rasgon, J. Ordonez, H. Yeoh, D. Law, J. B. Robbins, R. Schneerson, L. Muenz, S. Fuller, J. Johnson, B. Fireman, H. Alcorn, and R. Naso. 2002. Use of a Staphylococcus aureus conjugate vaccine in patients receiving hemodialysis. N. Engl. J. Med. 346:491-496.

Smith, W., J. H. Hale, and M. M. Smith. 1947. The role of coagulase in Staphylococcal infections. Brit. J. Exp. Pathol. 28:57.

Spaan, A. N., B. G. J. Surewaard, R. Nijland, and J. A. G. van Strijp. 2013. Neutrophils versus Staphylococcus aureus: a biological tug of war. Annu. Rev. Microbiol. 67:629-650.

Spellberg, B., and R. S. Daum. 2012. Development of a vaccine against Staphylococcus aureus. Semin. Immunopathol. 34:335-348.

Tager, M. 1956. Studies on the nature and the purification of coagulase-reacting factor and its relation to prothrombin. J. Exp. Med. 104:675-686.

Thammavongsa, V., D. M. Missiakas, and O. Schneewind. 2013. *Staphylococcus aureus* conversion of neutrophil extracellular traps into deoxyadenosine promotes immune cell death *Science* 342:863-866.

Thomer, L., O. Schneewind, and D. Missiakas. 2013. Multiple ligands of von Willebrand factor-binding protein (vWbp) promote *Staphylococcus aureus* clot formation in human plasma. *J. Biol. Chem.* 288:28283-28292.

Watanabe, S., T. Ito, T. Sasaki, S. Li, I. Uchiyama, K. Kishii, K. Kikuchi, R. L. Skov, and K. Hiramatsu. 2009. Genetic diversity of staphylocoagulase genes (coa): insight into the evolution of variable chromosomal virulence factors in *Staphylococcus aureus*. *PLoS One* 4:e5714.

The invention claimed is:

1. An immunogenic composition comprising a polypeptide consisting of two repeated tandem R-repeat units, wherein each R-repeat unit has at least 95% sequence identity to SEQ ID NO:120.

2. The immunogenic composition of claim 1, wherein the R-repeat unit has 95-99% sequence identity to SEQ ID NO:120.

3. The immunogenic composition of claim 1, further comprising an adjuvant.

4. A polypeptide consisting of at least one Staphylococcal coagulase R Domain wherein the R Domain consists of two repeated tandem R-repeat units, wherein each R-repeat unit has at least 95% sequence identity to SEQ ID NO: 120.

5. The polypeptide of claim 4, wherein the R-repeat unit has 95-99% sequence identity to SEQ ID NO:120.

* * * * *

UNITED STATES PATENT AND TRADEMARK OFFICE
CERTIFICATE OF CORRECTION

| | |
|---|---|
| PATENT NO. | : 11,214,600 B2 |
| APPLICATION NO. | : 16/077213 |
| DATED | : January 4, 2022 |
| INVENTOR(S) | : Dominique Missiakas et al. |

It is certified that error appears in the above-identified patent and that said Letters Patent is hereby corrected as shown below:

In the Specification

In Column 1, at Line 19, the paragraph should read as follows:
-- This invention was made with government support under grant numbers AI052747, AI110937, and HD009007 awarded by the National Institutes of Health. The government has certain rights in the invention. --

Signed and Sealed this
Sixteenth Day of August, 2022

*Katherine Kelly Vidal*

Katherine Kelly Vidal
*Director of the United States Patent and Trademark Office*

SEQUENCE LISTING

```
<160> NUMBER OF SEQ ID NOS: 127

<210> SEQ ID NO 1
<211> LENGTH: 609
<212> TYPE: PRT
<213> ORGANISM: Staphylococcus aureus

<400> SEQUENCE: 1

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Gly Lys Ser Gln Val Asn Ala Gly Ser Lys Asn Gly Thr Leu Ile
        35                  40                  45

Asp Ser Arg Tyr Leu Asn Ser Ala Leu Tyr Tyr Leu Glu Asp Tyr Ile
    50                  55                  60

Ile Tyr Ala Ile Gly Leu Thr Asn Lys Tyr Glu Tyr Gly Asp Asn Ile
65                  70                  75                  80

Tyr Lys Glu Ala Lys Asp Arg Leu Leu Glu Lys Val Leu Arg Glu Asp
                85                  90                  95

Gln Tyr Leu Leu Glu Arg Lys Lys Ser Gln Tyr Glu Asp Tyr Lys Gln
            100                 105                 110

Trp Tyr Ala Asn Tyr Lys Lys Glu Asn Pro Arg Thr Asp Leu Lys Met
        115                 120                 125

Ala Asn Phe His Lys Tyr Asn Leu Glu Glu Leu Ser Met Lys Glu Tyr
    130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
        195                 200                 205

Glu His Ala Lys Glu Leu Arg Ala Lys Leu Asp Leu Ile Leu Gly Asp
    210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Asp Phe Phe Met Glu Thr Lys
                245                 250                 255

Gln Asn Arg Pro Lys Ser Ile Thr Lys Tyr Asn Pro Thr Thr His Asn
            260                 265                 270

Tyr Lys Thr Asn Ser Asp Asn Lys Pro Asn Phe Asp Lys Leu Val Glu
        275                 280                 285

Glu Thr Lys Lys Ala Val Lys Glu Ala Asp Asp Ser Trp Lys Lys Lys
    290                 295                 300

Thr Val Lys Lys Tyr Gly Glu Thr Glu Thr Lys Ser Pro Val Val Lys
```

```
            305                 310                 315                 320
Glu Glu Lys Lys Val Glu Pro Gln Ala Pro Lys Val Asp Asn Gln
                325                 330                 335

Gln Glu Val Lys Thr Thr Ala Gly Lys Ala Glu Glu Thr Thr Gln Pro
                340                 345                 350

Val Ala Gln Pro Leu Val Lys Ile Pro Gln Gly Thr Ile Thr Gly Glu
                355                 360                 365

Ile Val Lys Gly Pro Glu Tyr Pro Thr Met Glu Asn Lys Thr Val Gln
    370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
                405                 410                 415

Leu Glu Gly Leu Glu Gly Ser Ser Ser Lys Leu Glu Ile Lys Pro Gln
                420                 425                 430

Gly Thr Glu Ser Thr Leu Lys Gly Thr Gln Gly Glu Ser Ser Asp Ile
                435                 440                 445

Glu Val Lys Pro Gln Ala Thr Glu Thr Thr Glu Ala Ser Gln Tyr Gly
    450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
                500                 505                 510

Thr Thr His Ala Asn Gly Gln Val Ser Tyr Gly Ala Arg Pro Thr Gln
                515                 520                 525

Asn Lys Pro Ser Lys Thr Asn Ala Tyr Asn Val Thr Thr His Gly Asn
                530                 535                 540

Gly Gln Val Ser Tyr Gly Ala Arg Pro Thr Gln Asn Lys Pro Ser Lys
545                 550                 555                 560

Thr Asn Ala Tyr Asn Val Thr Thr His Ala Asn Gly Gln Val Ser Tyr
                565                 570                 575

Gly Ala Arg Pro Thr Tyr Lys Lys Pro Ser Lys Thr Asn Ala Tyr Asn
                580                 585                 590

Val Thr Thr His Ala Asp Gly Thr Ala Thr Tyr Gly Pro Arg Val Thr
                595                 600                 605

Lys

<210> SEQ ID NO 2
<211> LENGTH: 658
<212> TYPE: PRT
<213> ORGANISM: Staphylococcus aureus

<400> SEQUENCE: 2

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Lys Glu Ser Arg Val Asn Glu Lys Ser Lys Lys Gly Ala Thr Val
                35                  40                  45

Ser Asp Tyr Tyr Tyr Trp Lys Ile Ile Asp Ser Leu Glu Ala Gln Phe
    50                  55                  60

Thr Gly Ala Ile Asp Leu Leu Glu Asp Tyr Lys Tyr Gly Asp Pro Ile
```

```
                65                  70                  75                  80
Tyr Lys Glu Ala Lys Asp Arg Leu Met Thr Arg Val Leu Gly Glu Asp
                85                  90                  95

Gln Tyr Leu Leu Lys Lys Ile Asp Glu Tyr Glu Leu Tyr Lys Lys
                100                 105                 110

Trp Tyr Lys Ser Ser Asn Lys Asn Thr Asn Met Leu Thr Phe His Lys
                115                 120                 125

Tyr Asn Leu Tyr Asn Leu Thr Met Asn Glu Tyr Asn Asp Ile Phe Asn
                130                 135                 140

Ser Leu Lys Asp Ala Val Tyr Gln Phe Asn Lys Glu Val Lys Glu Ile
145                 150                 155                 160

Glu His Lys Asn Val Asp Leu Lys Gln Phe Asp Lys Asp Gly Glu Asp
                165                 170                 175

Lys Ala Thr Lys Glu Val Tyr Asp Leu Val Ser Glu Ile Asp Thr Leu
                180                 185                 190

Val Val Thr Tyr Tyr Ala Asp Lys Asp Tyr Gly Glu His Ala Lys Glu
                195                 200                 205

Leu Arg Ala Lys Leu Asp Leu Ile Leu Gly Asp Thr Asp Asn Pro His
                210                 215                 220

Lys Ile Thr Asn Glu Arg Ile Lys Lys Glu Met Ile Asp Asp Leu Asn
225                 230                 235                 240

Ser Ile Ile Asp Asp Phe Phe Met Glu Thr Lys Gln Asn Arg Pro Asn
                245                 250                 255

Ser Ile Thr Lys Tyr Asp Pro Thr Lys His Asn Phe Lys Glu Lys Ser
                260                 265                 270

Glu Asn Lys Pro Asn Phe Asp Lys Leu Val Glu Thr Lys Lys Ala
                275                 280                 285

Val Lys Glu Ala Asp Glu Ser Trp Lys Asn Lys Thr Val Lys Lys Tyr
                290                 295                 300

Glu Glu Thr Val Thr Lys Ser Pro Val Val Lys Glu Glu Lys Lys Val
305                 310                 315                 320

Glu Glu Pro Gln Leu Pro Lys Val Gly Asn Gln Gln Glu Val Lys Thr
                325                 330                 335

Thr Ala Gly Lys Ala Glu Glu Thr Thr Gln Pro Val Ala Gln Pro Leu
                340                 345                 350

Val Lys Ile Pro Gln Glu Thr Ile Tyr Gly Glu Thr Val Lys Gly Pro
                355                 360                 365

Glu Tyr Pro Thr Met Glu Asn Lys Thr Leu Gln Gly Glu Ile Val Gln
                370                 375                 380

Gly Pro Asp Phe Leu Thr Met Glu Gln Asn Arg Pro Ser Leu Ser Asp
385                 390                 395                 400

Asn Tyr Thr Gln Pro Thr Pro Asn Pro Ile Leu Glu Gly Leu Glu
                405                 410                 415

Gly Ser Ser Ser Lys Leu Glu Ile Lys Pro Gln Gly Thr Glu Ser Thr
                420                 425                 430

Leu Lys Gly Ile Gln Gly Glu Ser Ser Asp Ile Glu Val Lys Pro Gln
                435                 440                 445

Ala Thr Glu Thr Thr Glu Ala Ser Gln Tyr Gly Pro Arg Pro Gln Phe
                450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495
```

```
Asn Lys Pro Ser Glu Thr Asn Ala Tyr Asn Val Thr Asn Gln Asp
            500                 505                 510

Gly Thr Val Ser Tyr Gly Ala Arg Pro Thr Gln Asn Lys Pro Ser Glu
            515                 520                 525

Thr Asn Ala Tyr Asn Val Thr Thr His Ala Asn Gly Gln Val Ser Tyr
            530                 535                 540

Gly Ala Arg Pro Thr Gln Lys Lys Pro Ser Lys Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr Thr His Ala
            580                 585                 590

Asn Gly Gln Val Ser Tyr Gly Ala Arg Pro Thr Tyr Lys Lys Pro Ser
            595                 600                 605

Glu Thr Asn Ala Tyr Asn Val Thr Thr His Ala Asn Gly Gln Val Ser
            610                 615                 620

Tyr Gly Ala Arg Pro Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys

<210> SEQ ID NO 3
<211> LENGTH: 633
<212> TYPE: PRT
<213> ORGANISM: Staphylococcus aureus

<400> SEQUENCE: 3

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Gly Lys Ser Gln Val Asn Ala Gly Ser Lys Asn Gly Lys Gln Ile
            35                  40                  45

Ala Asp Gly Tyr Tyr Trp Gly Ile Ile Glu Asn Leu Glu Asn Gln Phe
    50                  55                  60

Tyr Asn Ile Phe His Leu Leu Asp Gln His Lys Tyr Ala Glu Lys Glu
65                  70                  75                  80

Tyr Lys Asp Ala Val Asp Lys Leu Lys Thr Arg Val Leu Glu Glu Asp
                85                  90                  95

Gln Tyr Leu Leu Glu Arg Lys Lys Glu Lys Tyr Glu Ile Tyr Lys Glu
            100                 105                 110

Leu Tyr Lys Lys Tyr Lys Lys Glu Asn Pro Asn Thr Gln Val Lys Met
            115                 120                 125

Lys Ala Phe Asp Lys Tyr Asp Leu Gly Asp Leu Thr Met Glu Glu Tyr
    130                 135                 140

Asn Asp Leu Ser Lys Leu Leu Thr Lys Ala Leu Asp Asn Phe Lys Leu
145                 150                 155                 160

Glu Val Lys Lys Ile Glu Ser Glu Asn Pro Asp Leu Lys Pro Tyr Ser
                165                 170                 175

Glu Ser Glu Glu Arg Thr Ala Tyr Gly Lys Ile Asp Ser Leu Val Asp
            180                 185                 190

Gln Ala Tyr Ser Val Tyr Phe Ala Tyr Val Thr Asp Ala Gln His Lys
            195                 200                 205
```

```
Thr Glu Ala Leu Asn Leu Arg Ala Lys Ile Asp Leu Ile Leu Gly Asp
            210                 215                 220

Glu Lys Asp Pro Ile Arg Val Thr Asn Gln Arg Thr Glu Lys Glu Met
225                 230                 235                 240

Ile Lys Asp Leu Glu Ser Ile Ile Asp Asp Phe Phe Ile Glu Thr Lys
                245                 250                 255

Leu Asn Arg Pro Lys His Ile Thr Arg Tyr Asp Gly Thr Lys His Asp
                260                 265                 270

Tyr His Lys His Lys Asp Gly Phe Asp Ala Leu Val Lys Glu Thr Arg
            275                 280                 285

Glu Ala Val Ala Lys Ala Asp Glu Ser Trp Lys Asn Lys Thr Val Lys
            290                 295                 300

Lys Tyr Glu Glu Thr Val Thr Lys Ser Pro Val Val Lys Glu Lys
305                 310                 315                 320

Lys Val Glu Glu Pro Gln Ser Pro Lys Phe Asp Asn Gln Gln Glu Val
                325                 330                 335

Lys Ile Thr Val Asp Lys Ala Glu Glu Thr Thr Gln Pro Val Ala Gln
                340                 345                 350

Pro Leu Val Lys Ile Pro Gln Gly Thr Ile Thr Gly Glu Ile Val Lys
            355                 360                 365

Gly Pro Glu Tyr Pro Thr Met Glu Asn Lys Thr Leu Gln Gly Glu Ile
370                 375                 380

Val Gln Gly Pro Asp Phe Pro Thr Met Glu Gln Asn Arg Pro Ser Leu
385                 390                 395                 400

Ser Asp Asn Tyr Thr Gln Pro Thr Thr Pro Asn Pro Ile Leu Glu Gly
                405                 410                 415

Leu Glu Gly Ser Ser Ser Lys Leu Glu Ile Lys Pro Gln Gly Thr Glu
            420                 425                 430

Ser Thr Leu Lys Gly Thr Gln Gly Glu Ser Ser Asp Ile Glu Val Lys
            435                 440                 445

Pro Gln Ala Ser Glu Thr Thr Glu Ala Ser His Tyr Pro Ala Arg Pro
450                 455                 460

Gln Phe Asn Lys Thr Pro Lys Tyr Val Lys Tyr Arg Asp Ala Gly Thr
465                 470                 475                 480

Gly Ile Arg Glu Tyr Asn Asp Gly Thr Phe Gly Tyr Glu Ala Arg Pro
                485                 490                 495

Arg Phe Asn Lys Pro Ser Glu Thr Asn Ala Tyr Asn Val Thr Thr Asn
                500                 505                 510

Gln Asp Gly Thr Val Thr Tyr Gly Ala Arg Pro Thr Gln Asn Lys Pro
            515                 520                 525

Ser Lys Thr Asn Ala Tyr Asn Val Thr Thr His Ala Asn Gly Gln Val
530                 535                 540

Ser Tyr Gly Ala Arg Pro Thr Gln Asn Lys Pro Ser Lys Thr Asn Ala
545                 550                 555                 560

Tyr Asn Val Thr Thr His Ala Asn Gly Gln Val Ser Tyr Gly Ala Arg
                565                 570                 575

Pro Thr Gln Asn Lys Pro Ser Lys Thr Asn Ala Tyr Asn Val Thr Thr
            580                 585                 590

His Ala Asn Gly Gln Val Ser Tyr Gly Ala Arg Pro Thr Tyr Lys Lys
            595                 600                 605

Pro Ser Lys Thr Asn Ala Tyr Asn Val Thr Thr His Ala Asp Gly Thr
            610                 615                 620
```

```
Ala Thr Tyr Gly Pro Arg Val Thr Lys
625                 630

<210> SEQ ID NO 4
<211> LENGTH: 609
<212> TYPE: PRT
<213> ORGANISM: Staphylococcus aureus

<400> SEQUENCE: 4

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Asn Ser Lys Tyr Asp Thr Pro Ile
        35                  40                  45

Pro Asp Trp Tyr Leu Gly Ser Ile Leu Asn Arg Leu Gly Asp Gln Ile
    50                  55                  60

Tyr Tyr Ala Lys Glu Leu Thr Asn Lys Tyr Glu Tyr Gly Lys Lys Glu
65                  70                  75                  80

Tyr Lys Gln Ala Ile Asp Lys Leu Met Thr Arg Val Leu Gly Glu Asp
                85                  90                  95

His Tyr Leu Leu Glu Lys Lys Ala Gln Tyr Glu Ala Tyr Lys Lys
            100                 105                 110

Trp Phe Glu Lys His Lys Ser Glu Asn Pro His Ser Ser Leu Lys Lys
            115                 120                 125

Ile Lys Phe Asp Asp Phe Asp Leu Tyr Arg Leu Thr Lys Lys Glu Tyr
        130                 135                 140

Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
            180                 185                 190

Glu Ile Asp Thr Leu Tyr Ala Ala Tyr Phe Asn His Ser Gln Tyr Gly
        195                 200                 205

His Asn Ala Lys Glu Leu Arg Ala Lys Leu Asp Ile Ile Leu Gly Asp
    210                 215                 220

Ala Lys Asp Pro Val Arg Ile Thr Asn Glu Arg Ile Arg Lys Glu Met
225                 230                 235                 240

Met Asp Asp Leu Asn Ser Ile Ile Asp Asp Phe Phe Met Asp Thr Asn
                245                 250                 255

Met Asn Arg Pro Leu Asn Ile Thr Lys Phe Asn Pro Asn Ile His Asp
            260                 265                 270

Tyr Thr Asn Lys Pro Glu Asn Arg Asp Asn Phe Asp Lys Leu Val Lys
        275                 280                 285

Glu Thr Arg Glu Ala Ile Ala Asn Ala Asp Glu Ser Trp Lys Thr Arg
    290                 295                 300

Thr Val Lys Asn Tyr Gly Glu Ser Glu Thr Lys Ser Pro Val Val Lys
305                 310                 315                 320

Glu Glu Lys Lys Val Glu Glu Pro Gln Leu Pro Lys Val Gly Asn Gln
                325                 330                 335

Gln Glu Asp Lys Ile Thr Val Gly Thr Thr Glu Glu Ala Pro Leu Pro
            340                 345                 350

Ile Ala Gln Pro Leu Val Lys Ile Pro Gln Gly Thr Ile Gln Gly Glu
        355                 360                 365
```

```
Ile Val Lys Gly Pro Glu Tyr Leu Thr Met Glu Asn Lys Thr Leu Gln
    370                 375                 380

Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Pro Asn Pro Ile
            405                 410                 415

Leu Lys Gly Ile Glu Gly Asn Ser Thr Lys Leu Glu Ile Lys Pro Gln
            420                 425                 430

Gly Thr Glu Ser Thr Leu Lys Gly Thr Gln Gly Glu Ser Ser Asp Ile
            435                 440                 445

Glu Val Lys Pro Gln Ala Thr Glu Thr Thr Glu Ala Ser His Tyr Pro
    450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
            485                 490                 495

Ala Arg Pro Arg Phe Asn Lys Pro Ser Glu Thr Asn Ala Tyr Asn Val
            500                 505                 510

Thr Thr Asn Gln Asp Gly Thr Val Ser Tyr Gly Ala Arg Pro Thr Gln
            515                 520                 525

Asn Lys Pro Ser Glu Thr Asn Ala Tyr Asn Val Thr Thr His Ala Asn
    530                 535                 540

Gly Gln Val Ser Tyr Gly Ala Arg Pro Thr Gln Asn Lys Pro Ser Glu
545                 550                 555                 560

Thr Asn Ala Tyr Asn Val Thr Thr His Ala Asn Gly Gln Val Ser Tyr
            565                 570                 575

Gly Ala Arg Pro Thr Gln Asn Lys Pro Ser Lys Thr Asn Ala Tyr Asn
            580                 585                 590

Val Thr Thr His Ala Asp Gly Thr Ala Thr Tyr Gly Pro Arg Val Thr
            595                 600                 605

Lys

<210> SEQ ID NO 5
<211> LENGTH: 671
<212> TYPE: PRT
<213> ORGANISM: Staphylococcus aureus

<400> SEQUENCE: 5

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Gly Lys Ser Gln Val Asn Ala Gly Ser Lys Asn Gly Lys Gln Ile
        35                  40                  45

Ala Asp Gly Tyr Tyr Trp Gly Ile Ile Glu Asn Leu Glu Asn Gln Phe
    50                  55                  60

Tyr Asn Ile Phe His Leu Leu Asp Gln His Lys Tyr Ala Glu Lys Glu
65                  70                  75                  80

Tyr Lys Asp Ala Leu Asp Lys Leu Lys Thr Arg Val Leu Glu Glu Asp
            85                  90                  95

Gln Tyr Leu Leu Glu Arg Lys Lys Glu Lys Tyr Glu Ile Tyr Lys Glu
            100                 105                 110

Leu Tyr Lys Lys Tyr Lys Lys Glu Asn Pro Asn Thr Gln Val Lys Met
        115                 120                 125
```

```
Lys Ala Phe Asp Lys Tyr Asp Leu Gly Asp Leu Thr Met Glu Glu Tyr
    130                 135                 140

Asn Asp Leu Ser Lys Leu Leu Thr Lys Ala Leu Asp Asn Phe Lys Leu
145                 150                 155                 160

Glu Val Lys Lys Ile Glu Ser Glu Asn Pro Asp Leu Arg Pro Tyr Ser
                165                 170                 175

Glu Ser Glu Glu Arg Thr Ala Tyr Gly Lys Ile Asp Ser Leu Val Asp
            180                 185                 190

Gln Ala Tyr Ser Val Tyr Phe Ala Tyr Val Thr Asp Ala Gln His Lys
        195                 200                 205

Thr Glu Ala Leu Asn Leu Arg Ala Lys Ile Asp Leu Ile Leu Gly Asp
    210                 215                 220

Glu Lys Asp Pro Ile Arg Val Thr Asn Gln Arg Thr Glu Lys Glu Met
225                 230                 235                 240

Ile Lys Asp Leu Glu Ser Ile Ile Asp Asp Phe Phe Ile Glu Thr Lys
                245                 250                 255

Leu Asn Arg Pro Gln His Ile Thr Arg Tyr Asp Gly Thr Lys His Asp
            260                 265                 270

Tyr His Lys His Lys Asp Gly Phe Asp Ala Leu Val Lys Glu Thr Arg
        275                 280                 285

Glu Ala Val Ser Lys Ala Asp Glu Ser Trp Lys Thr Lys Thr Val Lys
    290                 295                 300

Lys Tyr Gly Glu Thr Glu Thr Lys Tyr Pro Val Val Lys Glu Glu Lys
305                 310                 315                 320

Lys Val Glu Glu Pro Gln Ser Pro Lys Val Ser Glu Lys Val Asp Val
                325                 330                 335

Gln Glu Thr Val Gly Thr Thr Glu Glu Ala Pro Leu Pro Ile Ala Gln
            340                 345                 350

Pro Leu Val Lys Leu Pro Gln Ile Gly Thr Gln Gly Glu Ile Val Lys
        355                 360                 365

Gly Pro Asp Tyr Pro Thr Met Glu Asn Lys Thr Leu Gln Gly Val Ile
    370                 375                 380

Val Gln Gly Pro Asp Phe Pro Thr Met Glu Gln Asn Arg Pro Ser Leu
385                 390                 395                 400

Ser Asp Asn Tyr Thr Gln Pro Ser Val Thr Leu Pro Ser Ile Thr Gly
                405                 410                 415

Glu Ser Thr Pro Thr Asn Pro Ile Leu Lys Gly Ile Glu Gly Asn Ser
            420                 425                 430

Ser Lys Leu Glu Ile Lys Pro Gln Gly Thr Glu Ser Thr Leu Lys Gly
        435                 440                 445

Ile Gln Gly Glu Ser Ser Asp Ile Glu Val Lys Pro Gln Ala Thr Glu
    450                 455                 460

Thr Thr Glu Ala Ser His Tyr Pro Ala Arg Pro Gln Phe Asn Lys Thr
465                 470                 475                 480

Pro Lys Tyr Val Lys Tyr Arg Asp Ala Gly Thr Gly Ile Arg Glu Tyr
                485                 490                 495

Asn Asp Gly Thr Phe Gly Tyr Glu Ala Arg Pro Arg Phe Asn Lys Pro
            500                 505                 510

Ser Glu Thr Asn Ala Tyr Asn Val Thr Thr Asn Gln Asp Gly Thr Val
        515                 520                 525

Ser Tyr Gly Ala Arg Pro Thr Gln Asn Lys Pro Ser Lys Thr Asn Ala
    530                 535                 540
```

Tyr Asn Val Thr Thr His Ala Asn Gly Gln Val Ser Tyr Gly Ala Arg
545                 550                 555                 560

Pro Thr Tyr Asn Lys Pro Ser Glu Thr Asn Ala Tyr Asn Val Thr Thr
            565                 570                 575

Asn Arg Asp Gly Thr Val Ser Tyr Gly Ala Arg Pro Thr Gln Asn Lys
                580                 585                 590

Pro Ser Glu Thr Asn Ala Tyr Asn Val Thr Thr His Gly Asn Gly Gln
        595                 600                 605

Val Ser Tyr Gly Ala Arg Pro Thr Gln Lys Lys Pro Ser Lys Thr Asn
            610                 615                 620

Ala Tyr Asn Val Thr Thr His Ala Asn Gly Gln Val Ser Tyr Gly Ala
625                 630                 635                 640

Arg Pro Thr Tyr Asn Lys Pro Ser Lys Thr Asn Ala Tyr Asn Val Thr
                645                 650                 655

Thr His Ala Asp Gly Thr Ala Thr Tyr Gly Pro Arg Val Thr Lys
            660                 665                 670

<210> SEQ ID NO 6
<211> LENGTH: 658
<212> TYPE: PRT
<213> ORGANISM: Staphylococcus aureus

<400> SEQUENCE: 6

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Lys Ser Lys Gly Ala Thr Val
        35                  40                  45

Ser Asp Tyr Tyr Tyr Trp Lys Ile Ile Asp Ser Leu Glu Ala Gln Phe
    50                  55                  60

Thr Gly Ala Ile Asp Leu Leu Glu Asp Tyr Lys Tyr Gly Asp Pro Ile
65                  70                  75                  80

Tyr Lys Glu Ala Lys Asp Arg Leu Met Thr Arg Val Leu Gly Glu Asp
                85                  90                  95

Gln Tyr Leu Leu Lys Lys Ile Asp Glu Tyr Glu Leu Tyr Lys Lys
            100                 105                 110

Trp Tyr Lys Ser Ser Asn Lys Asn Thr Asn Met Leu Thr Phe His Lys
        115                 120                 125

Tyr Asn Leu Tyr Asn Leu Thr Met Asn Glu Tyr Asn Asp Ile Phe Asn
    130                 135                 140

Ser Leu Lys Asp Ala Val Tyr Gln Phe Asn Lys Glu Val Lys Glu Ile
145                 150                 155                 160

Glu His Lys Asn Val Asp Leu Lys Gln Phe Asp Lys Asp Gly Glu Asp
                165                 170                 175

Lys Ala Thr Lys Glu Val Tyr Asp Leu Val Ser Glu Ile Asp Thr Leu
            180                 185                 190

Val Val Thr Tyr Tyr Ala Asp Lys Asp Tyr Gly Glu His Ala Lys Glu
        195                 200                 205

Leu Arg Ala Lys Leu Asp Leu Ile Leu Gly Asp Thr Asp Asn Pro His
    210                 215                 220

Lys Ile Thr Asn Glu Arg Ile Lys Lys Glu Met Ile Asp Asp Leu Asn
225                 230                 235                 240

Ser Ile Ile Asp Asp Phe Phe Met Glu Thr Lys Gln Asn Arg Pro Asn
                245                 250                 255

```
Ser Ile Thr Lys Tyr Asp Pro Thr Lys His Asn Phe Lys Glu Lys Ser
        260                 265                 270

Glu Asn Lys Pro Asn Phe Asp Lys Leu Val Glu Thr Lys Lys Ala
        275                 280                 285

Val Lys Glu Ala Asp Glu Ser Trp Lys Asn Lys Thr Val Lys Lys Tyr
290                 295                 300

Glu Glu Thr Val Thr Lys Ser Pro Val Val Lys Glu Lys Lys Val
305                 310                 315                 320

Glu Glu Pro Gln Leu Pro Lys Val Gly Asn Gln Gln Glu Val Lys Thr
                325                 330                 335

Thr Ala Gly Lys Ala Glu Glu Thr Thr Gln Pro Val Ala Gln Pro Leu
        340                 345                 350

Val Lys Ile Pro Gln Glu Thr Ile Tyr Gly Glu Thr Val Lys Gly Pro
        355                 360                 365

Glu Tyr Pro Thr Met Glu Asn Lys Thr Leu Gln Gly Glu Ile Val Gln
        370                 375                 380

Gly Pro Asp Phe Leu Thr Met Glu Gln Asn Arg Pro Ser Leu Ser Asp
385                 390                 395                 400

Asn Tyr Thr Gln Pro Thr Thr Pro Asn Pro Ile Leu Glu Gly Leu Glu
                405                 410                 415

Gly Ser Ser Ser Lys Leu Glu Ile Lys Pro Gln Gly Thr Glu Ser Thr
                420                 425                 430

Leu Lys Gly Ile Gln Gly Glu Ser Ser Asp Ile Glu Val Lys Pro Gln
        435                 440                 445

Ala Thr Glu Thr Thr Glu Ala Ser Gln Tyr Gly Pro Arg Pro Gln Phe
        450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495

Asn Lys Pro Ser Glu Thr Asn Ala Tyr Asn Val Thr Thr Asn Gln Asp
                500                 505                 510

Gly Thr Val Ser Tyr Gly Ala Arg Pro Thr Gln Asn Lys Pro Ser Glu
        515                 520                 525

Thr Asn Ala Tyr Asn Val Thr Thr His Ala Asn Gly Gln Val Ser Tyr
        530                 535                 540

Gly Ala Arg Pro Thr Gln Lys Lys Pro Ser Lys Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr Thr His Ala
                580                 585                 590

Asn Gly Gln Val Ser Tyr Gly Ala Arg Pro Thr Tyr Lys Lys Pro Ser
        595                 600                 605

Glu Thr Asn Ala Tyr Asn Val Thr Thr His Ala Asn Gly Gln Val Ser
        610                 615                 620

Tyr Gly Ala Arg Pro Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys
```

```
<210> SEQ ID NO 7
<211> LENGTH: 663
<212> TYPE: PRT
<213> ORGANISM: Staphylococcus aureus

<400> SEQUENCE: 7
```

| | | | | | | | | | | | | | | |
|---|---|---|---|---|---|---|---|---|---|---|---|---|---|---|
| Met | Lys | Lys | Gln | Ile | Ile | Ser | Leu | Gly | Ala | Leu | Ala | Val | Ala | Ser | Ser |
| 1 | | | | 5 | | | | | 10 | | | | | 15 | |
| Leu | Phe | Thr | Trp | Asp | Asn | Lys | Ala | Asp | Ala | Ile | Val | Thr | Lys | Asp | Tyr |
| | | | 20 | | | | | 25 | | | | | 30 | | |
| Ser | Lys | Glu | Ser | Arg | Val | Asn | Glu | Asn | Ser | Lys | Tyr | Asp | Thr | Pro | Ile |
| | | 35 | | | | | 40 | | | | | 45 | | | |
| Pro | Asp | Trp | Tyr | Leu | Gly | Ser | Ile | Leu | Asn | Arg | Leu | Gly | Asp | Gln | Ile |
| | 50 | | | | | 55 | | | | | 60 | | | | |
| Tyr | Tyr | Ala | Lys | Glu | Leu | Thr | Asn | Lys | Tyr | Glu | Tyr | Gly | Glu | Lys | Glu |
| 65 | | | | | 70 | | | | | 75 | | | | | 80 |
| Tyr | Lys | Gln | Ala | Ile | Asp | Lys | Leu | Met | Thr | Arg | Val | Leu | Gly | Glu | Asp |
| | | | | 85 | | | | | 90 | | | | | 95 | |
| His | Tyr | Leu | Leu | Glu | Lys | Lys | Ala | Gln | Tyr | Glu | Ala | Tyr | Lys | Lys | |
| | | | 100 | | | | | 105 | | | | | 110 | | |
| Trp | Phe | Glu | Lys | His | Lys | Ser | Glu | Asn | Pro | His | Ser | Leu | Lys | Lys | |
| | | | 115 | | | | | 120 | | | | | 125 | | |
| Ile | Lys | Phe | Asp | Asp | Phe | Asp | Leu | Tyr | Arg | Leu | Thr | Lys | Lys | Glu | Tyr |
| | 130 | | | | | 135 | | | | | 140 | | | | |
| Asn | Glu | Leu | His | Gln | Ser | Leu | Lys | Glu | Ala | Val | Asp | Glu | Phe | Asn | Ser |
| 145 | | | | | 150 | | | | | 155 | | | | | 160 |
| Glu | Val | Lys | Asn | Ile | Gln | Ser | Lys | Gln | Lys | Asp | Leu | Leu | Pro | Tyr | Asp |
| | | | | 165 | | | | | 170 | | | | | 175 | |
| Glu | Ala | Thr | Glu | Asn | Arg | Val | Thr | Asn | Gly | Ile | Tyr | Asp | Phe | Val | Cys |
| | | | 180 | | | | | 185 | | | | | 190 | | |
| Glu | Ile | Asp | Thr | Leu | Tyr | Ala | Ala | Tyr | Phe | Asn | His | Ser | Gln | Tyr | Gly |
| | | 195 | | | | | 200 | | | | | 205 | | | |
| His | Asn | Ala | Lys | Glu | Leu | Arg | Ala | Lys | Leu | Asp | Ile | Ile | Leu | Gly | Asp |
| | 210 | | | | | 215 | | | | | 220 | | | | |
| Ala | Lys | Asp | Pro | Val | Arg | Ile | Thr | Asn | Glu | Arg | Ile | Arg | Lys | Glu | Met |
| 225 | | | | | 230 | | | | | 235 | | | | | 240 |
| Met | Asp | Asp | Leu | Asn | Ser | Ile | Ile | Asp | Asp | Phe | Phe | Met | Asp | Thr | Asn |
| | | | | 245 | | | | | 250 | | | | | 255 | |
| Met | Asn | Arg | Pro | Leu | Asn | Ile | Thr | Lys | Phe | Asn | Pro | Asn | Ile | His | Asp |
| | | | 260 | | | | | 265 | | | | | 270 | | |
| Tyr | Thr | Asn | Lys | Pro | Glu | Asn | Arg | Asp | Asn | Phe | Asp | Lys | Leu | Val | Lys |
| | | 275 | | | | | 280 | | | | | 285 | | | |
| Glu | Thr | Arg | Glu | Ala | Val | Ala | Asn | Ala | Asp | Glu | Ser | Trp | Lys | Thr | Arg |
| | 290 | | | | | 295 | | | | | 300 | | | | |
| Thr | Val | Lys | Asn | Tyr | Gly | Glu | Ser | Glu | Thr | Lys | Ser | Pro | Val | Val | Lys |
| 305 | | | | | 310 | | | | | 315 | | | | | 320 |
| Glu | Glu | Lys | Lys | Val | Glu | Glu | Pro | Gln | Leu | Pro | Lys | Val | Gly | Asn | Gln |
| | | | | 325 | | | | | 330 | | | | | 335 | |
| Gln | Glu | Asp | Lys | Ile | Thr | Val | Gly | Thr | Thr | Glu | Glu | Ala | Pro | Leu | Pro |
| | | | 340 | | | | | 345 | | | | | 350 | | |
| Ile | Ala | Gln | Pro | Leu | Val | Lys | Ile | Pro | Gln | Gly | Thr | Ile | Gln | Gly | Glu |
| | | 355 | | | | | 360 | | | | | 365 | | | |
| Ile | Val | Lys | Gly | Pro | Glu | Tyr | Leu | Thr | Met | Glu | Asn | Lys | Thr | Leu | Gln |
| | 370 | | | | | 375 | | | | | 380 | | | | |

```
Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Pro Asn Pro Ile
            405                 410                 415

Leu Lys Gly Ile Glu Gly Asn Ser Thr Lys Leu Glu Ile Lys Pro Gln
        420                 425                 430

Gly Thr Glu Ser Thr Leu Lys Gly Thr Gln Gly Glu Ser Ser Asp Ile
            435                 440                 445

Glu Val Lys Pro Gln Ala Thr Glu Thr Thr Glu Ala Ser His Tyr Pro
450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
            485                 490                 495

Ala Arg Pro Arg Phe Asn Lys Pro Ser Glu Thr Asn Ala Tyr Asn Val
            500                 505                 510

Thr Thr Asn Gln Asp Gly Thr Val Ser Tyr Gly Ala Arg Pro Thr Gln
            515                 520                 525

Asn Lys Pro Ser Glu Thr Asn Ala Tyr Asn Val Thr Thr His Ala Asn
530                 535                 540

Gly Gln Val Ser Tyr Gly Ala Arg Pro Thr Tyr Lys Lys Pro Ser Glu
545                 550                 555                 560

Thr Asn Ala Tyr Asn Val Thr Thr Asn Gln Asp Gly Thr Val Ser Tyr
            565                 570                 575

Gly Ala Arg Pro Thr Gln Asn Lys Pro Ser Glu Thr Asn Ala Tyr Asn
            580                 585                 590

Val Thr Thr His Ala Asn Gly Gln Val Ser Tyr Gly Ala Arg Pro Thr
            595                 600                 605

Gln Asn Lys Pro Ser Glu Thr Asn Ala Tyr Asn Val Thr Thr His Ala
        610                 615                 620

Asn Gly Gln Val Ser Tyr Gly Ala Arg Pro Thr Gln Asn Lys Pro Ser
625                 630                 635                 640

Lys Thr Asn Ala Tyr Asn Val Thr Thr His Ala Asp Gly Thr Ala Thr
            645                 650                 655

Tyr Gly Pro Arg Val Thr Lys
            660

<210> SEQ ID NO 8
<211> LENGTH: 636
<212> TYPE: PRT
<213> ORGANISM: Staphylococcus aureus

<400> SEQUENCE: 8

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Gly Lys Ser Gln Val Asn Ala Gly Ser Lys Asn Gly Thr Leu Ile
        35                  40                  45

Asp Ser Arg Tyr Leu Asn Ser Ala Leu Tyr Tyr Leu Glu Asp Tyr Ile
    50                  55                  60

Ile Tyr Ala Ile Gly Leu Thr Asn Lys Tyr Glu Tyr Gly Asp Asn Ile
65                  70                  75                  80

Tyr Lys Glu Ala Lys Asp Arg Leu Leu Glu Lys Val Leu Arg Glu Asp
            85                  90                  95
```

-continued

```
Gln Tyr Leu Leu Glu Arg Lys Lys Ser Gln Tyr Glu Asp Tyr Lys Gln
            100                 105                 110

Trp Tyr Ala Asn Tyr Lys Lys Glu Asn Pro Arg Thr Asp Leu Lys Met
            115                 120                 125

Ala Asn Phe His Lys Tyr Asn Leu Glu Glu Leu Ser Met Lys Glu Tyr
            130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
            195                 200                 205

Glu His Ala Lys Glu Leu Arg Ala Lys Leu Asp Leu Ile Leu Gly Asp
            210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Asp Phe Phe Met Glu Thr Lys
                245                 250                 255

Gln Asn Arg Pro Lys Ser Ile Thr Lys Tyr Asn Pro Thr Thr His Asn
            260                 265                 270

Tyr Lys Thr Asn Ser Asp Asn Lys Pro Asn Phe Asp Lys Leu Val Glu
            275                 280                 285

Glu Thr Lys Lys Ala Val Lys Glu Ala Asp Asp Ser Trp Lys Lys Lys
            290                 295                 300

Thr Val Lys Lys Tyr Gly Glu Thr Glu Thr Lys Ser Pro Val Val Lys
305                 310                 315                 320

Glu Glu Lys Lys Val Glu Glu Pro Gln Ala Pro Lys Val Asp Asn Gln
                325                 330                 335

Gln Glu Val Lys Thr Thr Ala Gly Lys Ala Glu Glu Thr Thr Gln Pro
            340                 345                 350

Val Ala Gln Pro Leu Val Lys Ile Pro Gln Gly Thr Ile Thr Gly Glu
            355                 360                 365

Ile Val Lys Gly Pro Glu Tyr Pro Thr Met Glu Asn Lys Thr Val Gln
            370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
                405                 410                 415

Leu Glu Gly Leu Glu Gly Ser Ser Ser Lys Leu Glu Ile Lys Pro Gln
            420                 425                 430

Gly Thr Glu Ser Thr Leu Lys Gly Thr Gln Gly Glu Ser Ser Asp Ile
            435                 440                 445

Glu Val Lys Pro Gln Ala Thr Glu Thr Thr Glu Ala Ser Gln Tyr Gly
            450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510
```

```
Thr Thr His Ala Asn Gly Gln Val Ser Tyr Gly Ala Arg Pro Thr Tyr
            515                 520                 525

Lys Lys Pro Ser Glu Thr Asn Ala Tyr Asn Val Thr Thr His Ala Asn
    530                 535                 540

Gly Gln Val Ser Tyr Gly Ala Arg Pro Thr Gln Asn Lys Pro Ser Lys
545                 550                 555                 560

Thr Asn Ala Tyr Asn Val Thr His Gly Asn Gly Gln Val Ser Tyr
                565                 570                 575

Gly Ala Arg Pro Thr Gln Asn Lys Pro Ser Lys Thr Asn Ala Tyr Asn
            580                 585                 590

Val Thr Thr His Ala Asn Gly Gln Val Ser Tyr Gly Ala Arg Pro Thr
        595                 600                 605

Tyr Lys Lys Pro Ser Lys Thr Asn Ala Tyr Asn Val Thr Thr His Ala
        610                 615                 620

Asp Gly Thr Ala Thr Tyr Gly Pro Arg Val Thr Lys
625                 630                 635
```

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

```
Gly Ala Ser Ile Thr Thr Ser Tyr
1               5
```

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

```
Ile Ser Tyr Ser Gly Asn Thr
1               5
```

<210> SEQ ID NO 11
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 11

```
Ala Thr Tyr Tyr Asp Phe Asn Tyr Asp Gly Tyr Leu Asp Val
1               5                   10
```

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 12

```
Ser Ser Val Ser Ser Ser Tyr
1               5
```

<210> SEQ ID NO 13
<211> LENGTH: 3

```
<212> TYPE: PRT
<213> ORGANISM: Artificial Sequence
<220> FEATURE:
<223> OTHER INFORMATION: Synthetic Peptide

<400> SEQUENCE: 13

Ser Thr Ser
1

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Gln Gln Tyr His Arg Ser Pro Pro Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 15

Gly Tyr Thr Phe Thr Ser Phe Asp
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 16

Ile Phe Pro Gly Asp Gly Ser Ala
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 17

Val Lys Asn His Gly Gly Trp Tyr Phe Asp Val
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 18

Gln Ser Ile Val His Ser Asn Gly Asn Thr Tyr
1               5                   10

<210> SEQ ID NO 19
<211> LENGTH: 3
<212> TYPE: PRT
```

<213> ORGANISM: Artificial Sequence
<220> FEATURE:
<223> OTHER INFORMATION: Synthetic Peptide

<400> SEQUENCE: 19

Lys Val Ser
1

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

Phe Gln Gly Ser His Val Pro Leu Thr
1               5

<210> SEQ ID NO 21
<211> LENGTH: 609
<212> TYPE: PRT
<213> ORGANISM: Artificial Sequence
<220> FEATURE:
<223> OTHER INFORMATION: Synthetic Peptide

<400> SEQUENCE: 21

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Gly Lys Ser Gln Val Asn Ala Gly Ser Lys Asn Gly Thr Leu Ile
            35                  40                  45

Asp Ser Arg Tyr Leu Asn Ser Ala Leu Tyr Tyr Leu Glu Asp Tyr Ile
        50                  55                  60

Ile Tyr Ala Ile Gly Leu Thr Asn Lys Tyr Glu Tyr Gly Asp Asn Ile
65                  70                  75                  80

Tyr Lys Glu Ala Lys Asp Arg Leu Leu Glu Lys Val Leu Arg Glu Asp
                85                  90                  95

Gln Tyr Leu Leu Glu Arg Lys Lys Ser Gln Tyr Glu Asp Tyr Lys Gln
                100                 105                 110

Trp Tyr Ala Asn Tyr Lys Lys Glu Asn Pro Arg Thr Asp Leu Lys Met
            115                 120                 125

Ala Asn Phe His Lys Tyr Asn Leu Glu Glu Leu Ser Met Lys Glu Tyr
        130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
        195                 200                 205

Glu His Ala Lys Glu Leu Arg Ala Lys Leu Asp Leu Ile Leu Gly Asp
    210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Asp Phe Phe Met Glu Thr Lys
                245                 250                 255

```
Gln Asn Arg Pro Lys Ser Ile Thr Lys Tyr Asn Pro Thr Thr His Asn
            260                 265                 270

Tyr Lys Thr Asn Ser Asp Asn Lys Pro Asn Phe Asp Lys Leu Val Glu
            275                 280                 285

Glu Thr Lys Lys Ala Val Lys Glu Ala Asp Asp Ser Trp Lys Lys Lys
            290                 295                 300

Thr Val Lys Lys Tyr Gly Glu Thr Thr Lys Ser Pro Val Val Lys
305                 310                 315                 320

Glu Glu Lys Lys Val Glu Glu Pro Gln Ala Pro Lys Val Asp Asn Gln
                325                 330                 335

Gln Glu Val Lys Thr Thr Ala Gly Lys Ala Glu Thr Thr Gln Pro
            340                 345                 350

Val Ala Gln Pro Leu Val Lys Ile Pro Gln Gly Thr Ile Thr Gly Glu
            355                 360                 365

Ile Val Lys Gly Pro Glu Tyr Pro Thr Met Glu Asn Lys Thr Val Gln
370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
            405                 410                 415

Leu Glu Gly Leu Glu Gly Ser Ser Ser Lys Leu Glu Ile Lys Pro Gln
            420                 425                 430

Gly Thr Glu Ser Thr Leu Lys Gly Thr Gln Gly Glu Ser Ser Asp Ile
            435                 440                 445

Glu Val Lys Pro Gln Ala Thr Glu Thr Thr Glu Ala Ser Gln Tyr Gly
            450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
            485                 490                 495

Ala Arg Pro Arg Phe Asn Lys Pro Ser Glu Thr Asn Ala Tyr Asn Val
            500                 505                 510

Thr Thr His Ala Asn Gly Gln Val Ser Tyr Gly Ala Arg Pro Thr Gln
            515                 520                 525

Asn Lys Pro Ser Lys Thr Asn Ala Tyr Asn Val Thr Thr His Gly Asn
            530                 535                 540

Gly Gln Val Ser Tyr Gly Ala Arg Pro Thr Gln Asn Lys Pro Ser Lys
545                 550                 555                 560

Thr Asn Ala Tyr Asn Val Thr Thr His Ala Asn Gly Gln Val Ser Tyr
                565                 570                 575

Gly Ala Arg Pro Thr Tyr Lys Lys Pro Ser Lys Thr Asn Ala Tyr Asn
            580                 585                 590

Val Thr Thr His Ala Asp Gly Thr Ala Thr Tyr Gly Pro Arg Val Thr
            595                 600                 605

Lys

<210> SEQ ID NO 22
<211> LENGTH: 658
<212> TYPE: PRT
<213> ORGANISM: Artificial Sequence
<220> FEATURE:
<223> OTHER INFORMATION: Synthetic Peptide

<400> SEQUENCE: 22
```

```
Met Lys Lys Gln Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
        20                  25                  30

Ser Lys Glu Ser Arg Val Asn Glu Lys Ser Lys Lys Gly Ala Thr Val
            35                  40                  45

Ser Asp Tyr Tyr Tyr Trp Lys Ile Ile Asp Ser Leu Glu Ala Gln Phe
    50                  55                  60

Thr Gly Ala Ile Asp Leu Leu Glu Asp Tyr Lys Tyr Gly Asp Pro Ile
65                  70                  75                  80

Tyr Lys Glu Ala Lys Asp Arg Leu Met Thr Arg Val Leu Gly Glu Asp
                85                  90                  95

Gln Tyr Leu Leu Lys Lys Ile Asp Glu Tyr Glu Leu Tyr Lys Lys
            100                 105                 110

Trp Tyr Lys Ser Ser Asn Lys Asn Thr Asn Met Leu Thr Phe His Lys
            115                 120                 125

Tyr Asn Leu Tyr Asn Leu Thr Met Asn Glu Tyr Asn Asp Ile Phe Asn
    130                 135                 140

Ser Leu Lys Asp Ala Val Tyr Gln Phe Asn Lys Glu Val Lys Glu Ile
145                 150                 155                 160

Glu His Lys Asn Val Asp Leu Lys Gln Phe Asp Lys Asp Gly Glu Asp
                165                 170                 175

Lys Ala Thr Lys Glu Val Tyr Asp Leu Val Ser Glu Ile Asp Thr Leu
            180                 185                 190

Val Val Thr Tyr Tyr Ala Asp Lys Asp Tyr Gly Glu His Ala Lys Glu
        195                 200                 205

Leu Arg Ala Lys Leu Asp Leu Ile Leu Gly Asp Thr Asp Asn Pro His
    210                 215                 220

Lys Ile Thr Asn Glu Arg Ile Lys Lys Glu Met Ile Asp Asp Leu Asn
225                 230                 235                 240

Ser Ile Ile Asp Asp Phe Phe Met Glu Thr Lys Gln Asn Arg Pro Asn
                245                 250                 255

Ser Ile Thr Lys Tyr Asp Pro Thr Lys His Asn Phe Lys Glu Lys Ser
            260                 265                 270

Glu Asn Lys Pro Asn Phe Asp Lys Leu Val Glu Thr Lys Lys Ala
    275                 280                 285

Val Lys Glu Ala Asp Glu Ser Trp Lys Asn Lys Thr Val Lys Lys Tyr
        290                 295                 300

Glu Glu Thr Val Thr Lys Ser Pro Val Val Lys Glu Glu Lys Lys Val
305                 310                 315                 320

Glu Glu Pro Gln Leu Pro Lys Val Gly Asn Gln Gln Glu Val Lys Thr
                325                 330                 335

Thr Ala Gly Lys Ala Glu Glu Thr Thr Gln Pro Val Ala Gln Pro Leu
            340                 345                 350

Val Lys Ile Pro Gln Glu Thr Ile Tyr Gly Glu Thr Val Lys Gly Pro
        355                 360                 365

Glu Tyr Pro Thr Met Glu Asn Lys Thr Leu Gln Gly Glu Ile Val Gln
    370                 375                 380

Gly Pro Asp Phe Leu Thr Met Glu Gln Asn Arg Pro Ser Leu Ser Asp
385                 390                 395                 400

Asn Tyr Thr Gln Pro Thr Thr Pro Asn Pro Ile Leu Glu Gly Leu Glu
                405                 410                 415

Gly Ser Ser Ser Lys Leu Glu Ile Lys Pro Gln Gly Thr Glu Ser Thr
```

```
                420                 425                 430
Leu Lys Gly Ile Gln Gly Glu Ser Ser Asp Ile Glu Val Lys Pro Gln
            435                 440                 445

Ala Thr Glu Thr Thr Glu Ala Ser Gln Tyr Gly Pro Arg Pro Gln Phe
        450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495

Asn Lys Pro Ser Glu Thr Asn Ala Tyr Asn Val Thr Thr Asn Gln Asp
            500                 505                 510

Gly Thr Val Ser Tyr Gly Ala Arg Pro Thr Gln Asn Lys Pro Ser Glu
        515                 520                 525

Thr Asn Ala Tyr Asn Val Thr Thr His Ala Asn Gly Gln Val Ser Tyr
    530                 535                 540

Gly Ala Arg Pro Thr Gln Lys Lys Pro Ser Lys Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr Thr His Ala
            580                 585                 590

Asn Gly Gln Val Ser Tyr Gly Ala Arg Pro Thr Tyr Lys Lys Pro Ser
        595                 600                 605

Glu Thr Asn Ala Tyr Asn Val Thr Thr His Ala Asn Gly Gln Val Ser
    610                 615                 620

Tyr Gly Ala Arg Leu Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys

<210> SEQ ID NO 23
<211> LENGTH: 658
<212> TYPE: PRT
<213> ORGANISM: Artificial Sequence
<220> FEATURE:
<223> OTHER INFORMATION: Synthetic Peptide

<400> SEQUENCE: 23

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Lys Ser Lys Lys Gly Ala Thr Val
        35                  40                  45

Ser Asp Tyr Tyr Tyr Trp Lys Ile Ile Asp Ser Leu Glu Ala Gln Phe
    50                  55                  60

Thr Gly Ala Ile Asp Leu Leu Glu Asp Tyr Lys Tyr Gly Asp Pro Ile
65                  70                  75                  80

Tyr Lys Glu Ala Lys Asp Arg Leu Met Thr Arg Val Leu Gly Glu Asp
                85                  90                  95

Gln Tyr Leu Leu Lys Lys Lys Ile Asp Glu Tyr Glu Leu Tyr Lys Lys
            100                 105                 110

Trp Tyr Lys Ser Ser Asn Lys Asn Thr Asn Met Leu Thr Phe His Lys
        115                 120                 125
```

```
Tyr Asn Leu Tyr Asn Leu Thr Met Asn Glu Tyr Asn Asp Ile Phe Asn
    130                 135                 140

Ser Leu Lys Asp Ala Val Tyr Gln Phe Asn Lys Glu Val Lys Glu Ile
145                 150                 155                 160

Glu His Lys Asn Val Asp Leu Lys Gln Phe Asp Lys Asp Gly Glu Asp
                165                 170                 175

Lys Ala Thr Lys Glu Val Tyr Asp Leu Val Ser Glu Ile Asp Thr Leu
            180                 185                 190

Val Val Thr Tyr Tyr Ala Asp Lys Asp Tyr Gly Glu His Ala Lys Glu
        195                 200                 205

Leu Arg Ala Lys Leu Asp Leu Ile Leu Gly Asp Thr Asp Asn Pro His
    210                 215                 220

Lys Ile Thr Asn Glu Arg Ile Lys Lys Glu Met Ile Asp Asp Leu Asn
225                 230                 235                 240

Ser Ile Ile Asp Asp Phe Phe Met Glu Thr Lys Gln Asn Arg Pro Asn
                245                 250                 255

Ser Ile Thr Lys Tyr Asp Pro Thr Lys His Asn Phe Lys Glu Lys Ser
            260                 265                 270

Glu Asn Lys Pro Asn Phe Asp Lys Leu Val Glu Thr Lys Lys Ala
        275                 280                 285

Val Lys Glu Ala Asp Glu Ser Trp Lys Asn Lys Thr Val Lys Lys Tyr
    290                 295                 300

Glu Glu Thr Val Thr Lys Ser Pro Val Val Lys Glu Lys Lys Val
305                 310                 315                 320

Glu Glu Pro Gln Leu Pro Lys Val Gly Asn Gln Glu Val Lys Thr
                325                 330                 335

Thr Ala Gly Lys Ala Glu Glu Thr Thr Gln Pro Val Ala Gln Pro Leu
            340                 345                 350

Val Lys Ile Pro Gln Glu Thr Ile Tyr Gly Glu Thr Val Lys Gly Pro
        355                 360                 365

Glu Tyr Pro Thr Met Glu Asn Lys Thr Leu Gln Gly Glu Ile Val Gln
    370                 375                 380

Gly Pro Asp Phe Leu Thr Met Glu Gln Asn Arg Pro Ser Leu Ser Asp
385                 390                 395                 400

Asn Tyr Thr Gln Pro Thr Thr Pro Asn Pro Ile Leu Glu Gly Leu Glu
                405                 410                 415

Gly Ser Ser Ser Lys Leu Glu Ile Lys Pro Gln Gly Thr Glu Ser Thr
            420                 425                 430

Leu Lys Gly Ile Gln Gly Glu Ser Asp Ile Glu Val Lys Pro Gln
        435                 440                 445

Ala Thr Glu Thr Thr Glu Ala Ser Gln Tyr Gly Pro Arg Pro Gln Phe
450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495

Asn Lys Pro Ser Glu Thr Asn Ala Tyr Asn Val Thr Thr Asn Gln Asp
            500                 505                 510

Gly Thr Val Ser Tyr Gly Ala Arg Pro Thr Gln Asn Lys Pro Ser Glu
        515                 520                 525

Thr Asn Ala Tyr Asn Val Thr Thr His Ala Asn Gly Gln Val Ser Tyr
    530                 535                 540
```

-continued

Gly Ala Arg Pro Thr Gln Lys Lys Pro Ser Lys Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr Thr His Ala
            580                 585                 590

Asn Gly Gln Val Ser Tyr Gly Ala Arg Pro Thr Tyr Lys Lys Pro Ser
        595                 600                 605

Glu Thr Asn Ala Tyr Asn Val Thr Thr His Ala Asn Gly Gln Val Ser
610                 615                 620

Tyr Gly Ala Arg Pro Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys

<210> SEQ ID NO 24
<211> LENGTH: 658
<212> TYPE: PRT
<213> ORGANISM: Artificial Sequence
<220> FEATURE:
<223> OTHER INFORMATION: Synthetic Peptide

<400> SEQUENCE: 24

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Lys Glu Ser Arg Val Asn Glu Lys Ser Lys Lys Gly Ala Thr Val
            35                  40                  45

Ser Asp Tyr Tyr Tyr Trp Lys Ile Ile Asp Ser Leu Glu Ala Gln Phe
        50                  55                  60

Thr Gly Ala Ile Asp Leu Leu Glu Asp Tyr Lys Tyr Gly Asp Pro Ile
65                  70                  75                  80

Tyr Lys Glu Ala Lys Asp Arg Leu Met Thr Arg Val Leu Gly Glu Asp
                85                  90                  95

Gln Tyr Leu Leu Lys Lys Ile Asp Glu Tyr Glu Leu Tyr Lys Lys
                100                 105                 110

Trp Tyr Lys Ser Ser Asn Lys Asn Thr Asn Met Leu Thr Phe His Lys
            115                 120                 125

Tyr Asn Leu Tyr Asn Leu Thr Met Asn Glu Tyr Asn Asp Ile Phe Asn
        130                 135                 140

Ser Leu Lys Asp Ala Val Tyr Gln Phe Asn Lys Glu Val Lys Glu Ile
145                 150                 155                 160

Glu His Lys Asn Val Asp Leu Lys Gln Phe Asp Lys Asp Gly Glu Asp
                165                 170                 175

Lys Ala Thr Lys Glu Val Tyr Asp Leu Val Ser Glu Ile Asp Thr Leu
            180                 185                 190

Val Val Thr Tyr Tyr Ala Asp Lys Asp Tyr Gly Glu His Ala Lys Glu
        195                 200                 205

Leu Arg Ala Lys Leu Asp Leu Ile Leu Gly Asp Thr Asp Asn Pro His
        210                 215                 220

Lys Ile Thr Asn Glu Arg Ile Lys Lys Glu Met Ile Asp Asp Leu Asn
225                 230                 235                 240

Ser Ile Ile Asp Asp Phe Phe Met Glu Thr Lys Gln Asn Arg Pro Asn

```
                245                 250                 255
Ser Ile Thr Lys Tyr Asp Pro Thr Lys His Asn Phe Lys Glu Lys Ser
            260                 265                 270

Glu Asn Lys Pro Asn Phe Asp Lys Leu Val Glu Glu Thr Lys Lys Ala
        275                 280                 285

Val Lys Glu Ala Asp Glu Ser Trp Lys Asn Lys Thr Val Lys Lys Tyr
    290                 295                 300

Glu Glu Thr Val Thr Lys Ser Pro Val Val Lys Glu Glu Lys Lys Val
305                 310                 315                 320

Glu Glu Pro Gln Leu Pro Lys Val Gly Asn Gln Gln Glu Val Lys Thr
                325                 330                 335

Thr Ala Gly Lys Ala Glu Glu Thr Thr Gln Pro Val Ala Gln Pro Leu
            340                 345                 350

Val Lys Ile Pro Gln Glu Thr Ile Tyr Gly Glu Thr Val Lys Gly Pro
        355                 360                 365

Glu Tyr Pro Thr Met Glu Asn Lys Thr Leu Gln Gly Glu Ile Val Gln
    370                 375                 380

Gly Pro Asp Phe Leu Thr Met Glu Gln Asn Arg Pro Ser Leu Ser Asp
385                 390                 395                 400

Asn Tyr Thr Gln Pro Thr Thr Pro Asn Pro Ile Leu Glu Gly Leu Glu
                405                 410                 415

Gly Ser Ser Ser Lys Leu Glu Ile Lys Pro Gln Gly Thr Glu Ser Thr
            420                 425                 430

Leu Lys Gly Ile Gln Gly Glu Ser Ser Asp Ile Glu Val Lys Pro Gln
        435                 440                 445

Ala Thr Glu Thr Thr Glu Ala Ser Gln Tyr Gly Pro Arg Pro Gln Phe
    450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495

Asn Lys Pro Ser Glu Thr Asn Ala Tyr Asn Val Thr Thr Asn Gln Asp
            500                 505                 510

Gly Thr Val Ser Tyr Gly Ala Arg Pro Thr Gln Asn Lys Pro Ser Glu
        515                 520                 525

Thr Asn Ala Tyr Asn Val Thr Thr His Ala Asn Gly Gln Val Ser Tyr
    530                 535                 540

Gly Ala Arg Pro Thr Tyr Lys Lys Pro Ser Glu Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr Thr His Ala
            580                 585                 590

Asn Gly Gln Val Ser Tyr Gly Ala Arg Pro Thr Tyr Lys Lys Pro Ser
        595                 600                 605

Glu Thr Asn Ala Tyr Asn Val Thr Thr His Ala Asn Gly Gln Val Ser
    610                 615                 620

Tyr Gly Ala Arg Pro Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys
```

<210> SEQ ID NO 25
<211> LENGTH: 636
<212> TYPE: PRT
<213> ORGANISM: Artificial Sequence
<220> FEATURE:
<223> OTHER INFORMATION: Synthetic Peptide

<400> SEQUENCE: 25

```
Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Gly Lys Ser Gln Val Asn Ala Gly Ser Lys Asn Gly Thr Leu Ile
        35                  40                  45

Asp Ser Arg Tyr Leu Asn Ser Ala Leu Tyr Tyr Leu Glu Asp Tyr Ile
    50                  55                  60

Ile Tyr Ala Ile Gly Leu Thr Asn Lys Tyr Glu Tyr Gly Asp Asn Ile
65                  70                  75                  80

Tyr Lys Glu Ala Lys Asp Arg Leu Leu Glu Lys Val Leu Arg Glu Asp
                85                  90                  95

Gln Tyr Leu Leu Glu Arg Lys Lys Ser Gln Tyr Glu Asp Tyr Lys Gln
            100                 105                 110

Trp Tyr Ala Asn Tyr Lys Lys Glu Asn Pro Arg Thr Asp Leu Lys Met
        115                 120                 125

Ala Asn Phe His Lys Tyr Asn Leu Glu Glu Leu Ser Met Lys Glu Tyr
    130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
        195                 200                 205

Glu His Ala Lys Glu Leu Arg Ala Lys Leu Asp Leu Ile Leu Gly Asp
    210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Phe Phe Met Glu Thr Lys
                245                 250                 255

Gln Asn Arg Pro Lys Ser Ile Thr Lys Tyr Asn Pro Thr Thr His Asn
            260                 265                 270

Tyr Lys Thr Asn Ser Asp Asn Lys Pro Asn Phe Asp Lys Leu Val Glu
        275                 280                 285

Glu Thr Lys Lys Ala Val Lys Glu Ala Asp Asp Ser Trp Lys Lys Lys
    290                 295                 300

Thr Val Lys Lys Tyr Gly Glu Thr Glu Thr Lys Ser Pro Val Val Lys
305                 310                 315                 320

Glu Glu Lys Lys Val Glu Glu Pro Gln Ala Pro Lys Val Asp Asn Gln
                325                 330                 335

Gln Glu Val Lys Thr Thr Ala Gly Lys Ala Glu Glu Thr Thr Gln Pro
            340                 345                 350

Val Ala Gln Pro Leu Val Lys Ile Pro Gln Gly Thr Ile Thr Gly Glu
        355                 360                 365
```

```
Ile Val Lys Gly Pro Glu Tyr Pro Thr Met Glu Asn Lys Thr Val Gln
    370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
                405                 410                 415

Leu Glu Gly Leu Glu Gly Ser Ser Lys Leu Glu Ile Lys Pro Gln
                420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Thr Glu Ala Ser Gln Tyr Gly
450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
                500                 505                 510

Thr Thr His Ala Asn Gly Gln Val Ser Tyr Gly Ala Arg Pro Thr Tyr
            515                 520                 525

Lys Lys Pro Ser Glu Thr Asn Ala Tyr Asn Val Thr Thr His Ala Asn
    530                 535                 540

Gly Gln Val Ser Tyr Gly Ala Arg Pro Thr Gln Asn Lys Pro Ser Lys
545                 550                 555                 560

Thr Asn Ala Tyr Asn Val Thr Thr His Gly Asn Gly Gln Val Ser Tyr
                565                 570                 575

Gly Ala Arg Pro Thr Gln Asn Lys Pro Ser Lys Thr Asn Ala Tyr Asn
                580                 585                 590

Val Thr Thr His Ala Asn Gly Gln Val Ser Tyr Gly Ala Arg Pro Thr
            595                 600                 605

Tyr Lys Lys Pro Ser Lys Thr Asn Ala Tyr Asn Val Thr Thr His Ala
    610                 615                 620

Asp Gly Thr Ala Thr Tyr Gly Pro Arg Val Thr Lys
625                 630                 635

<210> SEQ ID NO 26
<211> LENGTH: 609
<212> TYPE: PRT
<213> ORGANISM: Artificial Sequence
<220> FEATURE:
<223> OTHER INFORMATION: Synthetic Peptide

<400> SEQUENCE: 26

Met Lys Lys Gln Ile Ile Ser Leu Gly Ala Leu Ala Val Ala Ser Ser
1                   5                   10                  15

Leu Phe Thr Trp Asp Asn Lys Ala Asp Ala Ile Val Thr Lys Asp Tyr
                20                  25                  30

Ser Gly Lys Ser Gln Val Asn Ala Gly Ser Lys Asn Gly Thr Leu Ile
            35                  40                  45

Asp Ser Arg Tyr Leu Asn Ser Ala Leu Tyr Tyr Leu Glu Asp Tyr Ile
        50                  55                  60

Ile Tyr Ala Ile Gly Leu Thr Asn Lys Tyr Glu Tyr Gly Asp Asn Ile
65                  70                  75                  80

Tyr Lys Glu Ala Lys Asp Arg Leu Leu Glu Lys Val Leu Arg Glu Asp
                85                  90                  95
```

```
Gln Tyr Leu Leu Glu Arg Lys Lys Ser Gln Tyr Glu Asp Tyr Lys Gln
                100                 105                 110

Trp Tyr Ala Asn Tyr Lys Lys Glu Asn Pro Arg Thr Asp Leu Lys Met
            115                 120                 125

Ala Asn Phe His Lys Tyr Asn Leu Glu Glu Leu Ser Met Lys Glu Tyr
        130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
        195                 200                 205

Glu His Ala Lys Glu Leu Arg Ala Lys Leu Asp Leu Ile Leu Gly Asp
    210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Asp Phe Phe Met Glu Thr Lys
                245                 250                 255

Gln Asn Arg Pro Lys Ser Ile Thr Lys Tyr Asn Pro Thr Thr His Asn
            260                 265                 270

Tyr Lys Thr Asn Ser Asp Asn Lys Pro Asn Phe Asp Lys Leu Val Glu
        275                 280                 285

Glu Thr Lys Lys Ala Val Lys Glu Ala Asp Asp Ser Trp Lys Lys Lys
    290                 295                 300

Thr Val Lys Lys Tyr Gly Glu Thr Glu Thr Lys Ser Pro Val Val Lys
305                 310                 315                 320

Glu Glu Lys Lys Val Glu Pro Gln Ala Pro Lys Val Asp Asn Gln
                325                 330                 335

Gln Glu Val Lys Thr Thr Ala Gly Lys Ala Glu Glu Thr Gln Pro
            340                 345                 350

Val Ala Gln Pro Leu Val Lys Ile Pro Gln Gly Thr Ile Thr Gly Glu
        355                 360                 365

Ile Val Lys Gly Pro Glu Tyr Pro Thr Met Glu Asn Lys Thr Val Gln
    370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
                405                 410                 415

Leu Glu Gly Leu Glu Gly Ser Ser Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Thr Glu Ala Ser Gln Tyr Gly
    450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr His Ala Asn Gly Gln Val Ser Tyr Gly Ala Arg Pro Thr Gln
```

```
                    515                 520                 525
Asn Lys Pro Ser Lys Thr Asn Ala Tyr Asn Val Thr Thr His Gly Asn
        530                 535                 540

Gly Gln Val Ser Tyr Gly Ala Arg Pro Thr Gln Asn Lys Pro Ser Lys
545                 550                 555                 560

Thr Asn Ala Tyr Asn Val Thr Thr His Ala Asn Gly Gln Val Ser Tyr
                565                 570                 575

Gly Ala Arg Pro Thr Tyr Lys Lys Pro Ser Lys Thr Asn Ala Tyr Asn
            580                 585                 590

Val Thr Thr His Ala Asp Gly Thr Ala Thr Tyr Gly Pro Arg Val Thr
                595                 600                 605

Lys

<210> SEQ ID NO 27
<211> LENGTH: 656
<212> TYPE: PRT
<213> ORGANISM: Artificial Sequence
<220> FEATURE:
<223> OTHER INFORMATION: Synthetic Peptide

<400> SEQUENCE: 27

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Asn Gly Lys Ser Gln Val Lys Lys Glu Ser Lys Asn Gly Thr Leu Ile
        35                  40                  45

Asp Ser Arg Tyr Tyr Trp Glu Lys Ile Glu Ala Leu Glu Lys Gln Phe
    50                  55                  60

Ser Ser Ala Leu Ala Leu Thr Asp Glu Tyr Gln Tyr Gly Gly Asn Glu
65                  70                  75                  80

Tyr Lys Glu Ala Lys Asp Lys Leu Met Glu Arg Ile Leu Gly Glu Asp
                85                  90                  95

Gln Tyr Leu Leu Lys Lys Ile Asp Glu Tyr Asp Tyr Tyr Lys Lys
            100                 105                 110

Trp Tyr Lys Ala Thr Tyr Pro Asn Asp Asn Ser Lys Met Tyr Ser Phe
            115                 120                 125

His Lys Tyr Asn Val Tyr Tyr Leu Thr Met Asn Glu Tyr Asn Glu Ile
        130                 135                 140

Thr Asn Ser Leu Lys Asp Ala Val Glu Lys Phe Asn Asn Glu Val Arg
145                 150                 155                 160

Asp Ile Gln Ser Lys Asn Glu Asp Leu Lys Pro Tyr Asp Glu Asn Thr
                165                 170                 175

Glu Lys Gln Glu Thr Asp Lys Ile Tyr Glu Phe Val Ser Glu Ile Asp
            180                 185                 190

Thr Val Phe Ala Ala Tyr Tyr Ser His Glu Lys Phe Gly Ile His Ala
            195                 200                 205

Lys Glu Leu Arg Ala Lys Leu Asp Ile Ile Leu Gly Asp Val His Asn
        210                 215                 220

Pro Asn Arg Ile Thr Asn Glu Arg Ile Lys Lys Glu Met Met Glu Asp
225                 230                 235                 240

Leu Asn Ser Ile Val Asp Asp Phe Phe Met Glu Thr Asn Gln Asn Arg
                245                 250                 255

Pro Thr Thr Ile Lys Lys Tyr Asp Pro Asn Ile His Asp Tyr Thr Lys
            260                 265                 270
```

Lys Lys Glu Asn Lys Glu Asn Phe Asp Lys Leu Val Lys Glu Thr Arg
            275                 280                 285

Glu Ala Val Glu Lys Ala Asp Glu Ser Trp Lys Asn Lys Thr Val Lys
        290                 295                 300

Lys Tyr Glu Glu Thr Val Thr Lys Ser Pro Phe Val Lys Glu Glu Lys
305                 310                 315                 320

Lys Val Glu Glu Pro Gln Leu Pro Lys Val Gly Asn Gln Gln Glu Val
                325                 330                 335

Lys Thr Thr Ala Gly Lys Ala Glu Glu Thr Thr Gln Pro Leu Val Lys
            340                 345                 350

Ile Pro Gln Gly Thr Ile Thr Gly Glu Ile Val Lys Gly Pro Asp Tyr
        355                 360                 365

Pro Thr Met Glu Asn Lys Thr Leu Gln Gly Glu Ile Val Gln Gly Pro
    370                 375                 380

Asp Phe Pro Thr Met Glu Gln Asn Arg Pro Ser Leu Ser Asp Asn Tyr
385                 390                 395                 400

Thr Gln Pro Thr Thr Thr Asn Pro Ile Leu Glu Gly Leu Glu Gly Ser
                405                 410                 415

Ser Ser Lys Leu Glu Ile Lys Pro Gln Gly Thr Glu Ser Thr Leu Gln
            420                 425                 430

Gly Thr Gln Gly Glu Ser Ser Asp Ile Glu Val Lys Pro Gln Ala Thr
        435                 440                 445

Glu Thr Thr Glu Ala Ser Gln Tyr Gly Pro Arg Pro Gln Phe Asn Lys
    450                 455                 460

Thr Pro Lys Tyr Val Lys Tyr Arg Asp Ala Gly Thr Gly Ile Arg Glu
465                 470                 475                 480

Tyr Asn Asp Gly Thr Phe Gly Tyr Glu Ala Arg Pro Arg Phe Asn Lys
                485                 490                 495

Pro Ser Glu Thr Asn Ala Tyr Asn Val Thr Thr Asn Gln Asp Gly Thr
            500                 505                 510

Val Thr Tyr Gly Ala Arg Pro Thr Gln Asn Lys Pro Ser Lys Thr Asn
        515                 520                 525

Ala Tyr Asn Val Thr Thr His Ala Asn Gly Gln Val Ser Tyr Gly Ala
    530                 535                 540

Arg Pro Thr Tyr Lys Lys Pro Ser Glu Thr Asn Ala Tyr Asn Val Thr
545                 550                 555                 560

Thr His Ala Asn Gly Gln Val Ser Tyr Gly Ala Arg Pro Thr Gln Asn
                565                 570                 575

Lys Ala Ser Glu Thr Asn Ala Tyr Asn Val Thr His Ala Asn Gly
            580                 585                 590

Gln Val Ser Tyr Gly Ala Arg Pro Thr Gln Asn Lys Pro Ser Lys Thr
        595                 600                 605

Asn Ala Tyr Asn Val Thr Thr His Gly Asn Gly Gln Val Ser Tyr Gly
    610                 615                 620

Ala Arg Pro Thr Tyr Lys Lys Pro Ser Glu Thr Asn Ala Tyr Asn Val
625                 630                 635                 640

Thr Thr His Ala Asp Gly Thr Ala Thr Tyr Gly Pro Arg Val Thr Lys
                645                 650                 655

<210> SEQ ID NO 28
<211> LENGTH: 656
<212> TYPE: PRT
<213> ORGANISM: Artificial Sequence
<220> FEATURE:

<223> OTHER INFORMATION: Synthetic Peptide

<400> SEQUENCE: 28

```
Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Asn Gly Lys Ser Gln Val Lys Lys Glu Ser Lys Asn Gly Thr Leu Ile
        35                  40                  45

Asp Ser Arg Tyr Tyr Trp Glu Lys Ile Glu Ala Leu Glu Lys Gln Phe
    50                  55                  60

Ser Ser Ala Leu Ala Leu Thr Asp Glu Tyr Gln Tyr Gly Gly Asn Glu
65                  70                  75                  80

Tyr Lys Glu Ala Lys Asp Lys Leu Met Glu Arg Ile Leu Gly Glu Asp
                85                  90                  95

Gln Tyr Leu Leu Lys Lys Ile Asp Glu Tyr Asp Tyr Tyr Lys Lys
            100                 105                 110

Trp Tyr Lys Ala Thr Tyr Pro Asn Asp Asn Ser Lys Met Tyr Ser Phe
            115                 120                 125

His Lys Tyr Asn Val Tyr Leu Thr Met Asn Glu Tyr Asn Glu Ile
    130                 135                 140

Ser Asn Ser Leu Lys Asp Ala Val Glu Lys Phe Asn Asn Glu Val Arg
145                 150                 155                 160

Asp Ile Gln Ser Lys Asn Glu Asp Leu Lys Pro Tyr Asp Glu Asn Thr
                165                 170                 175

Glu Lys Gln Glu Thr Asp Lys Ile Tyr Glu Phe Val Ser Glu Ile Asp
            180                 185                 190

Thr Val Phe Ala Ala Tyr Tyr Ser His Glu Lys Phe Gly Ile His Ala
        195                 200                 205

Lys Glu Leu Arg Ala Lys Leu Asp Ile Ile Leu Gly Asp Val His Asn
210                 215                 220

Pro Asn Arg Ile Thr Asn Glu Arg Ile Lys Lys Glu Met Met Glu Asp
225                 230                 235                 240

Leu Asn Ser Ile Val Asp Asp Phe Phe Met Glu Thr Asn Gln Asn Arg
                245                 250                 255

Pro Thr Thr Ile Lys Lys Tyr Asp Pro Asn Ile His Asp Tyr Thr Lys
            260                 265                 270

Lys Lys Glu Asn Lys Glu Asn Phe Asp Lys Leu Val Lys Glu Thr Arg
        275                 280                 285

Glu Ala Val Glu Lys Ala Asp Glu Ser Trp Lys Asn Lys Thr Val Lys
    290                 295                 300

Lys Tyr Glu Glu Thr Val Thr Lys Ser Pro Phe Val Lys Glu Glu Lys
305                 310                 315                 320

Lys Val Glu Glu Pro Gln Leu Pro Lys Val Gly Asn Gln Glu Val
                325                 330                 335

Lys Thr Thr Ala Gly Lys Ala Glu Glu Thr Thr Gln Pro Leu Val Lys
            340                 345                 350

Ile Pro Gln Gly Thr Ile Thr Gly Glu Ile Val Lys Gly Pro Asp Tyr
        355                 360                 365

Pro Thr Met Glu Asn Lys Thr Leu Gln Gly Glu Ile Val Gln Gly Pro
    370                 375                 380

Asp Phe Pro Thr Met Glu Gln Asn Arg Pro Ser Leu Ser Asp Asn Tyr
385                 390                 395                 400
```

```
Thr Gln Pro Thr Thr Thr Asn Pro Ile Leu Glu Gly Leu Glu Gly Ser
                405                 410                 415

Ser Ser Lys Leu Glu Ile Lys Pro Gln Gly Thr Glu Ser Thr Leu Gln
        420                 425                 430

Gly Thr Gln Gly Glu Ser Ser Asp Ile Glu Val Lys Pro Gln Ala Thr
            435                 440                 445

Glu Thr Thr Glu Ala Ser Gln Tyr Gly Pro Arg Pro Gln Phe Asn Lys
450                 455                 460

Thr Pro Lys Tyr Val Lys Tyr Arg Asp Ala Gly Thr Gly Ile Arg Glu
465                 470                 475                 480

Tyr Asn Asp Gly Thr Phe Gly Tyr Glu Ala Arg Pro Arg Phe Asn Lys
                485                 490                 495

Pro Ser Glu Thr Asn Ala Tyr Asn Val Thr Thr Asn Gln Asp Gly Thr
            500                 505                 510

Val Thr Tyr Gly Ala Arg Pro Thr Gln Asn Lys Pro Ser Lys Thr Asn
        515                 520                 525

Ala Tyr Asn Val Thr Thr His Ala Asn Gly Gln Val Ser Tyr Gly Ala
    530                 535                 540

Arg Pro Thr Tyr Lys Lys Pro Ser Glu Thr Asn Ala Tyr Asn Val Thr
545                 550                 555                 560

Thr His Ala Asn Gly Gln Val Ser Tyr Gly Ala Arg Pro Thr Gln Asn
                565                 570                 575

Lys Ala Ser Glu Thr Asn Ala Tyr Asn Val Thr Thr His Ala Asn Gly
            580                 585                 590

Gln Val Ser Tyr Gly Ala Arg Pro Thr Gln Asn Lys Pro Ser Lys Thr
        595                 600                 605

Asn Ala Tyr Asn Val Thr Thr His Gly Asn Gly Gln Val Ser Tyr Gly
    610                 615                 620

Ala Arg Pro Thr Tyr Lys Lys Pro Ser Glu Thr Asn Ala Tyr Asn Val
625                 630                 635                 640

Thr Thr His Ala Asp Gly Thr Ala Thr Tyr Gly Pro Arg Val Thr Lys
                645                 650                 655

<210> SEQ ID NO 29
<211> LENGTH: 575
<212> TYPE: PRT
<213> ORGANISM: Artificial Sequence
<220> FEATURE:
<223> OTHER INFORMATION: Synthetic Peptide

<400> SEQUENCE: 29

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Asn Gly Lys Ser Gln Val Lys Lys Glu Ser Lys Asn Gly Thr Leu Ile
            35                  40                  45

Asp Ser Arg Tyr Tyr Trp Glu Lys Ile Glu Ala Leu Glu Lys Gln Phe
        50                  55                  60

Ser Ser Ala Leu Ala Leu Thr Asp Glu Tyr Gln Tyr Gly Gly Asn Glu
65                  70                  75                  80

Tyr Lys Glu Ala Lys Asp Lys Leu Met Glu Arg Ile Leu Gly Glu Asp
                85                  90                  95

Gln Tyr Leu Leu Lys Lys Ile Asp Glu Tyr Asp Tyr Tyr Lys Lys
            100                 105                 110
```

-continued

```
Trp Tyr Lys Ala Thr Tyr Pro Asn Asp Asn Ser Lys Met Tyr Ser Phe
            115                 120                 125

His Lys Tyr Asn Val Tyr Tyr Leu Thr Met Asn Glu Tyr Asn Glu Ile
        130                 135                 140

Thr Asn Ser Leu Lys Asp Ala Val Glu Lys Phe Asn Asn Glu Val Arg
145                 150                 155                 160

Asp Ile Gln Ser Lys Asn Glu Asp Leu Lys Pro Tyr Asp Glu Asn Thr
                165                 170                 175

Glu Lys Gln Glu Thr Asp Lys Ile Tyr Glu Phe Val Ser Glu Ile Asp
            180                 185                 190

Thr Val Phe Ala Ala Tyr Tyr Ser His Glu Lys Phe Gly Ile His Ala
        195                 200                 205

Lys Glu Leu Arg Ala Lys Leu Asp Ile Ile Leu Gly Asp Val His Asn
210                 215                 220

Pro Asn Arg Ile Thr Asn Glu Arg Ile Lys Lys Glu Met Met Glu Asp
225                 230                 235                 240

Leu Asn Ser Ile Val Asp Asp Phe Phe Met Glu Thr Asn Gln Asn Arg
                245                 250                 255

Pro Thr Thr Ile Lys Lys Tyr Asp Pro Asn Ile His Asp Tyr Thr Lys
            260                 265                 270

Lys Lys Glu Asn Lys Glu Asn Phe Asp Lys Leu Val Lys Glu Thr Arg
        275                 280                 285

Glu Ala Val Glu Lys Ala Asp Glu Ser Trp Lys Asn Lys Thr Val Lys
290                 295                 300

Lys Tyr Glu Glu Thr Val Thr Lys Ser Pro Phe Val Lys Glu Glu Lys
305                 310                 315                 320

Lys Val Glu Glu Pro Gln Leu Pro Lys Val Gly Asn Gln Gln Glu Val
                325                 330                 335

Lys Thr Thr Ala Gly Lys Ala Glu Glu Thr Thr Gln Pro Leu Val Lys
            340                 345                 350

Ile Pro Gln Gly Thr Ile Thr Gly Glu Ile Val Lys Gly Pro Asp Tyr
        355                 360                 365

Pro Thr Met Glu Asn Lys Thr Leu Gln Gly Glu Ile Val Gln Gly Pro
370                 375                 380

Asp Phe Pro Thr Met Glu Gln Asn Arg Pro Ser Leu Ser Asp Asn Tyr
385                 390                 395                 400

Thr Gln Pro Thr Thr Asn Pro Ile Leu Glu Gly Leu Glu Gly Ser
                405                 410                 415

Ser Ser Lys Leu Glu Ile Lys Pro Gln Gly Thr Glu Ser Thr Leu Gln
            420                 425                 430

Gly Thr Gln Gly Glu Ser Ser Asp Ile Glu Val Lys Pro Gln Ala Thr
        435                 440                 445

Glu Thr Thr Glu Ala Ser Gln Tyr Gly Pro Arg Pro Gln Phe Asn Lys
450                 455                 460

Thr Pro Lys Tyr Val Lys Tyr Arg Asp Ala Gly Thr Gly Ile Arg Glu
465                 470                 475                 480

Tyr Asn Asp Gly Thr Phe Gly Tyr Glu Ala Arg Pro Arg Phe Asn Lys
                485                 490                 495

Pro Ser Glu Thr Asn Ala Tyr Asn Val Thr Thr Asn Gln Asp Gly Thr
            500                 505                 510

Val Thr Tyr Gly Ala Arg Pro Thr Gln Asn Lys Pro Ser Lys Thr Asn
        515                 520                 525

Ala Tyr Asn Val Thr Thr His Ala Asn Gly Gln Val Ser Tyr Gly Ala
```

```
                     530                 535                 540
Arg Pro Thr Tyr Lys Lys Pro Ser Glu Thr Asn Ala Tyr Asn Val Thr
545                 550                 555                 560

Thr His Ala Asn Gly Thr Ala Thr Tyr Gly Pro Arg Val Thr Lys
                    565                 570                 575

<210> SEQ ID NO 30
<211> LENGTH: 609
<212> TYPE: PRT
<213> ORGANISM: Artificial Sequence
<220> FEATURE:
<223> OTHER INFORMATION: Synthetic Peptide

<400> SEQUENCE: 30

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Lys Glu Ser Arg Val Asn Glu Asn Ser Lys Tyr Asp Thr Pro Ile
            35                  40                  45

Pro Asp Trp Tyr Leu Gly Ser Ile Leu Asn Arg Leu Gly Asp Gln Ile
        50                  55                  60

Tyr Tyr Ala Lys Glu Leu Thr Asn Lys Tyr Glu Tyr Gly Glu Lys Glu
65                  70                  75                  80

Tyr Lys Gln Ala Ile Asp Lys Leu Met Thr Arg Val Leu Gly Glu Asp
                85                  90                  95

His Tyr Leu Leu Glu Lys Lys Ala Gln Tyr Glu Ala Tyr Lys Lys
            100                 105                 110

Trp Phe Glu Lys His Lys Ser Glu Asn Pro His Ser Ser Leu Lys Lys
        115                 120                 125

Ile Lys Phe Asp Asp Phe Asp Leu Tyr Arg Leu Thr Lys Lys Glu Tyr
130                 135                 140

Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
            180                 185                 190

Glu Ile Asp Thr Leu Tyr Ala Ala Tyr Phe Asn His Ser Gln Tyr Gly
        195                 200                 205

His Asn Ala Lys Glu Leu Arg Ala Lys Leu Asp Ile Ile Leu Gly Asp
210                 215                 220

Ala Lys Asp Pro Val Arg Ile Thr Asn Glu Arg Ile Arg Lys Glu Met
225                 230                 235                 240

Met Asp Asp Leu Asn Ser Ile Ile Asp Phe Phe Met Asp Thr Asn
                245                 250                 255

Met Asn Arg Pro Leu Asn Ile Thr Lys Phe Asn Pro Asn Ile His Asp
            260                 265                 270

Tyr Thr Asn Lys Pro Glu Asn Arg Asp Asn Phe Asp Lys Leu Val Lys
        275                 280                 285

Glu Thr Arg Glu Ala Ile Ala Asn Ala Asp Glu Ser Trp Lys Thr Arg
290                 295                 300

Thr Val Lys Asn Tyr Gly Glu Ser Glu Thr Lys Ser Pro Val Val Lys
305                 310                 315                 320

Glu Glu Lys Lys Val Glu Glu Pro Gln Leu Pro Lys Val Gly Asn Gln
```

```
                    325                 330                 335

Gln Glu Asp Lys Ile Thr Val Gly Thr Thr Glu Glu Ala Pro Leu Pro
            340                 345                 350

Ile Ala Gln Pro Leu Val Lys Ile Pro Gln Gly Thr Ile Gln Gly Glu
        355                 360                 365

Ile Val Lys Gly Pro Glu Tyr Leu Thr Met Glu Asn Lys Thr Leu Gln
    370                 375                 380

Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Pro Asn Pro Ile
                405                 410                 415

Leu Lys Gly Ile Glu Gly Asn Ser Thr Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Glu Ala Ser His Tyr Pro
    450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr Asn Gln Asp Gly Thr Val Ser Tyr Gly Ala Arg Pro Thr Gln
        515                 520                 525

Asn Lys Pro Ser Glu Thr Asn Ala Tyr Asn Val Thr Thr His Ala Asn
    530                 535                 540

Gly Gln Val Ser Tyr Gly Ala Arg Pro Thr Gln Asn Lys Pro Ser Glu
545                 550                 555                 560

Thr Asn Ala Tyr Asn Val Thr Thr His Ala Asn Gly Gln Val Ser Tyr
                565                 570                 575

Gly Ala Arg Pro Thr Gln Asn Lys Pro Ser Lys Thr Asn Ala Tyr Asn
            580                 585                 590

Val Thr Thr His Ala Asp Gly Thr Ala Thr Gly Pro Arg Val Thr
        595                 600                 605

Lys

<210> SEQ ID NO 31
<211> LENGTH: 663
<212> TYPE: PRT
<213> ORGANISM: Artificial Sequence
<220> FEATURE:
<223> OTHER INFORMATION: Synthetic Peptide

<400> SEQUENCE: 31

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Lys Glu Ser Arg Val Asn Glu Asn Ser Lys Tyr Asp Thr Pro Ile
            35                  40                  45

Pro Asp Trp Tyr Leu Gly Ser Ile Leu Asn Arg Leu Gly Asp Gln Ile
        50                  55                  60

Tyr Tyr Ala Lys Glu Leu Thr Asn Lys Tyr Glu Tyr Gly Glu Lys Glu
65                  70                  75                  80
```

```
Tyr Lys Gln Ala Ile Asp Lys Leu Met Thr Arg Val Leu Gly Glu Asp
                85                  90                  95

His Tyr Leu Leu Glu Lys Lys Ala Gln Tyr Glu Ala Tyr Lys Lys
            100                 105                 110

Trp Phe Glu Lys His Lys Ser Glu Asn Pro His Ser Ser Leu Lys Lys
            115                 120                 125

Ile Lys Phe Asp Asp Phe Asp Leu Tyr Arg Leu Thr Lys Lys Glu Tyr
        130                 135                 140

Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
            180                 185                 190

Glu Ile Asp Thr Leu Tyr Ala Ala Tyr Phe Asn His Ser Gln Tyr Gly
            195                 200                 205

His Asn Ala Lys Glu Leu Arg Ala Lys Leu Asp Ile Ile Leu Gly Asp
    210                 215                 220

Ala Lys Asp Pro Val Arg Ile Thr Asn Glu Arg Ile Arg Lys Glu Met
225                 230                 235                 240

Met Asp Asp Leu Asn Ser Ile Ile Asp Asp Phe Phe Met Asp Thr Asn
                245                 250                 255

Met Asn Arg Pro Leu Asn Ile Thr Lys Phe Asn Pro Asn Ile His Asp
            260                 265                 270

Tyr Thr Asn Lys Pro Glu Asn Arg Asp Asn Phe Asp Lys Leu Val Lys
        275                 280                 285

Glu Thr Arg Glu Ala Val Ala Asn Ala Asp Glu Ser Trp Lys Thr Arg
        290                 295                 300

Thr Val Lys Asn Tyr Gly Glu Ser Glu Thr Lys Ser Pro Val Val Lys
305                 310                 315                 320

Glu Glu Lys Lys Val Glu Glu Pro Gln Leu Pro Lys Val Gly Asn Gln
                325                 330                 335

Gln Glu Asp Lys Ile Thr Val Gly Thr Thr Glu Glu Ala Pro Leu Pro
            340                 345                 350

Ile Ala Gln Pro Leu Val Lys Ile Pro Gln Gly Thr Ile Gln Gly Glu
        355                 360                 365

Ile Val Lys Gly Pro Glu Tyr Leu Thr Met Glu Asn Lys Thr Leu Gln
        370                 375                 380

Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Asn Pro Ile
                405                 410                 415

Leu Lys Gly Ile Glu Gly Asn Ser Thr Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Glu Ala Ser His Tyr Pro
            450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495
```

```
Ala Arg Pro Arg Phe Asn Lys Pro Ser Glu Thr Asn Ala Tyr Asn Val
            500                 505                 510

Thr Thr Asn Gln Asp Gly Thr Val Ser Tyr Gly Ala Arg Pro Thr Gln
        515                 520                 525

Asn Lys Pro Ser Glu Thr Asn Ala Tyr Asn Val Thr Thr His Ala Asn
    530                 535                 540

Gly Gln Val Ser Tyr Gly Ala Arg Pro Thr Tyr Lys Pro Ser Glu
545                 550                 555                 560

Thr Asn Ala Tyr Asn Val Thr Thr Asn Gln Asp Gly Thr Val Ser Tyr
                565                 570                 575

Gly Ala Arg Pro Thr Gln Asn Lys Pro Ser Glu Thr Asn Ala Tyr Asn
            580                 585                 590

Val Thr Thr His Ala Asn Gly Gln Val Ser Tyr Gly Ala Arg Pro Thr
        595                 600                 605

Gln Asn Lys Pro Ser Glu Thr Asn Ala Tyr Asn Val Thr Thr His Ala
    610                 615                 620

Asn Gly Gln Val Ser Tyr Gly Ala Arg Pro Thr Gln Asn Lys Pro Ser
625                 630                 635                 640

Lys Thr Asn Ala Tyr Asn Val Thr Thr His Ala Asp Gly Thr Ala Thr
                645                 650                 655

Tyr Gly Pro Arg Val Thr Lys
            660

<210> SEQ ID NO 32
<211> LENGTH: 663
<212> TYPE: PRT
<213> ORGANISM: Artificial Sequence
<220> FEATURE:
<223> OTHER INFORMATION: Synthetic Peptide

<400> SEQUENCE: 32

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Lys Glu Ser Arg Val Asn Glu Asn Ser Lys Tyr Asp Thr Pro Ile
            35                  40                  45

Pro Asp Trp Tyr Leu Gly Ser Ile Leu Asn Arg Leu Gly Asp Gln Ile
        50                  55                  60

Tyr Tyr Ala Lys Glu Leu Thr Asn Lys Tyr Glu Tyr Gly Glu Lys Glu
65                  70                  75                  80

Tyr Lys Gln Ala Ile Asp Lys Leu Met Thr Arg Val Leu Gly Glu Asp
                85                  90                  95

His Tyr Leu Leu Glu Lys Lys Ala Gln Tyr Glu Ala Tyr Lys Lys
            100                 105                 110

Trp Phe Glu Lys His Lys Ser Glu Asn Pro His Ser Ser Leu Lys Lys
        115                 120                 125

Ile Lys Phe Asp Asp Phe Asp Leu Tyr Arg Leu Thr Lys Lys Glu Tyr
    130                 135                 140

Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
            180                 185                 190
```

-continued

```
Glu Ile Asp Thr Leu Tyr Ala Ala Tyr Phe Asn His Ser Gln Tyr Gly
            195                 200                 205

His Asn Ala Lys Glu Leu Arg Ala Lys Leu Asp Ile Ile Leu Gly Asp
        210                 215                 220

Ala Lys Asp Pro Val Arg Ile Thr Asn Glu Arg Ile Arg Lys Glu Met
225                 230                 235                 240

Met Asp Asp Leu Asn Ser Ile Ile Asp Asp Phe Phe Met Asp Thr Asn
                245                 250                 255

Met Asn Arg Pro Leu Asn Ile Thr Lys Phe Asn Pro Asn Ile His Asp
            260                 265                 270

Tyr Thr Asn Lys Pro Glu Asn Arg Asp Asn Phe Asp Lys Leu Val Lys
        275                 280                 285

Glu Thr Arg Glu Ala Ile Ala Asn Ala Asp Glu Ser Trp Lys Thr Arg
    290                 295                 300

Thr Val Lys Asn Tyr Gly Glu Ser Glu Thr Lys Ser Pro Val Val Lys
305                 310                 315                 320

Glu Glu Lys Lys Val Glu Glu Pro Gln Leu Pro Lys Val Gly Asn Gln
                325                 330                 335

Gln Glu Asp Lys Ile Thr Val Gly Thr Thr Glu Glu Ala Pro Leu Pro
            340                 345                 350

Ile Ala Gln Pro Leu Val Lys Ile Pro Gln Gly Thr Ile Gln Gly Glu
        355                 360                 365

Ile Val Lys Gly Pro Glu Tyr Leu Thr Met Glu Asn Lys Thr Leu Gln
    370                 375                 380

Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Pro Asn Pro Ile
                405                 410                 415

Leu Lys Gly Ile Glu Gly Asn Ser Thr Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Thr Glu Ala Ser His Tyr Pro
    450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr Asn Gln Asp Gly Thr Val Ser Tyr Gly Ala Arg Pro Thr Gln
        515                 520                 525

Asn Lys Pro Ser Glu Thr Asn Ala Tyr Asn Val Thr His Ala Asn
    530                 535                 540

Gly Gln Val Ser Tyr Gly Ala Arg Pro Thr Tyr Lys Lys Pro Ser Glu
545                 550                 555                 560

Thr Asn Ala Tyr Asn Val Thr Asn Gln Asp Gly Thr Val Ser Tyr
                565                 570                 575

Gly Ala Arg Pro Thr Gln Asn Lys Pro Ser Glu Thr Asn Ala Tyr Asn
            580                 585                 590

Val Thr Thr His Ala Asn Gly Gln Val Ser Tyr Gly Ala Arg Pro Thr
        595                 600                 605

Gln Asn Lys Pro Ser Glu Thr Asn Ala Tyr Asn Val Thr Thr His Ala
```

```
                   610                 615                 620
Asn Gly Gln Val Ser Tyr Gly Ala Arg Pro Thr Gln Asn Lys Pro Ser
625                 630                 635                 640

Lys Thr Asn Ala Tyr Asn Val Thr Thr His Ala Asp Gly Thr Ala Thr
                    645                 650                 655

Tyr Gly Pro Arg Val Thr Lys
                660

<210> SEQ ID NO 33
<211> LENGTH: 590
<212> TYPE: PRT
<213> ORGANISM: Artificial Sequence
<220> FEATURE:
<223> OTHER INFORMATION: Synthetic Peptide

<400> SEQUENCE: 33

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Gly Lys Ser Gln Val Asn Ala Gly Ser Lys Asn Gly Lys Gln Ile
            35                  40                  45

Ala Asp Gly Tyr Tyr Trp Gly Ile Ile Glu Asn Leu Glu Asn Gln Phe
        50                  55                  60

Tyr Asn Ile Phe His Leu Leu Asp Gln His Lys Tyr Ala Glu Lys Glu
65                  70                  75                  80

Tyr Lys Asp Ala Leu Asp Lys Leu Lys Thr Arg Val Leu Glu Glu Asp
                85                  90                  95

Gln Tyr Leu Leu Glu Arg Lys Lys Glu Lys Tyr Glu Ile Tyr Lys Glu
            100                 105                 110

Leu Tyr Lys Lys Tyr Lys Lys Glu Asn Pro Asn Thr Gln Val Lys Met
        115                 120                 125

Lys Ala Phe Asp Lys Tyr Asp Leu Gly Asp Leu Thr Met Glu Glu Tyr
    130                 135                 140

Asn Asp Leu Ser Lys Leu Leu Thr Lys Ala Leu Asp Asn Phe Lys Leu
145                 150                 155                 160

Glu Val Lys Lys Ile Glu Ser Glu Asn Pro Asp Leu Arg Pro Tyr Ser
                165                 170                 175

Glu Ser Glu Glu Arg Thr Ala Tyr Gly Lys Ile Asp Ser Leu Val Asp
            180                 185                 190

Gln Ala Tyr Ser Val Tyr Phe Ala Tyr Val Thr Asp Ala Gln His Lys
        195                 200                 205

Thr Glu Ala Leu Asn Leu Arg Ala Lys Ile Asp Leu Ile Leu Gly Asp
    210                 215                 220

Glu Lys Asp Pro Ile Arg Val Thr Asn Gln Arg Thr Glu Lys Glu Met
225                 230                 235                 240

Ile Lys Asp Leu Glu Ser Ile Ile Asp Asp Phe Phe Ile Glu Thr Lys
                245                 250                 255

Leu Asn Arg Pro Gln His Ile Thr Arg Tyr Asp Gly Thr Lys His Asp
            260                 265                 270

Tyr His Lys His Lys Asp Gly Phe Asp Ala Leu Val Lys Glu Thr Arg
        275                 280                 285

Glu Ala Val Ser Lys Ala Asp Glu Ser Trp Lys Thr Lys Thr Val Lys
    290                 295                 300

Lys Tyr Gly Glu Thr Glu Thr Lys Tyr Pro Val Val Lys Glu Glu Lys
```

```
            305                 310                 315                 320
Lys Val Glu Glu Pro Gln Ser Pro Lys Val Ser Glu Lys Val Asp Val
                325                 330                 335

Gln Glu Thr Val Gly Thr Thr Glu Glu Ala Pro Leu Pro Ile Ala Gln
                340                 345                 350

Pro Leu Val Lys Leu Pro Gln Ile Gly Thr Gln Gly Glu Ile Val Lys
                355                 360                 365

Gly Pro Asp Tyr Pro Thr Met Glu Asn Lys Thr Leu Gln Gly Val Ile
            370                 375                 380

Val Gln Gly Pro Asp Phe Pro Thr Met Glu Gln Asn Arg Pro Ser Leu
385                 390                 395                 400

Ser Asp Asn Tyr Thr Gln Pro Ser Val Thr Leu Pro Ser Ile Thr Gly
                405                 410                 415

Glu Ser Thr Pro Thr Asn Pro Ile Leu Lys Gly Ile Glu Gly Asn Ser
                420                 425                 430

Ser Lys Leu Glu Ile Lys Pro Gln Gly Thr Glu Ser Thr Leu Lys Gly
                435                 440                 445

Ile Gln Gly Glu Ser Ser Asp Ile Glu Val Lys Pro Gln Ala Thr Glu
            450                 455                 460

Thr Thr Glu Ala Ser His Tyr Pro Ala Arg Pro Gln Phe Asn Lys Thr
465                 470                 475                 480

Pro Lys Tyr Val Lys Tyr Arg Asp Ala Gly Thr Gly Ile Arg Glu Tyr
                485                 490                 495

Asn Asp Gly Thr Phe Gly Tyr Glu Ala Arg Pro Arg Phe Asn Lys Pro
                500                 505                 510

Ser Glu Thr Asn Ala Tyr Asn Val Thr Thr Asn Gln Asp Gly Thr Val
                515                 520                 525

Ser Tyr Gly Ala Arg Pro Thr Gln Asn Lys Pro Ser Lys Thr Asn Ala
            530                 535                 540

Tyr Asn Val Thr Thr His Ala Asn Gly Gln Val Ser Tyr Gly Ala Arg
545                 550                 555                 560

Pro Thr Tyr Asn Lys Pro Ser Lys Thr Asn Ala Tyr Asn Val Thr Thr
                565                 570                 575

His Ala Asp Gly Thr Ala Thr Tyr Gly Pro Arg Val Thr Lys
            580                 585                 590

<210> SEQ ID NO 34
<211> LENGTH: 671
<212> TYPE: PRT
<213> ORGANISM: Artificial Sequence
<220> FEATURE:
<223> OTHER INFORMATION: Synthetic Peptide

<400> SEQUENCE: 34

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Gly Lys Ser Gln Val Asn Ala Gly Ser Lys Asn Gly Lys Gln Ile
            35                  40                  45

Ala Asp Gly Tyr Tyr Trp Gly Ile Ile Glu Asn Leu Glu Asn Gln Phe
        50                  55                  60

Tyr Asn Ile Phe His Leu Leu Asp Gln His Lys Tyr Ala Glu Lys Glu
65                  70                  75                  80

Tyr Lys Asp Ala Leu Asp Lys Leu Lys Thr Arg Val Leu Glu Glu Asp
```

```
                    85                  90                  95
Gln Tyr Leu Leu Glu Arg Lys Glu Lys Tyr Glu Ile Tyr Lys Glu
                   100                 105                 110
Leu Tyr Lys Lys Tyr Lys Lys Glu Asn Pro Asn Thr Gln Val Lys Met
                   115                 120                 125
Lys Ala Phe Asp Lys Tyr Asp Leu Gly Asp Leu Thr Met Glu Glu Tyr
                   130                 135                 140
Asn Asp Leu Ser Lys Leu Leu Thr Lys Ala Leu Asp Asn Phe Lys Leu
145                150                 155                 160
Glu Val Lys Lys Ile Glu Ser Glu Asn Pro Asp Leu Arg Pro Tyr Ser
                   165                 170                 175
Glu Ser Glu Glu Arg Thr Ala Tyr Gly Lys Ile Asp Ser Leu Val Asp
                   180                 185                 190
Gln Ala Tyr Ser Val Tyr Phe Ala Tyr Val Thr Asp Ala Gln His Lys
                   195                 200                 205
Thr Glu Ala Leu Asn Leu Arg Ala Lys Ile Asp Leu Ile Leu Gly Asp
                   210                 215                 220
Glu Lys Asp Pro Ile Arg Val Thr Asn Gln Arg Thr Glu Lys Glu Met
225                230                 235                 240
Ile Lys Asp Leu Glu Ser Ile Ile Asp Asp Phe Phe Ile Glu Thr Lys
                   245                 250                 255
Leu Asn Arg Pro Gln His Ile Thr Arg Tyr Asp Gly Thr Lys His Asp
                   260                 265                 270
Tyr His Lys His Lys Asp Gly Phe Asp Ala Leu Val Lys Glu Thr Arg
                   275                 280                 285
Glu Ala Val Ser Lys Ala Asp Glu Ser Trp Lys Thr Lys Thr Val Lys
                   290                 295                 300
Lys Tyr Gly Glu Thr Glu Thr Lys Tyr Pro Val Val Lys Glu Glu Lys
305                310                 315                 320
Lys Val Glu Glu Pro Gln Ser Pro Lys Val Ser Glu Lys Val Asp Val
                   325                 330                 335
Gln Glu Thr Val Gly Thr Thr Glu Glu Ala Pro Leu Pro Ile Ala Gln
                   340                 345                 350
Pro Leu Val Lys Leu Pro Gln Ile Gly Thr Gln Gly Glu Ile Val Lys
                   355                 360                 365
Gly Pro Asp Tyr Pro Thr Met Glu Asn Lys Thr Leu Gln Gly Val Ile
                   370                 375                 380
Val Gln Gly Pro Asp Phe Pro Thr Met Glu Gln Asn Arg Pro Ser Leu
385                390                 395                 400
Ser Asp Asn Tyr Thr Gln Pro Ser Val Thr Leu Pro Ser Ile Thr Gly
                   405                 410                 415
Glu Ser Thr Pro Thr Asn Pro Ile Leu Lys Gly Ile Glu Gly Asn Ser
                   420                 425                 430
Ser Lys Leu Glu Ile Lys Pro Gln Gly Thr Glu Ser Thr Leu Lys Gly
                   435                 440                 445
Ile Gln Gly Glu Ser Ser Asp Ile Glu Val Lys Pro Gln Ala Thr Glu
                   450                 455                 460
Thr Thr Glu Ala Ser His Tyr Pro Ala Arg Pro Gln Phe Asn Lys Thr
465                470                 475                 480
Pro Lys Tyr Val Lys Tyr Arg Asp Ala Gly Thr Gly Ile Arg Glu Tyr
                   485                 490                 495
Asn Asp Gly Thr Phe Gly Tyr Glu Ala Arg Pro Arg Phe Asn Lys Pro
                   500                 505                 510
```

Ser Glu Thr Asn Ala Tyr Asn Val Thr Thr Asn Gln Asp Gly Thr Val
            515                 520                 525

Ser Tyr Gly Ala Arg Pro Thr Gln Asn Lys Pro Ser Lys Thr Asn Ala
        530                 535                 540

Tyr Asn Val Thr Thr His Ala Asn Gly Gln Val Ser Tyr Gly Ala Arg
545                 550                 555                 560

Pro Thr Tyr Asn Lys Pro Ser Glu Thr Asn Ala Tyr Asn Val Thr Thr
                565                 570                 575

Asn Arg Asp Gly Thr Val Ser Tyr Gly Ala Arg Pro Thr Gln Asn Lys
            580                 585                 590

Pro Ser Glu Thr Asn Ala Tyr Asn Val Thr Thr His Gly Asn Gly Gln
        595                 600                 605

Val Ser Tyr Gly Ala Arg Pro Thr Gln Lys Lys Pro Ser Lys Thr Asn
        610                 615                 620

Ala Tyr Asn Val Thr Thr His Ala Asn Gly Gln Val Ser Tyr Gly Ala
625                 630                 635                 640

Arg Pro Thr Tyr Asn Lys Pro Ser Lys Thr Asn Ala Tyr Asn Val Thr
                645                 650                 655

Thr His Ala Asp Gly Thr Ala Thr Tyr Gly Pro Arg Val Thr Lys
            660                 665                 670

<210> SEQ ID NO 35
<211> LENGTH: 671
<212> TYPE: PRT
<213> ORGANISM: Artificial Sequence
<220> FEATURE:
<223> OTHER INFORMATION: Synthetic Peptide

<400> SEQUENCE: 35

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Gly Lys Ser Gln Val Asn Ala Gly Ser Lys Asn Gly Lys Gln Ile
        35                  40                  45

Ala Asp Gly Tyr Tyr Trp Gly Ile Ile Glu Asn Leu Glu Asn Gln Phe
    50                  55                  60

Tyr Asn Ile Phe His Leu Leu Asp Gln His Lys Tyr Ala Glu Lys Glu
65                  70                  75                  80

Tyr Lys Asp Ala Leu Asp Lys Leu Lys Thr Arg Val Leu Glu Glu Asp
                85                  90                  95

Gln Tyr Leu Leu Glu Arg Lys Lys Glu Lys Tyr Glu Ile Tyr Lys Glu
            100                 105                 110

Leu Tyr Lys Lys Tyr Lys Lys Glu Asn Pro Asn Thr Gln Val Lys Met
        115                 120                 125

Lys Ala Phe Asp Lys Tyr Asp Leu Gly Asp Leu Thr Met Glu Glu Tyr
    130                 135                 140

Asn Asp Leu Ser Lys Leu Leu Thr Lys Ala Leu Asp Asn Phe Lys Leu
145                 150                 155                 160

Glu Val Lys Lys Ile Glu Ser Glu Asn Pro Asp Leu Arg Pro Tyr Ser
                165                 170                 175

Glu Ser Glu Glu Arg Thr Ala Tyr Gly Lys Ile Asp Ser Leu Val Asp
            180                 185                 190

Gln Ala Tyr Ser Val Tyr Phe Ala Tyr Val Thr Asp Ala Gln His Lys
        195                 200                 205

```
Thr Glu Ala Leu Asn Leu Arg Ala Lys Ile Asp Leu Ile Leu Gly Asp
    210                 215                 220

Glu Lys Asp Pro Ile Arg Val Thr Asn Gln Arg Thr Glu Lys Glu Met
225                 230                 235                 240

Ile Lys Asp Leu Glu Ser Ile Ile Asp Asp Phe Phe Ile Glu Thr Lys
                245                 250                 255

Leu Asn Arg Pro Gln His Ile Thr Arg Tyr Asp Gly Thr Lys His Asp
                260                 265                 270

Tyr His Lys His Lys Asp Gly Phe Asp Ala Leu Val Lys Glu Thr Arg
            275                 280                 285

Glu Ala Val Ser Lys Ala Asp Glu Ser Trp Lys Thr Lys Thr Val Lys
    290                 295                 300

Lys Tyr Gly Glu Thr Glu Thr Lys Tyr Pro Val Val Lys Glu Glu Lys
305                 310                 315                 320

Lys Val Glu Glu Pro Gln Ser Pro Lys Val Ser Glu Lys Val Asp Val
                325                 330                 335

Gln Glu Thr Val Gly Thr Thr Glu Glu Ala Pro Leu Pro Ile Ala Gln
                340                 345                 350

Pro Leu Val Lys Leu Pro Gln Ile Gly Thr Gln Gly Glu Ile Val Lys
                355                 360                 365

Gly Pro Asp Tyr Pro Thr Met Glu Asn Lys Thr Leu Gln Gly Val Ile
370                 375                 380

Val Gln Gly Pro Asp Phe Pro Thr Met Glu Gln Asn Arg Pro Ser Leu
385                 390                 395                 400

Ser Asp Asn Tyr Thr Gln Pro Ser Val Thr Leu Pro Ser Ile Thr Gly
                405                 410                 415

Glu Ser Thr Ser Thr Asn Pro Ile Leu Lys Gly Ile Glu Gly Asn Ser
                420                 425                 430

Ser Lys Leu Glu Ile Lys Pro Gln Gly Thr Glu Ser Thr Leu Lys Gly
            435                 440                 445

Ile Gln Gly Glu Ser Ser Asp Ile Glu Val Lys Pro Gln Ala Thr Glu
    450                 455                 460

Thr Thr Glu Ala Ser His Tyr Pro Ala Arg Pro Gln Phe Asn Lys Thr
465                 470                 475                 480

Pro Lys Tyr Val Lys Tyr Arg Asp Ala Gly Thr Gly Ile Arg Glu Tyr
                485                 490                 495

Asn Asp Gly Thr Phe Gly Tyr Glu Ala Arg Pro Arg Phe Asn Lys Pro
                500                 505                 510

Ser Glu Thr Asn Ala Tyr Asn Val Thr Thr Asn Gln Asp Gly Thr Val
            515                 520                 525

Ser Tyr Gly Ala Arg Pro Thr Gln Asn Lys Pro Ser Lys Thr Asn Ala
    530                 535                 540

Tyr Asn Val Thr Thr His Ala Asn Gly Gln Val Ser Tyr Gly Ala Arg
545                 550                 555                 560

Pro Thr Tyr Asn Lys Pro Ser Glu Thr Asn Ala Tyr Asn Val Thr Thr
                565                 570                 575

Asn Arg Asp Gly Thr Val Ser Tyr Gly Ala Arg Pro Thr Gln Asn Lys
                580                 585                 590

Pro Ser Glu Thr Asn Ala Tyr Asn Val Thr Thr His Gly Asn Gly Gln
            595                 600                 605

Val Ser Tyr Gly Ala Arg Pro Thr Gln Lys Lys Pro Ser Lys Thr Asn
    610                 615                 620
```

Ala Tyr Asn Val Thr Thr His Ala Asn Gly Gln Val Ser Tyr Gly Ala
625                 630                 635                 640

Arg Pro Thr Gln Lys Lys Pro Ser Lys Thr Asn Ala Tyr Asn Val Thr
            645                 650                 655

Thr His Ala Asp Gly Thr Ala Thr Tyr Gly Pro Arg Val Thr Lys
            660                 665                 670

<210> SEQ ID NO 36
<211> LENGTH: 663
<212> TYPE: PRT
<213> ORGANISM: Artificial Sequence
<220> FEATURE:
<223> OTHER INFORMATION: Synthetic Peptide

<400> SEQUENCE: 36

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Asn Ser Lys Tyr Asp Thr Pro Ile
            35                  40                  45

Pro Asp Trp Tyr Leu Gly Ser Ile Leu Asn Arg Leu Gly Asp Gln Ile
    50                  55                  60

Tyr Tyr Ala Lys Glu Leu Thr Asn Lys Tyr Glu Tyr Gly Lys Glu
65                  70                  75                  80

Tyr Lys Gln Ala Ile Asp Lys Leu Met Thr Arg Val Leu Gly Glu Asp
                85                  90                  95

His Tyr Leu Leu Glu Lys Lys Lys Ala Gln Tyr Glu Ala Tyr Lys Lys
            100                 105                 110

Trp Phe Glu Lys His Lys Ser Glu Asn Pro His Ser Ser Leu Lys Lys
            115                 120                 125

Ile Lys Phe Asp Asp Phe Asp Leu Tyr Arg Leu Thr Lys Lys Glu Tyr
    130                 135                 140

Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
            180                 185                 190

Glu Ile Asp Thr Leu Tyr Ala Ala Tyr Phe Asn His Ser Gln Tyr Gly
            195                 200                 205

His Asn Ala Lys Glu Leu Arg Ala Lys Leu Asp Ile Ile Leu Gly Asp
    210                 215                 220

Ala Lys Asp Pro Val Arg Ile Thr Asn Glu Arg Ile Arg Lys Glu Met
225                 230                 235                 240

Met Asp Asp Leu Asn Ser Ile Ile Asp Asp Phe Phe Met Asp Thr Asn
                245                 250                 255

Met Asn Arg Pro Leu Asn Ile Thr Lys Phe Asn Pro Asn Ile His Asp
            260                 265                 270

Tyr Thr Asn Lys Pro Glu Asn Arg Asp Asn Phe Asp Lys Leu Val Lys
            275                 280                 285

Glu Thr Arg Glu Ala Val Ala Asn Ala Asp Glu Ser Trp Lys Thr Arg
    290                 295                 300

Thr Val Lys Asn Tyr Gly Glu Ser Glu Thr Lys Ser Pro Val Val Lys
305                 310                 315                 320

-continued

```
Glu Glu Lys Lys Val Glu Glu Pro Gln Leu Pro Lys Val Gly Asn Gln
                325                 330                 335
Gln Glu Asp Lys Ile Thr Val Gly Thr Thr Glu Glu Ala Pro Leu Pro
            340                 345                 350
Ile Ala Gln Pro Leu Val Lys Ile Pro Gln Gly Thr Ile Gln Gly Glu
        355                 360                 365
Ile Val Lys Gly Pro Glu Tyr Leu Thr Met Glu Asn Lys Thr Leu Gln
    370                 375                 380
Gly Glu Ile Val Gln Gly Pro Asp Phe Pro Thr Met Glu Gln Asn Arg
385                 390                 395                 400
Pro Ser Leu Ser Asp Asn Tyr Thr Gln Pro Thr Thr Pro Asn Pro Ile
                405                 410                 415
Leu Lys Gly Ile Glu Gly Asn Ser Thr Lys Leu Glu Ile Lys Pro Gln
            420                 425                 430
Gly Thr Glu Ser Thr Leu Lys Gly Thr Gln Gly Glu Ser Ser Asp Ile
        435                 440                 445
Glu Val Lys Pro Gln Ala Thr Glu Thr Thr Glu Ala Ser His Tyr Pro
    450                 455                 460
Ala Arg Pro Gln Phe Asn Lys Thr Pro Lys Tyr Val Lys Tyr Arg Asp
465                 470                 475                 480
Ala Gly Thr Gly Ile Arg Glu Tyr Asn Asp Gly Thr Phe Gly Tyr Glu
                485                 490                 495
Ala Arg Pro Arg Phe Asn Lys Pro Ser Glu Thr Asn Ala Tyr Asn Val
            500                 505                 510
Thr Thr Asn Gln Asp Gly Thr Val Ser Tyr Gly Ala Arg Pro Thr Gln
        515                 520                 525
Asn Lys Pro Ser Glu Thr Asn Ala Tyr Asn Val Thr Thr His Ala Asn
    530                 535                 540
Gly Gln Val Ser Tyr Gly Ala Arg Pro Thr Tyr Lys Lys Pro Ser Glu
545                 550                 555                 560
Thr Asn Ala Tyr Asn Val Thr Thr Asn Gln Asp Gly Thr Val Ser Tyr
                565                 570                 575
Gly Ala Arg Pro Thr Gln Asn Lys Pro Ser Glu Thr Asn Ala Tyr Asn
            580                 585                 590
Val Thr Thr His Ala Asn Gly Gln Val Ser Tyr Gly Ala Arg Pro Thr
        595                 600                 605
Gln Asn Lys Pro Ser Glu Thr Asn Ala Tyr Asn Val Thr Thr His Ala
    610                 615                 620
Asn Gly Gln Val Ser Tyr Gly Ala Arg Pro Thr Gln Asn Lys Pro Ser
625                 630                 635                 640
Lys Thr Asn Ala Tyr Asn Val Thr Thr His Ala Asp Gly Thr Ala Thr
                645                 650                 655
Tyr Gly Pro Arg Val Thr Lys
            660
```

<210> SEQ ID NO 37
<211> LENGTH: 663
<212> TYPE: PRT
<213> ORGANISM: Artificial Sequence
<220> FEATURE:
<223> OTHER INFORMATION: Synthetic Peptide

<400> SEQUENCE: 37

```
Met Lys Lys Gln Ile Ile Ser Leu Gly Ala Leu Ala Val Ala Ser Ser
1               5                   10                  15
```

-continued

```
Leu Phe Thr Trp Asp Asn Lys Ala Asp Ala Ile Val Thr Lys Asp Tyr
             20                  25                  30
Ser Lys Glu Ser Arg Val Asn Glu Asn Ser Lys Tyr Asp Thr Pro Ile
         35                  40                  45
Pro Asp Trp Tyr Leu Gly Ser Ile Leu Asn Arg Leu Gly Asp Gln Ile
 50                  55                  60
Tyr Tyr Ala Lys Glu Leu Thr Asn Lys Tyr Glu Tyr Gly Glu Lys Glu
 65                  70                  75                  80
Tyr Lys Gln Ala Ile Asp Lys Leu Met Thr Arg Val Leu Gly Glu Asp
                 85                  90                  95
His Tyr Leu Leu Glu Lys Lys Ala Gln Tyr Glu Ala Tyr Lys Lys
            100                 105                 110
Trp Phe Glu Lys His Lys Ser Glu Asn Pro His Ser Ser Leu Lys Lys
        115                 120                 125
Ile Lys Phe Asp Asp Phe Asp Leu Tyr Arg Leu Thr Lys Lys Glu Tyr
    130                 135                 140
Asn Glu Leu His Gln Ser Leu Lys Glu Ala Val Asp Glu Phe Asn Ser
145                 150                 155                 160
Glu Val Lys Asn Ile Gln Ser Lys Gln Lys Asp Leu Leu Pro Tyr Asp
                165                 170                 175
Glu Ala Thr Glu Asn Arg Val Thr Asn Gly Ile Tyr Asp Phe Val Cys
            180                 185                 190
Glu Ile Asp Thr Leu Tyr Ala Ala Tyr Phe Asn His Ser Gln Tyr Gly
        195                 200                 205
His Asn Ala Lys Glu Leu Arg Ala Lys Leu Asp Ile Ile Leu Gly Asp
    210                 215                 220
Ala Lys Asp Pro Val Arg Ile Thr Asn Glu Arg Ile Arg Lys Glu Lys
225                 230                 235                 240
Met Asp Asp Leu Asn Ser Ile Ile Asp Asp Phe Phe Met Asp Thr Asn
                245                 250                 255
Met Asn Arg Pro Leu Asn Ile Thr Lys Phe Asn Pro Asn Ile His Asp
            260                 265                 270
Tyr Thr Asn Lys Pro Glu Asn Arg Asp Asn Phe Asp Lys Leu Val Lys
        275                 280                 285
Glu Thr Arg Glu Ala Val Ala Asn Ala Asp Glu Ser Trp Lys Thr Arg
    290                 295                 300
Thr Val Lys Asn Tyr Gly Glu Ser Glu Thr Lys Ser Pro Val Val Lys
305                 310                 315                 320
Glu Glu Lys Lys Val Glu Glu Pro Gln Leu Pro Lys Val Gly Asn Gln
                325                 330                 335
Gln Glu Asp Lys Ile Thr Val Gly Thr Thr Glu Glu Ala Pro Leu Pro
            340                 345                 350
Ile Ala Gln Pro Leu Val Lys Ile Pro Gln Gly Thr Ile Gln Gly Glu
        355                 360                 365
Ile Val Lys Gly Pro Glu Tyr Leu Thr Met Glu Asn Lys Thr Leu Gln
    370                 375                 380
Gly Glu Ile Val Gln Gly Pro Asp Phe Pro Thr Met Glu Gln Asn Arg
385                 390                 395                 400
Pro Ser Leu Ser Asp Asn Tyr Thr Gln Pro Thr Thr Pro Asn Pro Ile
                405                 410                 415
Leu Lys Gly Ile Glu Gly Asn Ser Thr Lys Leu Glu Ile Lys Pro Gln
            420                 425                 430
Gly Thr Glu Ser Thr Leu Lys Gly Thr Gln Gly Glu Ser Ser Asp Ile
```

-continued

```
                435                 440                 445

Glu Val Lys Pro Gln Ala Thr Glu Thr Thr Glu Ala Ser His Tyr Pro
    450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr Asn Gln Asp Gly Thr Val Ser Tyr Gly Ala Arg Pro Thr Gln
                515                 520                 525

Asn Lys Pro Ser Glu Thr Asn Ala Tyr Asn Val Thr Thr His Ala Asn
530                 535                 540

Gly Gln Val Ser Tyr Gly Ala Arg Pro Thr Tyr Lys Lys Pro Ser Glu
545                 550                 555                 560

Thr Asn Ala Tyr Asn Val Thr Asn Gln Asp Gly Thr Val Ser Tyr
                565                 570                 575

Gly Ala Arg Pro Thr Gln Asn Lys Pro Ser Glu Thr Asn Ala Tyr Asn
            580                 585                 590

Val Thr Thr His Ala Asn Gly Gln Val Ser Tyr Gly Ala Arg Pro Thr
                595                 600                 605

Gln Asn Lys Pro Ser Glu Thr Asn Ala Tyr Asn Val Thr Thr His Ala
        610                 615                 620

Asn Gly Gln Val Ser Tyr Gly Ala Arg Pro Thr Gln Asn Lys Pro Ser
625                 630                 635                 640

Lys Thr Asn Ala Tyr Asn Val Thr Thr His Ala Asp Gly Thr Ala Thr
                645                 650                 655

Tyr Gly Pro Arg Val Thr Lys
            660

<210> SEQ ID NO 38
<211> LENGTH: 609
<212> TYPE: PRT
<213> ORGANISM: Artificial Sequence
<220> FEATURE:
<223> OTHER INFORMATION: Synthetic Peptide

<400> SEQUENCE: 38

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Asn Ser Lys Tyr Asp Thr Pro Ile
        35                  40                  45

Pro Asp Trp Tyr Leu Gly Ser Ile Leu Asn Arg Leu Gly Asp Gln Ile
    50                  55                  60

Tyr Tyr Ala Lys Glu Leu Thr Asn Lys Tyr Glu Tyr Gly Glu Lys Glu
65                  70                  75                  80

Tyr Lys Gln Ala Ile Asp Lys Leu Met Thr Arg Val Leu Gly Glu Asp
                85                  90                  95

His Tyr Leu Leu Glu Lys Lys Ala Gln Tyr Glu Ala Tyr Lys Lys
            100                 105                 110

Trp Phe Glu Lys His Lys Ser Glu Asn Pro His Ser Ser Leu Lys Lys
        115                 120                 125

Ile Lys Phe Asp Asp Phe Asp Leu Tyr Arg Leu Thr Lys Lys Glu Tyr
```

```
                130                 135                 140
Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
                180                 185                 190

Glu Ile Asp Thr Leu Tyr Ala Ala Tyr Phe Asn His Ser Gln Tyr Gly
                195                 200                 205

His Asn Ala Lys Glu Leu Arg Ala Lys Leu Asp Ile Ile Leu Gly Asp
            210                 215                 220

Ala Lys Asp Pro Val Arg Ile Thr Asn Glu Arg Ile Arg Lys Glu Lys
225                 230                 235                 240

Met Asp Asp Leu Asn Ser Ile Ile Asp Asp Phe Phe Met Asp Thr Asn
                245                 250                 255

Met Asn Arg Pro Leu Asn Ile Thr Lys Phe Asn Pro Asn Ile His Asp
                260                 265                 270

Tyr Thr Asn Lys Pro Glu Asn Arg Asp Asn Phe Asp Lys Leu Val Lys
            275                 280                 285

Glu Thr Arg Glu Ala Val Ala Asn Ala Asp Glu Ser Trp Lys Thr Arg
            290                 295                 300

Thr Val Lys Asn Tyr Gly Glu Ser Glu Thr Lys Ser Pro Val Val Lys
305                 310                 315                 320

Glu Glu Lys Lys Val Glu Glu Pro Gln Leu Pro Lys Val Gly Asn Gln
                325                 330                 335

Gln Glu Asp Lys Ile Thr Val Gly Thr Thr Glu Glu Ala Pro Leu Pro
            340                 345                 350

Ile Ala Gln Pro Leu Val Lys Ile Pro Gln Gly Thr Ile Gln Gly Glu
            355                 360                 365

Ile Val Lys Gly Pro Glu Tyr Leu Thr Met Glu Asn Lys Thr Leu Gln
            370                 375                 380

Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Pro Asn Pro Ile
                405                 410                 415

Leu Lys Gly Ile Glu Gly Asn Ser Thr Lys Leu Glu Ile Lys Pro Gln
                420                 425                 430

Gly Thr Glu Ser Thr Leu Lys Gly Thr Gln Gly Glu Ser Ser Asp Ile
                435                 440                 445

Glu Val Lys Pro Gln Ala Thr Glu Thr Thr Glu Ala Ser His Tyr Pro
450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
                500                 505                 510

Thr Thr Asn Gln Asp Gly Thr Val Ser Tyr Gly Ala Arg Pro Thr Gln
            515                 520                 525

Asn Lys Pro Ser Glu Thr Asn Ala Tyr Asn Val Thr Thr His Ala Asn
            530                 535                 540

Gly Gln Val Ser Tyr Gly Ala Arg Pro Thr Gln Asn Lys Pro Ser Glu
545                 550                 555                 560
```

```
Thr Asn Ala Tyr Asn Val Thr His Ala Asn Gly Gln Val Ser Tyr
            565                 570                 575

Gly Ala Arg Pro Thr Gln Asn Lys Pro Ser Lys Thr Asn Ala Tyr Asn
            580                 585                 590

Val Thr Thr His Ala Asp Gly Thr Ala Thr Tyr Gly Pro Arg Val Thr
            595                 600                 605

Lys

<210> SEQ ID NO 39
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 39

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Gln Lys Lys Pro Ser Lys Thr
    50                  55                  60

Asn Ala Tyr Asn Val Thr Thr His Ala Asn Gly Gln Val Ser Tyr Gly
65                  70                  75                  80

Ala Arg Pro Thr Gln Lys Lys Pro Ser Lys Thr Asn Ala Tyr Asn Val
                85                  90                  95

Thr Thr His Ala Asn Gly Gln Val Ser Tyr Gly Ala Arg Pro Thr Tyr
            100                 105                 110

Lys Lys Pro Ser Glu Thr Asn Ala Tyr Asn Val Thr Thr His Ala Asn
        115                 120                 125

Gly Gln Val Ser Tyr Gly Ala Arg Leu Thr Gln Lys Lys Pro Ser Glu
    130                 135                 140

Thr Asn Ala Tyr Asn Val Thr Thr His Ala Asp Gly Thr Ala Thr Tyr
145                 150                 155                 160

Gly Pro

<210> SEQ ID NO 40
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 40

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Gln Lys Lys Pro Ser Lys Thr
    50                  55                  60

Asn Ala Tyr Asn Val Thr Thr His Ala Asn Gly Gln Val Ser Tyr Gly
65                  70                  75                  80
```

Ala Arg Pro Thr Gln Lys Lys Pro Ser Lys Thr Asn Ala Tyr Asn Val
                    85                  90                  95

Thr Thr His Ala Asn Gly Gln Val Ser Tyr Gly Ala Arg Pro Thr Tyr
            100                 105                 110

Lys Lys Pro Ser Glu Thr Asn Ala Tyr Asn Val Thr Thr His Ala Asn
        115                 120                 125

Gly Gln Val Ser Tyr Gly Ala Arg Pro Thr Gln Lys Lys Pro Ser Glu
    130                 135                 140

Thr Asn Ala Tyr Asn Val Thr Thr His Ala Asp Gly Thr Ala Thr Tyr
145                 150                 155                 160

Gly Pro

<210> SEQ ID NO 41
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 41

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr His Ala Asn Gly Gln Val Ser Tyr Gly
65                  70                  75                  80

Ala Arg Pro Thr Gln Lys Lys Pro Ser Lys Thr Asn Ala Tyr Asn Val
                85                  90                  95

Thr Thr His Ala Asn Gly Gln Val Ser Tyr Gly Ala Arg Pro Thr Tyr
            100                 105                 110

Lys Lys Pro Ser Glu Thr Asn Ala Tyr Asn Val Thr Thr His Ala Asn
        115                 120                 125

Gly Gln Val Ser Tyr Gly Ala Arg Pro Thr Gln Lys Lys Pro Ser Glu
    130                 135                 140

Thr Asn Ala Tyr Asn Val Thr Thr His Ala Asp Gly Thr Ala Thr Tyr
145                 150                 155                 160

Gly Pro

<210> SEQ ID NO 42
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 42

Arg Pro Arg Phe Asn Lys Pro Ser Glu Thr Asn Ala Tyr Asn Val Thr
1               5                   10                  15

Thr His Ala Asn Gly Gln Val Ser Tyr Gly Ala Arg Pro Thr Tyr Lys
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Gln Asn Lys Pro Ser Lys Thr

```
            50                  55                  60

Asn Ala Tyr Asn Val Thr Thr His Gly Asn Gly Gln Val Ser Tyr Gly
 65                  70                  75                  80

Ala Arg Pro Thr Gln Asn Lys Pro Ser Lys Thr Asn Ala Tyr Asn Val
                 85                  90                  95

Thr Thr His Ala Asn Gly Gln Val Ser Tyr Gly Ala Arg Pro Thr Tyr
            100                 105                 110

Lys Lys Pro Ser Lys Thr Asn Ala Tyr Asn Val Thr Thr His Ala Asp
        115                 120                 125

Gly Thr Ala Thr Tyr Gly Pro
        130                 135

<210> SEQ ID NO 43
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 43

Arg Pro Arg Phe Asn Lys Pro Ser Glu Thr Asn Ala Tyr Asn Val Thr
  1               5                  10                  15

Thr His Ala Asn Gly Gln Val Ser Tyr Gly Ala Arg Pro Thr Gln Asn
             20                  25                  30

Lys Pro Ser Lys Thr Asn Ala Tyr Asn Val Thr Thr His Gly Asn Gly
         35                  40                  45

Gln Val Ser Tyr Gly Ala Arg Pro Thr Gln Asn Lys Pro Ser Lys Thr
     50                  55                  60

Asn Ala Tyr Asn Val Thr Thr His Ala Asn Gly Gln Val Ser Tyr Gly
 65                  70                  75                  80

Ala Arg Pro Thr Tyr Lys Lys Pro Ser Lys Thr Asn Ala Tyr Asn Val
                 85                  90                  95

Thr Thr His Ala Asp Gly Thr Ala Thr Tyr Gly Pro
            100                 105

<210> SEQ ID NO 44
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 44

Arg Pro Arg Phe Asn Lys Pro Ser Glu Thr Asn Ala Tyr Asn Val Thr
  1               5                  10                  15

Thr Asn Gln Asp Gly Thr Val Thr Tyr Gly Ala Arg Pro Thr Gln Asn
             20                  25                  30

Lys Pro Ser Lys Thr Asn Ala Tyr Asn Val Thr Thr His Ala Asn Gly
         35                  40                  45

Gln Val Ser Tyr Gly Ala Arg Pro Thr Tyr Lys Lys Pro Ser Glu Thr
     50                  55                  60

Asn Ala Tyr Asn Val Thr Thr His Ala Asn Gly Gln Val Ser Tyr Gly
 65                  70                  75                  80

Ala Arg Pro Thr Gln Asn Lys Ala Ser Glu Thr Asn Ala Tyr Asn Val
                 85                  90                  95

Thr Thr His Ala Asn Gly Gln Val Ser Tyr Gly Ala Arg Pro Thr Gln
            100                 105                 110
```

```
Asn Lys Pro Ser Lys Thr Asn Ala Tyr Asn Val Thr His Gly Asn
            115                 120                 125

Gly Gln Val Ser Tyr Gly Ala Arg Pro Thr Tyr Lys Lys Pro Ser Glu
        130                 135                 140

Thr Asn Ala Tyr Asn Val Thr Thr His Ala Asp Gly Thr Ala Thr Tyr
145                 150                 155                 160

Gly Pro

<210> SEQ ID NO 45
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 45

Arg Pro Arg Phe Asn Lys Pro Ser Glu Thr Asn Ala Tyr Asn Val Thr
1               5                   10                  15

Thr Asn Gln Asp Gly Thr Val Thr Tyr Gly Ala Arg Pro Thr Gln Asn
            20                  25                  30

Lys Pro Ser Lys Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr His Ala Asn Gly Gln Val Ser Tyr Gly
65                  70                  75                  80

Ala Arg Pro Thr Gln Asn Lys Ala Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Lys Thr Asn Ala Tyr Asn Val Thr Thr His Gly Asn
        115                 120                 125

Gly Gln Val Ser Tyr Gly Ala Arg Pro Thr Tyr Lys Lys Pro Ser Glu
    130                 135                 140

Thr Asn Ala Tyr Asn Val Thr Thr His Ala Asp Gly Thr Ala Thr Tyr
145                 150                 155                 160

Gly Pro

<210> SEQ ID NO 46
<211> LENGTH: 81
<212> TYPE: PRT
<213> ORGANISM: Artificial Sequence
<220> FEATURE:
<223> OTHER INFORMATION: Synthetic Peptide

<400> SEQUENCE: 46

Arg Pro Arg Phe Asn Lys Pro Ser Glu Thr Asn Ala Tyr Asn Val Thr
1               5                   10                  15

Thr Asn Gln Asp Gly Thr Val Thr Tyr Gly Ala Arg Pro Thr Gln Asn
            20                  25                  30

Lys Pro Ser Lys Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr His Ala Asn Gly Thr Ala Thr Tyr Gly
65                  70                  75                  80

Pro
```

<210> SEQ ID NO 47
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 47

```
Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Gln Asn Lys Pro Ser Glu Thr
    50                  55                  60

Asn Ala Tyr Asn Val Thr Thr His Ala Asn Gly Gln Val Ser Tyr Gly
65                  70                  75                  80

Ala Arg Pro Thr Gln Asn Lys Pro Ser Lys Thr Asn Ala Tyr Asn Val
                85                  90                  95

Thr Thr His Ala Asp Gly Thr Ala Thr Tyr Gly Pro
            100                 105
```

<210> SEQ ID NO 48
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 48

```
Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Pro Ser Glu Thr
    50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Glu Thr Asn Ala Tyr Asn Val Thr Thr His Ala Asn
        115                 120                 125

Gly Gln Val Ser Tyr Gly Ala Arg Pro Thr Gln Asn Lys Pro Ser Lys
    130                 135                 140

Thr Asn Ala Tyr Asn Val Thr Thr His Ala Asp Gly Thr Ala Thr Tyr
145                 150                 155                 160

Gly Pro
```

<210> SEQ ID NO 49
<211> LENGTH: 162
<212> TYPE: PRT
<213> ORGANISM: Artificial Sequence

```
<220> FEATURE:
<223> OTHER INFORMATION: Synthetic Peptide

<400> SEQUENCE: 49

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
            35                  40                  45

Gln Val Ser Tyr Gly Ala Arg Pro Thr Tyr Lys Lys Pro Ser Glu Thr
        50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Ala Asn Gly Gln Val Ser Tyr Gly Ala Arg Pro Thr Gln
                100                 105                 110

Asn Lys Pro Ser Glu Thr Asn Ala Tyr Asn Val Thr His Ala Asn
            115                 120                 125

Gly Gln Val Ser Tyr Gly Ala Arg Pro Thr Gln Asn Lys Pro Ser Lys
        130                 135                 140

Thr Asn Ala Tyr Asn Val Thr Thr His Ala Asp Gly Thr Ala Thr Tyr
145                 150                 155                 160

Gly Pro

<210> SEQ ID NO 50
<211> LENGTH: 81
<212> TYPE: PRT
<213> ORGANISM: Artificial Sequence
<220> FEATURE:
<223> OTHER INFORMATION: Synthetic Peptide

<400> SEQUENCE: 50

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Lys Thr Asn Ala Tyr Asn Val Thr Thr His Ala Asn Gly
            35                  40                  45

Gln Val Ser Tyr Gly Ala Arg Pro Thr Tyr Asn Lys Pro Ser Lys Thr
        50                  55                  60

Asn Ala Tyr Asn Val Thr Thr His Ala Asp Gly Thr Ala Thr Tyr Gly
65                  70                  75                  80

Pro

<210> SEQ ID NO 51
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 51

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30
```

```
Lys Pro Ser Lys Thr Asn Ala Tyr Asn Val Thr Thr His Ala Asn Gly
            35                  40                  45

Gln Val Ser Tyr Gly Ala Arg Pro Thr Tyr Asn Lys Pro Ser Glu Thr
    50                  55                  60

Asn Ala Tyr Asn Val Thr Thr Asn Arg Asp Gly Thr Val Ser Tyr Gly
 65                  70                  75                  80

Ala Arg Pro Thr Gln Asn Lys Pro Ser Glu Thr Asn Ala Tyr Asn Val
                85                  90                  95

Thr Thr His Gly Asn Gly Gln Val Ser Tyr Gly Ala Arg Pro Thr Gln
            100                 105                 110

Lys Lys Pro Ser Lys Thr Asn Ala Tyr Asn Val Thr Thr His Ala Asn
            115                 120                 125

Gly Gln Val Ser Tyr Gly Ala Arg Pro Thr Tyr Asn Lys Pro Ser Lys
            130                 135                 140

Thr Asn Ala Tyr Asn Val Thr Thr His Ala Asp Gly Thr Ala Thr Tyr
145                 150                 155                 160

Gly Pro

<210> SEQ ID NO 52
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 52

Arg Pro Arg Phe Asn Lys Pro Ser Glu Thr Asn Ala Tyr Asn Val Thr
 1               5                  10                  15

Thr Asn Gln Asp Gly Thr Val Ser Tyr Gly Ala Arg Pro Thr Gln Asn
                20                  25                  30

Lys Pro Ser Lys Thr Asn Ala Tyr Asn Val Thr Thr His Ala Asn Gly
            35                  40                  45

Gln Val Ser Tyr Gly Ala Arg Pro Thr Tyr Asn Lys Pro Ser Glu Thr
    50                  55                  60

Asn Ala Tyr Asn Val Thr Thr Asn Arg Asp Gly Thr Val Ser Tyr Gly
 65                  70                  75                  80

Ala Arg Pro Thr Gln Asn Lys Pro Ser Glu Thr Asn Ala Tyr Asn Val
                85                  90                  95

Thr Thr His Gly Asn Gly Gln Val Ser Tyr Gly Ala Arg Pro Thr Gln
            100                 105                 110

Lys Lys Pro Ser Lys Thr Asn Ala Tyr Asn Val Thr Thr His Ala Asn
            115                 120                 125

Gly Gln Val Ser Tyr Gly Ala Arg Pro Thr Gln Lys Lys Pro Ser Lys
            130                 135                 140

Thr Asn Ala Tyr Asn Val Thr Thr His Ala Asp Gly Thr Ala Thr Tyr
145                 150                 155                 160

Gly Pro

<210> SEQ ID NO 53
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 53
```

```
Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Glu Thr Asn Ala Tyr Asn Val Thr Thr His Ala Asn
        115                 120                 125

Gly Gln Val Ser Tyr Gly Ala Arg Pro Thr Gln Asn Lys Pro Ser Lys
    130                 135                 140

Thr Asn Ala Tyr Asn Val Thr Thr His Ala Asp Gly Thr Ala Thr Tyr
145                 150                 155                 160

Gly Pro

<210> SEQ ID NO 54
<211> LENGTH: 162
<212> TYPE: PRT
<213> ORGANISM: Artificial Sequence
<220> FEATURE:
<223> OTHER INFORMATION: Synthetic Peptide

<400> SEQUENCE: 54

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Glu Thr Asn Ala Tyr Asn Val Thr Thr His Ala Asn
        115                 120                 125

Gly Gln Val Ser Tyr Gly Ala Arg Pro Thr Gln Asn Lys Pro Ser Lys
    130                 135                 140

Thr Asn Ala Tyr Asn Val Thr Thr His Ala Asp Gly Thr Ala Thr Tyr
145                 150                 155                 160

Gly Pro

<210> SEQ ID NO 55
<211> LENGTH: 108
<212> TYPE: PRT
<213> ORGANISM: Artificial Sequence
```

-continued

<220> FEATURE:
<223> OTHER INFORMATION: Synthetic Peptide

<400> SEQUENCE: 55

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Gln Asn Lys Pro Ser Glu Thr
    50                  55                  60

Asn Ala Tyr Asn Val Thr Thr His Ala Asn Gly Gln Val Ser Tyr Gly
65                  70                  75                  80

Ala Arg Pro Thr Gln Asn Lys Pro Ser Lys Thr Asn Ala Tyr Asn Val
                85                  90                  95

Thr Thr His Ala Asp Gly Thr Ala Thr Tyr Gly Pro
            100                 105

<210> SEQ ID NO 56
<211> LENGTH: 114
<212> TYPE: PRT
<213> ORGANISM: Artificial Sequence
<220> FEATURE:
<223> OTHER INFORMATION: Synthetic Peptide

<400> SEQUENCE: 56

Glu Ala Arg Pro Arg Phe Asn Lys Pro Ser Glu Thr Asn Ala Tyr Asn
1               5                   10                  15

Val Thr Thr His Ala Asn Gly Gln Val Ser Tyr Gly Ala Arg Pro Thr
            20                  25                  30

Gln Asn Lys Pro Ser Lys Thr Asn Ala Tyr Asn Val Thr Thr His Gly
        35                  40                  45

Asn Gly Gln Val Ser Tyr Gly Ala Arg Pro Thr Gln Asn Lys Pro Ser
    50                  55                  60

Lys Thr Asn Ala Tyr Asn Val Thr Thr His Ala Asn Gly Gln Val Ser
65                  70                  75                  80

Tyr Gly Ala Arg Pro Thr Tyr Lys Lys Pro Ser Lys Thr Asn Ala Tyr
                85                  90                  95

Asn Val Thr Thr His Ala Asp Gly Thr Ala Thr Tyr Gly Pro Arg Val
            100                 105                 110

Thr Lys

<210> SEQ ID NO 57
<211> LENGTH: 81
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: X is T or R
<220> FEATURE:
<221> NAME/KEY: MISC_FEATURE
<222> LOCATION: (4)..(4)
<223> OTHER INFORMATION: X is F or Q
<220> FEATURE:
<221> NAME/KEY: MISC_FEATURE
<222> LOCATION: (5)..(5)
<223> OTHER INFORMATION: X is N or K
<220> FEATURE:

```
<221> NAME/KEY: MISC_FEATURE
<222> LOCATION: (7)..(7)
<223> OTHER INFORMATION: X is P or A
<220> FEATURE:
<221> NAME/KEY: MISC_FEATURE
<222> LOCATION: (9)..(9)
<223> OTHER INFORMATION: X is E or K
<220> FEATURE:
<221> NAME/KEY: MISC_FEATURE
<222> LOCATION: (18)..(18)
<223> OTHER INFORMATION: X is H or N
<220> FEATURE:
<221> NAME/KEY: MISC_FEATURE
<222> LOCATION: (19)..(19)
<223> OTHER INFORMATION: X is A, G or Q
<220> FEATURE:
<221> NAME/KEY: MISC_FEATURE
<222> LOCATION: (20)..(20)
<223> OTHER INFORMATION: X is N or D
<220> FEATURE:
<221> NAME/KEY: MISC_FEATURE
<222> LOCATION: (22)..(22)
<223> OTHER INFORMATION: X is Q or T
<220> FEATURE:
<221> NAME/KEY: MISC_FEATURE
<222> LOCATION: (24)..(24)
<223> OTHER INFORMATION: X is S or T
<220> FEATURE:
<221> NAME/KEY: MISC_FEATURE
<222> LOCATION: (31)..(31)
<223> OTHER INFORMATION: X is Y or Q
<220> FEATURE:
<221> NAME/KEY: MISC_FEATURE
<222> LOCATION: (32)..(32)
<223> OTHER INFORMATION: X is K or N
<220> FEATURE:
<221> NAME/KEY: MISC_FEATURE
<222> LOCATION: (36)..(36)
<223> OTHER INFORMATION: X is E or K
<220> FEATURE:
<221> NAME/KEY: MISC_FEATURE
<222> LOCATION: (46)..(46)
<223> OTHER INFORMATION: X is A or G
<220> FEATURE:
<221> NAME/KEY: MISC_FEATURE
<222> LOCATION: (56)..(56)
<223> OTHER INFORMATION: X is L or P
<220> FEATURE:
<221> NAME/KEY: MISC_FEATURE
<222> LOCATION: (58)..(58)
<223> OTHER INFORMATION: X is Q or Y
<220> FEATURE:
<221> NAME/KEY: MISC_FEATURE
<222> LOCATION: (59)..(59)
<223> OTHER INFORMATION: X is N or K
<220> FEATURE:
<221> NAME/KEY: MISC_FEATURE
<222> LOCATION: (63)..(63)
<223> OTHER INFORMATION: X is K or E
<220> FEATURE:
<221> NAME/KEY: MISC_FEATURE
<222> LOCATION: (74)..(74)
<223> OTHER INFORMATION: X is D or N

<400> SEQUENCE: 57

Arg Pro Xaa Xaa Xaa Lys Xaa Ser Xaa Thr Asn Ala Tyr Asn Val Thr
 1               5                  10                  15

Thr Xaa Xaa Xaa Gly Xaa Val Xaa Tyr Gly Ala Arg Pro Thr Xaa Xaa
             20                  25                  30

Lys Pro Ser Xaa Thr Asn Ala Tyr Asn Val Thr Thr His Xaa Asn Gly
         35                  40                  45

Gln Val Ser Tyr Gly Ala Arg Xaa Thr Xaa Xaa Lys Pro Ser Xaa Thr
     50                  55                  60

Asn Ala Tyr Asn Val Thr Thr His Ala Xaa Gly Thr Ala Thr Tyr Gly
```

<210> SEQ ID NO 58
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(24)
<223> OTHER INFORMATION: X is S or T

<400> SEQUENCE: 58

Arg Pro Arg Phe Asn Lys Pro Ser Glu Thr Asn Ala Tyr Asn Val Thr
1               5                   10                  15

Thr Asn Gln Asp Gly Thr Val Xaa Tyr Gly Ala
            20                  25

<210> SEQ ID NO 59
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: X is T or R
<220> FEATURE:
<221> NAME/KEY: MISC_FEATURE
<222> LOCATION: (4)..(4)
<223> OTHER INFORMATION: X is Q or F
<220> FEATURE:
<221> NAME/KEY: MISC_FEATURE
<222> LOCATION: (9)..(9)
<223> OTHER INFORMATION: X is K or E

<400> SEQUENCE: 59

Arg Pro Xaa Xaa Asn Lys Pro Ser Xaa Thr Asn Ala Tyr Asn Val Thr
1               5                   10                  15

Thr His Ala Asn Gly Gln Val Ser Tyr Gly Ala
            20                  25

<210> SEQ ID NO 60
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: X is T or R
<220> FEATURE:
<221> NAME/KEY: MISC_FEATURE
<222> LOCATION: (4)..(4)
<223> OTHER INFORMATION: X is F, Y or Q
<220> FEATURE:
<221> NAME/KEY: MISC_FEATURE
<222> LOCATION: (5)..(5)
<223> OTHER INFORMATION: X is N or K
<220> FEATURE:
<221> NAME/KEY: MISC_FEATURE
<222> LOCATION: (9)..(9)
<223> OTHER INFORMATION: X is E or K
<220> FEATURE:
<221> NAME/KEY: MISC_FEATURE
<222> LOCATION: (18)..(18)
<223> OTHER INFORMATION: X is H or N

```
<220> FEATURE:
<221> NAME/KEY: MISC_FEATURE
<222> LOCATION: (19)..(19)
<223> OTHER INFORMATION: X is Q, A or R
<220> FEATURE:
<221> NAME/KEY: MISC_FEATURE
<222> LOCATION: (20)..(20)
<223> OTHER INFORMATION: X is N or D
<220> FEATURE:
<221> NAME/KEY: MISC_FEATURE
<222> LOCATION: (22)..(22)
<223> OTHER INFORMATION: X is Q or T

<400> SEQUENCE: 60

Arg Pro Xaa Xaa Xaa Lys Pro Ser Xaa Thr Asn Ala Tyr Asn Val Thr
1               5                   10                  15

Thr Xaa Xaa Xaa Gly Xaa Val Ser Tyr Gly Ala
            20                  25

<210> SEQ ID NO 61
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid

<400> SEQUENCE: 61

Ala Arg Xaa Xaa Xaa Xaa Lys Xaa Ser Xaa Thr Asn Ala Tyr Asn Val
1               5                   10                  15

Thr Thr Xaa Xaa Xaa Gly Xaa Xaa Xaa Tyr Gly
            20                  25

<210> SEQ ID NO 62
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(25)
```

<223> OTHER INFORMATION: Xaa can be any naturally occurring amino acid

<400> SEQUENCE: 62

Ala Arg Pro Thr Xaa Xaa Lys Pro Ser Xaa Thr Asn Ala Tyr Asn Val
1               5                   10                  15

Thr Thr His Xaa Xaa Gly Xaa Xaa Xaa Tyr Gly
            20                  25

<210> SEQ ID NO 63
<211> LENGTH: 1830
<212> TYPE: DNA
<213> ORGANISM: Staphylococcus aureus

<400> SEQUENCE: 63

| | | | | | |
|---|---|---|---|---|---|
| atgaaaaagc | aaataatttc | gctaggcgca | ttagcagttg | catctagctt | atttacatgg | 60 |
| gataacaaag | cagatgcgat | agtaacaaag | gattatagtg | ggaaatcaca | agttaatgct | 120 |
| gggagtaaaa | atgggacatt | aatagatagc | agatatttaa | attcagctct | atattatttg | 180 |
| gaagactata | taatttatgc | tataggatta | actaataaat | atgaatatgg | agataatatt | 240 |
| tataaagaag | ctaaagatag | gttgttggaa | aaggtattaa | gggaagatca | atatcttttg | 300 |
| gagagaaaga | aatctcaata | tgaagattat | aaacaatggt | atgcaaatta | taaaaaagaa | 360 |
| aatcctcgta | cagatttaaa | aatggctaat | tttcataaat | ataatttaga | agaactttcg | 420 |
| atgaaagaat | acaatgaact | acaggatgca | ttaaagagag | cactggatga | ttttcacaga | 480 |
| gaagttaaag | atattaagga | taagaattca | gacttgaaaa | cttttaatgc | agcagaagaa | 540 |
| gataaagcaa | ctaaggaagt | atacgatctc | gtatctgaaa | ttgatacatt | agttgtatca | 600 |
| tattatggtg | ataaggatta | tggggagcac | gcgaaagagt | tacgagcaaa | actggactta | 660 |
| atccttggag | atacagacaa | tccacataaa | attacaaatg | aacgtattaa | aaaagaaatg | 720 |
| attgatgact | taaattcaat | tattgatgat | ttctttatgg | aaactaaaca | aaatagaccg | 780 |
| aaatctataa | cgaaatataa | tcctacaaca | cataactata | aacaaatag | tgataataaa | 840 |
| cctaattttg | ataaattagt | tgaagaaacg | aaaaaagcag | ttaaagaagc | agatgattct | 900 |
| tggaaaaaga | aaactgtcaa | aaaatacgga | gaaactgaaa | caaaatcgcc | agtagtaaaa | 960 |
| gaagagaaga | agttgaaga | acctcaagca | cctaaagttg | ataaccaaca | agaggttaaa | 1020 |
| actacggctg | gtaaagctga | agaaacaaca | caaccagttg | cacaaccatt | agttaaaatt | 1080 |
| ccacagggca | caattacagg | tgaaattgta | aaaggtccgg | aatatccaac | gatggaaaat | 1140 |
| aaaacggtac | aaggtgaaat | cgttcaaggt | cccgattttc | taacaatgga | acaaagcggc | 1200 |
| ccatcattaa | gcaataatta | tacaaaccca | ccgttaacga | accctatttt | agaaggtctt | 1260 |
| gaaggtagct | catctaaact | tgaaataaaa | ccacaaggta | ctgaatcaac | gttaaaaggt | 1320 |
| actcaaggag | aatcaagtga | tattgaagtt | aaacctcaag | caactgaaac | aacagaagct | 1380 |
| tctcaatatg | gtccgagacc | gcaatttaac | aaaacaccta | aatatgttaa | atatagagat | 1440 |
| gctggtacag | gtatccgtga | atacaacgat | ggaacatttg | gatatgaagc | gagaccaaga | 1500 |
| ttcaataagc | catcagaaac | aaatgcatat | aacgtaacaa | cacatgcaaa | tggtcaagta | 1560 |
| tcatacggag | ctcgtccgac | acaaaacaag | ccaagcaaaa | caaacgcata | taacgtaaca | 1620 |
| acacatggaa | acggccaagt | atcatatggc | gctcgcccaa | cacaaaacaa | gccaagcaaa | 1680 |
| acaaatgcat | acaacgtaac | aacacatgca | aacggtcaag | tgtcatacgg | agctcgcccg | 1740 |
| acatacaaga | agccaagtaa | aacaaatgca | tacaatgtaa | caacacatgc | agatggtact | 1800 |
| gcgacatatg | ggcctagagt | aacaaaataa | | | | 1830 |

<210> SEQ ID NO 64
<211> LENGTH: 1977
<212> TYPE: DNA
<213> ORGANISM: Staphylococcus aureus

<400> SEQUENCE: 64

```
atgaaaaagc aaataatttc gctaggcgca ttagcagttg catctagctt atttacatgg      60
gataacaaag cagatgcgat agtaacaaag gattatagta aagaatcaag agtgaatgag     120
aaaagtaaaa agggagctac tgtttcagat tattactatt ggaaaataat tgatagttta     180
gaggcacaat ttactggagc aatagactta ttggaagatt ataaatatgg agatcctatc     240
tataagaag cgaaagatag attgatgaca agagtattag gagaagacca gtatttatta      300
aagaaaaga ttgatgaata tgagctttat aaaaagtggt ataaaagttc aaataagaac      360
actaatatgc ttactttcca taaatataat ctttacaatt taacaatgaa tgaatataac     420
gatatttta actctttgaa agatgcagtt tatcaattta ataagaagt taagaaata       480
gagcataaaa atgttgactt gaagcagttt gataaagatg gagaagacaa ggcaactaaa     540
gaagtttatg accttgtttc tgaaattgat acattagttg taacttatta tgctgataag     600
gattatgggg agcatgcgaa agagttacga gcaaaactgg acttaatcct tggagataca     660
gacaatccac ataaaattac aaatgagcgt ataaaaaaag aaatgatcga tgacttaaat     720
tcaattatag atgatttctt tatggagact aaacaaaata gaccgaattc tataacaaaa     780
tatgatccaa caaaacacaa ttttaaagag aagagtgaaa ataaacctaa ttttgataaa     840
ttagttgaag aaacaaaaaa agcagttaaa gaagcagacg aatcttggaa aaataaaact     900
gtcaaaaaat acgaggaaac tgtaacaaaa tctcctgttg taaaagaaga gaagaaagtt     960
gaagaacctc aattacctaa agttggaaac cagcaagagg ttaaaactac ggctggtaaa    1020
gctgaagaaa caacacaacc agtggcacag ccattagtaa aaattccaca agaaacaatc    1080
tatggtgaaa ctgtaaaagg tccagaatat ccaacgatgg aaaataaaac gttacaaggt    1140
gaaatcgttc aaggtcccga ttttctaaca atggaacaaa acagaccatc tttaagcgat    1200
aattatactc aaccgacgac accgaaccct attttagaag gtcttgaagg tagctcatct    1260
aaacttgaaa taaaaccaca aggtactgaa tcaacgttga aggtattca aggagaatca    1320
agtgatattg aagttaaacc tcaagcaact gaaacaacag aagcttctca atatggtccg    1380
agaccgcaat ttaacaaaac acctaagtat gtgaaatata gagatgctgg tacaggtatc    1440
cgtgaataca acgatggaac atttggatat gaagcgagac caagattcaa caagccaagt    1500
gaaacaaatg catacaacgt aacgacaaat caagatggca cagtatcata cggagctcgc    1560
ccaacacaaa acaagccaag tgaaacaaac gcatataacg taacaacaca tgcaaatggt    1620
caagtatcat acggtgctcg cccaacacaa aaaagccaa gcaaaacaaa tgcatacaac    1680
gtaacaacac atgcaaatgg tcaagtatca tatggcgctc gcccgacaca aaaaaagcca    1740
agcaaaacaa atgcatataa cgtaacaaca catgcaaatg gtcaagtatc atacggagct    1800
cgcccgacat acaagaagcc aagcgaaaca aatgcataca acgtaacaac acatgcaaat    1860
ggtcaagtat catatggcgc tcgcccgaca caaaaaaagc caagcgaaac aaacgcatat    1920
aacgtaacaa cacatgcaga tggtactgcg acatatgggc ctagagtaac aaaataa      1977
```

<210> SEQ ID NO 65
<211> LENGTH: 1830
<212> TYPE: DNA

<213> ORGANISM: Staphylococcus aureus

<400> SEQUENCE: 65

```
atgaaaaagc aaataatttc gctaggcgca ttagcagttg catctagctt atttacatgg      60
gataacaaag cagatgcgat agtaactaaa gattatagta agaatcaag agtgaatgag     120
aacagtaaat acgatacacc aattccagat tggtatctag gtagtatttt aaacagatta    180
ggggatcaaa tatactacgc taaggaatta actaataaat acgaatatgg tgagaaagag    240
tataagcaag cgatagataa attgatgact agagttttgg gagaagatca ttatctatta    300
gaaaaaaga aagcacaata tgaagcatac aaaaaatggt ttgaaaaaca taaaagtgaa     360
aatccacatt ctagttttaaa aaagattaaa tttgacgatt ttgatttata tagattaacg   420
aagaaagaat acaatgagtt acatcaatca ttaaaagaag ctgttgatga gtttaatagt    480
gaagtgaaaa atattcaatc taaacaaaag gatttattac cttatgatga agcaactgaa    540
aatcgagtaa caaatggaat atatgatttt gtttgcgaga ttgacacatt atacgcagca    600
tattttaatc atagccaata tggtcataat gctaaagaat aagagcaaa gctagatata    660
attcttggtg atgctaaaga tcctgttaga attacgaatg aaagaataag aaaagaaatg    720
atggatgatt taaattctat tattgatgat ttctttatgg atacaaacat gaatagacca    780
ttaaacataa ctaaatttaa tccgaatatt catgactata ctaataagcc tgaaaataga    840
gataacttcg ataaattagt caaagaaaca agagaagcaa tcgcaaacgc tgacgaatct    900
tggaaaacaa gaaccgtcaa aaattacggt gaatctgaaa caaaatctcc tgttgtaaaa    960
gaagagaaga agttgaaga acctcaatta cctaaagttg aaaccagca agaggataaa     1020
attacagttg gtacaactga agaagcacca ttaccaattg cgcaaccact agttaaaatt   1080
ccacagggca caattcaagg tgaaattgta aaaggtccgg aatatctaac gatggaaaat   1140
aaaacgttac aaggtgaaat cgttcaaggt ccagatttcc caacaatgga acaaaacaga   1200
ccatctttaa gcgataatta tactcaaccg acgacaccga accctatttt aaaaggtatt   1260
gaaggaaact caactaaact tgaaataaaa ccacaaggta ctgaatcaac gttaaaggt    1320
actcaaggag aatcaagtga tattgaagtt aaacctcaag caactgaaac aacagaagca   1380
tcacattatc cagcgagacc tcaatttaac aaaacaccta gtatgtgaa atatagagat    1440
gctggtacag gtatccgtga atacaacgat ggaacatttg gatatgaagc gagaccaaga   1500
ttcaacaagc caagcgaaac aaatgcatac aacgtaacga caaatcaaga tggcacagta   1560
tcatatggcg ctcgcccgac acaaaacaag ccaagcgaaa caaacgcata taacgtaaca   1620
acacatgcaa acggccaagt atcatacgga gctcgtccga cacaaaacaa gccaagcgaa   1680
acgaacgcat ataacgtaac aacacatgca acggtcaag tgtcatacgg agctcgccca    1740
acacaaaaca agccaagtaa acaaatgca tacaatgtaa caacacatgc agatggtact   1800
gcgacatatg gtcctagagt aacaaaataa                                    1830
```

<210> SEQ ID NO 66
<211> LENGTH: 1902
<212> TYPE: DNA
<213> ORGANISM: Staphylococcus aureus

<400> SEQUENCE: 66

```
atgaaaaagc aaataatttc gctaggcgca ttagcagttg catctagctt atttacatgg      60
gataacaaag cagatgcgat agtaacaaag gattatagtg gaaatcaca agttaatgct     120
gggagtaaaa atgggaaaca aattgcagat ggatattatt ggggaataat tgaaaatcta   180
```

```
gaaaaccagt tttacaatat ttttcattta ctggatcagc ataaatatgc agaaaaagaa      240
tataaagatg cagtagataa attaaaaact agagttttag aggaagacca atacctgcta      300
gaaagaaaaa aagaaaaata cgaaatttat aaagaactat ataaaaaata caaaaagag       360 aatcctaata ctcaagttaa aatgaaagca tttgataaat acgatcttgg cgatttaact      420
atggaagaat acaatgactt atcaaaatta ttaacaaaag cattggataa ctttaagtta      480
gaagtaaaga aaattgaatc agagaatcca gatttaaaac catattctga agcgaagaa       540 agaacagcat atggtaaaat agattcactt gttgatcaag catatagtgt atattttgcc      600
tacgttacag atgcacaaca taaaacagaa gcattaaatc ttagggcgaa aattgatttg      660
attttaggtg atgaaaaaga tccaattaga gttacgaatc aacgtactga aaagaaatg       720 attaaagatt tagaatctat tattgatgat ttcttcattg aaaccaagtt gaatagacct      780
aaacacatta ctaggtatga tggaactaaa catgattacc ataaacataa agatggattt      840
gatgctctag ttaaagaaac aagagaagcg gttgcaaagg ctgacgaatc ttggaaaaat      900
aaaactgtca aaaatacga ggaaactgta acaaaatctc cagttgtaaa agaagagaag       960
aaagttgaag aacctcaatc acctaaattt gataaccaac aagaggttaa aattacagtt     1020
gataaagctg aagaacaac acaaccagtg gcacagccat tagttaaaat tccacagggc      1080
acaattacag gtgaaattgt aaaaggtccg aatatccaa cgatggaaaa taaaacgtta      1140
caaggtgaaa tcgttcaagg tccagatttc ccaacaatgg aacaaaacag accatcttta     1200
agcgataatt atactcaacc gacgacaccg aaccctattt tagaaggtct tgaaggtagc     1260
tcatctaaac ttgaaataaa accacaaggt actgaatcaa cgttaaaagg tactcaagga     1320
gaatcaagtg atattgaagt taaacctcaa gcatctgaaa caacagaagc atcacattat     1380
ccagcaagac ctcaatttaa caaaacacct aaatatgtta atatagaga tgctggtaca      1440 ggtatccgtg aatacaacga tggaacattt ggatatgaag cgagaccaag attcaataag     1500
ccatcagaaa caaacgcata aacgtaacg acaaatcaag atggcacagt aacatatggc      1560
gctcgcccaa cacaaaacaa accagcaaa acaaatgcat acaacgtaac aacacatgca     1620
aatggtcaag tatcatatgg cgctcgcccg acacaaaaca agccaagcaa acaaatgca     1680 tataacgtaa caacacatgc aaatggtcaa gtatcatacg gagctcgccc gacacaaaac     1740
aagccaagca aaacaaatgc atataacgta acaacacacg caaacggtca agtgtcatac     1800
ggagctcgcc cgacatacaa gaagccaagt aaaacaaatg catacaatgt aacaacacat     1860
gcagatggta ctgcgacata tgggcctaga gtaacaaaat aa                        1902

<210> SEQ ID NO 67
<211> LENGTH: 1938
<212> TYPE: DNA
<213> ORGANISM: Staphylococcus aureus

<400> SEQUENCE: 67
atagtaacaa aggattatag tgggaaatca caagttaatg ctgggagtaa aaatgggaaa       60
caaattgcag atggatatta ttggggaata attgaaaatc tagagaacca gttttacaat      120
atttttcatt tattgatca gcataaatat gcagaaaaag aatataaaga tgcattagat      180
aaattaaaaa ctagagtttt agaggaagac caatacctgc tagaaagaaa aaagaaaaa       240 tacgaaattt ataagaact atataaaaaa tacaaaaaag agaatcctaa tactcaggtt      300
aaaatgaaag catttgataa atacgatctt ggcgatttaa ctatggaaga atacaatgac      360
```

```
ttatcaaaat tattaacaaa agcattggat aactttaagt tagaagtaaa gaaaattgaa      420
tcagagaatc cagatttaag accatattct gaaagtgaag agagaacagc atatggtaaa      480
atagattcac ttgttgatca agcatatagt gtatattttg cctacgttac agatgctcaa      540
cataaaacag aagcattaaa tcttagggca aaaatagatt tgattttagg tgatgaaaaa      600
gatccaatta gagtgacgaa tcaacgtact gaaaagaaa tgattaaaga tttagaatct       660
attattgatg atttcttcat tgaaacaaag ttgaatagac ctcaacacat tactagatat      720
gatggaacta acatgattta ccataaacat aaagatggat ttgatgcttt agttaaagaa      780
acaagagaag cggtttctaa ggctgacgaa tcttggaaaa ctaaaactgt caaaaaatac      840
ggggaaactg aaacaaaata tcctgttgta aagaagaga agaaagttga agaacctcaa       900
tcacctaaag tttctgaaaa agtggatgtt caggaaacgg ttggtacaac tgaagaagca      960
ccattaccaa ttgcgcaacc actagttaaa ttaccacaaa ttgggactca aggcgaaatt     1020
gtaaaaggtc ccgactatcc aactatgaa aataaaacgt acaaggtgt aattgttcaa       1080 ggtccagatt tcccaacaat ggaacaaaac agaccatctt taagtgacaa ttatacacaa     1140
ccatctgtga ctttaccgtc aattacaggt gaaagtacac caacgaaccc tattttaaaa     1200
ggtattgaag gaaactcatc taaacttgaa ataaaaccac aaggtactga atcaacgttg     1260
aaaggtattc aaggagaatc aagtgatatt gaagttaaac ctcaagcaac tgaaacaaca     1320
gaagcatcac attatccagc gagaccgcaa tttaacaaaa cacctaaata tgtgaaatat     1380
agagatgctg gtacaggtat tcgtgaatac aacgatggaa cttttggata tgaagcgaga     1440
ccaagattca acaagccatc agaaacaaac gcatacaacg taacgacaaa tcaagatggc     1500
acagtatcat atggggctcg cccaacacaa aacaagccaa gcaaaacaaa tgcatataac     1560
gtaacaacac atgcaaacgg ccaagtatca tatggcgctc gcccgacata caacaagcca     1620
agtgaaacaa atgcatacaa cgtaacgaca atcgagatg gcacagtatc atatggcgct      1680
cgcccgacac aaaacaagcc aagcgaaacg aatgcatata acgtaacaac acacggaaat     1740
ggccaagtat catatggcgc tcgtccgaca caaaagaagc caagcaaaac aaatgcatat     1800
aacgtaacaa cacatgcaaa cggccaagta tcatatggcg ctcgtccgac atacaacaag     1860
ccaagtaaaa caaatgcata caatgtaaca acacatgcag atggtactgc gacatatggt     1920
cctagagtaa caaaataa                                                   1938
```

<210> SEQ ID NO 68
<211> LENGTH: 162
<212> TYPE: PRT
<213> ORGANISM: Staphylococcus aureus

<400> SEQUENCE: 68

```
Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Gln Lys Lys Pro Ser Lys Thr
    50                  55                  60

Asn Ala Tyr Asn Val Thr Thr His Ala Asn Gly Gln Val Ser Tyr Gly
65                  70                  75                  80

Ala Arg Pro Thr Gln Lys Lys Pro Ser Lys Thr Asn Ala Tyr Asn Val
                85                  90                  95
```

```
Thr Thr His Ala Asn Gly Gln Val Ser Tyr Gly Ala Arg Pro Thr Tyr
            100                 105                 110
Lys Lys Pro Ser Glu Thr Asn Ala Tyr Asn Val Thr Thr His Ala Asn
        115                 120                 125
Gly Gln Val Ser Tyr Gly Ala Arg Leu Thr Gln Lys Lys Pro Ser Glu
    130                 135                 140
Thr Asn Ala Tyr Asn Val Thr Thr His Ala Asp Gly Thr Ala Thr Tyr
145                 150                 155                 160
Gly Pro

<210> SEQ ID NO 69
<211> LENGTH: 162
<212> TYPE: PRT
<213> ORGANISM: Staphylococcus aureus

<400> SEQUENCE: 69

Arg Pro Arg Phe Asn Lys Pro Ser Glu Thr Asn Ala Tyr Asn Val Thr
1               5                   10                  15
Thr Asn Gln Asp Gly Thr Val Ser Tyr Gly Ala Arg Pro Thr Gln Asn
            20                  25                  30
Lys Pro Ser Glu Thr Asn Ala Tyr Asn Val Thr Thr His Ala Asn Gly
        35                  40                  45
Gln Val Ser Tyr Gly Ala Arg Pro Thr Gln Lys Lys Pro Ser Lys Thr
    50                  55                  60
Asn Ala Tyr Asn Val Thr Thr His Ala Asn Gly Gln Val Ser Tyr Gly
65                  70                  75                  80
Ala Arg Pro Thr Gln Lys Lys Pro Ser Lys Thr Asn Ala Tyr Asn Val
                85                  90                  95
Thr Thr His Ala Asn Gly Gln Val Ser Tyr Gly Ala Arg Pro Thr Tyr
            100                 105                 110
Lys Lys Pro Ser Glu Thr Asn Ala Tyr Asn Val Thr Thr His Ala Asn
        115                 120                 125
Gly Gln Val Ser Tyr Gly Ala Arg Pro Thr Gln Lys Lys Pro Ser Glu
    130                 135                 140
Thr Asn Ala Tyr Asn Val Thr Thr His Ala Asp Gly Thr Ala Thr Tyr
145                 150                 155                 160
Gly Pro

<210> SEQ ID NO 70
<211> LENGTH: 162
<212> TYPE: PRT
<213> ORGANISM: Staphylococcus aureus

<400> SEQUENCE: 70

Arg Pro Arg Phe Asn Lys Pro Ser Glu Thr Asn Ala Tyr Asn Val Thr
1               5                   10                  15
Thr Asn Gln Asp Gly Thr Val Ser Tyr Gly Ala Arg Pro Thr Gln Asn
            20                  25                  30
Lys Pro Ser Glu Thr Asn Ala Tyr Asn Val Thr Thr His Ala Asn Gly
        35                  40                  45
Gln Val Ser Tyr Gly Ala Arg Pro Thr Tyr Lys Lys Pro Ser Glu Thr
    50                  55                  60
Asn Ala Tyr Asn Val Thr Thr His Ala Asn Gly Gln Val Ser Tyr Gly
65                  70                  75                  80
Ala Arg Pro Thr Gln Lys Lys Pro Ser Lys Thr Asn Ala Tyr Asn Val
```

85                  90                  95
Thr Thr His Ala Asn Gly Gln Val Ser Tyr Gly Ala Arg Pro Thr Tyr
                100                 105                 110
Lys Lys Pro Ser Glu Thr Asn Ala Tyr Asn Val Thr Thr His Ala Asn
            115                 120                 125
Gly Gln Val Ser Tyr Gly Ala Arg Pro Thr Gln Lys Lys Pro Ser Glu
    130                 135                 140
Thr Asn Ala Tyr Asn Val Thr Thr His Ala Asp Gly Thr Ala Thr Tyr
145                 150                 155                 160
Gly Pro

<210> SEQ ID NO 71
<211> LENGTH: 135
<212> TYPE: PRT
<213> ORGANISM: Staphylococcus aureus

<400> SEQUENCE: 71

Arg Pro Arg Phe Asn Lys Pro Ser Glu Thr Asn Ala Tyr Asn Val Thr
1               5                   10                  15
Thr His Ala Asn Gly Gln Val Ser Tyr Gly Ala Arg Pro Thr Tyr Lys
            20                  25                  30
Lys Pro Ser Glu Thr Asn Ala Tyr Asn Val Thr Thr His Ala Asn Gly
        35                  40                  45
Gln Val Ser Tyr Gly Ala Arg Pro Thr Gln Asn Lys Pro Ser Lys Thr
    50                  55                  60
Asn Ala Tyr Asn Val Thr Thr His Gly Asn Gly Gln Val Ser Tyr Gly
65                  70                  75                  80
Ala Arg Pro Thr Gln Asn Lys Pro Ser Lys Thr Asn Ala Tyr Asn Val
                85                  90                  95
Thr Thr His Ala Asn Gly Gln Val Ser Tyr Gly Ala Arg Pro Thr Tyr
                100                 105                 110
Lys Lys Pro Ser Lys Thr Asn Ala Tyr Asn Val Thr Thr His Ala Asp
            115                 120                 125
Gly Thr Ala Thr Tyr Gly Pro
    130                 135

<210> SEQ ID NO 72
<211> LENGTH: 108
<212> TYPE: PRT
<213> ORGANISM: Staphylococcus aureus

<400> SEQUENCE: 72

Arg Pro Arg Phe Asn Lys Pro Ser Glu Thr Asn Ala Tyr Asn Val Thr
1               5                   10                  15
Thr His Ala Asn Gly Gln Val Ser Tyr Gly Ala Arg Pro Thr Gln Asn
            20                  25                  30
Lys Pro Ser Lys Thr Asn Ala Tyr Asn Val Thr Thr His Ala Asn Gly
        35                  40                  45
Gln Val Ser Tyr Gly Ala Arg Pro Thr Gln Asn Lys Pro Ser Lys Thr
    50                  55                  60
Asn Ala Tyr Asn Val Thr Thr His Gly Asn Gly Gln Val Ser Tyr Gly
65                  70                  75                  80
Ala Arg Pro Thr Tyr Lys Lys Pro Ser Lys Thr Asn Ala Tyr Asn Val
                85                  90                  95
Thr Thr His Ala Asp Gly Thr Ala Thr Tyr Gly Pro
                100                 105

<210> SEQ ID NO 73
<211> LENGTH: 162
<212> TYPE: PRT
<213> ORGANISM: Staphylococcus aureus

<400> SEQUENCE: 73

```
Arg Pro Arg Phe Asn Lys Pro Ser Glu Thr Asn Ala Tyr Asn Val Thr
1               5                   10                  15

Thr Asn Gln Asp Gly Thr Val Thr Tyr Gly Ala Arg Pro Thr Gln Asn
            20                  25                  30

Lys Pro Ser Lys Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr His Ala Asn Gly Gln Val Ser Tyr Gly
65                  70                  75                  80

Ala Arg Pro Thr Gln Asn Lys Ala Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Lys Thr Asn Ala Tyr Asn Val Thr Thr His Gly Asn
        115                 120                 125

Gly Gln Val Ser Tyr Gly Ala Arg Pro Thr Tyr Lys Lys Pro Ser Glu
    130                 135                 140

Thr Asn Ala Tyr Asn Val Thr Thr His Ala Asp Gly Thr Ala Thr Tyr
145                 150                 155                 160

Gly Pro
```

<210> SEQ ID NO 74
<211> LENGTH: 162
<212> TYPE: PRT
<213> ORGANISM: Staphylococcus aureus

<400> SEQUENCE: 74

```
Arg Pro Arg Phe Asn Lys Pro Ser Glu Thr Asn Ala Tyr Asn Val Thr
1               5                   10                  15

Thr Asn Gln Asp Gly Thr Val Thr Tyr Gly Ala Arg Pro Thr Gln Asn
            20                  25                  30

Lys Pro Ser Lys Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr His Ala Asn Gly Gln Val Ser Tyr Gly
65                  70                  75                  80

Ala Arg Pro Thr Gln Asn Lys Ala Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Lys Thr Asn Ala Tyr Asn Val Thr Thr His Gly Asn
        115                 120                 125

Gly Gln Val Ser Tyr Gly Ala Arg Pro Thr Tyr Lys Lys Pro Ser Glu
    130                 135                 140

Thr Asn Ala Tyr Asn Val Thr Thr His Ala Asp Gly Thr Ala Thr Tyr
145                 150                 155                 160
```

Gly Pro

<210> SEQ ID NO 75
<211> LENGTH: 81
<212> TYPE: PRT
<213> ORGANISM: Staphylococcus aureus

<400> SEQUENCE: 75

Arg Pro Arg Phe Asn Lys Pro Ser Glu Thr Asn Ala Tyr Asn Val Thr
1               5                   10                  15

Thr Asn Gln Asp Gly Thr Val Thr Tyr Gly Ala Arg Pro Thr Gln Asn
            20                  25                  30

Lys Pro Ser Lys Thr Asn Ala Tyr Asn Val Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr His Ala Asn Gly Thr Ala Thr Tyr Gly
65                  70                  75                  80

Pro

<210> SEQ ID NO 76
<211> LENGTH: 108
<212> TYPE: PRT
<213> ORGANISM: Staphylococcus aureus

<400> SEQUENCE: 76

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Lys
            20                  25                  30

Lys Pro Ser Glu Thr Asn Ala Tyr Asn Val Thr His Ala Asn Gly
        35                  40                  45

Gln Val Ser Tyr Gly Ala Arg Pro Thr Gln Asn Lys Pro Ser Glu Thr
    50                  55                  60

Asn Ala Tyr Asn Val Thr Thr His Gly Asn Gly Gln Val Ser Tyr Gly
65                  70                  75                  80

Ala Arg Pro Thr Gln Asn Lys Pro Ser Lys Thr Asn Ala Tyr Asn Val
            85                  90                  95

Thr Thr His Ala Asp Gly Thr Ala Thr Tyr Gly Pro
            100                 105

<210> SEQ ID NO 77
<211> LENGTH: 162
<212> TYPE: PRT
<213> ORGANISM: Staphylococcus aureus

<400> SEQUENCE: 77

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                    85                  90                  95

Thr Thr His Ala Asn Gly Gln Val Ser Tyr Gly Ala Arg Pro Thr Gln
            100                 105                 110

Asn Lys Pro Ser Glu Thr Asn Ala Tyr Asn Val Thr Thr His Ala Asn
        115                 120                 125

Gly Gln Val Ser Tyr Gly Ala Arg Pro Thr Gln Asn Lys Pro Ser Lys
    130                 135                 140

Thr Asn Ala Tyr Asn Val Thr Thr His Ala Asp Gly Thr Ala Thr Tyr
145                 150                 155                 160

Gly Pro

<210> SEQ ID NO 78
<211> LENGTH: 162
<212> TYPE: PRT
<213> ORGANISM: Staphylococcus aureus

<400> SEQUENCE: 78

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Glu Thr Asn Ala Tyr Asn Val Thr Thr His Ala Asn
        115                 120                 125

Gly Gln Val Ser Tyr Gly Ala Arg Pro Thr Gln Asn Lys Pro Ser Lys
    130                 135                 140

Thr Asn Ala Tyr Asn Val Thr Thr His Ala Asp Gly Thr Ala Thr Tyr
145                 150                 155                 160

Gly Pro

<210> SEQ ID NO 79
<211> LENGTH: 81
<212> TYPE: PRT
<213> ORGANISM: Staphylococcus aureus

<400> SEQUENCE: 79

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Lys Thr Asn Ala Tyr Asn Val Thr Thr His Ala Asn Gly
        35                  40                  45

Gln Val Ser Tyr Gly Ala Arg Pro Thr Tyr Lys Pro Ser Lys Thr
    50                  55                  60

Asn Ala Tyr Asn Val Thr Thr His Ala Asp Gly Thr Ala Thr Tyr Gly
65                  70                  75                  80

Pro

<210> SEQ ID NO 80
<211> LENGTH: 162
<212> TYPE: PRT
<213> ORGANISM: Staphylococcus aureus

<400> SEQUENCE: 80

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Lys Thr Asn Ala Tyr Asn Val Thr Thr His Ala Asn Gly
        35                  40                  45

Gln Val Ser Tyr Gly Ala Arg Pro Thr Tyr Asn Lys Pro Ser Glu Thr
    50                  55                  60

Asn Ala Tyr Asn Val Thr Thr Asn Arg Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Gly Asn Gly Gln Val Ser Tyr Gly Ala Arg Pro Thr Gln
            100                 105                 110

Lys Lys Pro Ser Lys Thr Asn Ala Tyr Asn Val Thr Thr His Ala Asn
        115                 120                 125

Gly Gln Val Ser Tyr Gly Ala Arg Pro Thr Tyr Asn Lys Pro Ser Lys
    130                 135                 140

Thr Asn Ala Tyr Asn Val Thr Thr His Ala Asp Gly Thr Ala Thr Tyr
145                 150                 155                 160

Gly Pro

<210> SEQ ID NO 81
<211> LENGTH: 162
<212> TYPE: PRT
<213> ORGANISM: Staphylococcus aureus

<400> SEQUENCE: 81

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Lys Thr Asn Ala Tyr Asn Val Thr Thr His Ala Asn Gly
        35                  40                  45

Gln Val Ser Tyr Gly Ala Arg Pro Thr Tyr Asn Lys Pro Ser Glu Thr
    50                  55                  60

Asn Ala Tyr Asn Val Thr Thr Asn Arg Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Gly Asn Gly Gln Val Ser Tyr Gly Ala Arg Pro Thr Gln
            100                 105                 110

Lys Lys Pro Ser Lys Thr Asn Ala Tyr Asn Val Thr Thr His Ala Asn
        115                 120                 125

Gly Gln Val Ser Tyr Gly Ala Arg Pro Thr Gln Lys Lys Pro Ser Lys
    130                 135                 140

Thr Asn Ala Tyr Asn Val Thr Thr His Ala Asp Gly Thr Ala Thr Tyr

```
145                 150                 155                 160

Gly Pro

<210> SEQ ID NO 82
<211> LENGTH: 162
<212> TYPE: PRT
<213> ORGANISM: Staphylococcus aureus

<400> SEQUENCE: 82

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Glu Thr Asn Ala Tyr Asn Val Thr Thr His Ala Asn
        115                 120                 125

Gly Gln Val Ser Tyr Gly Ala Arg Pro Thr Gln Asn Lys Pro Ser Lys
    130                 135                 140

Thr Asn Ala Tyr Asn Val Thr Thr His Ala Asp Gly Thr Ala Thr Tyr
145                 150                 155                 160

Gly Pro

<210> SEQ ID NO 83
<211> LENGTH: 162
<212> TYPE: PRT
<213> ORGANISM: Staphylococcus aureus

<400> SEQUENCE: 83

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Tyr Lys Lys Pro Ser Glu Thr
    50                  55                  60

Asn Ala Tyr Asn Val Thr Thr Asn Gln Asp Gly Thr Val Ser Tyr Gly
65                  70                  75                  80

Ala Arg Pro Thr Gln Asn Lys Pro Ser Glu Thr Asn Ala Tyr Asn Val
                85                  90                  95

Thr Thr His Ala Asn Gly Gln Val Ser Tyr Gly Ala Arg Pro Thr Gln
            100                 105                 110

Asn Lys Pro Ser Glu Thr Asn Ala Tyr Asn Val Thr Thr His Ala Asn
        115                 120                 125

Gly Gln Val Ser Tyr Gly Ala Arg Pro Thr Gln Asn Lys Pro Ser Lys
    130                 135                 140
```

```
Thr Asn Ala Tyr Asn Val Thr Thr His Ala Asp Gly Thr Ala Thr Tyr
145                 150                 155                 160

Gly Pro

<210> SEQ ID NO 84
<211> LENGTH: 108
<212> TYPE: PRT
<213> ORGANISM: Staphylococcus aureus

<400> SEQUENCE: 84

Arg Pro Arg Phe Asn Lys Pro Ser Glu Thr Asn Ala Tyr Asn Val Thr
1               5                   10                  15

Thr Asn Gln Asp Gly Thr Val Ser Tyr Gly Ala Arg Pro Thr Gln Asn
            20                  25                  30

Lys Pro Ser Glu Thr Asn Ala Tyr Asn Val Thr Thr His Ala Asn Gly
        35                  40                  45

Gln Val Ser Tyr Gly Ala Arg Pro Thr Gln Asn Lys Pro Ser Glu Thr
    50                  55                  60

Asn Ala Tyr Asn Val Thr Thr His Ala Asn Gly Gln Val Ser Tyr Gly
65                  70                  75                  80

Ala Arg Pro Thr Gln Asn Lys Pro Ser Lys Thr Asn Ala Tyr Asn Val
                85                  90                  95

Thr Thr His Ala Asp Gly Thr Ala Thr Tyr Gly Pro
            100                 105

<210> SEQ ID NO 85
<211> LENGTH: 162
<212> TYPE: PRT
<213> ORGANISM: Staphylococcus aureus

<400> SEQUENCE: 85

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Glu Thr Asn Ala Tyr Asn Val Thr Thr His Ala Asn
        35                  40                  45

Gly Gln Val Ser Tyr Gly Ala Arg Pro Thr Gln Lys Lys Pro Ser Lys
    50                  55                  60

Thr Asn Ala Tyr Asn Val Thr Thr His Ala Asn Gly Gln Val Ser Tyr
65                  70                  75                  80

Gly Ala Arg Pro Thr Gln Lys Lys Pro Ser Lys Thr Asn Ala Tyr Asn
                85                  90                  95

Val Thr Thr His Ala Asn Gly Gln Val Ser Tyr Gly Ala Arg Pro Thr
            100                 105                 110

Tyr Lys Lys Pro Ser Glu Thr Asn Ala Tyr Asn Val Thr Thr His Ala
        115                 120                 125

Asn Gly Gln Val Ser Tyr Gly Ala Arg Leu Thr Gln Lys Lys Pro Ser
    130                 135                 140

Glu Thr Asn Ala Tyr Asn Val Thr Thr His Ala Asp Gly Thr Ala Thr
145                 150                 155                 160

Tyr Gly

<210> SEQ ID NO 86
<211> LENGTH: 162
<212> TYPE: PRT
<213> ORGANISM: Staphylococcus aureus
```

<400> SEQUENCE: 86

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Glu Thr Asn Ala Tyr Asn Val Thr Thr His Ala Asn
        35                  40                  45

Gly Gln Val Ser Tyr Gly Ala Arg Pro Thr Gln Lys Lys Pro Ser Lys
    50                  55                  60

Thr Asn Ala Tyr Asn Val Thr Thr His Ala Asn Gly Gln Val Ser Tyr
65                  70                  75                  80

Gly Ala Arg Pro Thr Gln Lys Lys Pro Ser Lys Thr Asn Ala Tyr Asn
                85                  90                  95

Val Thr Thr His Ala Asn Gly Gln Val Ser Tyr Gly Ala Arg Pro Thr
            100                 105                 110

Tyr Lys Lys Pro Ser Glu Thr Asn Ala Tyr Asn Val Thr Thr His Ala
        115                 120                 125

Asn Gly Gln Val Ser Tyr Gly Ala Arg Pro Thr Gln Lys Lys Pro Ser
    130                 135                 140

Glu Thr Asn Ala Tyr Asn Val Thr Thr His Ala Asp Gly Thr Ala Thr
145                 150                 155                 160

Tyr Gly

<210> SEQ ID NO 87
<211> LENGTH: 162
<212> TYPE: PRT
<213> ORGANISM: Staphylococcus aureus

<400> SEQUENCE: 87

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Glu Thr Asn Ala Tyr Asn Val Thr Thr His Ala Asn
        35                  40                  45

Gly Gln Val Ser Tyr Gly Ala Arg Pro Thr Tyr Lys Lys Pro Ser Glu
    50                  55                  60

Thr Asn Ala Tyr Asn Val Thr Thr His Ala Asn Gly Gln Val Ser Tyr
65                  70                  75                  80

Gly Ala Arg Pro Thr Gln Lys Lys Pro Ser Lys Thr Asn Ala Tyr Asn
                85                  90                  95

Val Thr Thr His Ala Asn Gly Gln Val Ser Tyr Gly Ala Arg Pro Thr
            100                 105                 110

Tyr Lys Lys Pro Ser Glu Thr Asn Ala Tyr Asn Val Thr Thr His Ala
        115                 120                 125

Asn Gly Gln Val Ser Tyr Gly Ala Arg Pro Thr Gln Lys Lys Pro Ser
    130                 135                 140

Glu Thr Asn Ala Tyr Asn Val Thr Thr His Ala Asp Gly Thr Ala Thr
145                 150                 155                 160

Tyr Gly

<210> SEQ ID NO 88
<211> LENGTH: 135
<212> TYPE: PRT

<213> ORGANISM: Staphylococcus aureus

<400> SEQUENCE: 88

```
Ala Arg Pro Arg Phe Asn Lys Pro Ser Glu Thr Asn Ala Tyr Asn Val
1               5                   10                  15
Thr Thr His Ala Asn Gly Gln Val Ser Tyr Gly Ala Arg Pro Thr Tyr
            20                  25                  30
Lys Lys Pro Ser Glu Thr Asn Ala Tyr Asn Val Thr Thr His Ala Asn
        35                  40                  45
Gly Gln Val Ser Tyr Gly Ala Arg Pro Thr Gln Asn Lys Pro Ser Lys
    50                  55                  60
Thr Asn Ala Tyr Asn Val Thr Thr His Gly Asn Gly Gln Val Ser Tyr
65                  70                  75                  80
Gly Ala Arg Pro Thr Gln Asn Lys Pro Ser Lys Thr Asn Ala Tyr Asn
                85                  90                  95
Val Thr Thr His Ala Asn Gly Gln Val Ser Tyr Gly Ala Arg Pro Thr
            100                 105                 110
Tyr Lys Lys Pro Ser Lys Thr Asn Ala Tyr Asn Val Thr Thr His Ala
        115                 120                 125
Asp Gly Thr Ala Thr Tyr Gly
    130                 135
```

<210> SEQ ID NO 89
<211> LENGTH: 108
<212> TYPE: PRT
<213> ORGANISM: Staphylococcus aureus

<400> SEQUENCE: 89

```
Ala Arg Pro Arg Phe Asn Lys Pro Ser Glu Thr Asn Ala Tyr Asn Val
1               5                   10                  15
Thr Thr His Ala Asn Gly Gln Val Ser Tyr Gly Ala Arg Pro Thr Gln
            20                  25                  30
Asn Lys Pro Ser Lys Thr Asn Ala Tyr Asn Val Thr Thr His Gly Asn
        35                  40                  45
Gly Gln Val Ser Tyr Gly Ala Arg Pro Thr Gln Asn Lys Pro Ser Lys
    50                  55                  60
Thr Asn Ala Tyr Asn Val Thr Thr His Ala Asn Gly Gln Val Ser Tyr
65                  70                  75                  80
Gly Ala Arg Pro Thr Tyr Lys Lys Pro Ser Lys Thr Asn Ala Tyr Asn
                85                  90                  95
Val Thr Thr His Ala Asp Gly Thr Ala Thr Tyr Gly
            100                 105
```

<210> SEQ ID NO 90
<211> LENGTH: 162
<212> TYPE: PRT
<213> ORGANISM: Staphylococcus aureus

<400> SEQUENCE: 90

```
Ala Arg Pro Arg Phe Asn Lys Pro Ser Glu Thr Asn Ala Tyr Asn Val
1               5                   10                  15
Thr Thr Asn Gln Asp Gly Thr Val Thr Tyr Gly Ala Arg Pro Thr Gln
            20                  25                  30
Asn Lys Pro Ser Lys Thr Asn Ala Tyr Asn Val Thr Thr His Ala Asn
        35                  40                  45
Gly Gln Val Ser Tyr Gly Ala Arg Pro Thr Tyr Lys Lys Pro Ser Glu
    50                  55                  60
```

```
Thr Asn Ala Tyr Asn Val Thr His Ala Asn Gly Gln Val Ser Tyr
 65                  70                  75                  80

Gly Ala Arg Pro Thr Gln Asn Lys Ala Ser Glu Thr Asn Ala Tyr Asn
             85                  90                  95

Val Thr Thr His Ala Asn Gly Gln Val Ser Tyr Gly Ala Arg Pro Thr
            100                 105                 110

Gln Asn Lys Pro Ser Lys Thr Asn Ala Tyr Asn Val Thr Thr His Gly
        115                 120                 125

Asn Gly Gln Val Ser Tyr Gly Ala Arg Pro Thr Tyr Lys Lys Pro Ser
    130                 135                 140

Glu Thr Asn Ala Tyr Asn Val Thr Thr His Ala Asp Gly Thr Ala Thr
145                 150                 155                 160

Tyr Gly

<210> SEQ ID NO 91
<211> LENGTH: 162
<212> TYPE: PRT
<213> ORGANISM: Staphylococcus aureus

<400> SEQUENCE: 91

Ala Arg Pro Arg Phe Asn Lys Pro Ser Glu Thr Asn Ala Tyr Asn Val
 1               5                  10                  15

Thr Thr Asn Gln Asp Gly Thr Val Thr Tyr Gly Ala Arg Pro Thr Gln
             20                  25                  30

Asn Lys Pro Ser Lys Thr Asn Ala Tyr Asn Val Thr Thr His Ala Asn
         35                  40                  45

Gly Gln Val Ser Tyr Gly Ala Arg Pro Thr Tyr Lys Lys Pro Ser Glu
    50                  55                  60

Thr Asn Ala Tyr Asn Val Thr Thr His Ala Asn Gly Gln Val Ser Tyr
 65                  70                  75                  80

Gly Ala Arg Pro Thr Gln Asn Lys Ala Ser Glu Thr Asn Ala Tyr Asn
             85                  90                  95

Val Thr Thr His Ala Asn Gly Gln Val Ser Tyr Gly Ala Arg Pro Thr
            100                 105                 110

Gln Asn Lys Pro Ser Lys Thr Asn Ala Tyr Asn Val Thr Thr His Gly
        115                 120                 125

Asn Gly Gln Val Ser Tyr Gly Ala Arg Pro Thr Tyr Lys Lys Pro Ser
    130                 135                 140

Glu Thr Asn Ala Tyr Asn Val Thr Thr His Ala Asp Gly Thr Ala Thr
145                 150                 155                 160

Tyr Gly

<210> SEQ ID NO 92
<211> LENGTH: 81
<212> TYPE: PRT
<213> ORGANISM: Staphylococcus aureus

<400> SEQUENCE: 92

Ala Arg Pro Arg Phe Asn Lys Pro Ser Glu Thr Asn Ala Tyr Asn Val
 1               5                  10                  15

Thr Thr Asn Gln Asp Gly Thr Val Thr Tyr Gly Ala Arg Pro Thr Gln
             20                  25                  30

Asn Lys Pro Ser Lys Thr Asn Ala Tyr Asn Val Thr Thr His Ala Asn
         35                  40                  45

Gly Gln Val Ser Tyr Gly Ala Arg Pro Thr Tyr Lys Lys Pro Ser Glu
```

```
                50                  55                  60
Thr Asn Ala Tyr Asn Val Thr Thr His Ala Asn Gly Thr Ala Thr Tyr
65                  70                  75                  80

Gly

<210> SEQ ID NO 93
<211> LENGTH: 108
<212> TYPE: PRT
<213> ORGANISM: Staphylococcus aureus

<400> SEQUENCE: 93

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
                20                  25                  30

Asn Lys Pro Ser Glu Thr Asn Ala Tyr Asn Val Thr Thr His Ala Asn
            35                  40                  45

Gly Gln Val Ser Tyr Gly Ala Arg Pro Thr Gln Asn Lys Pro Ser Glu
        50                  55                  60

Thr Asn Ala Tyr Asn Val Thr Thr His Ala Asn Gly Gln Val Ser Tyr
65                  70                  75                  80

Gly Ala Arg Pro Thr Gln Asn Lys Pro Ser Lys Thr Asn Ala Tyr Asn
                85                  90                  95

Val Thr Thr His Ala Asp Gly Thr Ala Thr Tyr Gly
            100                 105

<210> SEQ ID NO 94
<211> LENGTH: 162
<212> TYPE: PRT
<213> ORGANISM: Staphylococcus aureus

<400> SEQUENCE: 94

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
                20                  25                  30

Asn Lys Pro Ser Glu Thr Asn Ala Tyr Asn Val Thr Thr His Ala Asn
            35                  40                  45

Gly Gln Val Ser Tyr Gly Ala Arg Pro Thr Tyr Lys Lys Pro Ser Glu
        50                  55                  60

Thr Asn Ala Tyr Asn Val Thr Thr Asn Gln Asp Gly Thr Val Ser Tyr
65                  70                  75                  80

Gly Ala Arg Pro Thr Gln Asn Lys Pro Ser Glu Thr Asn Ala Tyr Asn
                85                  90                  95

Val Thr Thr His Ala Asn Gly Gln Val Ser Tyr Gly Ala Arg Pro Thr
            100                 105                 110

Gln Asn Lys Pro Ser Glu Thr Asn Ala Tyr Asn Val Thr Thr His Ala
        115                 120                 125

Asn Gly Gln Val Ser Tyr Gly Ala Arg Pro Thr Gln Asn Lys Pro Ser
    130                 135                 140

Lys Thr Asn Ala Tyr Asn Val Thr Thr His Ala Asp Gly Thr Ala Thr
145                 150                 155                 160

Tyr Gly

<210> SEQ ID NO 95
<211> LENGTH: 162
```

```
<212> TYPE: PRT
<213> ORGANISM: Staphylococcus aureus

<400> SEQUENCE: 95

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Glu Thr Asn Ala Tyr Asn Val Thr Thr His Ala Asn
        35                  40                  45

Gly Gln Val Ser Tyr Gly Ala Arg Pro Thr Tyr Lys Lys Pro Ser Glu
    50                  55                  60

Thr Asn Ala Tyr Asn Val Thr Thr Asn Gln Asp Gly Thr Val Ser Tyr
65                  70                  75                  80

Gly Ala Arg Pro Thr Gln Asn Lys Pro Ser Glu Thr Asn Ala Tyr Asn
                85                  90                  95

Val Thr Thr His Ala Asn Gly Gln Val Ser Tyr Gly Ala Arg Pro Thr
            100                 105                 110

Gln Asn Lys Pro Ser Glu Thr Asn Ala Tyr Asn Val Thr Thr His Ala
        115                 120                 125

Asn Gly Gln Val Ser Tyr Gly Ala Arg Pro Thr Gln Asn Lys Pro Ser
    130                 135                 140

Lys Thr Asn Ala Tyr Asn Val Thr Thr His Ala Asp Gly Thr Ala Thr
145                 150                 155                 160

Tyr Gly

<210> SEQ ID NO 96
<211> LENGTH: 81
<212> TYPE: PRT
<213> ORGANISM: Staphylococcus aureus

<400> SEQUENCE: 96

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Lys Thr Asn Ala Tyr Asn Val Thr Thr His Ala Asn
        35                  40                  45

Gly Gln Val Ser Tyr Gly Ala Arg Pro Thr Tyr Asn Lys Pro Ser Lys
    50                  55                  60

Thr Asn Ala Tyr Asn Val Thr Thr His Ala Asp Gly Thr Ala Thr Tyr
65                  70                  75                  80

Gly

<210> SEQ ID NO 97
<211> LENGTH: 162
<212> TYPE: PRT
<213> ORGANISM: Staphylococcus aureus

<400> SEQUENCE: 97

Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Lys Thr Asn Ala Tyr Asn Val Thr Thr His Ala Asn
        35                  40                  45
```

```
Gly Gln Val Ser Tyr Gly Ala Arg Pro Thr Tyr Asn Lys Pro Ser Glu
    50                  55                  60

Thr Asn Ala Tyr Asn Val Thr Thr Asn Arg Asp Gly Thr Val Ser Tyr
65                  70                  75                  80

Gly Ala Arg Pro Thr Gln Asn Lys Pro Ser Glu Thr Asn Ala Tyr Asn
                85                  90                  95

Val Thr Thr His Gly Asn Gly Gln Val Ser Tyr Gly Ala Arg Pro Thr
                100                 105                 110

Gln Lys Lys Pro Ser Lys Thr Asn Ala Tyr Asn Val Thr Thr His Ala
            115                 120                 125

Asn Gly Gln Val Ser Tyr Gly Ala Arg Pro Thr Tyr Asn Lys Pro Ser
        130                 135                 140

Lys Thr Asn Ala Tyr Asn Val Thr Thr His Ala Asp Gly Thr Ala Thr
145                 150                 155                 160

Tyr Gly
```

<210> SEQ ID NO 98
<211> LENGTH: 162
<212> TYPE: PRT
<213> ORGANISM: Staphylococcus aureus

<400> SEQUENCE: 98

```
Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Lys Thr Asn Ala Tyr Asn Val Thr His Ala Asn
        35                  40                  45

Gly Gln Val Ser Tyr Gly Ala Arg Pro Thr Tyr Asn Lys Pro Ser Glu
    50                  55                  60

Thr Asn Ala Tyr Asn Val Thr Thr Asn Arg Asp Gly Thr Val Ser Tyr
65                  70                  75                  80

Gly Ala Arg Pro Thr Gln Asn Lys Pro Ser Glu Thr Asn Ala Tyr Asn
                85                  90                  95

Val Thr Thr His Gly Asn Gly Gln Val Ser Tyr Gly Ala Arg Pro Thr
                100                 105                 110

Gln Lys Lys Pro Ser Lys Thr Asn Ala Tyr Asn Val Thr Thr His Ala
            115                 120                 125

Asn Gly Gln Val Ser Tyr Gly Ala Arg Pro Thr Gln Lys Lys Pro Ser
        130                 135                 140

Lys Thr Asn Ala Tyr Asn Val Thr Thr His Ala Asp Gly Thr Ala Thr
145                 150                 155                 160

Tyr Gly
```

<210> SEQ ID NO 99
<211> LENGTH: 162
<212> TYPE: PRT
<213> ORGANISM: Staphylococcus aureus

<400> SEQUENCE: 99

```
Ala Arg Pro Arg Phe Asn Lys Pro Ser Glu Thr Asn Ala Tyr Asn Val
1               5                   10                  15

Thr Thr Asn Gln Asp Gly Thr Val Ser Tyr Gly Ala Arg Pro Thr Gln
            20                  25                  30

Asn Lys Pro Ser Glu Thr Asn Ala Tyr Asn Val Thr Thr His Ala Asn
        35                  40                  45
```

Gly Gln Val Ser Tyr Gly Ala Arg Pro Thr Tyr Lys Lys Pro Ser Glu
            50                  55                  60

Thr Asn Ala Tyr Asn Val Thr Thr Asn Gln Asp Gly Thr Val Ser Tyr
 65                  70                  75                  80

Gly Ala Arg Pro Thr Gln Asn Lys Pro Ser Glu Thr Asn Ala Tyr Asn
                85                  90                  95

Val Thr Thr His Ala Asn Gly Gln Val Ser Tyr Gly Ala Arg Pro Thr
            100                 105                 110

Gln Asn Lys Pro Ser Glu Thr Asn Ala Tyr Asn Val Thr Thr His Ala
            115                 120                 125

Asn Gly Gln Val Ser Tyr Gly Ala Arg Pro Thr Gln Asn Lys Pro Ser
            130                 135                 140

Lys Thr Asn Ala Tyr Asn Val Thr Thr His Ala Asp Gly Thr Ala Thr
145                 150                 155                 160

Tyr Gly

<210> SEQ ID NO 100
<211> LENGTH: 162
<212> TYPE: PRT
<213> ORGANISM: Staphylococcus aureus

<400> SEQUENCE: 100

Ala Arg Pro Arg Phe Asn Lys Pro Ser Glu Thr Asn Ala Tyr Asn Val
 1               5                  10                  15

Thr Thr Asn Gln Asp Gly Thr Val Ser Tyr Gly Ala Arg Pro Thr Gln
            20                  25                  30

Asn Lys Pro Ser Glu Thr Asn Ala Tyr Asn Val Thr Thr His Ala Asn
            35                  40                  45

Gly Gln Val Ser Tyr Gly Ala Arg Pro Thr Tyr Lys Lys Pro Ser Glu
            50                  55                  60

Thr Asn Ala Tyr Asn Val Thr Thr Asn Gln Asp Gly Thr Val Ser Tyr
 65                  70                  75                  80

Gly Ala Arg Pro Thr Gln Asn Lys Pro Ser Glu Thr Asn Ala Tyr Asn
                85                  90                  95

Val Thr Thr His Ala Asn Gly Gln Val Ser Tyr Gly Ala Arg Pro Thr
            100                 105                 110

Gln Asn Lys Pro Ser Glu Thr Asn Ala Tyr Asn Val Thr Thr His Ala
            115                 120                 125

Asn Gly Gln Val Ser Tyr Gly Ala Arg Pro Thr Gln Asn Lys Pro Ser
            130                 135                 140

Lys Thr Asn Ala Tyr Asn Val Thr Thr His Ala Asp Gly Thr Ala Thr
145                 150                 155                 160

Tyr Gly

<210> SEQ ID NO 101
<211> LENGTH: 108
<212> TYPE: PRT
<213> ORGANISM: Staphylococcus aureus

<400> SEQUENCE: 101

Ala Arg Pro Arg Phe Asn Lys Pro Ser Glu Thr Asn Ala Tyr Asn Val
 1               5                  10                  15

Thr Thr Asn Gln Asp Gly Thr Val Ser Tyr Gly Ala Arg Pro Thr Gln
            20                  25                  30

Asn Lys Pro Ser Glu Thr Asn Ala Tyr Asn Val Thr Thr His Ala Asn

```
            35                  40                  45
Gly Gln Val Ser Tyr Gly Ala Arg Pro Thr Gln Asn Lys Pro Ser Glu
     50                  55                  60

Thr Asn Ala Tyr Asn Val Thr Thr His Ala Asn Gly Gln Val Ser Tyr
 65                  70                  75                  80

Gly Ala Arg Pro Thr Gln Asn Lys Pro Ser Lys Thr Asn Ala Tyr Asn
                 85                  90                  95

Val Thr Thr His Ala Asp Gly Thr Ala Thr Tyr Gly
            100                 105

<210> SEQ ID NO 102
<211> LENGTH: 27
<212> TYPE: PRT
<213> ORGANISM: Staphylococcus aureus

<400> SEQUENCE: 102

Ala Arg Pro Thr Tyr Asn Lys Pro Ser Glu Thr Asn Ala Tyr Asn Val
 1               5                  10                  15

Thr Thr Asn Arg Asp Gly Thr Val Ser Tyr Gly
            20                  25

<210> SEQ ID NO 103
<211> LENGTH: 27
<212> TYPE: PRT
<213> ORGANISM: Staphylococcus aureus

<400> SEQUENCE: 103

Ala Arg Pro Thr Tyr Lys Lys Pro Ser Glu Thr Asn Ala Tyr Asn Val
 1               5                  10                  15

Thr Thr Asn Gln Asp Gly Thr Val Ser Tyr Gly
            20                  25

<210> SEQ ID NO 104
<211> LENGTH: 27
<212> TYPE: PRT
<213> ORGANISM: Staphylococcus aureus

<400> SEQUENCE: 104

Ala Arg Pro Arg Phe Asn Lys Pro Ser Glu Thr Asn Ala Tyr Asn Val
 1               5                  10                  15

Thr Thr Asn Gln Asp Gly Thr Val Ser Tyr Gly
            20                  25

<210> SEQ ID NO 105
<211> LENGTH: 27
<212> TYPE: PRT
<213> ORGANISM: Staphylococcus aureus

<400> SEQUENCE: 105

Ala Arg Pro Arg Phe Asn Lys Pro Ser Glu Thr Asn Ala Tyr Asn Val
 1               5                  10                  15

Thr Thr Asn Gln Asp Gly Thr Val Thr Tyr Gly
            20                  25

<210> SEQ ID NO 106
<211> LENGTH: 27
<212> TYPE: PRT
<213> ORGANISM: Staphylococcus aureus

<400> SEQUENCE: 106

Ala Arg Pro Thr Tyr Asn Lys Pro Ser Lys Thr Asn Ala Tyr Asn Val
```

```
                1               5                   10                  15
Thr Thr His Ala Asp Gly Thr Ala Thr Tyr Gly
            20                  25

<210> SEQ ID NO 107
<211> LENGTH: 27
<212> TYPE: PRT
<213> ORGANISM: Staphylococcus aureus

<400> SEQUENCE: 107

Ala Arg Pro Thr Tyr Lys Lys Pro Ser Lys Thr Asn Ala Tyr Asn Val
1               5                   10                  15

Thr Thr His Ala Asp Gly Thr Ala Thr Tyr Gly
            20                  25

<210> SEQ ID NO 108
<211> LENGTH: 27
<212> TYPE: PRT
<213> ORGANISM: Staphylococcus aureus

<400> SEQUENCE: 108

Ala Arg Pro Thr Tyr Lys Lys Pro Ser Glu Thr Asn Ala Tyr Asn Val
1               5                   10                  15

Thr Thr His Ala Asn Gly Thr Ala Thr Tyr Gly
            20                  25

<210> SEQ ID NO 109
<211> LENGTH: 27
<212> TYPE: PRT
<213> ORGANISM: Staphylococcus aureus

<400> SEQUENCE: 109

Ala Arg Pro Thr Tyr Lys Lys Pro Ser Glu Thr Asn Ala Tyr Asn Val
1               5                   10                  15

Thr Thr His Ala Asp Gly Thr Ala Thr Tyr Gly
            20                  25

<210> SEQ ID NO 110
<211> LENGTH: 27
<212> TYPE: PRT
<213> ORGANISM: Staphylococcus aureus

<400> SEQUENCE: 110

Ala Arg Pro Thr Gln Asn Lys Pro Ser Lys Thr Asn Ala Tyr Asn Val
1               5                   10                  15

Thr Thr His Ala Asp Gly Thr Ala Thr Tyr Gly
            20                  25

<210> SEQ ID NO 111
<211> LENGTH: 27
<212> TYPE: PRT
<213> ORGANISM: Staphylococcus aureus

<400> SEQUENCE: 111

Ala Arg Pro Thr Gln Lys Lys Pro Ser Lys Thr Asn Ala Tyr Asn Val
1               5                   10                  15

Thr Thr His Ala Asp Gly Thr Ala Thr Tyr Gly
            20                  25

<210> SEQ ID NO 112
<211> LENGTH: 27
<212> TYPE: PRT
```

<213> ORGANISM: Staphylococcus aureus

<400> SEQUENCE: 112

Ala Arg Pro Thr Gln Lys Lys Pro Ser Glu Thr Asn Ala Tyr Asn Val
1               5                   10                  15

Thr Thr His Ala Asp Gly Thr Ala Thr Tyr Gly
            20                  25

<210> SEQ ID NO 113
<211> LENGTH: 27
<212> TYPE: PRT
<213> ORGANISM: Staphylococcus aureus

<400> SEQUENCE: 113

Ala Arg Leu Thr Gln Lys Lys Pro Ser Glu Thr Asn Ala Tyr Asn Val
1               5                   10                  15

Thr Thr His Ala Asp Gly Thr Ala Thr Tyr Gly
            20                  25

<210> SEQ ID NO 114
<211> LENGTH: 27
<212> TYPE: PRT
<213> ORGANISM: Staphylococcus aureus

<400> SEQUENCE: 114

Ala Arg Pro Thr Tyr Lys Lys Pro Ser Glu Thr Asn Ala Tyr Asn Val
1               5                   10                  15

Thr Thr His Ala Asn Gly Gln Val Ser Tyr Gly
            20                  25

<210> SEQ ID NO 115
<211> LENGTH: 27
<212> TYPE: PRT
<213> ORGANISM: Staphylococcus aureus

<400> SEQUENCE: 115

Ala Arg Pro Arg Phe Asn Lys Pro Ser Glu Thr Asn Ala Tyr Asn Val
1               5                   10                  15

Thr Thr His Ala Asn Gly Gln Val Ser Tyr Gly
            20                  25

<210> SEQ ID NO 116
<211> LENGTH: 27
<212> TYPE: PRT
<213> ORGANISM: Staphylococcus aureus

<400> SEQUENCE: 116

Ala Arg Pro Thr Gln Lys Lys Pro Ser Lys Thr Asn Ala Tyr Asn Val
1               5                   10                  15

Thr Thr His Ala Asn Gly Gln Val Ser Tyr Gly
            20                  25

<210> SEQ ID NO 117
<211> LENGTH: 27
<212> TYPE: PRT
<213> ORGANISM: Staphylococcus aureus

<400> SEQUENCE: 117

Ala Arg Pro Thr Gln Asn Lys Pro Ser Lys Thr Asn Ala Tyr Asn Val
1               5                   10                  15

Thr Thr His Ala Asn Gly Gln Val Ser Tyr Gly
            20                  25

<210> SEQ ID NO 118
<211> LENGTH: 27
<212> TYPE: PRT
<213> ORGANISM: Staphylococcus aureus

<400> SEQUENCE: 118

Ala Arg Pro Thr Gln Asn Lys Pro Ser Lys Thr Asn Ala Tyr Asn Val
1               5                   10                  15

Thr Thr His Gly Asn Gly Gln Val Ser Tyr Gly
            20                  25

<210> SEQ ID NO 119
<211> LENGTH: 27
<212> TYPE: PRT
<213> ORGANISM: Staphylococcus aureus

<400> SEQUENCE: 119

Ala Arg Pro Thr Gln Asn Lys Ala Ser Glu Thr Asn Ala Tyr Asn Val
1               5                   10                  15

Thr Thr His Ala Asn Gly Gln Val Ser Tyr Gly
            20                  25

<210> SEQ ID NO 120
<211> LENGTH: 27
<212> TYPE: PRT
<213> ORGANISM: Staphylococcus aureus

<400> SEQUENCE: 120

Ala Arg Pro Thr Gln Asn Lys Pro Ser Glu Thr Asn Ala Tyr Asn Val
1               5                   10                  15

Thr Thr His Ala Asn Gly Gln Val Ser Tyr Gly
            20                  25

<210> SEQ ID NO 121
<211> LENGTH: 27
<212> TYPE: PRT
<213> ORGANISM: Staphylococcus aureus

<400> SEQUENCE: 121

Ala Arg Pro Thr Gln Asn Lys Pro Ser Glu Thr Asn Ala Tyr Asn Val
1               5                   10                  15

Thr Thr His Gly Asn Gly Gln Val Ser Tyr Gly
            20                  25

<210> SEQ ID NO 122
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 122

Ala Arg Pro Thr Gln Asn Lys Pro Ser Glu Thr Asn Ala Tyr Asn Val
1               5                   10                  15

Thr Thr His Ala Asn Gly Gln Val Ser Tyr Gly Ala Arg Pro Thr Gln
            20                  25                  30

Asn Lys Pro Ser Glu Thr Asn Ala Tyr Asn Val Thr Thr His Ala Asn
        35                  40                  45

Gly Gln Val Ser Tyr Gly
    50

```
<210> SEQ ID NO 123
<211> LENGTH: 80
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is T or R
<220> FEATURE:
<221> NAME/KEY: MISC_FEATURE
<222> LOCATION: (5)..(5)
<223> OTHER INFORMATION: X is F or Q
<220> FEATURE:
<221> NAME/KEY: MISC_FEATURE
<222> LOCATION: (6)..(6)
<223> OTHER INFORMATION: X is N or K
<220> FEATURE:
<221> NAME/KEY: MISC_FEATURE
<222> LOCATION: (8)..(8)
<223> OTHER INFORMATION: X is P or A
<220> FEATURE:
<221> NAME/KEY: MISC_FEATURE
<222> LOCATION: (10)..(10)
<223> OTHER INFORMATION: X is E or K
<220> FEATURE:
<221> NAME/KEY: MISC_FEATURE
<222> LOCATION: (19)..(19)
<223> OTHER INFORMATION: X is H or N
<220> FEATURE:
<221> NAME/KEY: MISC_FEATURE
<222> LOCATION: (20)..(20)
<223> OTHER INFORMATION: X is A, G or Q
<220> FEATURE:
<221> NAME/KEY: MISC_FEATURE
<222> LOCATION: (21)..(21)
<223> OTHER INFORMATION: X is N or D
<220> FEATURE:
<221> NAME/KEY: MISC_FEATURE
<222> LOCATION: (23)..(23)
<223> OTHER INFORMATION: X is Q or T
<220> FEATURE:
<221> NAME/KEY: MISC_FEATURE
<222> LOCATION: (25)..(25)
<223> OTHER INFORMATION: X is S or T
<220> FEATURE:
<221> NAME/KEY: MISC_FEATURE
<222> LOCATION: (32)..(32)
<223> OTHER INFORMATION: X is Y or Q
<220> FEATURE:
<221> NAME/KEY: MISC_FEATURE
<222> LOCATION: (33)..(33)
<223> OTHER INFORMATION: X is K or N
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: MISC_FEATURE
<222> LOCATION: (37)..(37)
<223> OTHER INFORMATION: X is E or K
<220> FEATURE:
<221> NAME/KEY: MISC_FEATURE
<222> LOCATION: (46)..(46)
<223> OTHER INFORMATION: X is A or G
<220> FEATURE:
<221> NAME/KEY: MISC_FEATURE
<222> LOCATION: (56)..(56)
<223> OTHER INFORMATION: X is L or P
<220> FEATURE:
<221> NAME/KEY: MISC_FEATURE
<222> LOCATION: (58)..(58)
<223> OTHER INFORMATION: X is Q or Y
<220> FEATURE:
<221> NAME/KEY: MISC_FEATURE
<222> LOCATION: (59)..(59)
<223> OTHER INFORMATION: X is N or K
```

```
<220> FEATURE:
<221> NAME/KEY: MISC_FEATURE
<222> LOCATION: (63)..(63)
<223> OTHER INFORMATION: X is K or E
<220> FEATURE:
<221> NAME/KEY: MISC_FEATURE
<222> LOCATION: (74)..(74)
<223> OTHER INFORMATION: X is D or N

<400> SEQUENCE: 123
```

Ala Arg Pro Xaa Xaa Xaa Lys Xaa Ser Xaa Thr Asn Ala Tyr Asn Val
1               5                   10                  15

Thr Thr Xaa Xaa Xaa Gly Xaa Val Xaa Tyr Gly Ala Arg Pro Thr Xaa
            20                  25                  30

Lys Pro Ser Xaa Thr Asn Ala Tyr Asn Val Thr Thr His Xaa Asn Gly
        35                  40                  45

Gln Val Ser Tyr Gly Ala Arg Xaa Thr Xaa Xaa Lys Pro Ser Xaa Thr
    50                  55                  60

Asn Ala Tyr Asn Val Thr Thr His Ala Xaa Gly Thr Ala Thr Tyr Gly
65                  70                  75                  80

```
<210> SEQ ID NO 124
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (25)..(25)
<223> OTHER INFORMATION: X is S or T

<400> SEQUENCE: 124
```

Ala Arg Pro Arg Phe Asn Lys Pro Ser Glu Thr Asn Ala Tyr Asn Val
1               5                   10                  15

Thr Thr Asn Gln Asp Gly Thr Val Xaa Tyr Gly
            20                  25

```
<210> SEQ ID NO 125
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is T or R
<220> FEATURE:
<221> NAME/KEY: MISC_FEATURE
<222> LOCATION: (5)..(5)
<223> OTHER INFORMATION: X is Q or F
<220> FEATURE:
<221> NAME/KEY: MISC_FEATURE
<222> LOCATION: (10)..(10)
<223> OTHER INFORMATION: X is K or E

<400> SEQUENCE: 125
```

Ala Arg Pro Xaa Xaa Asn Lys Pro Ser Xaa Thr Asn Ala Tyr Asn Val
1               5                   10                  15

Thr Thr His Ala Asn Gly Gln Val Ser Tyr Gly
            20                  25

```
<210> SEQ ID NO 126
<211> LENGTH: 27
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is R or T
<220> FEATURE:
<221> NAME/KEY: MISC_FEATURE
<222> LOCATION: (5)..(5)
<223> OTHER INFORMATION: X is F, Y or Q
<220> FEATURE:
<221> NAME/KEY: MISC_FEATURE
<222> LOCATION: (6)..(6)
<223> OTHER INFORMATION: X is N or K
<220> FEATURE:
<221> NAME/KEY: MISC_FEATURE
<222> LOCATION: (10)..(10)
<223> OTHER INFORMATION: X is E or K
<220> FEATURE:
<221> NAME/KEY: MISC_FEATURE
<222> LOCATION: (19)..(19)
<223> OTHER INFORMATION: X is H or N
<220> FEATURE:
<221> NAME/KEY: MISC_FEATURE
<222> LOCATION: (20)..(20)
<223> OTHER INFORMATION: X is Q, A, or R
<220> FEATURE:
<221> NAME/KEY: MISC_FEATURE
<222> LOCATION: (21)..(21)
<223> OTHER INFORMATION: X is N or D
<220> FEATURE:
<221> NAME/KEY: MISC_FEATURE
<222> LOCATION: (23)..(23)
<223> OTHER INFORMATION: X is Q or T

<400> SEQUENCE: 126

Ala Arg Pro Xaa Xaa Xaa Lys Pro Ser Xaa Thr Asn Ala Tyr Asn Val
1               5                   10                  15

Thr Thr Xaa Xaa Xaa Gly Xaa Val Ser Tyr Gly
            20                  25

<210> SEQ ID NO 127
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 127

Ala Arg Pro Lys Pro Ser Thr Asn Ala Tyr Asn Val Thr Thr Gly Tyr
1               5                   10                  15

Gly
```